US012274725B2

(12) United States Patent
Diamond et al.

(10) Patent No.: US 12,274,725 B2
(45) Date of Patent: Apr. 15, 2025

(54) ZIKA VIRUS STRAINS FOR TREATMENT OF GLIOMA

(71) Applicants: Washington University, St. Louis, MO (US); The Board of Regents of The University of Texas System, Austin, TX (US); The Cleveland Clinic Foundation, Cleveland, OH (US)

(72) Inventors: Michael Diamond, St. Louis, MO (US); Milan Chheda, St. Louis, MO (US); Jeremy Rich, Cleveland, OH (US); Pei-Yong Shi, Austin, TX (US); Zhe Zhu, Cleveland, OH (US); Matthew Gorman, St. Louis, MO (US)

(73) Assignees: Washington University, St. Louis, MO (US); The Cleveland Clinic Foundation, Cleveland, OH (US); The Board of Regents of the University of Texas System, Austin, TX (US)

(*) Notice: Subject to any disclaimer, the term of this patent is extended or adjusted under 35 U.S.C. 154(b) by 1152 days.

(21) Appl. No.: 16/622,180

(22) PCT Filed: Jun. 11, 2018

(86) PCT No.: PCT/US2018/036858
§ 371 (c)(1),
(2) Date: Dec. 12, 2019

(87) PCT Pub. No.: WO2018/231690
PCT Pub. Date: Dec. 20, 2018

(65) Prior Publication Data
US 2021/0145907 A1 May 20, 2021

Related U.S. Application Data

(60) Provisional application No. 62/574,537, filed on Oct. 19, 2017, provisional application No. 62/518,300, filed on Jun. 12, 2017.

(51) Int. Cl.
*A61K 35/768* (2015.01)
*A61K 45/06* (2006.01)
*A61P 35/00* (2006.01)
*C12N 7/04* (2006.01)

(52) U.S. Cl.
CPC ............ *A61K 35/768* (2013.01); *A61K 45/06* (2013.01); *A61P 35/00* (2018.01); *C12N 7/04* (2013.01); *C12N 2770/24121* (2013.01); *C12N 2770/24122* (2013.01); *C12N 2770/24132* (2013.01)

(58) Field of Classification Search
CPC ........ A61K 35/768; A61K 45/06; C12N 7/04; C12N 2770/24121; C12N 2770/24132
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,755,388 A | 7/1988 | Heath et al. | |
| 4,828,837 A | 5/1989 | Uster et al. | |
| 4,925,661 A | 5/1990 | Huang | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 2017/0000868 A1 | 1/2017 | Lyday | |
| 2017/0014502 A1 | 1/2017 | Sumathy et al. | |
| 2019/0202886 A1* | 7/2019 | Kaur | A61K 35/768 |

FOREIGN PATENT DOCUMENTS

| | | |
|---|---|---|
| JP | 2008530032 A | 8/2008 |
| JP | 2011516040 A | 5/2011 |
| WO | 2006086838 A1 | 8/2006 |
| WO | 2009114207 A2 | 9/2009 |
| WO | 2009114207 A3 | 1/2010 |
| WO | 2018035294 A1 | 2/2018 |
| WO | 2018231690 A1 | 12/2018 |
| WO | 2019126690 A1 | 6/2019 |

OTHER PUBLICATIONS

Shan C, Muruato AE, Nunes BTD, Luo H, Xie X, Medeiros DBA, Wakamiya M, Tesh RB, Barrett AD, Wang T, Weaver SC, Vasconcelos PFC, Rossi SL, Shi PY. A live-attenuated Zika virus vaccine candidate induces sterilizing immunity in mouse models. Nat Med. Jun. 2017;23(6):763-767. (Year: 2017).*

Wollmann G, Ozduman K, van den Pol AN. Oncolytic virus therapy for glioblastoma multiforme: concepts and candidates. Cancer J. Jan.-Feb. 2012;18(1):69-81. (Year: 2012).*

Fukuhara H, Ino Y, Todo T. Oncolytic virus therapy: A new era of cancer treatment at dawn. Cancer Sci. Oct. 2016;107(10):1373-1379. (Year: 2016).*

ScienceDaily. Scientists to test Zika virus on brain tumors. https://www.sciencedaily.com/releases/2017/05/170519084107.htm, May 19, 2017. (Year: 2017).*

Pickworth. From finding cancers' paper trail to harnessing the power of the Zika virus—our latest Pioneer Awards. https://news.cancerresearchuk.org/2017/05/19/from-finding-cancers-paper-trail-to-harnessing-the-power-of-the-zika-virus-our-latest-pioneer-awards/, May 19, 2017. (Year: 2017).*

(Continued)

*Primary Examiner* — Nicole Kinsey White
*Assistant Examiner* — Ruixue Wang
(74) *Attorney, Agent, or Firm* — Polsinelli PC

(57) ABSTRACT

The present disclosure involves a composition and method of treatment of glioblastoma, using ZIKA virus.

4 Claims, 93 Drawing Sheets
(92 of 93 Drawing Sheet(s) Filed in Color)
Specification includes a Sequence Listing.

(56) References Cited

OTHER PUBLICATIONS

Van Hemert F, Berkhout B. Nucleotide composition of the Zika virus RNA genome and its codon usage. Virol J. Jun. 8, 2016;13:95. (Year: 2016).*
Office Action dated Jan. 3, 2022 from related European Patent Application No. 18818114.3; 6 pgs.
Alonso, M. et al., "Targeting Brain Tumor Stem Cells with Oncolytic Adenoviruses.", David H. Kim et al. (eds.), Oncolytic Viruses: Methods and Protocols, Methods in Molecular Biology, 2012, pp. 111-125, vol. 797.
Alvarado, A. et al., "Glioblastoma Cancer Stem Cells Evade Innate Immune Suppression of Self-Renewal through Reduced TLR4 Expression," Cell Stem Cell, Apr. 2017, pp. 450-461, vol. 20, with Methods, pp. e1-e4.
Bao, S. et al., "Glioma stem cells promote radioresistance by preferential activation of the DNA damage response," Nature, Dec. 2006, pp. 756-760, vol. 444.
Brown, M. et al., "Cytotoxic and Immunogenic Mechanisms of Recombinant Oncolytic Poliovirus," HHS Public Access Author Manuscript, Aug. 2016, pp. 1-10, published in final edited form as: Curr. Opin. Virol., Aug. 2015, pp. 81-85, vol. 13.
Cassady, K. et al., "Pre-clinical Assessment of C134, a Chimeric Oncolytic Herpes Simplex Virus, in Mice and Non-human Primates," Mol. Ther. Oncol., Jun. 2017, pp. 1-10, vol. 5.
Cattaneo, R. et al., "How to develop viruses into anticancer weapons," PLOS Pathogens, Mar. 2017, pp. 1-6, vol. 13, No. 3, e1006190.
Chen, J. et al., "A restricted cell population propagates glioblastoma growth after chemotherapy," Nature, Aug. 2012, pp. 522-526, vol. 488.
Cho, H. et al., "Differential innate immune response programs in neuronal subtypes determine susceptibility to infection in the brain by positive-stranded RNA viruses," Nat. Med., Apr. 2013, pp. 458-464, vol. 19, No. 4.
Daffis, S. et al., "2'-O methylation of the viral mRNA cap evades host restriction γ IFIT family members," Nat., Nov. 2010, pp. 452-456, vol. 468.
Extended European Search Report dated Jan. 21, 2021 from related European Patent Application No. 18818114.3; 14 pgs.
Gabriel, E. et al., "Recent Zika Virus Isolates Induce Premature Differentiation of Neural Progenitors in Human Brain Organoids," Cell Stem Cell, Mar. 2017, pp. 397-406, vol. 20, with Methods, pp. e1-e5.
Garcez, P. et al., "Zika virus impairs growth in human neurospheres and brain organoids," Sci., Apr. 2016, pp. 1-7, vol. 352.
GenBank Accession No. KX280026.1, "Zika virus isolate Paraiba_01, complete genome," Nov. 2017; 6 pgs.
GenBank Accession No. KY785480.1, "Zika virus isolate Zika virus/H.sapiens-wt/BRA/2016/FC-DQ62D1-PLA polyprotein gene, partial cds," Jun. 2017; 7 pgs.
Gorman, M. et al., "An Immunocompetent Mouse Model of Zika Virus Infection," Cell Host & Microbe, May 2018, pp. 672-685, vol. 23.
Govero, J. et al., "Zika virus infection damages the testes in mice," HHS Public Access Author Manuscript, Dec. 2017, pp. 1-21, published in final edited form as: Nature, Dec. 2016, pp. 438-442, vol. 540, No. 7633.
Hubert, C. et al., "A Three-Dimensional Organoid Culture System Derived from Human Glioblastomas Recapitulates the Hypoxic Gradients and Cancer Stem Cell Heterogeneity of Tumors Found In Vivo," Cancer Res., Apr. 2016, pp. 2465-2477, vol. 76, No. 8.
International Search Report and Written Opinion dated Oct. 19, 2018 from related Patent Application No. PCT/US2018/036858; 13 pgs.
Jiang, H. et al., "Targeting focal adhesion kinase renders pancreatic cancers responsive to checkpoint immunotherapy," Nature Med., Aug. 2016, pp. 851-860, vol. 22, No. 8.
Kaufmann, J. et al., "Glioma virus therapies between bench and bedside," Neuro-Oncology, 2014, pp. 334-351, vol. 16, No. 3.
Lazear, H. et al., "A Mouse Model of Zika Virus Pathogenesis," Cell Host & Microbe, 2016, pp. 720-730, vol. 19, No. 5.
Li, S-H. et al., "Rational Design of a Flavivirus Vaccine by Abolishing Viral RNA 2'-O Methylation," J. Virol., May 2013, pp. 5812-5819, vol. 87, No. 10.
Li, H. et al., "Zika Virus Infects Neural Progenitors in the Adult Mouse Brain and Alters Proliferation," Cell Stem Cell, 2016, pp. 593-598, vol. 19.
Lima, E. et al., "Zika virus infection induces synthesis of Digoxin in glioblastoma cells," bioRxiv, Aug. 2017, pp. 1-18, DOI: 10.1101/174441.
Liu, C. et al., "Mosaic Analysis with Double Markers Reveals Tumor Cell of Origin in Glioma," Cell, Jul. 2011, pp. 209-221, vol. 146.
Martuza, R. et al., "Experimental Therapy of Human Glioma by Means of a Genetically Engineered Virus Mutant," Sci., May 1991, pp. 854-856, vol. 252, No. 5007.
Ming, G-I. et al., "Advances in Zika Virus Research: Stem Cell Models, Challenges, and Opportunities," Cell Stem Cell, Dec. 2016, pp. 690-702, vol. 19.
Miska, J. et al., "Anti-GITR therapy promotes immunity against malignant glioma in a murine model," HHS Public Access Author Manuscript, Dec. 2017, pp. 1-22, published in final edited form as: Cancer Immunol. Immunother., Dec. 2016, pp. 1555-1567, vol. 65, No. 12.
Moore, A., "Effects of Viruses On Tumors," Ann. Rev. Microbiol., Oct. 1954, pp. 393-410, vol. 8.
Oh, T. et al., "Immunocompetent murine models for the study of glioblastoma immunotherapy," J. Transl. Med., 2014, pp. 1-10, vol. 12, No. 107.
Parra, B. et al., "Guillain-Barre Syndrome Associated with Zika Virus Infection in Colombia," N. Engl. J. Med., Oct. 2016, pp. 1513-1523, vol. 375, No. 16.
Pastrana, E. et al., "Eyes Wide Open: A Critical Review of Sphere-Formation as an Assay for Stem Cells," Cell Stem Cell, May 2011, pp. 486-498, vol. 8.
Qian, X. et al., "Brain-Region-Specific Organoids Using Mini-bioreactors for Modeling ZIKV Exposure," Cell, May 2016, pp. 1238-1254, vol. 165, No. 5.
Reardon, D. et al., "Effect on Nivolumab vs Bevacizumab in Patients With Recurrent Glioblastoma," JAMA Oncol., Jul. 2020, pp. 1003-1010, vol. 6, No. 7.
Sapparapu, G. et al., "Neutralizing human antibodies prevent Zika virus replication and fetal disease in mice," HHS Public Access Author Manuscript, Sep. 2017, pp. 1-27, published in final edited form as: Nature, Dec. 2016, pp. 443-447, vol. 540, No. 7633.
Shan, C. et al., "An Infectious cDNA Clone of Zika Virus to Study Viral Virulence, Mosquito Transmission, and Antiviral Inhibitors," Cell Host & Microbe, Jun. 2016, pp. 891-900, vol. 19.
Shan, C. et al., "A live-attenuated Zika virus vaccine candidate induces sterilizing immunity in mouse models," Nat. Med., Jun. 2017, pp. 763-767, vol. 23, No. 6.
Singh, S. et al., "Identification of human brain tumour initiating cells, " Nature, Nov. 2004, pp. 396-401, vol. 432.
Southam, C. et al., "Clinical Studies of Viruses as Antineoplastic Agents, With Particular Reference To Egypt 101 VIRUS," Cancer, Sep. 1952, pp. 1025-1034, vol. 5.
Stupp, R. et al., "Effects of radiotherapy with concomitant and adjuvant temozolomide versus radiotherapy alone on survival in glioblastoma in a randomised phase III study: 5-year analysis of the EORTC-NCIC trial," The Lancet Oncol., May 2009, pp. 459-466, vol. 10.
Subramanian, A. et al., "Gene set enrichment analysis: A knowledge-based approach for interpreting genome-wide expression profiles," PNAS, Oct. 2005, pp. 15545-15550, vol. 102, No. 43.
Suva, M. et al., "Reconstructing and Reprogramming the Tumor-Propagating Potential of Glioblastoma Stem-like Cells," Cell, Apr. 2014, pp. 580-594, vol. 157.
Wallner, K. et al., "Patterns of Failure Following Treatment for Glioblastoma Multiforme and Anaplastic Astrocytoma," Internatl. J. Radiation Oncol. Biol. Phys., Jun. 1989, pp. 1405-1409, vol. 16, No. 6.
Wang, X. et al., "Purine synthesis promotes maintenance of brain tumor initiating cells in glioma," HHS Public Access Author Manu-

(56) References Cited

OTHER PUBLICATIONS script, Jun. 2018, pp. 1-34, published in final edited form as: Nat. Neurosci., May 2017, pp. 661-673, vol. 20, No. 5.
Zhao, H. et al., "Structural Basis of Zika Virus-Specific Antibody Protection," Cell, Aug. 2016, pp. 1016-1027, vol. 166.
Zhu, Z. et al., "Zika virus has oncolytic activity against glioblastoma stem cells," J. Exp. Med., 2017, pp. 2843-2857, vol. 214, No. 10.
Annamalai A.S., et al., "Zika Virus Encoding Nonglycosylated Envelope Protein Is Attenuated and Defective in Neuroinvasion," Journal of Virology, Dec. 2017, vol. 91, No. 23, pp. 1-16.
Examination Report No. 1 for Australian Patent Application No. 2018283957 dated Mar. 21, 2023, 4 pages.
International Preliminary Report on Patentability for International Application No. PCT/US2018/036858, mailed Dec. 26, 2019, 09 Pages.
Office Action for European Patent Application No. 18818114.3, mailed on Nov. 13, 2023, 160 Pages.
Office Action for European Patent Application No. 18818114.3, mailed on Jun. 17, 2022, 9 Pages.
Office Action for Japanese Patent Application No. 2019-569733, mailed on Dec. 5, 2023, 9 Pages.
Office Action for Japanese Patent Application No. 2019-569733, mailed on Jul. 5, 2022, 11 Pages.
Office Action for Japanese Patent Application No. 2019-569733, mailed on Apr. 11, 2023, 7 Pages.
Shan C., et al., "A Single-Dose Live-Attenuated Vaccine Prevents Zika Virus Pregnancy Transmission and Testis Damage," Nature communications, Sep. 22, 2017, vol. 8, No. 676. pp. 1-9.
Schnettler, et al., "Noncoding Flavivirus RNA Displays RNA Interference Suppressor Activity in Insect and Mammalian Cells," Journal of Virology, Dec. 2012, vol. 86, No. 24, 15 pages.
Schuessler, et al., "West Nile Virus Noncoding Subgenomic RNA Contributes to Vial Eveaion of the Type I Interferon-Mediated Antiviral Response," Journal of Virology, Feb. 29, 2012, 11 pages.
Clarke, et al., "Functional non-coding RNAs derived from the flavivirius 3' untranslated region," Virus Research, 2015. 9 pages, [http://dx.doi.org/10.1016/j.virusres.2015.01.026].
Whitehead, Stephen S., "Development of TV003/TV005, a single dose, highly immunogenic live attenuated dengue vaccine; what makes this vaccine different from the Sanofi-Pasteur CYD vaccine?" Expert Rev Vaccines, Apr. 2016, vol. 15(4), 19 pages.

* cited by examiner

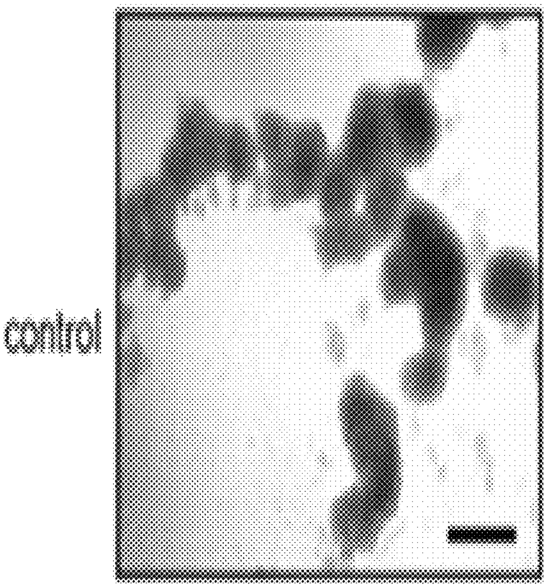
FIG. 1A
FIG. 1B
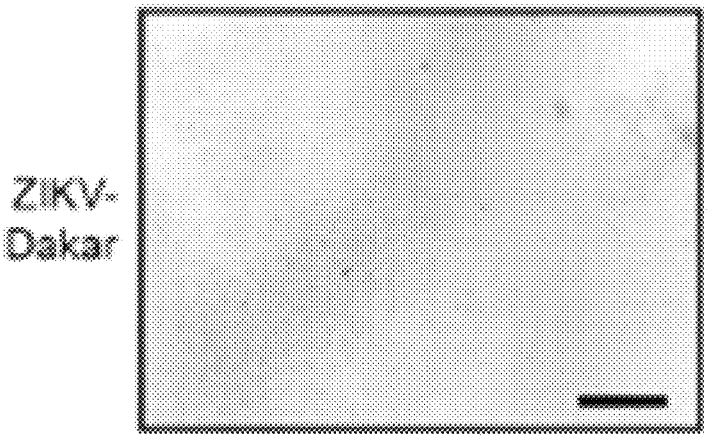
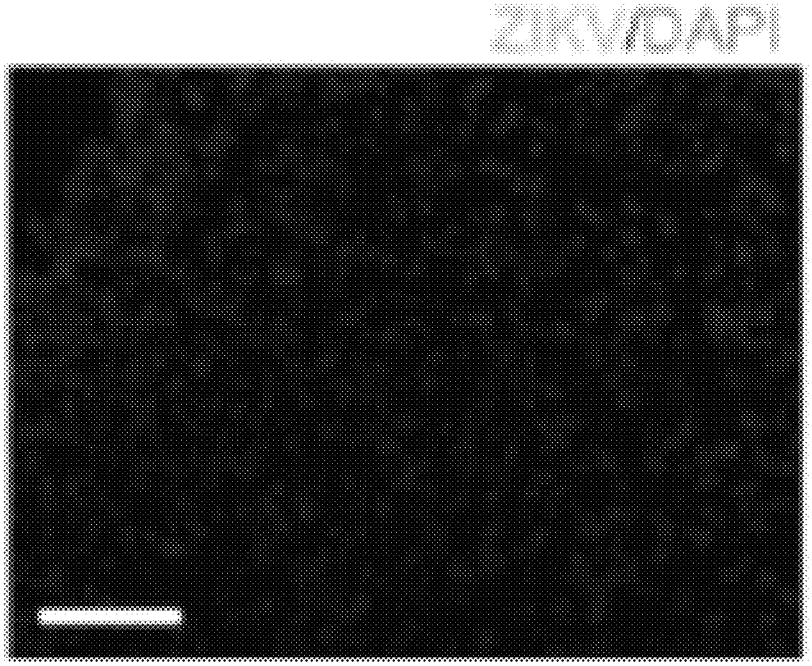
FIG. 1C

ZIKAV-Brazil

ZIKAV-Dakar

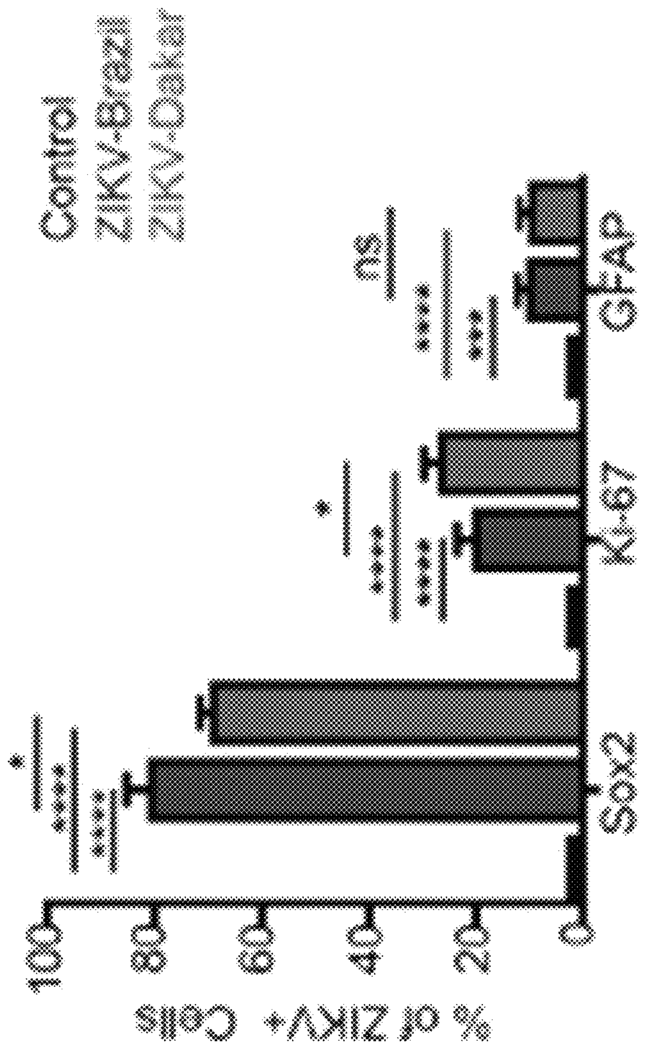
FIG. 3S
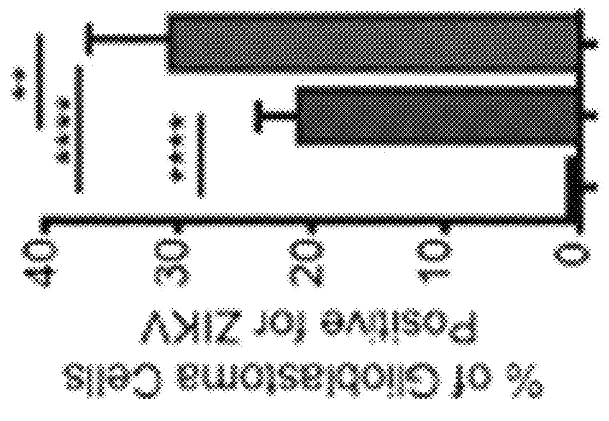

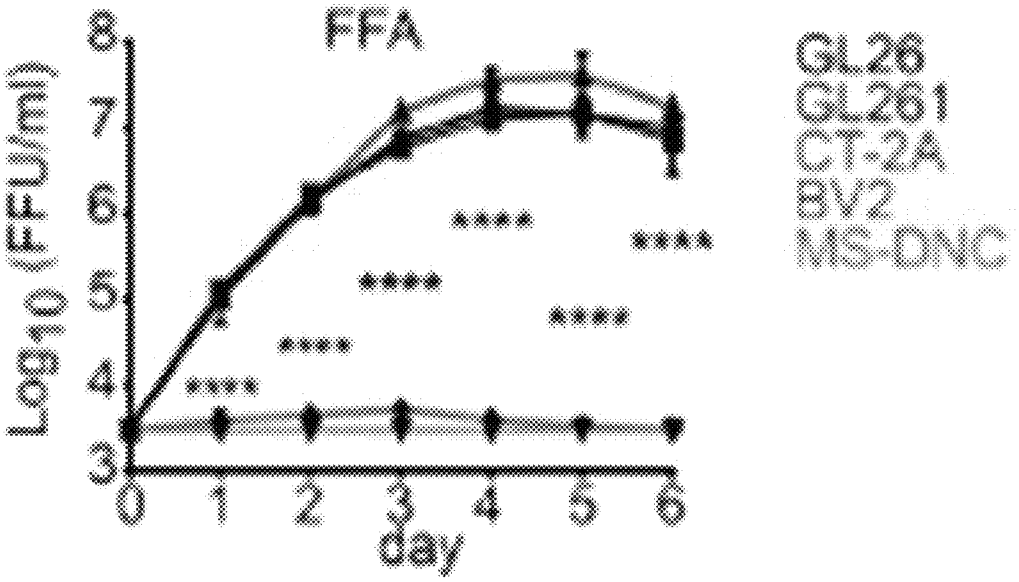
FIG. 4B
FIG. 4D
GL261
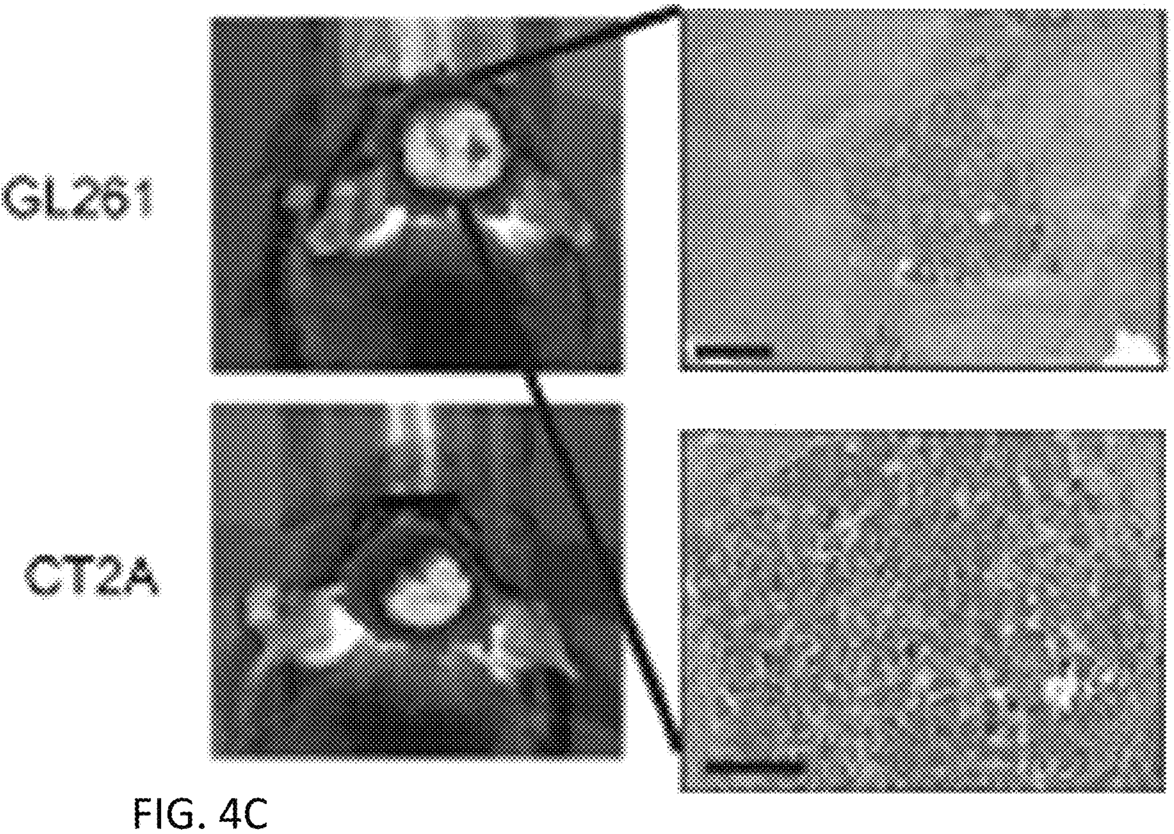
CT2A
FIG. 4C
FIG. 4E

GL261

Control

Adapted
ZIKV-Dakar

CT2A control

WNV-NY

GSC

DGC

DGC

DGC normal human neuronal cells normal human neuronal cells

| GO_Biological_Process | SIZE | NOM p-val | FWER p-val |
|---|---|---|---|
| GO:0060337 TYPE I INTERFERON SIGNALING PATHWAY | 62 | <0.0001 | 0 |
| GO:0071357 CELLULAR RESPONSE TO TYPE I INTERFERON | 62 | <0.0001 | 0 |
| GO:0034340 RESPONSE TO TYPE I INTERFERON | 63 | <0.0001 | 0.047 |
| GO:0034341 RESPONSE TO INTERFERON-GAMMA | 105 | <0.0001 | 0.047 |
| GO:0060333 INTERFERON-GAMMA-MEDIATED SIGNALING PATHWAY | 68 | <0.0001 | 0.047 |
| GO:0071346 CELLULAR RESPONSE TO INTERFERON-GAMMA | 91 | <0.0001 | 0.047 |

- Cloned ZIKV Dakar NS4B(G18R) ($10^7$) (n=10)
- Passaged Mouse Adapted ZIKV Dakar ($10^5$) (n=10)
- Cloned ZIKV Dakar NS4B(G18R) ($10^5$) (n=9)
- PBS (n=9)

Confirm tumors with imaging; Treat Mice (day 7)

SEQUENCE LISTING

```
<160> NUMBER OF SEQ ID NOS: 22

<210> SEQ ID NO 1
<211> LENGTH: 28
<212> TYPE: DNA
```

-continued

<213> ORGANISM: Artificial Sequence
<220> FEATURE:
<223> OTHER INFORMATION: SYNTHESIZED/PRIMER 1

<400> SEQUENCE: 1
ccaccaatgt tctcttgcag acatattg 28

<210> SEQ ID NO 2
<211> LENGTH: 26
<212> TYPE: DNA
<213> ORGANISM: Artificial Sequence
<220> FEATURE:
<223> OTHER INFORMATION: SYNTHESIZED/PRIMER 2

<400> SEQUENCE: 2
ttcggacagc cgttgtccaa cacaag 26

<210> SEQ ID NO 3
<211> LENGTH: 21
<212> TYPE: DNA
<213> ORGANISM: Artificial Sequence
<220> FEATURE:
<223> OTHER INFORMATION: SYNTHESIZED/PRIMER 3

<400> SEQUENCE: 3
agcctacctt gacaagcagt c 21

<210> SEQ ID NO 4
<211> LENGTH: 21
<212> TYPE: DNA
<213> ORGANISM: Artificial Sequence
<220> FEATURE:
<223> OTHER INFORMATION: SYNTHESIZED/PRIMER 4

<400> SEQUENCE: 4
aacaggagcg atgagtctgt c 21

<210> SEQ ID NO 5
<211> LENGTH: 23
<212> TYPE: DNA
<213> ORGANISM: Artificial Sequence
<220> FEATURE:
<223> OTHER INFORMATION: SYNTHESIZED/PRIMER 5

<400> SEQUENCE: 5
tgcgaaatgg tgtaaatgag tca 23

<210> SEQ ID NO 6
<211> LENGTH: 23
<212> TYPE: DNA
<213> ORGANISM: Artificial Sequence
<220> FEATURE:
<223> OTHER INFORMATION: SYNTHESIZED/PRIMER 6

<400> SEQUENCE: 6
cagcttgact caaaattcct gga 23

<210> SEQ ID NO 7
<211> LENGTH: 23
<212> TYPE: DNA
<213> ORGANISM: Artificial Sequence
<220> FEATURE:
<223> OTHER INFORMATION: SYNTHESIZED/PRIMER 7

<400> SEQUENCE: 7
tgaagattac gcttgctttt cct 23

<210> SEQ ID NO 8
<211> LENGTH: 19
<212> TYPE: DNA
<213> ORGANISM: Artificial Sequence
<220> FEATURE:
<223> OTHER INFORMATION: SYNTHESIZED/PRIMER 8

<400> SEQUENCE: 8
atgcccatca ctcggatgc 19

<210> SEQ ID NO 9
<211> LENGTH: 20
<212> TYPE: DNA
<213> ORGANISM: Artificial Sequence
<220> FEATURE:
<223> OTHER INFORMATION: SYNTHESIZED/PRIMER 9

<400> SEQUENCE: 9
ccctgctttg tatcggcctg 20

<210> SEQ ID NO 10
<211> LENGTH: 16
<212> TYPE: DNA
<213> ORGANISM: Artificial Sequence
<220> FEATURE:
<223> OTHER INFORMATION: SYNTHESIZED/PRIMER 10

<400> SEQUENCE: 10
acgatgaaat gcctga 16

<210> SEQ ID NO 11
<211> LENGTH: 20
<212> TYPE: DNA
<213> ORGANISM: Artificial Sequence
<220> FEATURE:
<223> OTHER INFORMATION: SYNTHESIZED/PRIMER 11

<400> SEQUENCE: 11
caggtcacca gactcctcac 20

<210> SEQ ID NO 12
<211> LENGTH: 22
<212> TYPE: DNA
<213> ORGANISM: Artificial Sequence
<220> FEATURE:
<223> OTHER INFORMATION: SYNTHESIZED/PRIMER 12

<400> SEQUENCE: 12
ctcagaagct gggttggttt at 22

<210> SEQ ID NO 13
<211> LENGTH: 21
<212> TYPE: DNA
<213> ORGANISM: Artificial Sequence
<220> FEATURE:
<223> OTHER INFORMATION: SYNTHESIZED/PRIMER 13

<400> SEQUENCE: 13
accatctcgt cgatcagtgt c 21

<210> SEQ ID NO 14
<211> LENGTH: 22
<212> TYPE: DNA
<213> ORGANISM: Artificial Sequence
<220> FEATURE:

<223> OTHER INFORMATION: SYNTHESIZED/PRIMER 14

<400> SEQUENCE: 14
tcgaatgggt attccacaga cg 22

<210> SEQ ID NO 15
<211> LENGTH: 19
<212> TYPE: DNA
<213> ORGANISM: Artificial Sequence
<220> FEATURE:
<223> OTHER INFORMATION: SYNTHESIZED/PRIMER 15

<400> SEQUENCE: 15
gtggcgactg tcctctgaa 19

<210> SEQ ID NO 16
<211> LENGTH: 18
<212> TYPE: DNA
<213> ORGANISM: Artificial Sequence
<220> FEATURE:
<223> OTHER INFORMATION: SYNTHESIZED/PRIMER 16

<400> SEQUENCE: 16
aacccgttga accccatt 18

<210> SEQ ID NO 17
<211> LENGTH: 20
<212> TYPE: DNA
<213> ORGANISM: Artificial Sequence
<220> FEATURE:
<223> OTHER INFORMATION: SYNTHESIZED/PRIMER 17

<400> SEQUENCE: 17
ccatccaatc ggtagtagcg 20

<210> SEQ ID NO 18
<211> LENGTH: 19
<212> TYPE: DNA
<213> ORGANISM: Artificial Sequence
<220> FEATURE:
<223> OTHER INFORMATION: SYNTHESIZED/PRIMER 18

<400> SEQUENCE: 18
cctgttcgac agtcagccg 19

<210> SEQ ID NO 19
<211> LENGTH: 20
<212> TYPE: DNA
<213> ORGANISM: Artificial Sequence
<220> FEATURE:
<223> OTHER INFORMATION: SYNTHESIZED/PRIMER 19

<400> SEQUENCE: 19
cgaccaaatc cgttgactcc 20

<210> SEQ ID NO 20
<211> LENGTH: 10123
<212> TYPE: DNA
<213> ORGANISM: Artificial Sequence
<220> FEATURE:
<223> OTHER INFORMATION: Zika virus
<220> FEATURE:
<221> NAME/KEY: misc_feature
<222> LOCATION: (2255)..(2387)
<223> OTHER INFORMATION: n is a, c, g, or t
<220> FEATURE:
<221> NAME/KEY: misc_feature
<222> LOCATION: (3700)..(3874)
<223> OTHER INFORMATION: n is a, c, g, or t
<220> FEATURE:
<221> NAME/KEY: misc_feature
<222> LOCATION: (4601)..(4779)
<223> OTHER INFORMATION: n is a, c, g, or t
<220> FEATURE:
<221> NAME/KEY: misc_feature
<222> LOCATION: (10044)..(10049)
<223> OTHER INFORMATION: n is a, c, g, or t

<400> SEQUENCE: 20
tggctgccat gctgagaata atcaatgcta ggaaggagaa gaagagacga ggcgcagaaa 60
ctagtgtcgg aattgttggc ctcctgctga ccacagctat ggcagcggag gtcactagac 120
gtgggagtgc atactatatg tacttggaca gaaacgatgc tggggaggcc atatcttttc 180
caaccacatt ggggatgaat aagtgttata tacagatcat ggatcttgga cacatgtgtg 240
atgccaccat gagctatgaa tgccctatgc tggatgaggg ggtggaacca gatgacgtcg 300
attgttggtg caacacgacg tcaacttggg ttgtgtacgg aacctgccat cacaaaaaag 360
gtgaagcacg gagatctaga agagctgtga cgctcccctc ccattccact aggaagctgc 420
aaacgcggtc gcaaacctgg ttggaatcaa gagaatacac aaagcacttg attagagtcg 480
aaaattggat attcaggaac cctggcttcg cgttagcagc agctgccatc gcttggcttt 540
tgggaagctc aacgagccaa aaagtcatat acttggtcat gatactgctg attgccccgg 600
catacagcat caggtgcata ggagtcagca atagggactt tgtggaaggt atgtcaggtg 660
ggacttgggt tgatgttgtc ttggaacatg gaggttgtgt caccgtaatg gcacaggaca 720
aaccgactgt cgacatagag ctggttacaa caacagtcag caacatggcg gaggtaagat 780
cctactgcta tgaggcatca atatcagaca tggcttcgga cagccgctgc ccaacacaag 840
gtgaagccta ccttgacaag caatcagaca ctcaatatgt ctgcaaaaga acgttagtgg 900
acagaggctg gggaaatgga tgtggacttt ttggcaaagg gagcctggtg acatgcgcta 960
agtttgcatg ctccaagaaa atgaccggga agagcatcca gccagagaat ctggagtacc 1020
ggataatgct gtcagttcat ggctcccagc acagtgggat gatcgttaat gacacaggac 1080
atgaaactga tgagaataga gcgaaggttg agataacgcc caattcacca agagccgaag 1140
ccaccctggg gggttttgga agcctaggac ttgattgtga accgaggaca ggccttgact 1200
tttcagattt gtattacttg actatgaata acaagcactg gttggttcac aaggagtggt 1260
tccacgacat tccattacct tggcatgctg ggcagacac cggaactcca cactggaaca 1320
acaaagaagc actggtagag ttcaaggacg cacatgccaa aaggcaaact gtcgtggttc 1380
tagggagtca agaaggagca gttcacacgg ccccttgctgg agctctggag gctgagatgg 1440
atggtgcaaa gggaaggctg tcctctggcc acttgaaatg tcgcctgaaa atggataaac 1500
ttagattgaa aggcgtgtca tactccttgt gtaccgcagc gttcacattc accaagatcc 1560
cggctgaaac actgcacggg acagtcacag tggaggtaca gtacgcaggg acagatggac 1620
cttgcaaggt tccagctcag atggcggtgg acatgcaaac tctgacccca gttgggaggt 1680
tgataaccgc taaccccgta atcactgaaa gcactgagaa ctctaagatg atgctggaac 1740
ttgatccacc atttggggac tcttacattg tcataggagt cggggagaag aagatcaccc 1800
accactggca caggagtggc agcaccattg gaaaagcatt tgaagccact gtgagaggtg 1860
ccaagagaat ggcagtcttg ggagacacag cctgggactt tggatcagtt ggaggcgctc 1920
tcaactcatt gggcaagggc atccatcaaa tttttggagc agctttcaaa tcattgtttg 1980

-continued

```
gaggaatgtc ctggttctca caaattctca ttggaacgtt gctgatgtgg ttgggtctga   2040
acacaaagaa tggatctatt tcccttatgt gcttggcctt agggggagtg ttgatcttct   2100
tatccacagc cgtctctgct gatgtggggt gctcggtgga cttctcaaag aaggagacga   2160
gatgtggtac aggggtgttc gtctataacg acgttgaagc ctggagggac aggtacaagt   2220
accatcctga ctccccccgt agattggcag cagcnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnngtg ggatctgtaa   2400
aaaaccccat gtggagaggt ccacagagat tgcccgtgcc tgtgaacgag ctgccccacg   2460
gctggaaggc ttgggggaaa tcgtacttcg tcagagcagc aaagacaaat aacagctttg   2520
tcgtggatgg tgacacactg aaggaatgcc cactcaaaca tagagcatgg aacagctttc   2580
ttgtggagga tcatgggttc ggggtatttc acactagtgt ctggctcaag gttagagaag   2640
attattcatt agagtgtgat ccagccgtta ttggaacagc tgttaaggga aaggaggctg   2700
tacacagtga tctaggctac tggattgaga gtgagaagaa tgacacatgg aggctgaaga   2760
gggcccatct gatcgagatg aaaacatgtg aatggccaaa gtcccacaca ttgtggacag   2820
atggaataga agagagtgat ctgatcatac ccaagtcttt agctgggcca ctcagccatc   2880
acaataccag agagggctac aggacccaaa tgaaagggcc atggcacagt gaagagcttg   2940
aaattcggtt tgaggaatgc ccaggcacta aggtccacgt ggaggaaaca tgtggaacaa   3000
gaggaccatc tctgagatca accactgcaa gcggaagggt gatcgaggaa tggtgctgca   3060
gggagtgcac aatgccccca ctgtcgttcc gggctaaaga tggctgttgg tatggaatgg   3120
agataaggcc caggaaagaa ccagaaagca acttagtaag gtcaatggtg actgcaggat   3180
caactgatca catggatcac ttctcccttg gagtgcttgt gattctgctc atggtgcagg   3240
aagggctgaa gaagagaatg accacaaaga tcatcataag cacatcaatg gcagtgctgg   3300
tagctatgat cctgggagga ttttcaatga gtgacctggc taagcttgca attttgatgg   3360
gtgccacctt cgcggaaatg aacactggag gagatgtagc tcatctggcg ctgatagcgg   3420
cattcaaagt cagaccagcg ttgctggtat ctttcatctt cagagctaat tggacacccc   3480
gtgaaagcat gctgctggcc ttggcctcgt gtcttttgca aactgcgatc tccgccttgg   3540
aaggcgacct gatggttctc atcaatggtt ttgctttggc ctggttggca atacgagcga   3600
tggttgttcc acgcactgat aacatcacct tggcaatcct ggctgctctg acaccactgg   3660
cccggggtac actgcttgtg gcgtggagag caggccttgn nnnnnnnnnn nnnnnnnnnn   3720
nnnnnnnnnn nnnnnnnnnn nnnnnnnnnn nnnnnnnnnn nnnnnnnnnn nnnnnnnnnn   3780
nnnnnnnnnn nnnnnnnnnn nnnnnnnnnn nnnnnnnnnn nnnnnnnnnn nnnnnnnnnn   3840
nnnnnnnnnn nnnnnnnnnn nnnnnnnnnn nnnnactcac agctgttggc ctgatatgcg   3900
cattggctgg agggttcgcc aaggcagata tagagatggc tgggcccatg gccgcggtcg   3960
gtctgctaat tgtcagttac gtggtctcag ggaagagtgt ggacatgtac attgaaagag   4020
caggtgacat cacatgggaa aaagatgcgg aagtcaccgg aaacagtccc cggctcgatg   4080
tggcgctaga tgagagtggt gatttctccc tggtggagga tgacggtccc cccatgagag   4140
agatcatact caaggtggtc ctgatgacca tctgtggcat gaacccaata gccataccct   4200
ttgcagctgg agcgtggtac gtatacgtga agactggaaa aaggagtggt gctctatggg   4260
atgtgcctgc tcccaaggaa gtaaaaaagg gggagaccac agatggagtg tacagagtaa   4320
tgactcgtag actgctaggt tcaacacaag ttggagtggg agttatgcaa gagggggtct   4380
```

-continued

```
ttcacactat gtggcacgtc acaaaaggat ccgcgctgag aagcggtgaa gggagacttg   4440
atccatactg gggagatgtc aagcaggatc tggtgtcata ctgtggtcca tggaagctag   4500
atgccgcctg ggacgggcac agcgaggtgc agctcttggc tgtgcccccc ggagagagag   4560
cgaggaacat ccagactctg cccggaatat ttaagacaaa nnnnnnnnnn nnnnnnnnnn   4620
nnnnnnnnnn nnnnnnnnnn nnnnnnnnnn nnnnnnnnnn nnnnnnnnnn nnnnnnnnnn   4680
nnnnnnnnnn nnnnnnnnnn nnnnnnnnnn nnnnnnnnnn nnnnnnnnnn nnnnnnnnnn   4740
nnnnnnnnnn nnnnnnnnnn nnnnnnnnnn nnnnnnnnnt cgagccttcg atgctgaaga   4800
agaagcagct aactgtctta gacttgcatc ctggagctgg gaaaaccagg agagttcttc   4860
ctgaaatagt ccgtgaagcc ataaaaacaa gactccgtac tgtgatctta gctccaacca   4920
gggttgtcgc tgctgaaatg gaggaagccc ttagagggct tccagtgcgt tatatgacaa   4980
cagcagtcaa tgtcacccac tctggaacag aaatcgtcga cttaatgtgc catgccacct   5040
tcacttcacg tctactacag ccaatcagag tccccaacta caatctgtat attatggatg   5100
aggcccactt cacagatccc tcaagtatag cagcaagagg atacatttca acaagggttg   5160
agatgggcga ggcggctgcc atcttcatga ccgccacgcc accaggaacc cgtgacgcat   5220
ttccggactc caactcacca attatggaca ccgaagtgga agtcccagag agagcctgga   5280
gctcaggctt tgattgggtg acggatcatt ctggaaaaac agtttggttt gttccaagcg   5340
tgaggaacgg caatgagatc gcagcttgtc tgacaaaggc tggaaaacgg gtcatacagc   5400
tcagcagaaa gacttttgag acagagttcc agaaaacaaa acatcaagag tgggactttg   5460
tcgtgacaac tgacatttca gagatgggcg ccaactttaa agctgaccgy gtcatagatt   5520
ccaggagatg cctaaagccg gtcatacttg atggcgagag agtcattctg gctggaccya   5580
tgcctgtcac acatgccagc gctgcccaga ggagggggcg cataggcagg aatcccaaca   5640
aacctggaga tgagtatctg tatggaggtg ggtgcgcaga gactgacgaa gaccatgcac   5700
actggcttga agcaagaatg ctccttgaca atatttacct ccaagatggc ctcatagcct   5760
cgctctatcg acctgaggcc gacaaagtag cagccattga gggagagttc aagcttagga   5820
cggagcaaag gaagaccttt gtggaactca tgaaaagagg agatcttcct gtttggctgg   5880
cctatcaggt tgcatctgcc ggaataacct acacagatag aagatggtgc tttgatggca   5940
cgaccaacaa caccataatg gaagacagtg tgccggcaga ggtgtggacc agacacggag   6000
agaaaagagt gctcaaaccg aggtggatgg acgccagagt ttgttcagat catgcggccc   6060
tgaagtcatt caaggagttt gccgctggga aaagaggagc ggcttttgga gtgatggaag   6120
ccctgggaac actgccagga cacatgacag agagattcca ggaagccatt gacaacctcg   6180
ctgtgctcat gcgggcagag actggaagca ggccttacaa agccgcggcg gcccaattgc   6240
cggagaccct agagaccatt atgcttttgg ggttgctggg aacagtctcg ctgggaatct   6300
tttttgtctt gatgaggaac aagggcatag ggaagatggg ctttggaatg gtgactcttg   6360
gggccagcgc atggctcatg tggctctcgg aaattgagcc agccagaatc gcatgtgtcc   6420
tcattgtcgt gttcctattg ctggtggtgc tcatacctga gccagaaaag caaagatctc   6480
cccaggacaa ccaaatggca atcatcatca tggtagcagt aggtcttctg ggcttgatta   6540
ccgccaatga actcggatgg ttggagagaa caaagagtga cctaagccat ctaatgggaa   6600
ggagagagga gggggcaacc ataggattct caatggacat tgacctgcgg ccagcctcag   6660
cttgggccat ctatgctgcc ttgacaactt tcattacccc agccgtccaa catgcagtga   6720
```

-continued

```
ccacttcata caacaactac tccttaatgg cgatggccac gcaagctgga gtgttgtttg   6780
gtatgggcaa agggatgcca ttctacgcat gggactttgg agtcccgctg ctaatgatag   6840
gttgctactc acaattaaca cccctgaccc taatagtggc catcattttg ctcgtggcgc   6900
actacatgta cttgatccca gggctgcagg cagcagctgc gcgtgctgcc cagaagagaa   6960
cggcagctgg catcatgaag aaccctgttg tggatggaat agtggtgact gacattgaca   7020
caatgacaat tgacccccaa gtggagaaaa agatgggaca ggtgctactc atagcagtag   7080
ccgtctccag cgccatactg tcgcggactg cctgggggtg gggggaggct ggggccttga   7140
tcacagccgc aacttccact ttgtgggaag gctctccgaa caagtactgg aactcctcta   7200
cagccacttc actgtgtaac atttttaggg gaagttactt ggctggagct tctctaatct   7260
acacagtaac aagaaacgct ggcttggtca agagacgtgg gggtggaaca ggagagaccc   7320
tgggagagaa atggaaggcc cgcttgaacc agatgtcggc cctggagttc tactcctaca   7380
aaaagtcagg catcaccgag gtgtgcagag aagaggcccg ccgcgccctc aaggacggtg   7440
tggcaacggg aggccatgct gtgtcccgag gaagtgcaaa gctgagatgg ttggtggagc   7500
ggggatacct gcagccctat ggaaaggtca ttgatcttgg atgtggcaga gggggctgga   7560
gttactacgc cgccaccatc cgtaaagttc aagaagtgaa aggatacaca aaaggaggcc   7620
ctggtcatga agaacccgtg ttggtgcaaa gctatgggtg gaacatagtc cgtctcaaga   7680
gtggggtgga cgtctttcat atggcggctg agccgtgtga cacgttgctg tgtgacatag   7740
gtgagtcatc atctagtcct gaagtggaag aagcacggac gctcagagtc ctctccatgg   7800
tgggggattg gcttgaaaaa cgaccaggag ccttttgtat aaaagtgttg tgcccataca   7860
ccagcactat gatggaaacc ctggagcgac tgcagcgtag gcatggggga ggactggtca   7920
gagtgccact ctcccgcaac tctacacatg agatgtactg ggtctctgga gcgaaaagca   7980
acaccataaa aagtgtgtcc accacgagcc agctcctctt ggggcgcatg gacgggccta   8040
ggaggccagt gaaatatgag gaggatgtga atctcggctc tggcacgcgg gctgtggtaa   8100
gctgcgctga agctcccaac atgaagatca ttggtaaccg cattgaaagg atccgcagtg   8160
agcacgcgga aacgtggttc tttgacgaga accacccata taggacatgg gcttaccatg   8220
gaagctatga ggcccccaca caagggtcag cgtcctctct aataaacggg gttgtcaggc   8280
tcctgtcaaa accctgggat gtggtgactg gagtcacagg aatagccatg accgacacca   8340
caccgtatgg tcagcaaaga gttttcaagg aaaaagtgga cactagggtg ccagaccccc   8400
aagaaggcac tcgtcaggtt atgagcatgg tctcttcctg gttgtggaaa gagctaggca   8460
aacacaaacg gccacgagtc tgtaccaaag aagagttcat taacaaggtt cgtagcaatg   8520
cagcattagg ggcaatattt gaagaggaaa aagagtggaa gactgcagtg gaagctgtga   8580
atgatccaag gttctgggct ctagtggaca aggaaagaga gcaccacctg agaggagagt   8640
gccagagttg tgtgtacaac atgatgggaa aaagagaaaa gaaacaaggg gaatttggaa   8700
aggccaaggg cagccgcgcc atctggtata tgtggctagg ggctagattt ctagagttcg   8760
aagcccttgg attcttgaac gaggatcact ggatggggag agagaactca ggaggtggtg   8820
ttgaagggct gggattacaa agactcggat atgtcctaga agagatgagt cgcataccag   8880
gagggaggat gtatgcagat gacactgctg gctgggacac ccgcatcagc aggtttgatc   8940
tggagaatga agctctaatc accaaccaaa tggagaaagg gcacagggcc ttggcattgg   9000
ccataatcaa gtacacatac caaaacaaag tggtaaaggt ccttagacca gctgaaaaag   9060
ggaaaacagt catggacatt atttcgagac aagaccaaag gggggagcgga caagttgtca   9120
```

cttacgctct taacacattt accaacctag tggtgcaact cattcggaat atggaggctg 9180
aggaagttct agagatgcaa gacttgtggc tgctgcggag gtcagagaaa gtgaccaact 9240
ggttgcagag caacggatgg gataggctca aacgaatggc agtcagtgga gatgattgcg 9300
ttgtgaagcc aattgatgat aggtttgcac atgccctcag gttcttgaat gatatgggaa 9360
aagttaggaa ggacacacaa gagtggaaac cctcaactgg atgggacaac tgggaagaag 9420
ttccgttttg ctcccaccac ttcaacaagc tccatctcaa ggacgggagg tccattgtgg 9480
ttccctgccg ccaccaagat gaactgattg gccgggcccg cgtctctcca ggggcgggat 9540
ggagcatccg ggagactgct tgccttgcaa aatcatatgc gcaaatgtgg cagctccttt 9600
atttccacag aagggacctc cgactgatgg ccaatgccat ttgttcatct gtgccagttg 9660
actgggttcc aactgggaga actacctggt caatccatgg aaagggagaa tggatgacca 9720
ctgaagacat gcttgtggtg tggaacagag tgtggattga ggagaacgac cacatggaag 9780
acaagacccc agttacgaaa tggacagaca ttccctattt gggaaaaagg gaagacttgt 9840
ggtgtggatc tctcataggg cacagaccgc gcaccacctg ggctgagaac attaaaaaca 9900
cagtcaacat ggtgcgcagg atcataggtg atgaagaaaa gtacatggac tacctatcca 9960
cccaagttcg ctacttgggt gaagaagggt ctacacctgg agtgctgtaa gcaccaatct 10020
taatgttgtc aggcctgcta gtcnnnnnna gcttggggaa agctgtgcag cctgtgaccc 10080
ccccaggaga agctgggaaa ccaagcctat agtcaggccg aga 10123

<210> SEQ ID NO 21
<211> LENGTH: 10807
<212> TYPE: DNA
<213> ORGANISM: Artificial Sequence
<220> FEATURE:
<223> OTHER INFORMATION: Zika virus

<400> SEQUENCE: 21
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
agaagaaatc cggaggattc cggattgtca atatgctaaa acgcggagta gcccgtgtga 180
gcccctttgg gggcttgaag aggctgccag ccggacttct gctgggtcat gggcccatca 240
ggatggtctt ggcgattcta gcctttttga gattcacggc aatcaagcca tcactgggtc 300
tcatcaatag atggggttca gtggggaaaa aagaggctat ggaaataata aagaagttta 360
agaaagatct ggctgccatg ctgagaataa tcaatgctag gaaggagaag aagagacgag 420
gcacagatac tagtgtcgga attgttggcc tcctgctgac cacagccatg gcagtggagg 480
tcactagacg tgggaatgca tactatatgt acttggacag aagcgatgct ggggaggcca 540
tatcttttcc aaccacaatg ggggatgaata agtgttatat acagatcatg gatcttggac 600
acatgtgtga tgccaccatg agctatgaat gccctatgct ggatgagggg gtagaaccag 660
atgacgtcga ttgttggtgc aacacgacgt caacttgggt tgtgtacgga acctgccacc 720
acaaaaaagg tgaagcacgg agatctagaa gagctgtgac gctcccctcc cattccacta 780
ggaagctgca aacgcggtcg cagacctggt tggaatcaag agaatacaca aagcacctga 840
ttagagtcga aaattggata ttcaggaacc ctggcttcgc gttagcagca gctgccatcg 900
cttggctttt gggaagctca acgagccaaa aagtcatata cttggtcatg atactgctga 960
ttgccccggc atacagcatc aggtgcatag gagtcagcaa tagggacttt gtggaaggta 1020

-continued

```
tgtcaggtgg gacttgggtt gatgttgtct tggaacatgg aggttgtgtt accgtaatgg   1080
cacaggacaa accgactgtc gacatagagc tggttacaac aacagtcagc aacatggcgg   1140
aggtaagatc ctactgctat gaggcatcaa tatcggacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcttgc tctaagaaaa tgaccgggaa gagcatccag ccagagaatc   1380
tggagtaccg gataatgctg tcagttcatg gctcccagca cagtgggatg atcgttaatg   1440
atacaggaca tgaaactgat gagaatagag cgaaggttga gataacgccc aattcaccaa   1500
gagccgaagc caccctgggg ggttttggaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcatgctgg ggcagacacc ggaactccac   1680
actggaacaa caaagaagca ctggtagagt tcaaggacgc acatgccaaa aggcagactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ctaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccctgtaa tcactgaaag cactgagaac tccaagatga   2100
tgctggaact ggatccacca tttggggact cttacattgt cataggagtc ggggaaaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
ggggtgctct caactcactg ggcaagggca tccatcaaat tttggagca gctttcaaat    2340
cattgtttgg aggaatgtcc tggttctcac aaattctcat tggaacgttg ctggtgtggt   2400
tgggtctgaa tacaaagaat ggatctattt cccttatgtg cttggcctta gggggagtgt   2460
tgatcttctt atccacagcc gtctctgctg atgtggggtg ctcggtggac ttctcaaaga   2520
aggaaacgag atgcggtaca ggggtgttcg tctataacga cgttgaagct tggagggaca   2580
ggtacaagta ccatcctgac tcccctcgta gattggcagc agcagtcaag caagcctggg   2640
aagatgggat ctgtgggatc tcctctgttt caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccatgg ctggaaggct tgggggaaat cgtacttcgt cagggcagca aagacaaata   2880
acagctttgt cgtggatggt gacacactga aggaatgccc actcaaacat agagcatgga   2940
acagctttct tgtggaggat catgggttcg gggtatttca cactagtgtc tggctcaagg   3000
ttagagaaga ttattcatta gagtgtgatc cagccgtcat tggaacagcc gctaagggaa   3060
aggaggctgt gcacagtgat ctaggctact ggattgagag tgagaagaac gacacatgga   3120
ggctgaagag ggcccacctg atcgagatga aaacatgtga atggccaaag tcccacacat   3180
tgtggacaga tggaatagaa gaaagtgatc tgatcatacc caagtcttta gctgggccac   3240
tcagccatca caacaccaga gagggctaca ggacccaaat gaaagggcca tggcatagtg   3300
aagagcttga aattcggttt gaggaatgcc caggcactaa ggtccacgtg gaggaaacat   3360
gtggaacaag aggaccatct ctgagatcaa ccactgcaag cggaagggtg atcgaggaat   3420
```

ggtgctgcag ggagtgcaca atgcccccac tgtcgttccg ggctaaagat ggttgttggt 3480
atggaatgga gataaggccc aggaaagaac cagaaagtaa cttagtaagg tcaatggtga 3540
ctgcaggatc aactgatcac atggatcact tctcccttgg agtgcttgtg attctgctca 3600
tggtacagga agggctaaag aagagaatga ccacaaagat catcataagc acatcaatgg 3660
cagtgctggt agctatgatc ctgggaggat tttcaatgag tgacctggct aagcttgcaa 3720
ttttgatggg tgccaccttc gcggaaatga acactggagg agatgttgct catctggcgc 3780
tgatagcggc attcaaagtc agacctgcgt tgctggtatc tttcattttc agagctaatt 3840
ggacaccccg tgagagcatg ctgctggcct tggcctcgtg tcttctgcaa actgcgatct 3900
ccgccttgga aggcgacctg atggttccca tcaatggttt tgctttggcc tggttggcaa 3960
tacgagcgat ggttgttcca cgcactgaca acatcacctt ggcaatcctg gctgctctga 4020
caccactggc ccggggcaca ctgcttgtgg cgtggagagc aggccttgct acttgcgggg 4080
ggttcatgct cctttctctg aaggggaaag gcagtgtgaa gaagaactta ccatttgtca 4140
tggccctggg actaaccgct gtgaggctgg tcgaccccat caacgtggtg ggactgctgt 4200
tgctcacaag gagtgggaag cggagctggc cccctagtga agtactcaca gctgttggcc 4260
tgatatgcgc attggctgga gggttcgcca aggcggatat agagatggct gggcccatgg 4320
ccgcggtcgg tctgctaatt gtcagttacg tggtctcagg aaagagtgtg gacatgtaca 4380
ttgaaagagc aggtgacatc acatgggaaa aagatgcgga agtcactgga aacagtcccc 4440
ggctcgatgt ggcactagat gagagtggtg atttctccct agtggaggat gatggtcccc 4500
ccatgagaga gatcatactc aaagtggtcc tgatggccat ctgtggcatg aacccaatag 4560
ccataccctt tgcagctgga gcgtggtacg tgtatgtgaa gactggaaaa aggagtggtg 4620
ctctatggga tgtgcctgct cccaaggaag taaaaaaggg ggagaccaca gatggagtgt 4680
acagagtaat gactcgtaga ctgctaggtt caacacaagt tggagtggga gtcatgcaag 4740
agggggtctt ccacactatg tggcacgtca caaaaggatc cgcgctgaga agcggtgaag 4800
ggagacttga tccatactgg ggagatgtca agcaggatct ggtgtcatac tgtggtccat 4860
ggaagctaga tgccgcctgg gacgggcaca gcgaggtgca gctcttggcc gtgccccccg 4920
gagagagagc gaggaacatc cagactctgc ccggaatatt taagacaaag gatggggaca 4980
ttggagcagt tgcgctggac tacccagcag gaacttcagg atctccaatc ctagataagt 5040
gtgggagagt gataggactc tatggtaatg ggtcgtgat caaaaatggg agttacgtta 5100
gtgccatcac ccaagggagg agggaggaag agactcctgt tgagtgcttc gagccttcga 5160
tgctgaagaa gaagcagcta actgtcttag acttgcatcc tggagctggg aaaaccagga 5220
gagttcttcc tgaaatagtc cgtgaagcca taaaaacaag actccgcact gtgatcttag 5280
ctccaaccag ggttgtcgct gctgaaatgg aggaagccct tagagggctt ccagtgcgtt 5340
atatgacaac agcagtcaat gtcacccatt ctgggacaga aatcgttgac ttaatgtgcc 5400
atgccacctt cacttcacgt ctactacagc caatcagagt ccccaactat aatctgtata 5460
ttatggatga ggcccacttc acagatccct caagtatagc agcaagagga tacatttcaa 5520
caagggttga gatgggcgag gcggctgcca tcttcatgac tgccacgcca ccaggaaccc 5580
gtgacgcatt cccggactcc aactcaccaa ttatggacac cgaagtggaa gtcccagaga 5640
gagcctggag ctcaggcttt gattgggtga cggatcattc tggaaaaaca gtttggtttg 5700
ttccaagcgt gaggaatggc aatgagatcg cagcttgtct gacaaaggct ggaaaacggg 5760

-continued

```
tcatacagct cagcagaaag acttttgaga cagagttcca gaaaacaaaa catcaagagt   5820
gggacttcgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
accccaacaa acctggagat gagtatctgt atggaggtgg gtgcgcagag actgatgaag   6060
accatgcaca ctggcttgaa gcaagaatgc ttcttgacaa catttacctc caagatggcc   6120
tcatagcctc gctctatcga cctgaggccg acaaagtagc agctattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcac gaccaacaac accataatgg aagacagtgt gccggcagag gtgtggacca   6360
gatacggaga gaaaagagtg ctcaaaccga ggtggatgga cgccagagtt tgttcagatc   6420
atgcggccct gaagtcattc aaagagtttg ccgctgggaa aagaggagcg gcctttggag   6480
tgatggaagc cctgggaaca ctgccaggac atatgacaga gagattccag gaggccattg   6540
acaacctcgc tgtgctcatg cgggcagaga ctggaagcag gccctacaaa gccgcggcgg   6600
cccaattacc ggagaccta gagactatca tgcttttggg gttgctggga acagtctcgc   6660
tgggaatctt tttcgtcttg atgcggaaca agggcatagg gaagatgggc tttggaatgg   6720
tgactcttgg ggccagcgca tggcttatgt ggctctcgga aattgagcca gccagaattg   6780
catgtgtcct cattgttgtg ttcctattgc tggtggtgct catacctgag ccagaaaagc   6840
aaagatctcc ccaggacaac caaatggcaa tcatcatcat ggtagcagtg ggtcttctgg   6900
gcttgattac cgccaatgaa ctcggatggt tggagagaac aaagagtgac ctaagccatc   6960
taatgggaag gagagaggag gggcaacta taggattctc aatggacatt gacctgcggc   7020
cagcctcagc ttgggctatc tatgctgctc tgacaacttt cattacccca gccgtccaac   7080
atgcagtgac cacttcatac aacaactact ccttaatggc gatggccacg caagctggag   7140
tgttgttcgg tatgggtaaa gggatgccat tctatgcatg ggactttgga gtcccgctgc   7200
taatgatagg ttgctactca caattaacac ccctgaccct aatagtggcc atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgacaatt gacccccaag tggagaaaaa gatgggacag gtgctactca   7440
tagcagtagc tgtctccagc gccatactgt cgcggaccgc ctgggggtgg ggtgaggctg   7500
gggccctgat cacagctgca acttccactt tgtgggaggg ctctccgaac aagtactgga   7560
actcctccac agccacctca ctgtgtaaca tttttagggg aagctacttg gctggagctt   7620
ctctaatcta cacagtaaca agaaacgctg gcttggtcaa gagacgtggg ggtggaacgg   7680
gagagaccct gggagagaaa tggaaggccc gcctgaacca gatgtcggcc ctggagttct   7740
actcctacaa aaagtcaggc atcaccgagg tgtgcagaga agaggcccgc cgcgccctca   7800
aggacggtgt ggcaacggga ggccacgctg tgtcccgagg aagtgcaaag ctgagatggt   7860
tggtggagag gggatacctg cagccctatg gaaaggtcat tgatcttgga tgtggcagag   7920
ggggctggag ttactatgcc gccaccatcc gcaaagttca agaagtgaaa ggatacacaa   7980
aaggaggccc tggtcatgaa gaacccatgt tggtgcaaag ctatgggtgg aacatagtcc   8040
gtcttaagag tggggtggac gtctttcata tggcggctga gccgtgtgac acgttgctgt   8100
gtgatatagg tgagtcatca tctagtcctg aagtggaaga agcacggacg ctcagagtcc   8160
```

-continued

```
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctccttttg ggcgcatgg    8400
acgggcccag gaggccagtg aaatatgaag aggatgtgaa tctcggctct ggcacgcggg   8460
ctgtggtaag ctgcgctgaa gctcccaaca tgaagatcat tggtaaccgc attgagagga   8520
tccgcagtga gcacgcggaa acgtggttct ttgacgagaa ccacccatat aggacatggg   8580
cttaccatgg aagctacgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agttaggcaa acacaaacgg ccacgagtct gtaccaaaga agagttcatc aacaaggttc   8880
gtagcaacgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagctgt gtgtacaaca tgatgggaaa aagagaaaag aaacaagggg   9060
aatttggaaa ggccaagggc agccgcgcca tctggtacat gtggctaggg gctagatttc   9120
tagagttcga agcccttgga ttcttgaacg aggatcactg gatggggaga gagaattcag   9180
gaggtggtgt tgaagggcta ggattacaaa gactcggata tgtcttagaa gagatgagtc   9240
gcataccagg aggaaggatg tatgcagatg atactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaagacagtt atggacatta tttcaagaca agaccaaagg gggagcggac   9480
aagttgtcac ttacgctctt aatacattta ccaacctagt ggtgcagctc attcggaata   9540
tggaggctga ggaagttcta gagatgcaag acttgtggct gctgcggagg tcagagaaag   9600
tgaccaactg gttgcagagc aatggatggg ataggctcaa acgaatggca gtcagtggag   9660
atgattgcgt tgtgaaacca attgatgata ggtttgcaca tgctctcagg ttcttgaatg   9720
atatgggaaa agttaggaag gacacacaag agtggaagcc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgagctcgc gtctcaccgg   9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatttg ggaaaaaggg  10200
aagacttgtg gtgtgggtct ctcatagggc acagaccgcg caccacctgg gctgagaaca  10260
ttaaaaacac agtcaacatg atgcgtagga tcataggtga tgaagaaaag tacgtggact  10320
acctatccac ccaagttcgc tacttgggcg aagaagggtc cacacctgga gtgctataag  10380
caccaatctt agtgttgtca ggcctgctag tcagccacag cttggggaaa gctgtgcagc  10440
ctgtgacccc cccaggagaa gctgggaaac caagcccata gtcaggccga gaacgccatg  10500
```

-continued gcacggaaga agccatgctg cctgtgagcc cctcagagga cactgagtca aaaaacccca 10560
cgcgcttgga ggcgcaggat gggaaaagaa ggtggcgacc ttccccaccc tttaatctgg 10620
ggcctgaact ggagatcagc tgtggatctc cagaagaggg actagtggtt agaggagacc 10680
ccccggaaaa cgcaaaacag catattgacg ctgggaaaga ccagagactc catgagtttc 10740
caccacgctg gccgccaggc acagatcgcc gaatagcggc ggccggtgtg gggaaatcca 10800
tgggtct 10807

<210> SEQ ID NO 22
<211> LENGTH: 10806
<212> TYPE: DNA
<213> ORGANISM: Artificial Sequence
<220> FEATURE:
<223> OTHER INFORMATION: Zika virus

<400> SEQUENCE: 22
agttgttgat ctgtgtgaat cagactgcga cagttcgagt ttgaagcgag agctaacaac 60
agtatcaaca ggtttaattt ggatttggaa acgagagttt ctggtcatga aaaacccaaa 120
gaagaaatcc ggaggattcc ggattgtcaa tatgctaaaa cgcggagtag cccgtgtaaa 180
ccccttgggg ggtttgaaga ggctgccagc cggacttctg ctgggccatg gacccatcag 240
aatggttttg gcgatactag ccttcttgag attcacagca atcaaaccat cactgggcct 300
catcaataga tggggttccg tggggaagaa ggaggctatg gaaataataa aaaagttcaa 360
gaaagacctt gctgccatgt tgagaattat caatgctagg aaggagagga agagacgtgg 420
cgctgacacc agcatcggaa tcgtcggcct cctgctgacc acagccatgg cagccgagat 480
cactagacgt gggagtgcat actacatgta cttggacagg agcgatgctg gtaaggccat 540
ttcttttgcc accacattgg gggtgaacaa atgccatgta cagatcatgg acctcgggca 600
catgtgtgac gccaccatga gttatgagtg ccccatgcta gacgagggag tggagccaga 660
tgacgtcgat tgctggtgca acacgacatc gacttgggtt gtgtacggaa cctgtcatca 720
taaaaaaggt gaagcacgac gatccagaag agccgtgacg cttccttctc actccacgag 780
gaagctgcaa acgcgatcgc agacttggct agagtcaaga gaatacacaa agcacctgat 840
caaggttgaa aattggatat ttaggaaccc cgggtttgcg ctagtggctg tagctatagc 900
ctggctcctg ggaagctcga cgagccaaaa agttatatac ttggtcatga tattgttgat 960
tgccccggca tacagcatta ggtgcatagg agttagcaat agagacttcg tggagggcat 1020
gtcaggtggg acctgggttg atgttgtctt ggaacatggg ggttgcgtca ccgtgatggc 1080
acaggacaag ccaacagttg atatcgagtt ggtcacgaca acggttagca acatggccga 1140
ggtaagatcc tactgctatg aggcatcaat atcggacatg gcttcggaca gccgttgtcc 1200
aacacaaggt gaagcctacc ttgacaagca gtcagacact caatatgtct gcaagagaac 1260
attggtggat agaggttggg gaaatgggtg tggacttttt ggcaaaggga gcttggtgac 1320
atgtgccaag tttacgtgct ccaagaaaat gacaggcaag agcatccagc cggagaactt 1380
ggagtaccgg ataatgctat cagtgcatgg atcccagcac agtgggatga ttgtgaatga 1440
cacaggacat gaaactgacg aaaacagagc aaaagtcgag gtcacaccca attcaccaag 1500
agcagaagca accttgggag gttttggaag cttgggactt gactgtgaac caaggacagg 1560
ccttgacttc tcagatctgt attacctgac catgaacaat aagcattggt tggtgcacaa 1620
ggagtggttt catgacatcc cattaccttg gcatgctggt gcagacactg gaactccaca 1680
ctggaacaac aaagaggcat tggtggagtt caaggacgcc cacgccaaga ggcaaactgt 1740

```
tgtggttctg gggagccaag agggagctgt tcatacggcc ctcgctggag ctttggaggc   1800
tgagatggat ggtgcaaagg gaaggctatt ctctggccat ttgaaatgcc gcctaaaaat   1860
ggacaagctt aggttgaagg gtgtgtcata ttccctgtgt accgcagcgt tcacatttac   1920
caaggtccca gctgaaacat tgcatggaac agtcacagtg gaggtgcagt atgcagggac   1980
agacggaccc tgcaaagtcc cagcccagat ggcggtggac atgcagaccc tgaccccagt   2040
tggaaggctg ataaccgcca atcctgtgat cactgaaagt actgagaatt caaagatgat   2100
gttggagctc gacccaccat ttggggattc ttacattgtc ataggagtcg gggacaagaa   2160
aatcacccat cactggcatc ggagtggtag caccatcgga aaggcatttg aagccactgt   2220
gagaggtgcc aagagaatgg cagtcttggg ggacacagcc tgggactttg gatcagttgg   2280
gggtgtgttt aattcattgg gtaagggtat tcaccagatc tttggagcag ctttcaaatc   2340
actgtttgga ggaatgtcct ggttctcaca gatcctcata ggcacactgt tggtgtggtt   2400
aggtttgaac acaaagaatg gatctatctc cctcacatgc ttagccctgg ggggagtgat   2460
gatcttcctt tccacggctg tttctgctga tgttgggtgc tcggtggact tctcaaaaaa   2520
ggaaacgaga tgtggcacgg gggtgttcgt ctacaatgac gttgaagcct ggagggaccg   2580
gtacaagtac catcctgact ccccccgcag attggcagca gctgttaagc aggcttggga   2640
agaggggatt tgtgggatct cctccgtttc gagaatggaa aacatcatgt ggaaatcagt   2700
ggaaggggag cttaatgcaa tcctagagga gaatggagtt caactgacag ttgtagtggg   2760
gtctgtaaaa aaccctatgt ggagaggtcc acagagattg ccagtgcctg tgaatgagct   2820
gccccatggc tggaaagcct gggggaaatc gtactttgtc agagcagcaa agaccaacaa   2880
cagttttgtt gtcgacggtg acacactgaa ggagtgtccg ctcaaacata gagcatggaa   2940
tagcttcctt gtggaggatc acgggtttgg gatcttccac accagtgttt ggctgaaggt   3000
cagagaggac tactcactag agtgtgaccc agccgtcata ggaacagctg tcaagggaaa   3060
ggaagctgca cacagtgatc taggctattg gattgagagt gaaaagaatg acacatggag   3120
gctgaggagg gctcatctga ttgagatgaa aacatgtgag tggccaaagt ctcacacact   3180
gtggacagat ggagtggaag aaagtgatct gatcataccc aagtccttag ctggtccact   3240
cagccaccac aacaccagag agggttacag aactcaagtg aaagggccat ggcatagtga   3300
agagctcgaa atccggtttg aggagtgccc aggaaccaag gttcacgtgg aggagacatg   3360
cggaactaga ggaccatctc tgagatcaac tactgctagt ggaagggtca tagaggaatg   3420
gtgctgtagg gaatgcacaa tgcctccact atcgttccgg gcgaaagacg gctgctggta   3480
tggaatggag ataaggccca gaaaggaacc agagagcaac ttagtgaggt ccatggtgac   3540
agcaggatca accgatcata tggatcactt ctctcttgga gtgcttgtga ttctactcat   3600
ggtgcaggaa ggtttgaaga agagaatgac cacaaagatc ataatgagca catcaatggc   3660
agtgctggta gccatggtct tgggaggatt ctcaatgagt gacctggcta agcttgtgat   3720
cctgatgggt gctactttcg cagaaatgaa cactggagga gatgtagctc acttggcatt   3780
ggttgcggca tttaaagtca gaccagcctt gttggtttcc ttcatcttca gagccaactg   3840
gacaccccgt gagagcatgc tgctagccct ggcttcgtgc ctcctgcaga ctgcgatctc   3900
tgctcttgaa ggcgagctga tggtcctcgt taatggattt gctttggcct ggttggcaat   3960
acgagcaatg gccgtgccac gcactgacaa tatcgctctg gcaattctgg ctgctctaac   4020
accattagcc agaggcacac tgctcgtggc atggagagcg ggcctcgcca cttgtggagg   4080
```

-continued

```
gttcatgctc ctttccctga aagggaaagg tagtgtgaag aagaacctgc cttttgtcat   4140
ggccttgggg ttgaccgctg tgaggatagt ggaccccatc aatgtggtag gactactgtt   4200
actcacaagg agtggaaaac ggagctggcc tcctagtgaa gtgcttacag ctgttggcct   4260
gatatgtgca ctggccggag ggtttgccaa ggcagacata gagatggctg ggcccatggc   4320
tgcagtgggc ctgctaattg tcagttatgt ggtctcggga aagagtgtgg acatgtacat   4380
cgaaagagca ggtgatatca catgggaaaa agacgcggaa gtcactggaa acagtcctcg   4440
gcttgacgtg gcactagatg agagtggtga tttctccttg gtagaggagg atggcccacc   4500
catgagagag atcatactca aggtggttct gatggccatc tgtggcatga acccaatagc   4560
catacccttc gctgcaggag cgtggtatgt gtatgtaaag actggaaaaa ggagtggtgc   4620
cctctgggac gtgcctgctc ccaaagaagt gaaaaaagga gagactacag atggagtgta   4680
cagagtgatg actcgcagac tgctgggttc aacacaggtt ggagtgggag tcatgcaaga   4740
gggagtcttc cacaccatgt ggcacgtcac aaaaggagcc gcattgagga gcggtgaagg   4800
aagacttgat ccatattggg gggacgtcaa gcaggacttg gtgtcatatt gtgggccttg   4860
gaagttggat gcagcctggg atggactaag tgaagtgcag cttttggccg taccccccgg   4920
agagagggct agaaacattc agactctgcc tggaatattc aagacaaagg atggggacat   4980
cggagcagtc gctctagact accccgcagg aacctcagga tctccaatcc tagacaaatg   5040
cggaagagtg ataggacttt atggcaatgg ggttgtgatc aagaatggaa gctatgttag   5100
tgccataacc cagggaaaaa gggaggagga ggctccagtt gagtgctttg aaccctcgat   5160
gctgaggaag aagcagctaa cagtcttgga tctgcatcca ggagccggga aaaccaggag   5220
ggttcttcct gaaatagtcc gtgaagccat aaagaagaga cttcgcacag tgatcctagc   5280
accaaccagg gtcgttgccg ctgagatgga ggaagcccta agaggactgc cggtgcgtta   5340
catgacaaca gcagtcaacg tcacccactc tgggacagaa atcgtcgatt tgatgtgcca   5400
tgccaccttc acttcacgcc tactacaacc catcagagtc cccaactaca acctttacat   5460
catggatgaa gctcatttca cagatccctc aagcatagct gcacgaggat atatatcaac   5520
aagggttgaa atgggcgagg cggctgctat cttcatgact gctacaccac caggaacccg   5580
cgatgcgttt ccggattcca actcaccaat catggacaca gaagtggaag ttccagagag   5640
agcctggagc tcaggctttg actgggtgac ggatcattct gggaaaacaa tttggtttgt   5700
tccaagtgtg agaaacggaa atgaaatcgc agcctgtctg acaaaggctg gaaagcgggt   5760
catacagctc agcaggaaga cttttgagac agagtttcag aagacaaaaa atcaagagtg   5820
ggactttgtc ataacaactg acatttcaga gatgggtgcc aatttcaagg ctgaccgggt   5880
catagattcc aggagatgcc taaagccagt catactcgat ggcgagagag tcatcctggc   5940
tgggcccatg cctgtcacgc atgccagtgc tgctcagagg agaggacgtg taggcaggaa   6000
ccccaacaaa cctggagatg agtacatgta tggaggtggg tgtgcagaga ctgatgaaga   6060
ccatgcacac tggcttgaag caagaatgct tcttgacaac atttacctcc aggatggcct   6120
catagcctcg ctctatcggc ctgaggccga caaggtagcc gccattgagg gagagttcaa   6180
gctgaggaca gagcaaagga agacctttgt ggaactcatg aagagaggag accttcccgt   6240
ttggctggcc tatcaagtag catctgccgg aataacttac acagatagaa gatggtgctt   6300
tgatggcact accaacaaca ccataatgga agacagtgta ccagcagagg tgtggaccaa   6360
gtatggagag aagagagtgc ttaaaccgag gtggatggat gctagggtct gttcagatca   6420
tgcggctctg aagtcgttca aagaatttgc cgctgggaag agaggagcgg ctttgggagt   6480
```

-continued

```
aatggatgcc ctgggaacat tgccaggaca catgacagag aggtttcagg aagccattga   6540
caatctcgct gtgctcatgc gagcagagac tggaagtagg ccctacaaag cagcggcagc   6600
tcaactgccg gagaccttag agactatcat gcttctgggc ttattgggaa cagtttcgct   6660
aggaatcttc tttgtcttga tgcggaacaa gggcatcggg aagatgggct tcggaatggt   6720
aacccttggg gccagcgcat ggctcatgtg gctttcggaa attgaaccag ccagaatcgc   6780
atgtgtcctc attgtcgtgt tttgttgct ggtggtgctc atacccgagc cagagaagca   6840
aagatctccc caggataatc aaatggcaat catcatcatg gtggcagttg gccttctggg   6900
tttgataact gcaaatgaac tcggatggct ggaaaggaca aaaagtgata tagctcatct   6960
aatgggaagg aaagaagagg ggacaaccat gggattctca atggatattg atctgcggcc   7020
agcctccgcc tgggctattt atgccgcatt gacaactctc atcaccccag ccgtccaaca   7080
tgcggtaacc acctcataca acaactactc cctgatggcg atggccacac aagctggagt   7140
gctgtttggc atgggcaaag ggatgccatt ttatgcatgg gactttggag tcccgctgct   7200
aatgatgggt tgctactcac aattaacacc cctgaccctg atagtggcca tcattctgct   7260
tgtggcacac tacatgtact tgatcccagg tttgcaggca gcagcagcac gtgctgccca   7320
gaagaggaca gcagctggca tcatgaagaa tcccgttgtg gatggaatag tggtgactga   7380
cattgacaca atgacaattg acccccaagt ggagaagaag atgggacaag tgttactcat   7440
agcagtagct gtctccagtg ctgtgctact gcggaccgct tggggatggg gggaggctgg   7500
ggctctgatc acagcagcaa cctccacctt atgggaaggc tctccaaaca aatactggaa   7560
ctcctccaca gccacctcac tgtgcaacat ctttagagga agttatttgg caggggcttc   7620
ccttatttac acagtgacaa gaaatgccgg tctggttaag agacgtggag gtggaacggg   7680
agagaccctg ggagagaagt ggaaagcccg cctgaaccag atgtcggcct tggagttcta   7740
ctcttacaaa aagtcaggca tcaccgaagt gtgtagggag gaggcgcgcc gcgccctcaa   7800
ggatggagtg gccacaggag gacatgctgt atcccgggga agcgcaaagc ttagatggtt   7860
ggtagagaga ggatacctgc agccccatgg aaaggttgtt gaccttggat gtggcagagg   7920
aggctggagt tattacgctg ccaccatccg taaagtgcag gaggtcagag gatacacaaa   7980
gggaggtcct ggccatgaag agcccatgct ggtgcaaagc tatgggtgga acatagttcg   8040
cctcaagagt ggagtggacg tcttccacat ggcggctgaa ccgtgtgaca ctctgctgtg   8100
tgacataggc gagtcatcat ccagtcctga agtggaagag acgcgaacac tcagagtgct   8160
ctccatggtg ggagactggc ttgaaaaaag accaggggcc ttctgcataa aggtgctgtg   8220
cccatacacc agcacaatga tggagaccat ggagcgactg caacgtaggc atgggggagg   8280
attagtcaga gtgccattgt cccgcaactc tacacatgag atgtattggg tctctggagc   8340
caaaagtaac atcataaaga gtgtgtccac cacaagtcag ctcctcttgg gacgcatgga   8400
agggcctagg aggccagtga aatatgagga ggatgtgaac ctcggctcag gcacacgagc   8460
tgtggcaagc tgcgctgagg ctcccaacat gaagatcatt ggtaggcgca ttgagagaat   8520
ccgcaatgaa catgcagaga catggttctt tgatgaaaac cacccataca ggacatgggc   8580
ctaccatggg agctacgaag cccccacgca ggggtcagcg tcatccctcg tgaacggggt   8640
tgttagactc ttgtcaaagc cctgggatgt ggtgactgga gttacaggaa tagctatgac   8700
tgacaccacg ccatacggcc aacaaagagt cttcaaggaa aaagtggaca ccagggtgcc   8760
agatccccaa gaaggcactc gccaagtgat gaacatggta tcgtcttggc tatggaagga   8820
```

-continued

```
gctgggaaaa cgcaagcgac cacgtgtctg caccaaagaa gagttcatta ataaggtgcg   8880

cagcaatgca gcactgggag caatatttga agaggaaaaa gaatggaaga cagctgtaga   8940

agctgtgaat gatccaagat tttgggctct agtggacaag gaaagagaac accacctgag   9000

aggagagtgt catagctgtg tgtacaacat gatgggcaaa agagaaaaga agcaaggaga   9060

attcgggaaa gcaaaaggca gccgcgcaat ctggtacatg tggttgggag ccagattttt   9120

ggagtttgaa gctcttgggt tcttgaacga ggaccactgg atggggagag aaaactcagg   9180

aggtggcgtt gaagggctag gactgcaaag gcttggatat atcctagaag aaatgaaccg   9240

ggcaccagga ggaaagatgt atgcagatga cactgctggc tgggacaccc gcattagcaa   9300

gtttgatcta gagaatgaag ccctgatcac taaccagatg gaagaagggc acagagctct   9360

ggcgttggcc gtgattaaat acacatacca aaacaaagtg gtgaaggttc tcagaccagc   9420

tgaaggaggg aaaacagtca tggacatcat ctcaagacaa gaccagagag ggagcggaca   9480

agttgttact tatgctctca acacattcac caacctggtg gtgcagctta tccggaacat   9540

ggaggctgag gaagtgctag agatgcatga tctgtggttg ttgaggaagc cagagaaagt   9600

gaccagatgg ttgcagagca atggatggga cagactcaaa cggatggcag ttagtggaga   9660

tgactgcgtt gtaaagccaa ttgatgatag gtttgcacat gccctcaggt tcttgaatga   9720

catgggaaag gttaggaaag acacacagga atggaaaccc tcgactggat ggagcaattg   9780

ggaagaggtc ccgttctgtt ctcaccactt caacaagctg cacctcaagg acgggagatc   9840

cattgtggtc ccctgccgcc accaagatga actgattggc cgagcccgtg tctcaccagg   9900

ggcaggatgg agcatccggg agactgcttg tcttgcaaaa tcatatgcac agatgtggca   9960

gcttctttat ttccacagaa gagacctccg actgatggcc aatgccattt gttcggctgt  10020

gccaattgac tgggtaccaa ctgggagaac cacctggtca atccatggaa agggagaatg  10080

gatgactact gaggacatgc tcatggtgtg gaatagagtg tggattgagg agaacgacca  10140

catggaggac aagacccctg taacaaaatg gacagacatt ccctatttgg gaaaaaggga  10200

ggacttatgg tgtggatccc ttatagggca tagacctcgc accacttggg ctgagaacat  10260

caaagacaca gtcaacatgg tgcgtaggat cataggtgat gaagaaaagt tcatggacta  10320

cctatccacc caagtacgct acttgggtga ggaagggtcc acacctggag tgctgtaagc  10380

atcaatttca atgttgtcag gcctgctagt cagccacagt ttggggaaag ctgtgcagcc  10440

tgtaaccccc ccaggagaag ctgggaaacc aagctcatag tcaggccgat aacgccatgg  10500

cacggaaaaa gccatgctgc ctgtgagccc ctcagaggac actgagtcaa aaaaccccac  10560

gcgcttggaa gcgcaggatg ggaaaagaag gtggcgacct tccccaccct ttaatctggg  10620

gcctgaactg gagattagct gtgaatctcc ggcagaagga ctagtggtta gaggagaccc  10680

cccggaaaac gcaaaacagc atattgacgc tgggaaagac cagagactcc atgagtttcc  10740

accacgctgg ccgccaggca cagatcgccg aacagcggcg gccggtgtgg ggaaatccat  10800

gggtct                                                             10806
```

ZIKA VIRUS STRAINS FOR TREATMENT OF GLIOMA

CROSS REFERENCE TO RELATED APPLICATIONS

This application claims the benefit of International Patent Application number PCT/US2018/36858, filed Jun. 11, 2018, which claims the benefit of U.S. Provisional Application No. 62/518,300, filed Jun. 12, 2017, and U.S. Provisional Application 62/574,537, filed Oct. 19, 2017, the disclosures of which are hereby incorporated by reference in their entirety.

FIELD OF THE INVENTION

The present disclosure provides viral therapy for the treatment of cancer. In particular, the present disclosure relates to compositions and method of using attenuated virus in oncolytic therapy.

INCORPORATION BY REFERENCE OF SEQUENCE LISTING PROVIDED ELECTRONICALLY

This application contains a Sequence Listing that has been submitted in ASCII format via Patent Center and is hereby incorporated by reference in its entirety. Said Sequence Listing was created on Dec. 6, 2024, is named 642319 ST25.txt and is 46,286 bytes in size.

BACKGROUND

Normal tissue homeostasis is a highly regulated process of cell proliferation and cell death. An imbalance of either cell proliferation or cell death can develop into a cancerous state. While cure rates for several malignancies have significantly improved, the outcome for patients with advanced solid tumors remains grimly unchanged over the last decades.

Currently, there are few effective options for the treatment of many common cancer types. The course of treatment for a given individual depends on the diagnosis, the stage to which the disease has developed and factors such as age, sex, and general health of the patient. The most conventional options of cancer treatment are surgery, radiation therapy and chemotherapy. Surgery plays a central role in the diagnosis and treatment of cancer. Typically, a surgical approach is required for biopsy and to remove cancerous growth. However, if the cancer has metastasized and is widespread, surgery is unlikely to result in a cure and an alternate approach must be taken.

Glioblastoma (GBM) is a primary intrinsic brain tumor. GBM may be resistant to traditional tumor therapy, and is usually lethal with a median survival of patients below two years. GBM is a heterogeneous disease, and the tumor mass includes non-transformed cells and transformed cells, including a precursor population of stem-like cells called the glioblastoma stem cells (GSC). The GSC are tumor initiating cells that are a self-renewing, tumorigenic stem-like tumor cell population. GSC contribute to tumor malignancy due to sustained proliferation, promotion of angiogenesis, invasive potential, immune escape, and therapeutic resistance. Unlike many deadly cancers, GBMs rarely metastasize and a majority (70 to 80%) of patients suffers recurrence within 2-3 cm of the original resection cavity; this tumor behavior has prompted investigation of local therapies, including oncolytic viruses. Some oncolytic viruses tested have proven to be toxic as they also infect and kill normal neighboring cells in the brain.

Zika Virus (ZIKV) is a member of Flaviviridae family. It has emerged as a major human pathogen and is associated with causing fetal developmental defects (microcephaly), poor pregnancy outcomes and Guillain-Barre syndrome. Infected individuals, especially adults can be symptomless or present with mild symptoms such as fever, headache, rash, conjunctivitis, and joint/muscle pain. The virus was first isolated from a sentinel monkey in Uganda's Zika forest in 1947. Based on serological evidence, the first human case was reported in 1952. Zika viral-mediated tissue injury and host responses to infection are just becoming understood. Apoptotic cell death contributes to varied clinical manifestation of Flavivirus infections.

An oncolytic virus that specifically kills cancer cells that contribute to tumor malignancy without killing other cells or causing toxicity is needed.

SUMMARY

In an aspect the disclosure provides a composition for treating a tumor. The composition comprises an oncolytic virus capable of inducing an oncolytic effect on the tumor. that specifically targets glioblastoma stem cells (GSC). The oncolytic virus may be Zika virus (ZIKV). The ZIKV may be attenuated by an E218A mutation that limits the replication capacity of the virus in the GSC surrounding non-GSCs due to enhanced sensitivity to type I interferon and particularly, the IFIT family of innate immune genes.

Another aspect of the disclosure provides a method of treating GBM in a subject, by administering an oncolytic virus composition to the subject that specifically kills GSC. The oncolytic virus may be ZIKV or an attenuated variant of ZIKV. The method of treatment may be a combination of the ZIKV composition and a chemotherapeutic agent.

In yet another aspect the disclosure provides a method of killing GSC by administering a composition of ZIKV. The ZIKV may be an attenuated variant of ZIKV. The ZIKV may specifically infect and kill GSC. Neighboring differentiated glioma cells, or adult neural cells or proliferating cells may not be infected or killed by the ZIKV.

BRIEF DESCRIPTION OF THE FIGURES

The application file contains at least one drawing executed in color. Copies of this patent application publication with color drawing(s) will be provided by the Office upon request and payment of the necessary fee.

FIG. 1A, FIG. 1B, FIG. 1C, FIG. 1D, FIG. 1E, FIG. 1F, FIG. 1G, FIG. 1H, FIG. 1I, FIG. 1J, FIG. 1K, FIG. 1L, FIG. 1M and FIG. 1N show ZIKV causes loss of human glioblastoma stem cell (GSC) self-renewal and proliferation. FIG. 1A and FIG. 1B show GSCs were uninfected (FIG. 1A) or infected (FIG. 1B) with ZIKV-Dakar, 7 dpi. FIG. 1C-FIG. 1F, GSCs uninfected (FIG. 1C, FIG. 1E) or infected (FIG. 1D, FIG. 1F) with ZIKV-Dakar, 48 hpi and underwent immunofluorescence staining for ZIKV envelope (E) protein (ZIKV, green) and DAPI (blue) (FIG. 1C-FIG. 1F), with Sox2 (red) (FIG. 1E, FIG. 1F). FIG. 1G, FIG. 1H, Relative cell viability of paired GSCs (387, 3565, and 4121) (FIG. 1G) and DGCs (FIG. 1H), infected with ZIKV-Dakar or ZIKV-Brazil, at an MOI of 5 for 7 days; all data was normalized to day 0. FIG. 1I, Sphere formation capacity of 387, 3565, 4121 GSCs infected with indicated ZIKV strains or control. FIG. 1J-FIG. 1M, GSCs were uninfected (FIG.

1J, FIG. 1L) or infected (FIG. 1K, FIG. 1M) with ZIKV-Dakar, 48 hpi and underwent immunofluorescence staining for ZIKV (green) and DAPI (blue), with Ki-67 (red) (FIG. 1J, FIG. 1K) or AC3 (red) (FIG. 1L, FIG. 1M). FIG. 1N, On day 4, the frequency of Sox2, Ki-67 and AC3 positive cells was measured by visual quantification in the three GSC lines with or without ZIKV infection. Data is derived from experiments performed in duplicate and pooled from three independent experiments. Error bars indicated standard deviations (SD); (*, P<0.05; , P<0.01; *, P<0.001; ****, P<0.0001; one-way ANOVA with Tukey's method for multiple comparisons). Scale bars, 200 μm for FIG. 1A, FIG. 1B. 100 μm for FIG. 1C-FIG. 1F, FIG. 1J-FIG. 1M.

FIG. 2A-FIG. 2F Bright-field images of GSC organoids after infection with two strains of ZIKV. GSCs were incubated in Matrigel for 3 days (a) or 3 weeks (FIG. 2B). Organoids were infected with ZIKV-Brazil (FIG. 2C, FIG. 2E) or ZIKV-Dakar (FIG. 2D, FIG. 2F), 2 (FIG. 2C, FIG. 2D) or 4 (FIG. 2E, FIG. 2F) weeks after infection. FIG. 2G, Organoid areas at 2 or 4 weeks after ZIKV infection were determined for three GSC organoid models (387, 3565, 4121). FIG. 2H-FIG. 2O, Representative images of uninfected control and ZIKV-Dakar infected GSC organoids at 2 weeks post infection, stained for ZIKV (green) (FIG. 2H-FIG. 2O) and DAPI (blue), with Sox2 (red) (FIG. 2H, FIG. 2I), AC3 (red) (FIG. 2J, FIG. 2K), Ki-67 (red) (FIG. 2L, FIG. 2M), or GFAP (red) (FIG. 2N, FIG. 2O). FIG. 2P, Quantification of $Sox2^+$, $Ki\text{-}67^+$, $AC3^+$ and $GFAP^+$ subpopulations of $DAPI^+$ cells; n=6 organoids for each condition. Values represent mean±SD. (, P<0.01; *, P<0.001; ****, P<0.0001; one-way ANOVA with Tukey's method for multiple comparisons). Scale bars, 400 μm for FIG. 2A-FIG. 2F, 200 μm for FIG. 2H-FIG. 2O.

FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, FIG. 3V, FIG. 3W, FIG. 3X, FIG. 3Y and FIG. 3Z show ZIKV can infect freshly isolated human glioblastoma but not normal brain tissue slices. a-c, Representative images showing freshly resected glioblastoma after staining with H & E (FIG. 3A), or for Ki-67 (FIG. 3B) or GFAP (FIG. 3C). FIG. 3D-FIG. 3R, Immunofluorescent staining of glioblastoma tissue uninfected (d-f), or infected with ZIKV-Dakar (FIG. 3G-FIG. 3L) or ZIKV-Brazil (FIG. 3M-FIG. 3R) after 7 days, for ZIKV (green) and DAPI (blue), with Sox2 (red) (FIG. 3D, FIG. 3G, FIG. 3J, FIG. 3M, FIG. 3P), Ki-67 (red) (FIG. 3E, FIG. 3H, FIG. 3K, FIG. 3N, FIG. 3Q), or GFAP (red) (FIG. 3F, FIG. 3I, FIG. 3L, FIG. 3O, FIG. 3R). FIG. 3S. Quantification of ZIKV-infected tumour cells, and Sox2, Ki-67, GFAP subpopulations of $ZIKV^+$ cells. FIG. 3T-FIG. 3Z, Representative images showing freshly resected normal brain after staining with H & E (FIG. 3T), or for Ki-67 (FIG. 3U) or GFAP (V). FIG. 3W-FIG. 3Z, Normal brain tissue uninfected (FIG. 3W, FIG. 3Y), or infected with ZIKV-Dakar (FIG. 3X, FIG. 3Z) after 7 days, stained for ZIKV (green) and DAPI (blue), with NeuN (red) (FIG. 3W, FIG. 3X) or GFAP (red) (FIG. 3Y, FIG. 3Z). In FIG. 3S, values represent mean±SD, and all results are pooled from three independent experiments. (Two-tailed unpaired t-test: , P<0.01; **, P<0.0001; ns, not significant). Scale bars, 100 μm for FIG. 3A-FIG. 3I, FIG. 3M-FIG. 3O, FIG. 3T-FIG. 3V, and 200 μm for FIG. 3J-FIG. 3L, FIG. 3P-FIG. 3R, and FIG. 3W-FIG. 3Z.

FIG. 4A, FIG. 4B, FIG. 4C, FIG. 4D, FIG. 4E, FIG. 4F, FIG. 4G, FIG. 4H, FIG. 4I, FIG. 4J, FIG. 4K, FIG. 4L, FIG. 4M, FIG. 4N, FIG. 4O, FIG. 4P, FIG. 4Q, FIG. 4R, FIG. 4S, FIG. 4T and FIG. 4U show Mouse-adapted ZIKV-Dakar attenuates growth of mouse glioma cells compared to differentiated cells in vitro, and prolongs survival of mice with glioma in vivo. FIG. 4A, Mouse glioma cells (C57BL/6 background: GL26, GL261 and CT-2A), microglial cells (BV2), and neural stem cell differentiated cells (MS-DNC) were infected with parental or mouse-adapted ZIKV-Dakar, and relative cell viability was assessed over a week, normalized to day 0. FIG. 4B, Viral titre from supernatant of ZIKV-Dakar-infected cells (GL26, GL261, CT-2A, BV2 and MS-DNC) was measured at one week by focus-forming assay (FFA). FIG. 4C-FIG. 4I, Murine glioma model with GL261 and CT-2A. One week after implantation, bioluminescence imaging (BLI) (FIG. 4C) and H & E staining (FIG. 4D, FIG. 4E) demonstrating glioma. Three weeks after GL261 (FIG. 4F, FIG. 4G) and CT-2A (FIG. 4H, FIG. 4I) implantation without (FIG. 4F, FIG. 4H) or with mouse-adapted ZIKV-Dakar treatment (FIG. 4G, FIG. 4I). FIG. 4J, FIG. 4K, Kaplan-Meier survival curves for glioma tumour models treated with PBS control or $10^3$ FFU (FIG. 4J) or $10^5$ FFU (FIG. 4K) of mouse adapted-ZIKV-Dakar. FIG. 4L-FIG. 4S, Immunofluorescence staining of GL261-glioma tumour-bearing mice at the endpoint after treatment with PBS control (FIG. 4L, FIG. 4N, FIG. 4P) or $10^3$ FFU adapted-ZIKV-Dakar (FIG. 4M, FIG. 4O, FIG. 4Q, FIG. 4R, FIG. 4S) for ZIKV (green) with DAPI (blue) (FIG. 4L-FIG. 4Q), Sox2 (red) (FIG. 4L, FIG. 4M, FIG. 4R), GFAP (red) (FIG. 4N, FIG. 4O), Ki-67 (red) (FIG. 4P, FIG. 4Q), and BrDU (blue) (FIG. 4R, FIG. 4S). FIG. 4T, Quantification of $ZIKV^+$ cells or $BrdU^+/Ki67^+$ cells in murine GL261 glioma (left), and Sox2, Ki67, $BrdU^+$ subpopulations of $ZIKV^+$ cells (right). In vitro experiments were pooled from three independent experiments, performed in duplicate. Animal survival experiments were pooled from two independent experiments (n=15 (control) or n=18 (ZIKV $10^3$ FFU treated) for GL26, n=7 (control) or n=8 (ZIKV $10^3$ FFU treated) for CT-2A, n=6 (control) or n=6 (ZIKV $10^5$ FFU treated) for GL261). (FIG. 4U, left) Representative low- and high-power images of in situ hybridization staining for viral RNA in mice with CT2A glioma 2 wk after treatment with ZIKV-Dakar or PBS (representative of two experiments). Arrow indicates positive staining. (FIG. 4U, right) Representative high-power images of cleaved caspase-3 staining on the same tumors. In vitro experiments were pooled from three independent experiments performed in duplicate. Quantification of immunostaining was from 6 mice. Values represent mean±SD, (One-way ANOVA with multiple comparison correction for FIG. 4A-FIG. 4B: ****, P<0.0001). The log-rank test was used for (FIG. 4J-FIG. 4K). Scale bar, 200 μm for FIG. 4D, FIG. 4F-FIG. 4I. Scale bar, 100 μm for FIG. 4E, FIG. 4L-FIG. 4S.

FIG. 5A, FIG. 5B, GSCs were mock treated or incubated with parental ZIKV (MOI of 5), ZIKV-E218A (MOI of 5), TMZ (250 μM), or ZIKV-E218A (MOI of 5) and TMZ (250 μM) combined (E218AT). After treatment for one week, three GSC lines (387, 3565, 4121) were assayed on day 7 for relative cell viability normalized to day 0 (FIG. 5A), and sphere formation (FIG. 5B). FIG. 5C-FIG. 5F, Immunofluorescence staining of uninfected control (FIG.

5C, FIG. 5E) and ZIKV-E218A treated (FIG. 5D, FIG. 5F) GSCs on day 7, for Sox2 (red), DAPI (blue) and ZIKV-E218A (green). FIG. 5G, FIG. 5H, Immunofluorescence staining of ZIKV-E218A-infected GSCs without (FIG. 5G) and with temozolomide (250 μM) (FIG. 5H) on day 7, for AC3 (red), DAPI (blue), and ZIKV-E218A (green). FIG. 5I. Quantification of $AC3^+$ apoptotic cells in three GSCs lines treated with temozolomide (TMZ), ZIKV-E218A, or ZIKV-E218A combined with TMZ (250 μM) (E218AT). FIG. 5J. Viral titre from supernatant of parental ZIKV-infected and E218A ZIKV-infected GSCs over one week, measured by focus-forming assay (FFA). All data were pooled from three independent experiments, performed in duplicate. Values represent mean±SD (One-way ANOVA with Tukey's method for multiple comparisons for FIG. 5A, FIG. 5B, and FIG. 5G. Two-tailed unpaired t-test for FIG. 5H. P<0.05; P<0.01; *P<0.001; **, P<0.0001).

FIG. 6A, Immunoblotting for stem cell (Sox2 and Olig2) and differentiation marker (GFAP) proteins from 4 lines of GSCs (387, 3565, 3691, and 4121) after 14 days of serum exposure. FIG. 6B, Quantification of $ZIKV^+$ cells in $DAPI^+$ cells, and $Sox2^+$ cells in $ZIKV^+$ GSCs, 48 hpi in 3565 GSCs (387 and 4121 not shown, with similar data). FIG. 6C-FIG. 6I, Flow cytometry histograms showing infection efficiency of GSCs (FIG. 6C-FIG. 6E) and DGCs (FIG. 6G-FIG. 6I). One representative experiment of four is shown. GSCs exposed to control (left), ZIKV-Dakar at an MOI of 0.01 (middle) or MOI of 5 (right) at 24 (FIG. 6C), 48 (FIG. 6D) and 72 h (FIG. 6E) and GDCs exposed to control (left), ZIKV at MOI of 0.01 (middle) or MOI of 5 (right) at 24 (FIG. 6G), 48 (FIG. 6H) and 72 h (FIG. 6I); quantification of ZIKV-Dakar infection efficiency in GSCs (FIG. 6F) and DGCs (FIG. 6J). For each experiment, data was pooled from four independent experiments. Values represent mean±SD.

FIG. 8A, FIG. 8B, Relative cell viability was determined for three matched GSC (FIG. 8A) and DGC (FIG. 8B) lines (387, 3565 and 4121) infected with WNV-NY (MOI 5), normalized to day 0. FIG. 8C, Viral titre was determined by FFA over one week based on supernatants from the three paired GSC and DGC lines after infection with WNV-NY (MOI 0.01). FIG. 8D-FIG. 8G, Flow cytometry histograms showing WNY-NY infection efficiency of GSCs (FIG. 8D), DGCs (FIG. 8E-FIG. 8G) at indicated MOIs and time points. One representative experiment of three is shown. FIG. 8H-FIG. 8K, Normal human brain tissues were uninfected (FIG. 8H, FIG. 8I) or infected by WNY-NY (MOI 0.01) (FIG. 8I, FIG. 8K) for one week. Immunofluorescence staining for WNV E (green) and DAPI (blue), with NeuN (red) or GFAP (red). FIG. 8L, WNV titre was determined by FFA over one week from supernatant from three independent normal human brain tissues (NM265, NM266, NM267) infected at an MOI of 0.01. FIG. 8M, Relative cell viability was determined for three normal human neuronal cell lines (NM55, NM177 and Hu-DNC) infected with WNV-NY at an MOI of 5, normalized to day 0. All data was pooled from three independent experiments, performed in duplicate. Values represent mean±SD (Two-tailed unpaired t-test, for FIG. 8A, FIG. 8B, FIG. 8C, FIG. 8M, P<0.01; *P<0.001; ****, P<0.0001).

FIG. 9A, FIG. 9B, Viruses in supernatants from infected tissues were titred by FFA. Fresh human glioblastoma specimens (143, 3788, and 3902) (FIG. 9A) or normal brain tissues (267, 266, 270) FIG. 9 (B) were exposed to ZIKV-Brazil or ZIKV-Dakar by direct injection or soaking. FIG. 9C-FIG. 9F, Immunofluorescence staining of GSCs (FIG. 9*c*) and DGCs (FIG. 9D) cultured in a monolayer and infected with ZIKV at an MOI of 5 (ZIKV, green; DAPI, blue) for 48 h. FIG. 9E, FIG. 9F, Immunofluorescence staining of DGCs, for ZIKV (green) and DAPI (blue), with GFAP (red) (FIG. 9E) or Tuj1 (red) (FIG. 9F). FIG. 9G, FIG. 9H, Immunofluorescence staining of normal human neuronal cells infected by ZIKV (MOI of 5) at 48 h, for ZIKV (green) and DAPI (blue), with GFAP (red) (FIG. 9G) or Tuj1 (red) (FIG. 9H). FIG. 9I, Relative cell viability was determined for three normal human neuronal cell lines (NM55, NM177 and Hu-DNC) infected with ZIKV-Brazil or ZIKV-Dakar at MOI of 5 for one week, normalized to day 0. FIG. 9J, FIG. 9K, FFA analysis of viral titre of supernatants from normal human neuronal cells (HDNC, NM55, NM177) (FIG. 9J) and DGCs (387, 3565, 4121)(FIG. 9K) infected with ZIKV-Brazil or ZIKV-Dakar. All experiments were performed in duplicate and pooled from three independent experiments. Values represent mean±SD (One-way ANOVA with multiple comparison correction was used for I, *P<0.05). Scale bar, 200 μm for FIG. 9A, 100 μm for FIG. 9C and FIG. 9E.

FIG. 10A, Unsupervised hierarchical clustering of transcripts from matched GSCs and DGCs (387, 3565, 4121), highlighting differential expression of ISGs. FIG. 10B, Gene set enrichment analysis for cellular response to type I IFN and to type II IFN-γ signalling pathways. FIG. 10C, Gene Ontology (GO) Consortium processes for type I and II IFN-γ response pathways significantly upregulated in DGCs compared to GSCs. FIG. 10D-G, Immunofluorescence staining of human glioblastoma uninfected FIG. 10D, FIG. 10E) or infected (FIG. 10F, FIG. 10G) with ZIKV-Dakar for ZIKV (green) and DAPI (blue), with Ifnar-1 (red) (FIG. 10D, FIG. 10F) and Stat1 (red) (FIG. 10E, FIG. 10G).

FIG. 11A, FIG. 11B, Heatmaps of GO processes for type I and II IFN-γ response pathways in uninfected and ZIKV-Dakar infected GSCs (387, 3565, 4121) FIG. 11C, qPCR for ISGs (Ifnar1, Stat1, Irf1, Ifh1, Oas2, and Ifh1) in 3565 and 4121 DGCs (red) normalized to their matched GSCs (black). FIG. 11D, Top-10 upregulated (red) and downregulated (blue) GO pathways after GSC infection with ZIKV-Dakar (MOI of 5) for 48 h. Each treatment condition was sequenced in duplicate.

DETAILED DESCRIPTION

Figure 1D:
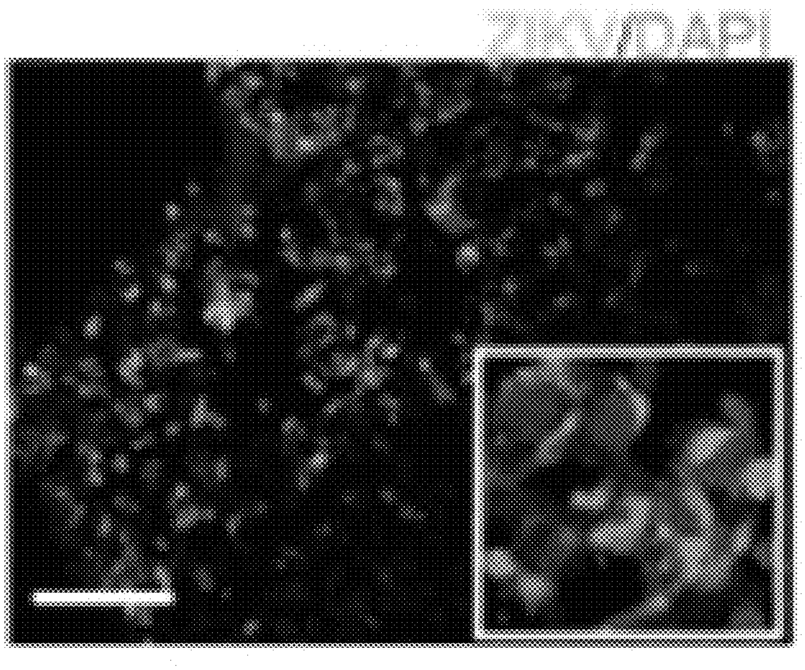
Figure 1E:
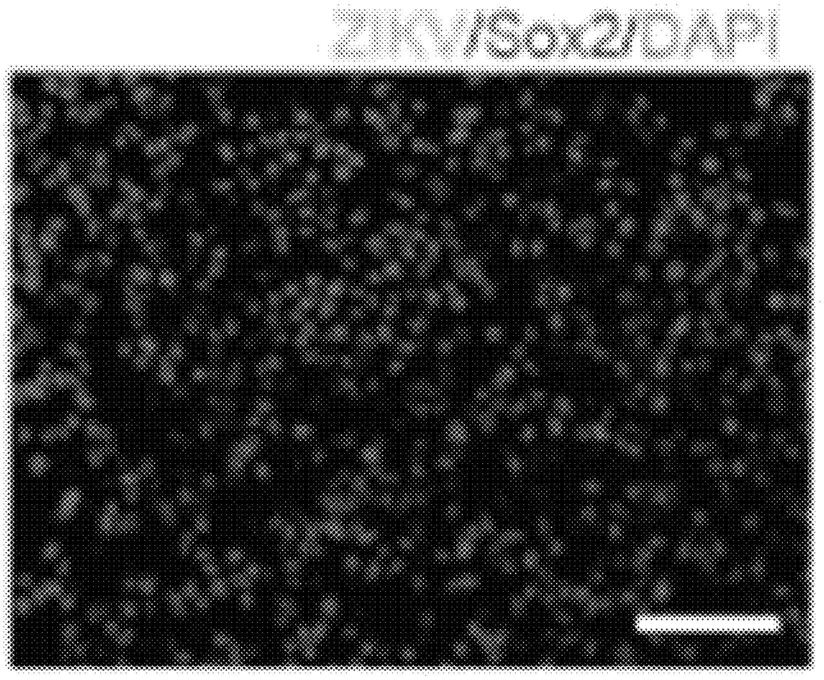

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

The present disclosure encompasses composition and methods for the treatment of a tumor with an oncolytic virus.

I. Composition

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular oncolytic virus is disclosed and discussed and a number of modifications that can be made to a number of molecules including the oncolytic virus are discussed, specifically contemplated is each and every combination and permutation of oncolytic virus and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

(a) Oncolytic Virus

Oncolytic viruses (OVs) which preferentially infect and kill cancer cells hold high promise as a cancer treatment. OVs selectively spread in cancer cells and cause a massive cytopathic effect. These virally infected, dying cancer cells further recruit immune cells such as NK cells or cytotoxic T cells to "clean up" infected cancer cells that escaped the viral killing.

Through the use of recombinant nucleic acid modification, it is understood and herein contemplated that oncolytic viruses can be engineered to or otherwise modified to be attenuated while maintaining the ability to target cancer cells. As used herein, "attenuated" can mean a virus that demonstrates reduced or no clinical signs of virus-related disease when administered to a subject compared to a wild-type virus. Accordingly, in one aspect, disclosed herein are engineered oncolytic viruses wherein the oncolytic viruses have increased efficacy against tumor cells and/or minimized toxicity to normal cells. In one aspect, the oncolytic viruses disclosed herein can be constructed from a viral backbone from the flavivirus family. Flaviviruses are positive-stranded RNA viruses that include Zika Virus (ZIKV), dengue, West Nile (WNV), and yellow fever viruses. While other flavivirus such as the WNV may have oncolytic properties, WNV infects and kill other normal neural cells in addition to GSC cells. In one aspect, the oncolytic viruses disclosed herein can be constructed from a Zika viral backbone. In one aspect, the virus is a modified or engineered Zika virus.

In some embodiment, the present disclosure provides a modified or engineered OV which may be efficiently and safely used in the treatment of a tumor. The engineered or modified ZIKV may promote infection and/or lysis of tumor cells with less toxicity to surrounding normal cells. In one aspect, modifying or engineering the OV results in a mutation of the OV. In particular, the term "mutation" or "mutant" is intended to include any polypeptide or representation thereof that differs from its corresponding wild-type polypeptide by having at least one amino acid substitution, addition or deletion, for example an arginine substitution. The single ORF of Flaviviruses encodes three structural (C-prM/M-E) and seven nonstructural (NS1-NS2A-NS2B-NS3-NS4A-NS4B-NS5) proteins. In some embodiments, the modified or engineered ZIKV may comprise mutations in one or more of the non-structural proteins. In one aspect, a modified or engineered ZIKV of the disclosure may comprise an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to GenBank Accession No. KX280026.1, herein incorporated by reference. In one aspect, a modified or engineered ZIKV of the disclosure may comprise a nucleotide sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to GenBank Accession No. KX280026.1. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (e.g. version 2.10.0) using e.g. the program "needle" (with the above mentioned GAP opening and extension penalties). Alternatively percent similarity or identity may be determined by searching against databases such as FASTA, BLAST, etc.

In some embodiments, the disclosure provides an engineered or modified ZIKV that is attenuated. In some embodiments, the engineered or modified ZIKV has limited replication capacity in a normal cell compared to the corresponding wild-type ZIKV. This limited replication may enhance the safety of the ZIKV composition. In one aspect, engineering or modifying the ZIKV sensitizes the virus to translational inhibition by type I interferon (IFN). In another aspect, the engineered or modified ZIKV has mutations affecting ZIKV 2'-O methyltransferase activity. In some embodiments, the present disclosure provides a modified or engineered ZIKV comprising an NS5 gene with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to GenBank Accession No. KY785480.1, herein incorporated by reference. In some embodiments, the present disclosure provides a modified or engineered ZIKV comprising at least one mutation in the NS5 protein. In another aspect, the present disclosure provides a modified or engineered ZIKV comprising one or more mutations to the NS5 protein, wherein at least one mutation occurs at the position corresponding to amino acid 218 as determined by sequence alignment with GenBank Accession No. KY785480.1. In one aspect, an engineered or modified ZIKV comprises a point mutant at the position corresponding to amino acid 218, wherein glutamic acid at position 218 is mutated to alanine.

In some embodiments, the disclosure provides a modified or engineered ZIKV which has reduced glycosylation compared to wild-type ZIKV. Any glycosylation site of a wild-type ZIKV is suitable to be mutated. In some embodiments, the modified or engineered ZIKV limit viral dissemination through endothelial barriers compared to wild-type ZIKV. In a non-limiting example, a modified or engineered ZIKV of the disclosure may comprise at least one mutation to the envelope (E) protein. In one aspect, a modified or engineered ZIKV may comprise one or more mutations to the E protein, wherein at least one mutation occurs in the VND sequence of the E protein as determined by sequence alignment with GenBank Accession No. KY785480.1. An engineered or modified ZIKV from which the VND motif is deleted or in which the N-linked glycosylation site is mutated by single-amino-acid substitution are highly attenuated and nonlethal. In some embodiments, a modified or engineered ZIKV comprise one or more mutations to the E protein, wherein at least one mutation occurs at the position corresponding to amino acid 154 and/or amino acid 156 of the E protein as determined by sequence alignment with GenBank Accession No. KY785480.1. In one aspect, an engineered or modified ZIKV comprises a point mutant at the position corresponding to amino acid 154 or to amino acid 156, wherein asparagine at position 154 is mutated to glutamine and threonine at position 156 is mutated to valine. In some embodiments, a modified or engineered ZIKV with reduced or absent glycosylation comprises at least one mutation in the NS1 protein.

In another aspect, the modified or engineered ZIKV comprise at least one mutation in the 3' untranslated region of the ZIKV genome. In some embodiments, the modified or engineered ZIKV disrupts short flaviviral RNA productions compared to wild-type ZIKV. In a non-limiting example, a modified or engineered ZIKV of the disclosure may contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleotides may be deleted from the 3' UTR.

In some embodiments, a modified or engineered ZIKV may comprise at least one mutation in the NS4B protein. In one aspect, the modified or engineered comprise mutations that affect interferon antagonism or autophagy pathways. In some embodiments, the present disclosure provides a modified or engineered ZIKV comprising one or more mutations to the NS4B protein, wherein at least one mutation occurs at the position corresponding to amino acid 18 as determined by sequence alignment with GenBank Accession No. KY785480.1. In one aspect, an engineered or modified ZIKV comprises a point mutant at the position corresponding to amino acid 18, wherein a glycine at position 18 is mutated to arginine. In some embodiments, a modified or engineered ZIKV may comprise at least one mutation in the NS3 protein. In some embodiments, the present disclosure provides a modified or engineered ZIKV comprising one or more mutations to the NS3 protein, wherein at least one mutation occurs at the position corresponding to amino acid 399 as determined by sequence alignment with GenBank Accession No. KY785480.1. In one aspect, an engineered or modified ZIKV comprises a point mutant at the position corresponding to amino acid 399, wherein a lysine at position 399 is mutated to arginine.

In one aspect, it is recognized that facilitating the membrane fusion of the virus to a target cell such as a cancer cell can increase the rate and efficiency of delivery of genetic material from the oncolytic virus to the target cell. One method that fusion of the oncolytic virus to the target cell can be facilitated is through the use of fusogenic peptides, polypeptide, and proteins. Fusogenic peptides, polypeptides, and proteins, can include, but are not limited to viral fusogenic peptides, polypeptides, and proteins such as, for example, influenza hemagglutinin peptide (HA), Dengue fusogenic peptide, HIV envelope (Env), paramyxovirus (for example, parainfluenza virus and SV5) fusion protein (F) and paramyxovirus hemmaglutinin-neuraminidase (HN). Accordingly, in one aspect, disclosed herein are oncolytic viruses comprising one or more exogenous membrane bound targeting ligand and an uncleaved signal anchor wherein the wherein the engineered oncolytic virus is a fusogenic oncolytic virus. In one aspect, the fusion peptide, polypeptide, or protein can be endogenous to the oncolytic virus or the virus can be engineered to express and exogenous fusion peptide, polypeptide, or protein. In other words, the oncolytic virus can either be natively or engineered/modified to be fusogenic. For example, the backbone oncolytic virus can be a ZIKV, which can be modified/engineered to comprise a fusogenic peptide, polypeptide, or protein and thus be fusogenic. Accordingly, in one aspect, disclosed herein are modified or engineered oncolytic viruses wherein the oncolytic virus expresses an exogenous membrane bound targeting ligand comprising an uncleaved signal anchor; wherein the modified or engineered oncolytic virus is a parainfluenza virus, such as, for example a modified or engineered ZIKV; and wherein the oncolytic virus expresses paramyxovirus F and/or HN. In one aspect, natively fusogenic oncolytic viruses can also be engineered to comprise further fusion peptides, polypeptides, or proteins. Such engineered fusogenic oncolytic viruses are hyperfusogenic. Thus, in one aspect, disclosed herein are fusogenic oncolytic viruses comprising a gene which codes for a peptide that allows a hyperfusogenic property that allows tumor cells to fuse.

In an aspect, the disclosure comprises a composition containing an oncolytic virus that specifically targets and kills glioblastoma stem cells (GSC). In an aspect an oncolytic virus is able to kill a tumor cell by infecting the tumor cell. The tumor cell that is targeted by the composition may be a GSC that is a precursor cell of the GBM. The killing efficiency of an oncolytic virus may depend on the ability to infect cells, replicate, and specifically kill tumor cells. In some embodiments, a modified or engineered ZIKV preferentially kills GSCs with minimal killing of other normal neural cells, and may be suitable for efficient and safe treatment of GBM (FIG. 8).

In an aspect the oncolytic virus used in the composition may be ZIKV. The ZIKV in the composition may be dispersed in a pharmacologically acceptable formulation. The composition may comprise a suitable carrier that may be saline or a buffer that does not affect the therapeutic potential of the composition. The carrier may be a pharmaceutically acceptable carrier that is suitable for injection intra-tumorally or by other desired route of injection. A suitable pharmaceutically acceptable carrier known in the art may be used in the composition.

(b) Components of the Composition

The present disclosure also provides pharmaceutical compositions. The pharmaceutical composition comprises a modified or engineered OV as disclosed herein, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylam ides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In various embodiments, the pharmaceutical composition comprising the OV comprises about 10e3 to 10e11 (log scale) viral particles (VP). In various embodiments, the pharmaceutical composition comprising the OV comprises about 10e4 to 10e11 (log scale) viral particles (VP). In various embodiments, the quantity of OV is about 10e3, 10e4, 10e5, 10e6, 10e7, 10e8, 10e9, 10e10, or 10e11. The actual quantity of viral particles can depend on the tumor volume or estimated tumor volume. For example, tumor volumes of in the about 1 $cm^3$ can be treated with about 10e3 to 10e9 viral particles and tumor volumes of about 100 $cm^3$ can be treated with about 10e6 to 10e11 viral particles.

In various embodiments, the composition comprising the OV comprises a quantity of viral particles for a multiplicity of infection (MOI) of 1, 2, 3, 4, 5, 10, 25, 50 or 100, or about 1, 2, 3, 4, 5, 10, 25, 50, or 100.

(c) Administration

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising an OV is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems.

Methods of incorporating compositions into delivery vehicles are known in the art.

In one alternative embodiment, a liposome delivery vehicle may be utilized. Liposomes, depending upon the embodiment, are suitable for delivery of an OV in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the OV may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a OV may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of the OV, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The OV may be encapsulated in a microemulsion by any method generally known in the art.

In yet another embodiment, an OV may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

In various embodiments, the pharmaceutical compositions comprising an OV according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

In some embodiments, the OV is administered via intratumoral delivery at a single site or multiple sites. In some embodiments, the OV is administered via intra-cerebral delivery. In other embodiments, the OV is administered intravenously or subcutaneously. In other embodiments, the OV is administered via intracarotid delivery. In other embodiments, the OV is administered via delivery to a body cavity, intraperitoneally. In other embodiments the OV is administered via intranasal delivery. In other embodiments, the OV is administered via oral delivery. In other embodiments, the OV is administered via intra-rectal delivery. In other embodiments, the OV is administered via intra-colon delivery. In other embodiments, the OV is administered via ocular delivery.

II. Method of Using the Composition

Oncolytic viruses have been shown in the art to be effective therapeutics for the treatment of cancer. The viruses lyse infected cancer cells at egress and the infection of cancer cells also stimulates the host immune response to kill the infected cells. The disclosed modified or engineered OVs are similarly useful in the treatment of cancer and improve upon the efficacy of such oncolytic viruses selectively target and kill cancer cells. Thus, in one aspect, the disclosed OVs can be used to treat cancer. In some embodiments, the OVs disclosed herein can be used to treat cancer by killing cancer stem cells in a subject in need thereof.

A tumor or cancer refers to a condition usually characterized by unregulated cell growth or cell death. A tumor may be malignant when nearby tissues or other parts of the body are invaded by the tumor. A tumor may be traditionally treated by surgical resection, radiation therapy, or chemotherapy. Any cancers or tumors, including both malignant and benign tumors as well as primary tumors and metastasis may be targets of oncolytic virus disclosed herein. In a specific embodiment the disclosure provides method to treat a cancer wherein the cancer is any solid tumor. In a some embodiments of the invention, the cancer is selected from a group consisting of glioblastoma, nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer, and tonsil cancer.

Accordingly, in one aspect, disclosed herein are methods of treating a cancer comprising administering to a subject a composition comprising one or more engineered oncolytic viruses. Suitable OVs are described above in Section I. By way of illustration, cancer patients or patients susceptible to cancer or suspected of having cancer may be treated as described herein. Oncolytic viruses as described herein may be administered to the individual and retained for extended periods of time. The individual may receive one or more administrations of the viruses. In some embodiments, the viruses are encapsulated to inhibit immune recognition and placed at the site of a tumor.

In various embodiments the expression constructs, nucleic acid sequences, vectors, host cells and/or pharmaceutical compositions comprising the OVs disclosed herein are used for the prevention, treatment or amelioration of a cancerous disease, such as a tumorous disease. In particular embodiments, the pharmaceutical composition of the present disclosure may be particularly useful in preventing, ameliorating and/or treating cancer, including cancer having solid tumors, for example.

In particular embodiments, the present invention contemplates, in part, viruses, expression constructs, nucleic acid molecules and/or vectors that can administered either alone or in any combination with another therapy, and in at least some aspects, together with a pharmaceutically acceptable carrier or excipient. In certain embodiments, prior to administration of the viruses, they may be combined with suitable pharmaceutical carriers and excipients that are well known in the art. The compositions prepared according to the disclosure can be used for the prevention or treatment or delaying of onset or worsening of cancer.

Furthermore, the disclosure relates to a method for the prevention, treatment or amelioration of a cancerous (including tumorous) disease comprising the step of administering to a subject in need thereof an effective amount of oncolytic viruses of the disclosure, wherein the virus is modified or engineered promote infection and/or lysis of tumor cells with less toxicity to surrounding normal cells. In some embodiments, the disclosure relates to inducing an oncolytic effect on a cancer. In some embodiments, the methods generally comprise administering to a subject in need thereof a composition comprising an effective amount of a modified or engineered ZIKV of the disclosure comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to GenBank Accession No. KX280026. In some embodiments, the methods generally comprise administering to a subject in need thereof a composition comprising an effective amount of a modified or engineered ZIKV of the disclosure may comprise a nucleotide sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to GenBank Accession No. KX280026.1. In another aspect, the method generally comprise administering to a subject in need thereof a composition comprising an effective amount of a modified or engineered ZIKV that has limited replication capacity in a normal cell compared to the corresponding wild-type ZIKV. In still another aspect, the methods generally comprise administering to a subject in need thereof a composition comprising an effective amount of a modified or engineered ZIKV which is susceptible to translational inhibition by type I interferon (IFN) compared to a wild-type ZIKV. In still yet another aspect, the methods generally comprise administering to a subject in need thereof a composition comprising an effective amount of a modified or engineered ZIKV with reduced 2'-O methyltransferase activity compared to a wild-type ZIKV. In another aspect, the methods generally comprise administering to a subject in need thereof a composition comprising an effective amount of a modified or engineered ZIKV with reduced viral dissemination across endothelial barriers compared to a wild-type ZIKV. In yet another aspect, the methods generally comprise administering to a subject in need thereof a composition comprising an effective amount of a modified or engineered ZIKV with disrupted short flaviviral RNA production compared to a wild-type ZIKV. In some embodiments, the methods generally comprise administering to a subject in need thereof a composition comprising an effective amount of a modified or engineered ZIKV comprising reduced glycosylation compared to wild-type ZIKV.

In some embodiments, the methods generally comprise administering to a subject in need thereof a composition comprising at least one mutation to the NS5 gene. In some embodiments, the methods generally comprise administering to a subject in need thereof a composition comprising an effective amount of a modified or engineered ZIKV comprising one or more mutations to the NS5 protein, wherein at least one mutation occurs at the position corresponding to amino acid 218 as determined by sequence alignment with GenBank Accession No. KY785480.1. In some embodiments, the methods generally comprise administering to a subject in need thereof a composition comprising an effective amount of an engineered or modified ZIKV comprises a point mutant at the position corresponding to amino acid 218, wherein glutamic acid at position 218 is mutated to alanine.

In some embodiments, the methods generally comprise administering to a subject in need thereof a composition comprising an effective amount of a modified or engineered ZIKV which has reduced glycosylation compared to wild-type ZIKV. In some embodiments, the methods generally comprise administering to a subject in need thereof a composition comprising an effective amount of a modified or engineered ZIKV comprising at least one mutation to the envelope (E) protein. In some embodiments, the methods generally comprise administering to a subject in need thereof a composition comprising an effective amount of a modified or engineered ZIKV comprising one or more mutations to the E protein, wherein at least one mutation occurs in the VND sequence of the E protein as determined by sequence alignment with GenBank Accession No. KY785480.1. In some embodiments, the methods generally comprise administering to a subject in need thereof a composition comprising an effective amount of a modified or engineered ZIKV comprise one or more mutations to the E protein, wherein at least one mutation occurs at the position corresponding to amino acid 154 or amino acid 156 of the E protein as determined by sequence alignment with GenBank Accession No. KY785480.1. In some embodiments, the methods generally comprise administering to a subject in need thereof a composition comprising an effective amount of an engineered or modified ZIKV comprising a point mutant at the position corresponding to amino acid 154 or amino acid 156, wherein asparagine at position amino acid 154 is mutated to glutamine and threonine at position amino acid 156 is mutated to valine. In some embodiments, the methods generally comprise administering to a subject in need thereof a composition comprising an effective amount of a modified or engineered ZIKV comprising at least one mutation in the NS1 protein.

In some embodiments, the methods generally comprise administering to a subject in need thereof a composition comprising an effective amount of a modified or engineered ZIKV comprising at least one mutation in the 3' untranslated region of the ZIKV genome. In some embodiments, the methods generally comprise administering to a subject in need thereof a composition comprising an effective amount of a modified or engineered ZIKV comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleotide deletions from the 3' UTR of the ZIKV genome.

In some embodiments, the methods generally comprise administering to a subject in need thereof a composition comprising an effective amount of a modified or engineered ZIKV comprising at least one mutation in the NS4B protein. [please provide the aa sequence for the NS4B protein. In some embodiments, the methods generally comprise administering to a subject in need thereof a composition comprising an effective amount of a modified or engineered ZIKV comprising one or more mutations to the NS4B protein, wherein at least one mutation occurs at the position corresponding to amino acid 18 as determined by sequence alignment with GenBank Accession No. KY785480.1. In some embodiments, the methods generally comprise administering to a subject in need thereof a composition comprising an effective amount of an engineered or modified ZIKV comprising one more mutations in the NS4B protein, wherein at least one mutation is a point mutant at the position corresponding to amino acid 18, wherein a glycine at position 18 is mutated to arginine. In some embodiments, the methods generally comprise administering to a subject in need thereof a composition comprising an effective amount of a modified or engineered ZIKV comprising at least one mutation in the NS3 protein. In some embodiments, the methods generally comprise administering to a subject in need thereof a composition comprising an effective amount of a modified or engineered ZIKV comprising one or more mutations to the NS3 protein, wherein at least one mutation occurs at the position corresponding to amino acid 399 as determined by sequence alignment with GenBank Accession No. KY785480.1. In some embodiments, the methods generally comprise administering to a subject in need thereof a composition comprising an effective amount of an engineered or modified ZIKV comprising a point mutant at the position corresponding to amino acid 399, wherein a lysine at position 399 is mutated to arginine.

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a “zoological animal” refers to an animal that may be found in a zoo. Such animals may include non-human primates, large cats, wolves, and bears. In a preferred embodiment, the subject is a human. In an aspect the subject may be a subject who has cancer or is at risk of developing cancer. The subject may have previously undergone resection of a tumor. In an aspect the subject may have previously undergone therapy for a cancer including surgical recession of the tumor, radiation therapy, and/or chemotherapy.

In some embodiments, the Zika virus composition may be administered to treat glioblastoma (GBM) in a subject, by killing glioblastoma stem cells (GSCs).

As used herein glioma may refer to any tumor arising from the supporting or connective tissue cells of the brain or spinal cord. As used herein glioblastoma (GBM) is a type of malignant glioma.

GBM may show very low response to traditional therapy such as surgery, radiation, and chemotherapy. Even when the tumor is surgically removed, GBM may recur in the proximity to the original resection cavity.

The tumor cells in GBM are heterogeneous, with contributions from non-transformed cells and from neoplastic cells. The main contributors of tumor cells are the glioblastoma stem cells (GSCs). The GSCs are self-renewing, tumorigenic stem-like tumor cell population. The GSCs are also known as tumor initiating cells or tumor precursor cells, and contribute to tumor malignancy due to sustained proliferation, promotion of angiogenesis, invasive potential, immune escape and therapeutic resistance. GSC is capable of proliferating to renew the pool of GSC and capable of differentiating into different cell types of the GBM. A successful treatment for GBM may require specifically killing these GSCs without killing neighboring cells.

In an aspect, GSC cells have stem-like properties and exhibit stem cell markers that aid in identification of the GSCs. As used herein stem-like properties may include characteristics such as being able to give rise to all cell types and being capable of sustained proliferation. In this instance the stem-like characteristics of the GSC cells may promote angiogenesis and invasive potential of the tumor. The GCSs may exhibit stem cell markers such as SOX2 and OLIG2 that enable identification of the GSCs. The GSCs may differentiate into differentiated glioma cells. The differentiated glioma cells may lose precursor markers such as SOX2 and OLIG2, and gain differentiation marker GFAP.

In an aspect the composition may target and kill a GSC in a quiescent state. As used herein, quiescent state is a non-dividing stage of the cell cycle. Quiescent stem cells, or a quiescent GCS, are essential for providing and maintaining a pool of self-renewing stem cells. These cells are an important factor in the recurrence of stem cell cancers, and are especially resistant to chemotherapy and other targeted therapies.

In an aspect the ZIKV composition may be administered directly into a tumor or site of tumor resection of the subject. In various aspects the composition may be administered through various routes such as intracranial, intravenous, intramuscular, intranasal, subcutaneous, intratracheal, or intratumoral.

An effective dose of the composition may be administered to the subject. As used herein, an effective dose is the dose of the composition that will have a therapeutic effect. In the case of a tumor, the therapeutically effective dose may reduce the number of cancer cells, reduce the size of the tumor, reduce invasion, stop the metastasis of the tumor to other parts of body or neighboring tissues, and/or inhibit tumor growth. In an aspect the therapeutic effect may be to kill cancer stem cells, decrease proliferation of the cancer stem cells, increase apoptosis of the GSC, treat GBM or stop the recurrence of cancer in a subject. In an aspect the therapeutic effect may be to kill GSC.

The effective dose may be a single dose or multiple doses. The dose may be determined by different subject factors including but not limited to body weight, stage of tumor, number of cancer cells, and prognosis of the cancer. In an aspect the effective dose of the ZIKV may be from about $10^2$ FFU to about $10^9$ FFU. The dose may be administered in a volume of composition ranging from about 5 ul to about 10 ml depending on different factors including but not limited to factors like characteristics of the subject, and route and site of administration.

The OV composition as disclosed herein is effective alone, but combination with any other therapies, such as traditional therapy, may be more effective than either one alone. For example, each agent of the combination therapy may work independently in the tumor tissue, the OVs may sensitize cells to chemotherapy or radiotherapy and/or chemotherapeutic agents may enhance the level of virus replication or effect the receptor status of the target cells. The agents of combination therapy may be administered simultaneously or sequentially.

In a preferred embodiment of the invention, the method or use further comprises administration of concurrent radiotherapy to a subject. In another preferred embodiment of the invention, the method or use further comprises administration of concurrent chemotherapy to a subject. As used herein "concurrent" refers to a therapy, which has been administered before, after or simultaneously with the gene therapy of the invention. The period for a concurrent therapy may vary from minutes to several weeks. Preferably the concurrent therapy lasts for some hours.

Agents suitable for combination therapy include but are not limited to All-trans retinoic acid, Azacitidine, Azathioprine, Bleomycin, Bevacizumab, Carboplatin, Capecitabine, CCNU, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Lenalidomide, Mechlorethamine, Mercaptopurine, Methotrexate, Mitoxantrone, Oxaliplatin, Paclitaxel, Pemetrexed, Pomalidomide, Procarbazine, Temozolomide, Teniposide, Tioguanine, Thalidomide, Valrubicin, Vinblastine, Vincristine, Vindesine and Vinorelbine. In some embodiments, agents suitable for combination therapy include but are not limited to immune checkpoint blockades. Non-limiting examples of immune checkpoint blockade agents include inhibitors of PD-1/PD-L1, CTLA-4, IDO, TIM3, LAG3, TIGIT, BTLA, VISTA, ICOS, KIRs, CD39, Pembrolizumab, Nivolumab, Ipilimumab, Atezolizumab, Avelumab, Durvalumab. In some embodiments, agents suitable for combination therapy include CAR T-cell therapy. In some embodiments, agents suitable for combination therapy include interleukin-based therapies; non-limiting examples include IL-7, IL-12, IL-21 and long-acting derivatives thereof. In some embodiments, agents suitable for combination therapy include interferon based therapies (e.g. IFN-alpha, beta, gamma).

III. Kits

The present invention is also directed to a kit to treat cancers. The kit is useful for practicing the inventive method of treating tumors. The kit is an assemblage of materials or components, including at least one of the inventive compositions. Thus, in some embodiments the kit contains a composition including a Zika virus as described above.

The exact nature of the components configured in the inventive kit depends on its intended purpose. For example, some embodiments are configured for the purpose of treating brain tumors such as glioma and glioblastomas. Other embodiments are configured for the purpose of treating inducing an oncolytic effect on a tumor/cancer, such as a brain tumor, an ocular tumor, skin cancer, gastrointestinal cancer, and lung cancer. In one embodiment, the kit is configured particularly for the purpose of treating or inducing an oncolytic effect on mammalian subjects. In another embodiment, the kit is configured particularly for the purpose of treating or inducing an oncolytic effect on human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat brain tumors such as glioma and glioblastomas, or to induce an oncolytic effect on a tumor. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in tumor treatment and/or administration of viral particles. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing a Zika virus. The packaging material generally has an external label which indicates the contents and/or purpose of the kit and/or its components.

Definitions

When introducing elements of the present disclosure or the preferred aspects(s) thereof, the articles "a," "an," "the," and "said" are intended to mean that there are one or more of the elements. Thus, for example, reference to "a pharmaceutical carrier" includes mixtures of two or more such carriers, and the like. The terms "comprising," "including," and "having" are intended to be inclusive and mean that there may be additional elements other than the listed elements.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Therapeutically effective amount" as used herein refers to that amount which is capable of achieving beneficial results in a patient with a tumor; for example, a brain tumor. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or lessen the disease even if the treatment is ultimately unsuccessful.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to Examples

Glioblastoma (GBM) is the most prevalent primary intrinsic brain tumour. Despite multimodal therapy of surgery, radiation, and chemotherapy, GBMs remain essentially lethal, with a median survival of patients below two years[1]. GBM is a heterogeneous disease, with extensive contributions from non-transformed cells, but also a cellular hierarchy within the neoplastic compartment. Atop the hierarchy resides a self-renewing, tumorigenic stem-like tumour cell population, termed GSCs or tumour initiating cells[2]. GSCs contribute to tumour malignancy due to sustained proliferation, promotion of angiogenesis, invasive potential, immune escape, and therapeutic resistance[3, 4].

Unlike many deadly cancers, GBMs rarely metastasize and a majority (70 to 80%) of patients suffer recurrence within 2-3 cm of the original resection cavity[5]; this tumour behaviour has prompted investigation of local therapies, including oncolytic viruses[6-10, 11]. Several oncolytic DNA viruses have been developed to achieve tumour cell killing with limited toxicity[9, 10]. Efficacy of virotherapy against tumours depends on the ability to infect cells, replicate, and specifically kill tumour cells[8]. ZIKV is a member of the flavivirus genus of positive stranded RNA viruses, which includes dengue, West Nile (WNV), and yellow fever viruses. The recent outbreak of ZIKV-induced fetal microcephaly have spurred extensive research into ZIKV biology[12-17]. ZIKV infects the developing central nervous system (CNS), with neural stem cells and progenitors prominently affected. Neural precursors infected with ZIKV undergo differentiation, loss of proliferation, and cell death[13, 15, 16, 18]. In contrast, the effects of ZIKV in adults generally are less severe, with only rare case reports of meningoencephalitis, suggesting that ZIKV infection has fewer deleterious effects in the adult brain[19]. We hypothesized that we could leverage the tropism of ZIKV for neuroprogenitor cells[13, 15-18].

To interrogate the effects of ZIKV on GSCs, well characterized patient-derived GSCs that express stem cell markers, self-renew and form tumours upon xenotransplantation and differentiated glioma cells (DGCs) were used[4, 20]. GSCs are defined functionally through measures of self-renewal, differentiation potential, and tumour propagation. GSCs frequently express stem and progenitor cell markers, including those of oligodendroglial progenitor cells (OPCs), which may serve as the cell-of-origin in gliomas[21].

Example 1: Viral Infection of Glioblastoma Cells

Figure 1F:
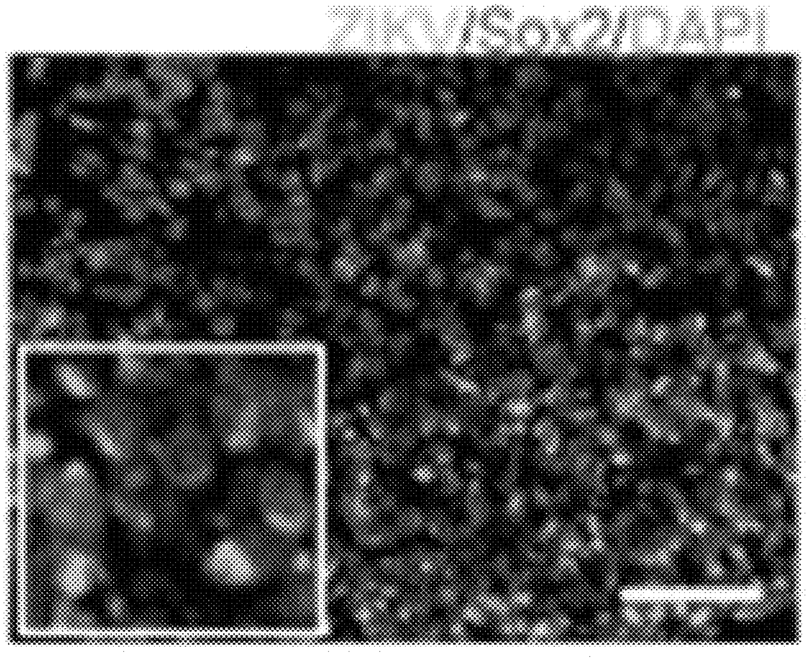
Figure 1G:
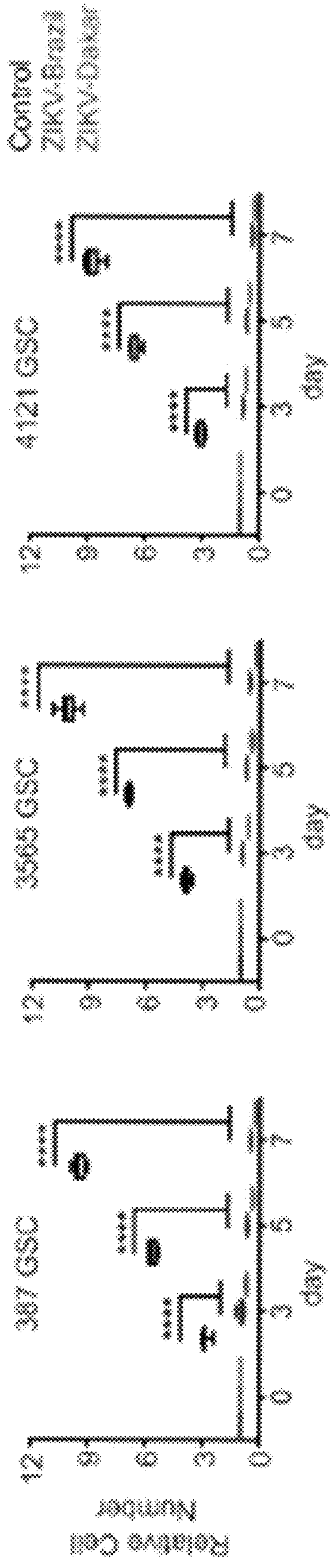
Figure 6A:
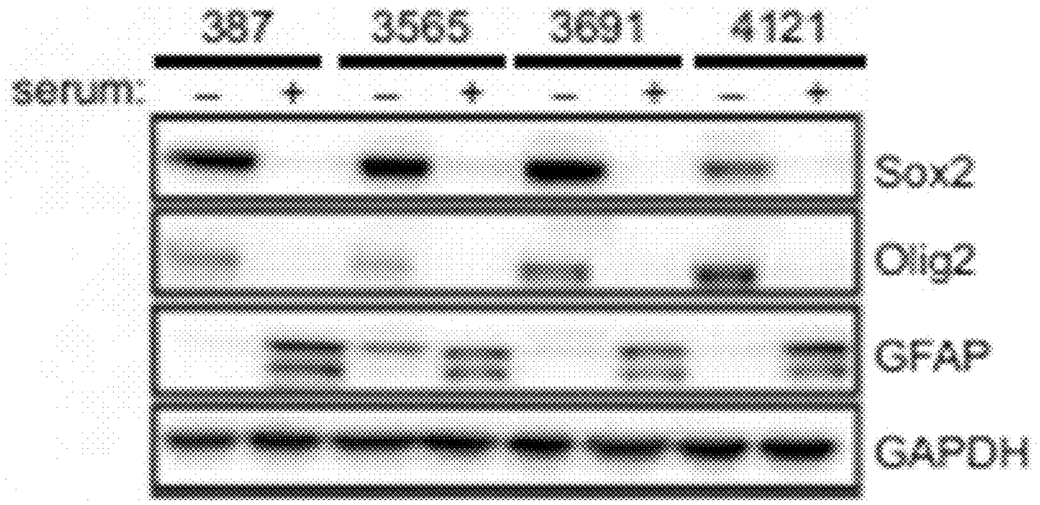
FIG. 6A, FIG. 6B, FIG. 6C, FIG. 6D, FIG. 6E, FIG. 6F, FIG. 6G, FIG. 6H, FIG. 6I and FIG. 6J show ZIKV infection efficiency is lower in DGCs than GSCs.
Figure 6B:
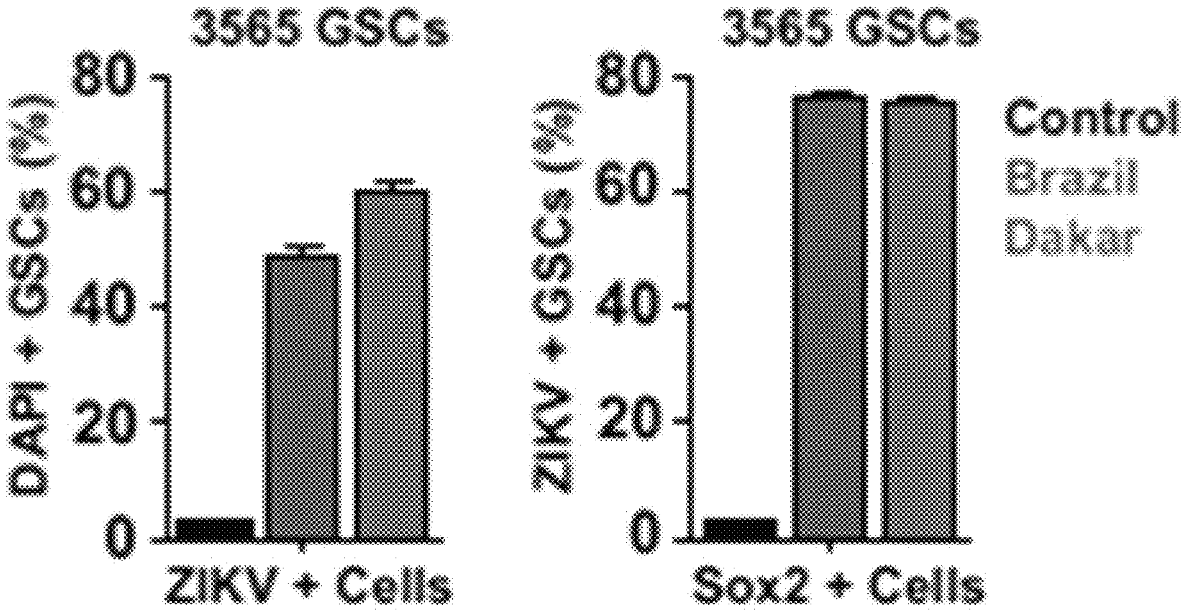

Four GSC models representing the major transcriptional GBM subtypes: proneural, classical, and mesenchymal were selected. Cellular differentiation was induced through exposure to serum[4]. As expected, all models showed loss of precursor markers (SOX2 and OLIG2) and gain of a differentiation marker (GFAP) upon induction of differentiation (FIG. 6A GSCs were infected (multiplicity of infection, MOI=5) with representative Asian/American (Brazil 2015) and African (Dakar 1984) ZIKV strains[12]. Forty-eight hours later, greater than 60% of GSCs were infected by either strain, as measured by immunofluorescence microscopy or flow cytometry (FIG. 1D, FIG. 6B, FIG. 7A-FIG. 7C and FIG. 7J, FIG. 9A). In contrast, DGCs supported a relatively low rate of viral infection (FIG. 7D-FIG. 7F, and FIG. 7K, FIG. 9B-FIG. 9D, and FIG. 9H), suggesting that ZIKV infects all tumour cells, but replicates better in GSCs. To confirm this observation fraction of ZIKV-infected cells that expressed a GSC marker (SOX2) were analysed; greater than 90% of infected cells were SOX2-positive (FIG. 1F and FIG. 6B).

Figure 1H:
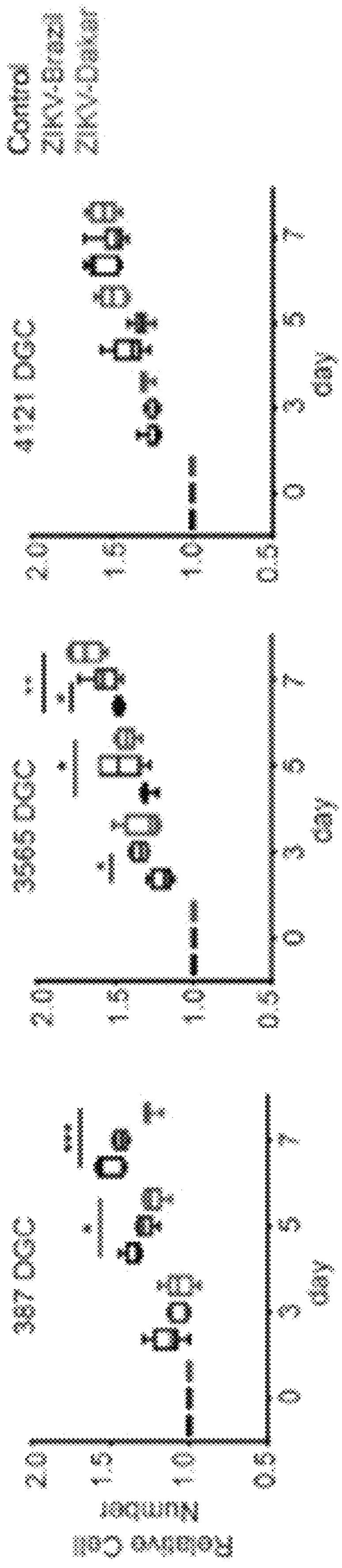
Figure 1I:
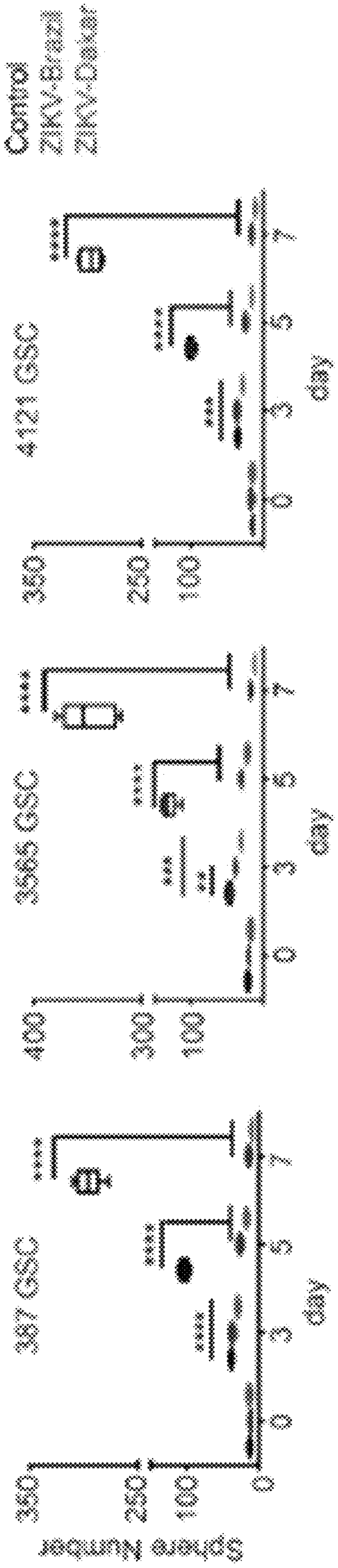
Figure 1J:
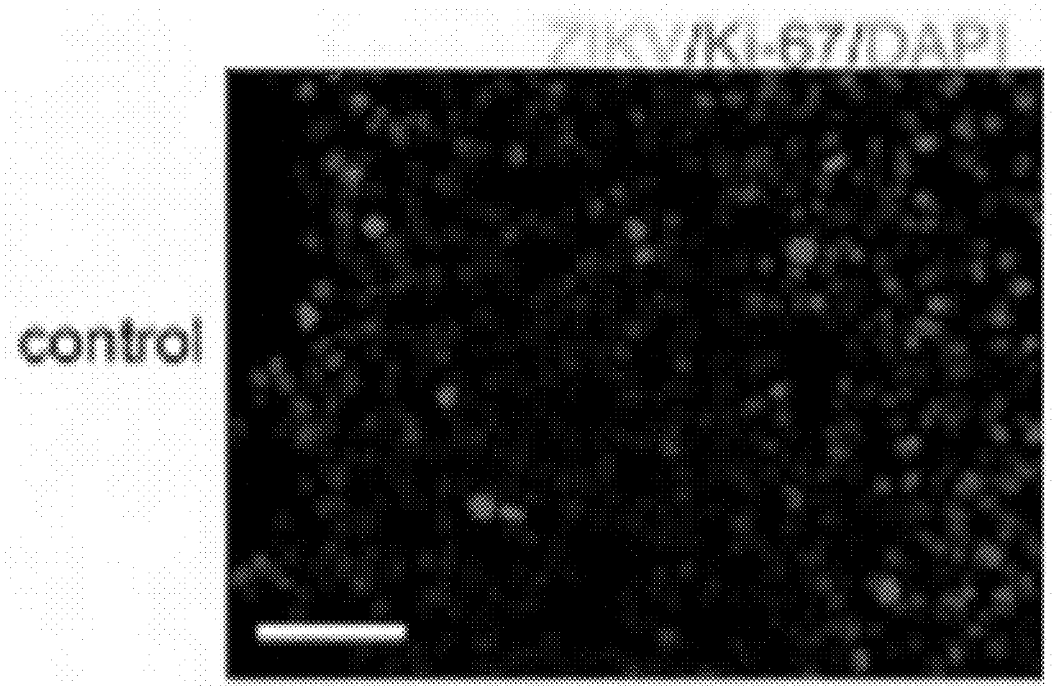
Figure 1K:
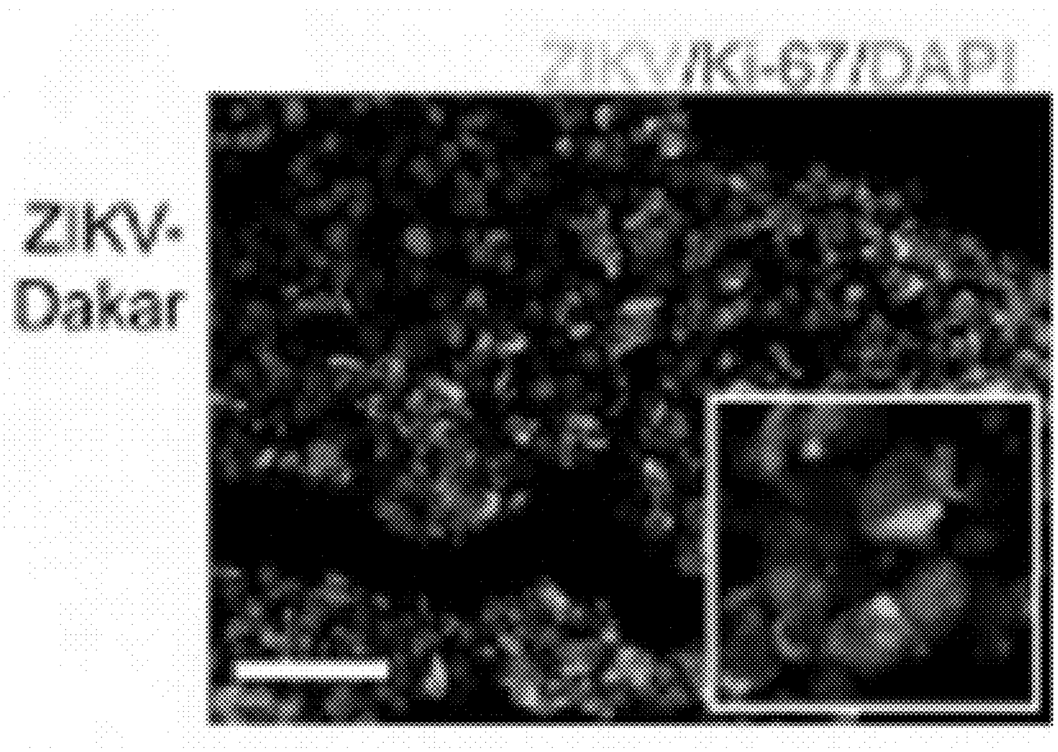
Figure 1L:
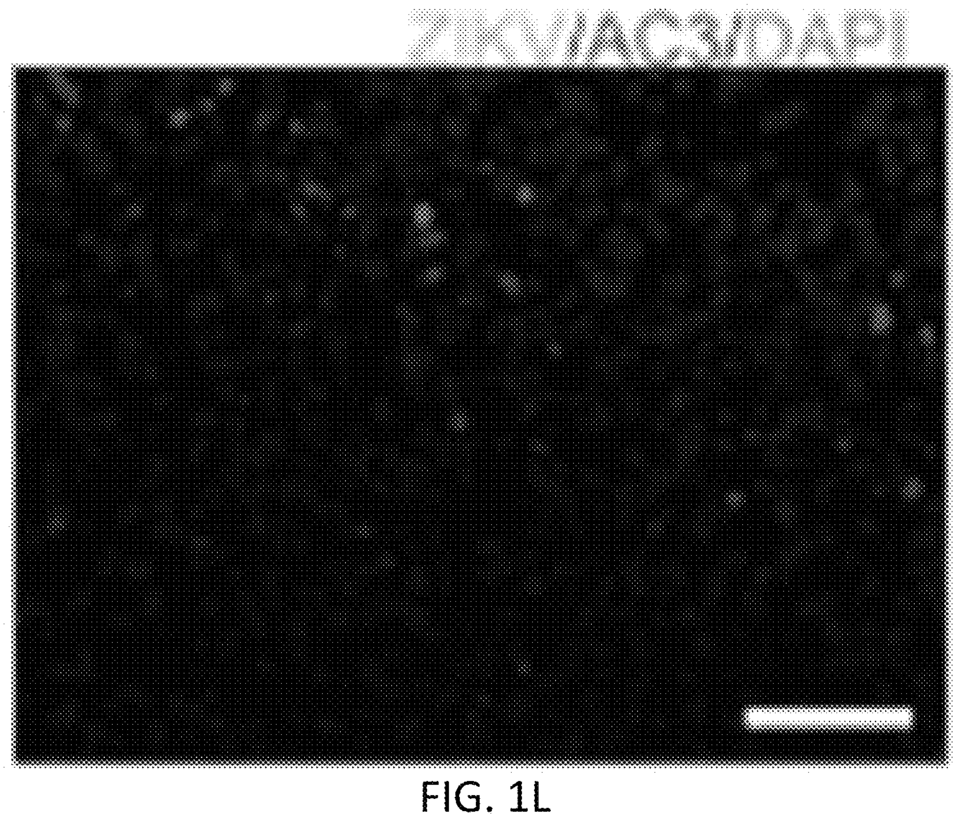
Figure 1M:
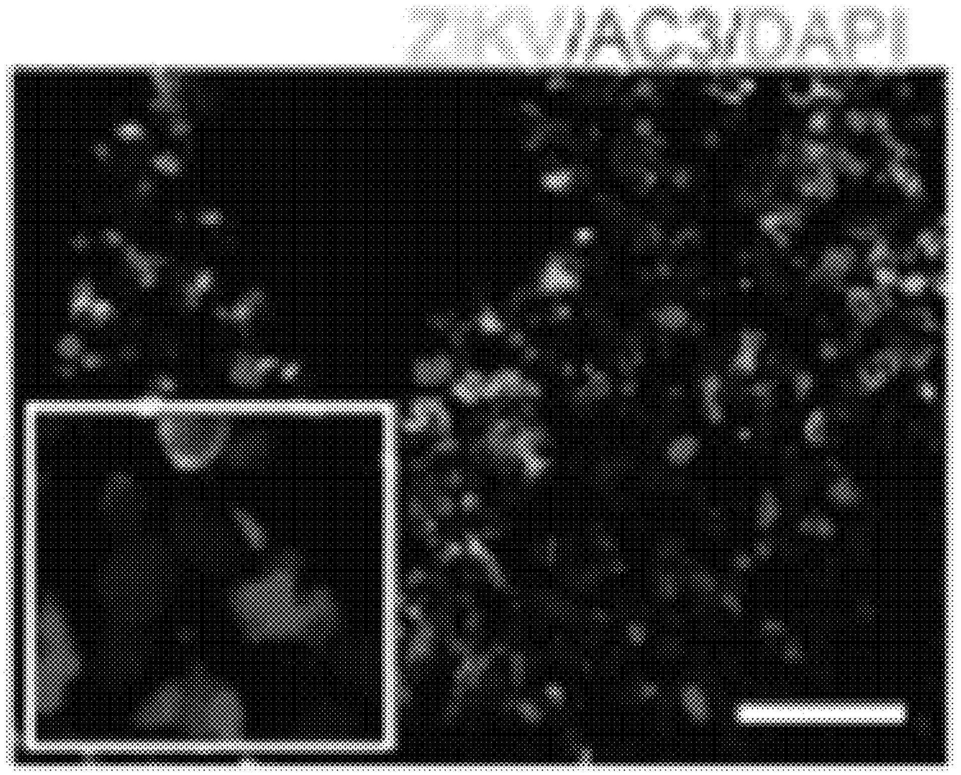
Figure 1N:
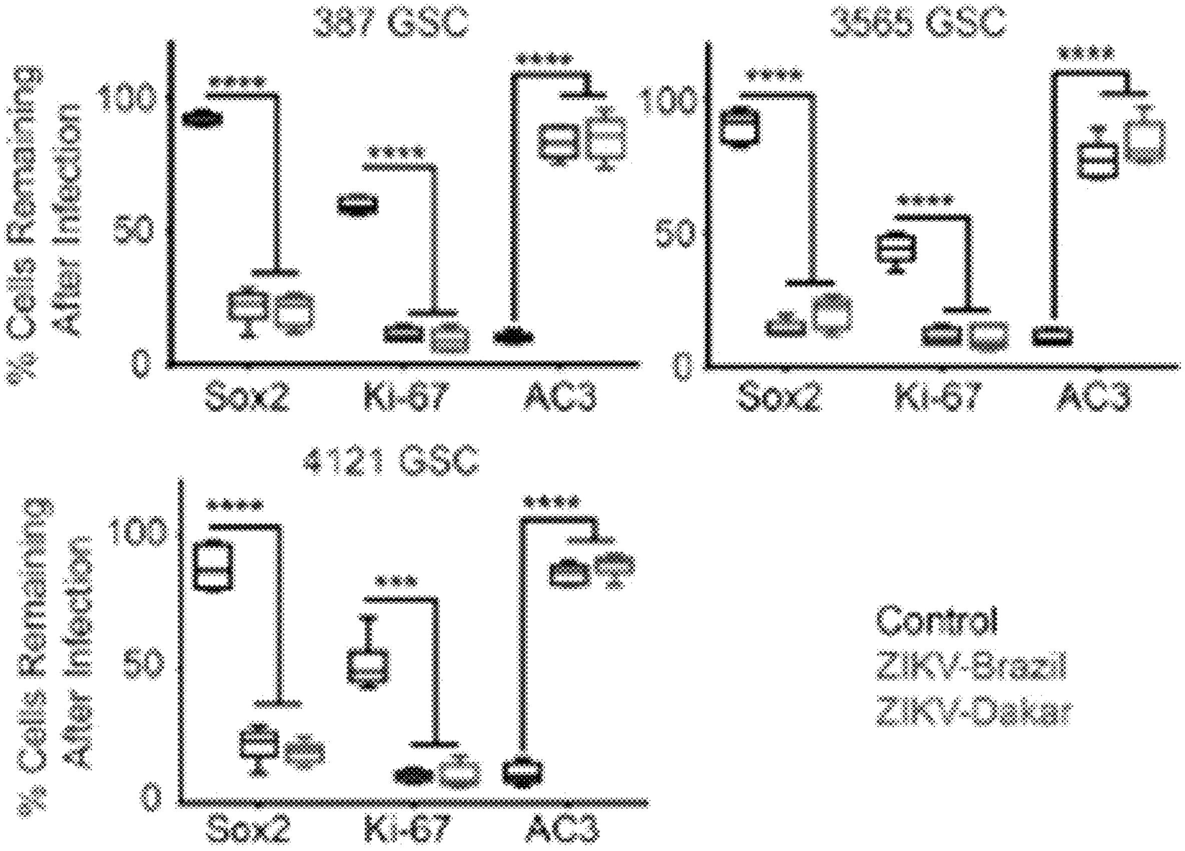
Figures 6C, 6D, 6E:
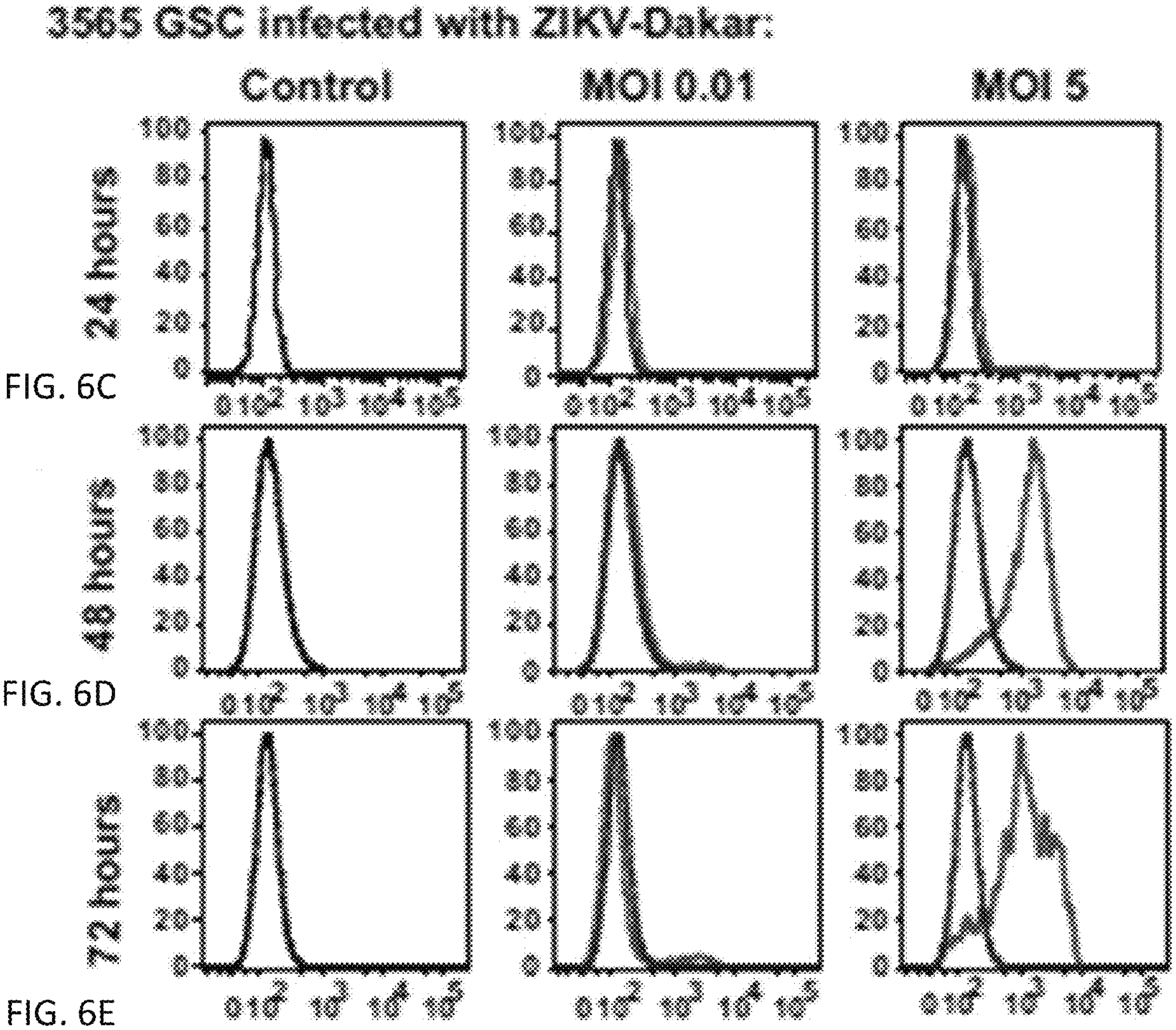

Example 2: Impact of Infection on the Proliferation of Matched GSCs and DGCs As ZIKV induces cell death in fetal neural precursors, the impact of infection on the proliferation of matched GSCs and DGCs was determined. Whereas GSC growth was nearly abolished by either ZIKV strain (FIG. 1B and FIG. 1K), DGCs were nearly unaffected (FIG. 1L, FIG. 6C-FIG. 6D). ZIKV infection resulted in reduced levels of a GSC marker (SOX2) (FIG. 1N) and diminished proliferation (measured by Ki-67) (FIG. 1H and FIG. 1N), but increased levels of an apoptotic marker (AC3) (FIG. 1J and FIG. 1N). Sphere formation in serum-free conditions has been used as a surrogate for self-renewal, albeit with caveats[22]. Consistent with its preferential targeting of GSCs, ZIKV also reduced GSC sphere formation (FIG. 1M).

Example 3: Comparing West Nile Disease Virus (WNV) to ZIKV

Figure 8A:
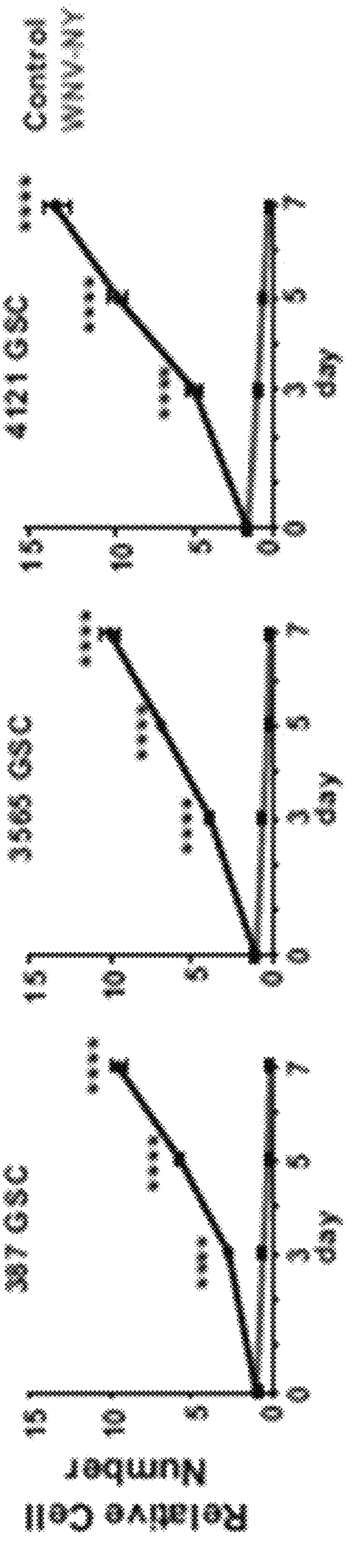
FIG. 8A, FIG. 8B, FIG. 8C, FIG. 8D, FIG. 8E, FIG. 8F, FIG. 8G, FIG. 8H, FIG. 8I, FIG. 8J, FIG. 8K, FIG. 8L and FIG. 8M show WNV infects and attenuates growth of GSCs, DGCs and normal neuronal cells (NNCs).
Figure 8B:
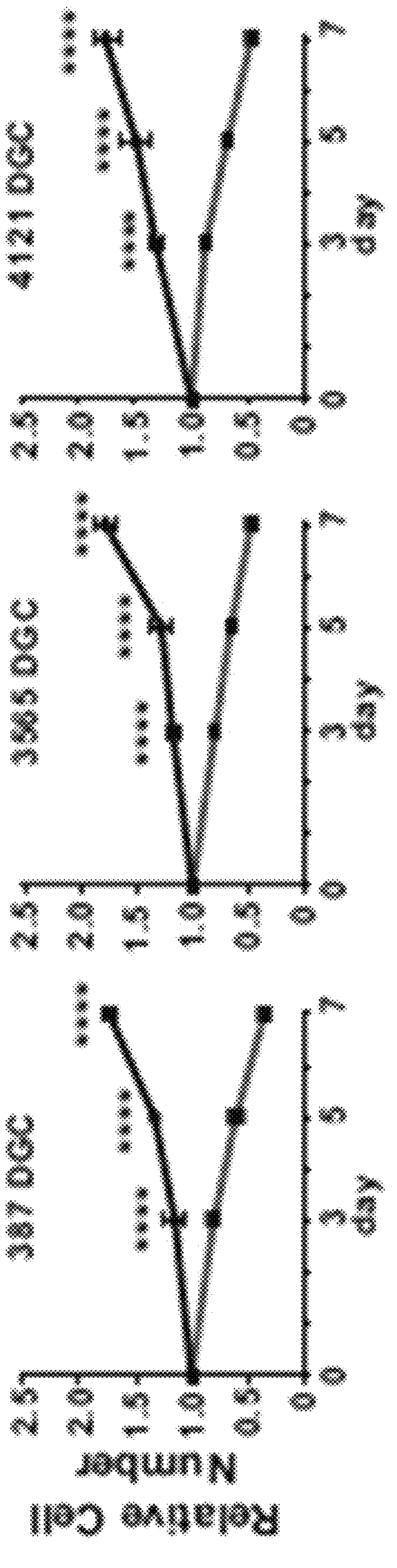
Figure 8C:
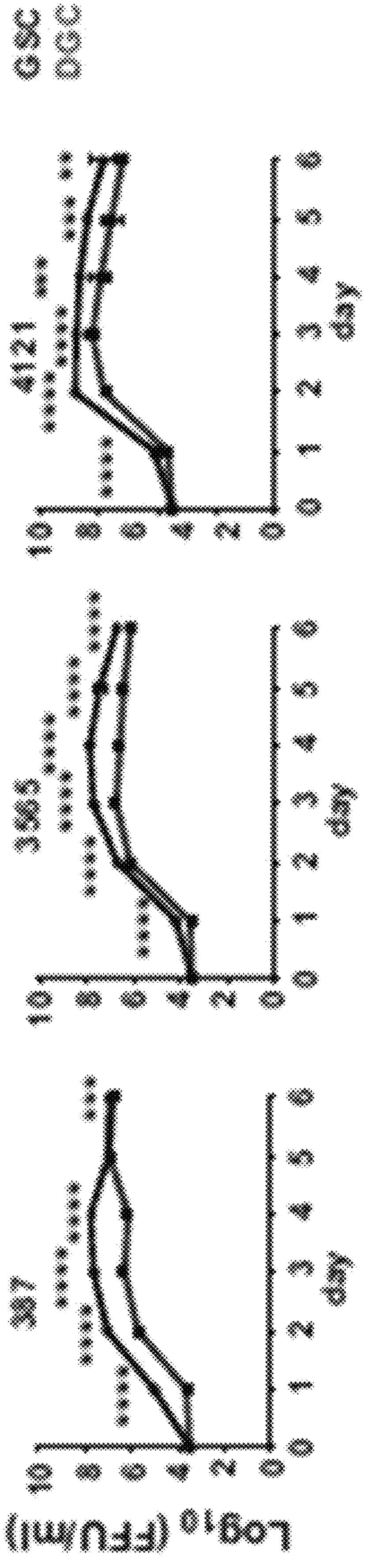
Figure 8D:
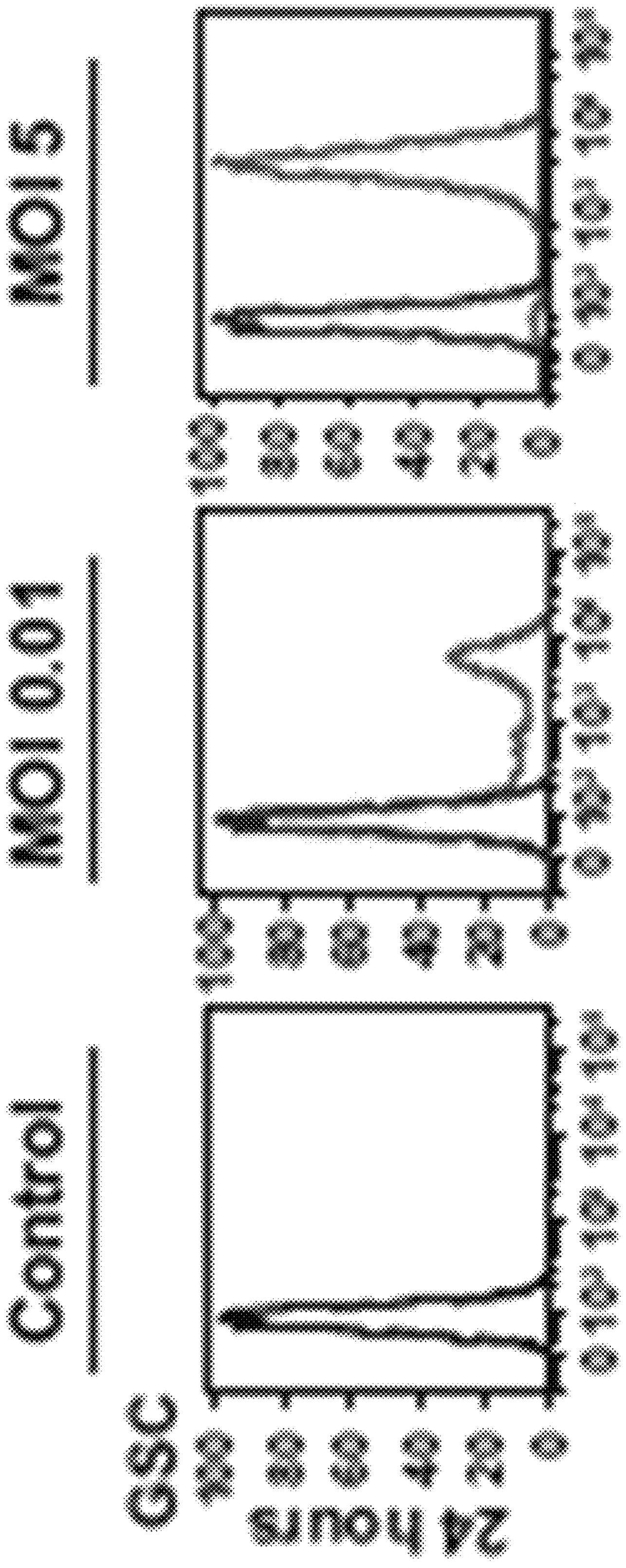
Figure 8E:
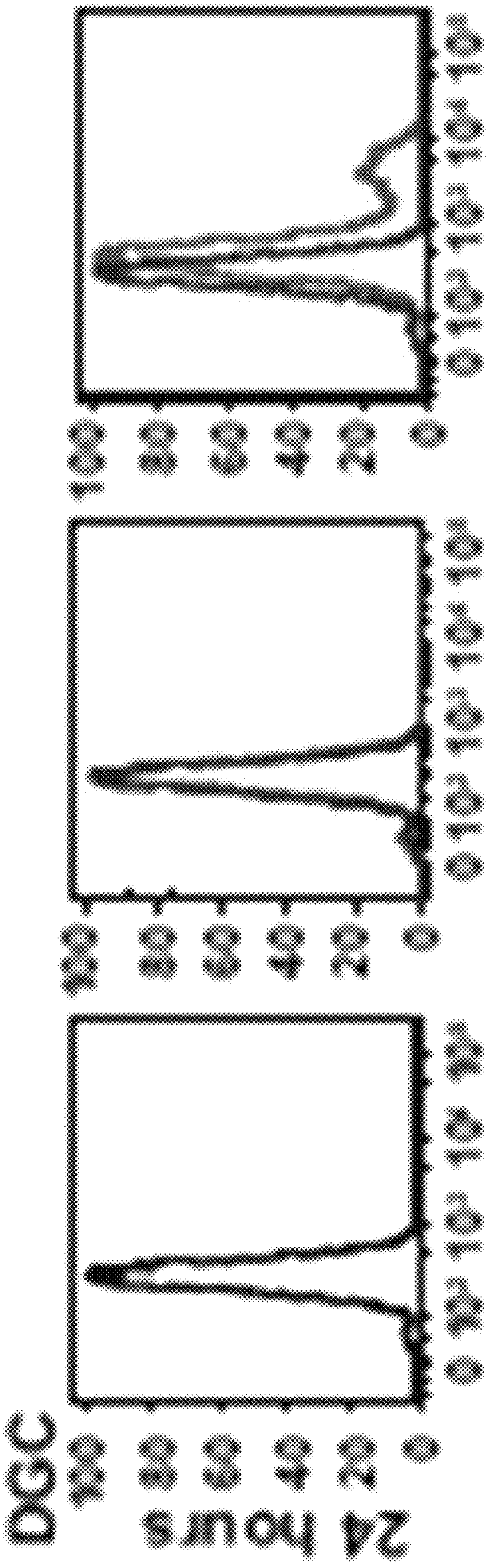
Figure 8F:
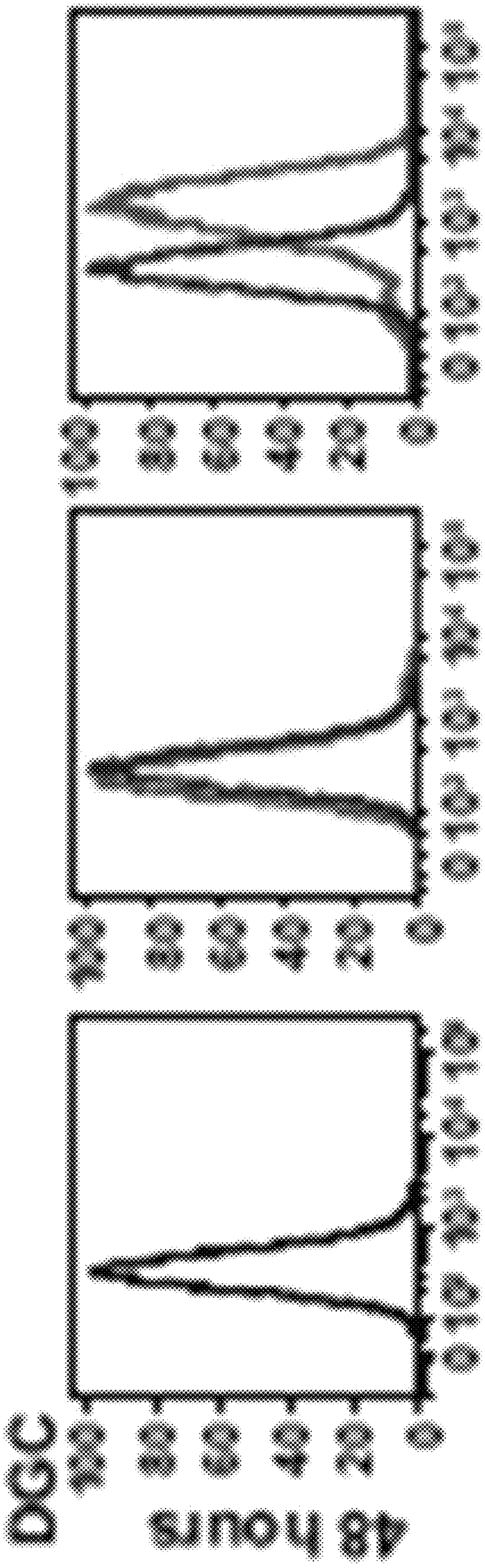
Figure 8G:
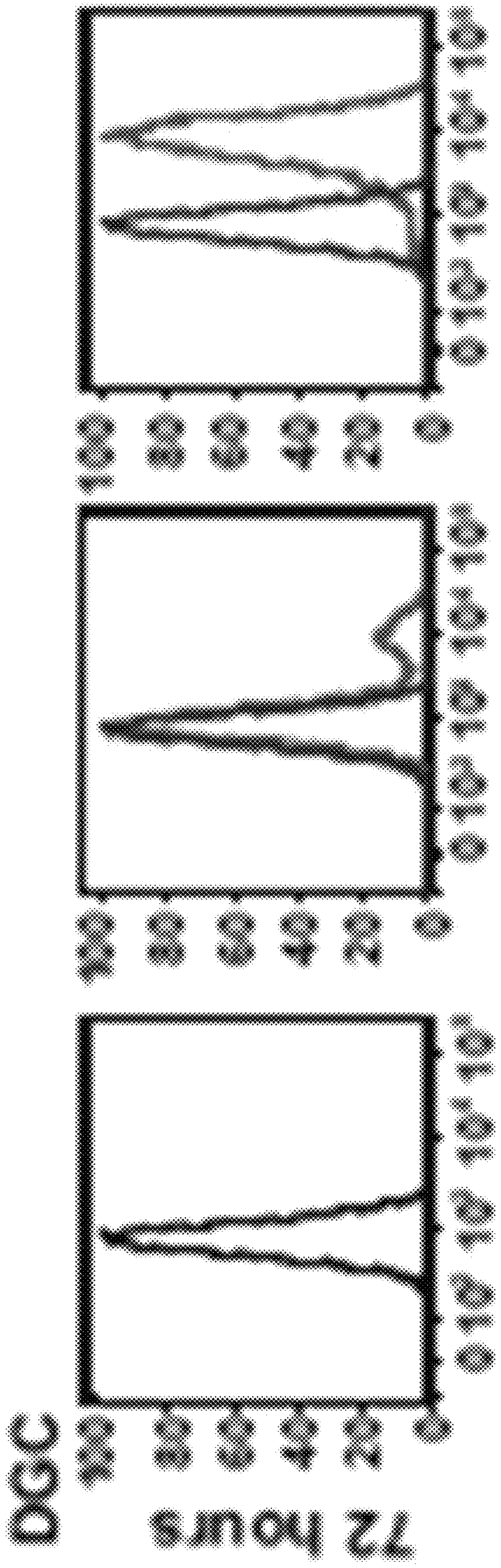
Figure 8H:
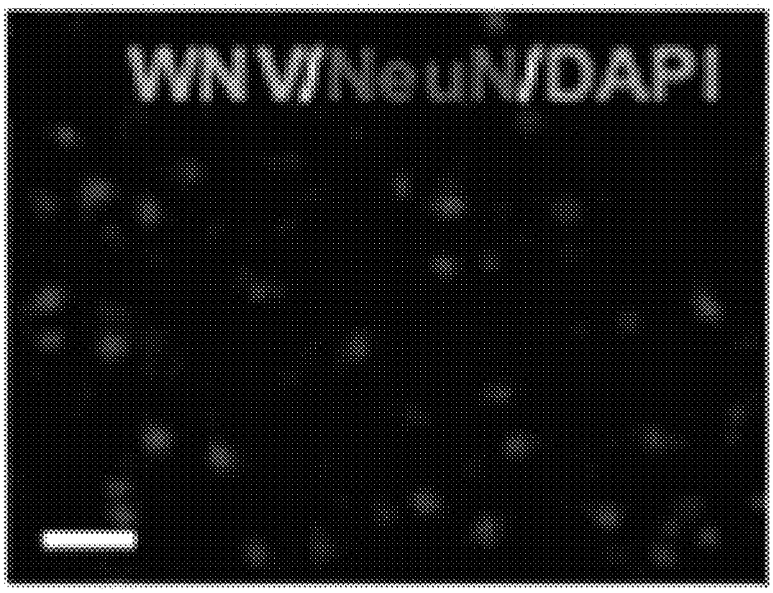
Figure 8I:
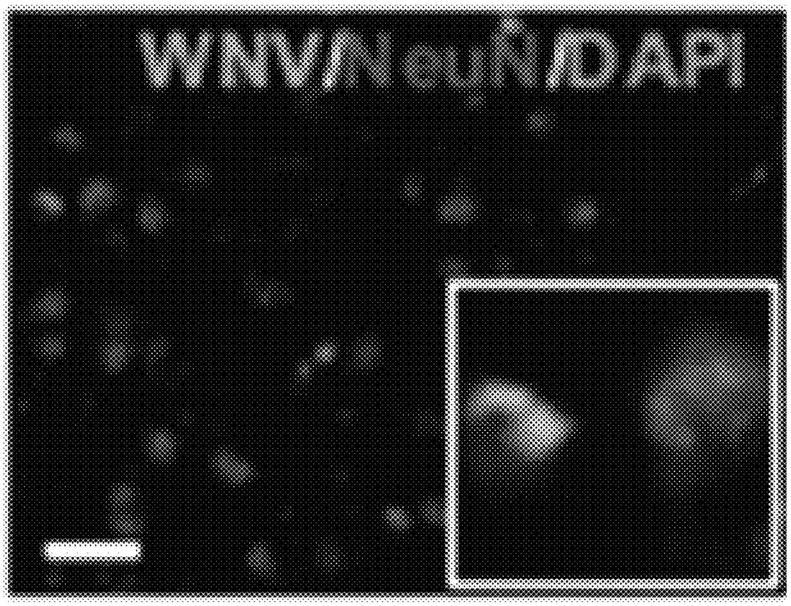
Figure 8J:
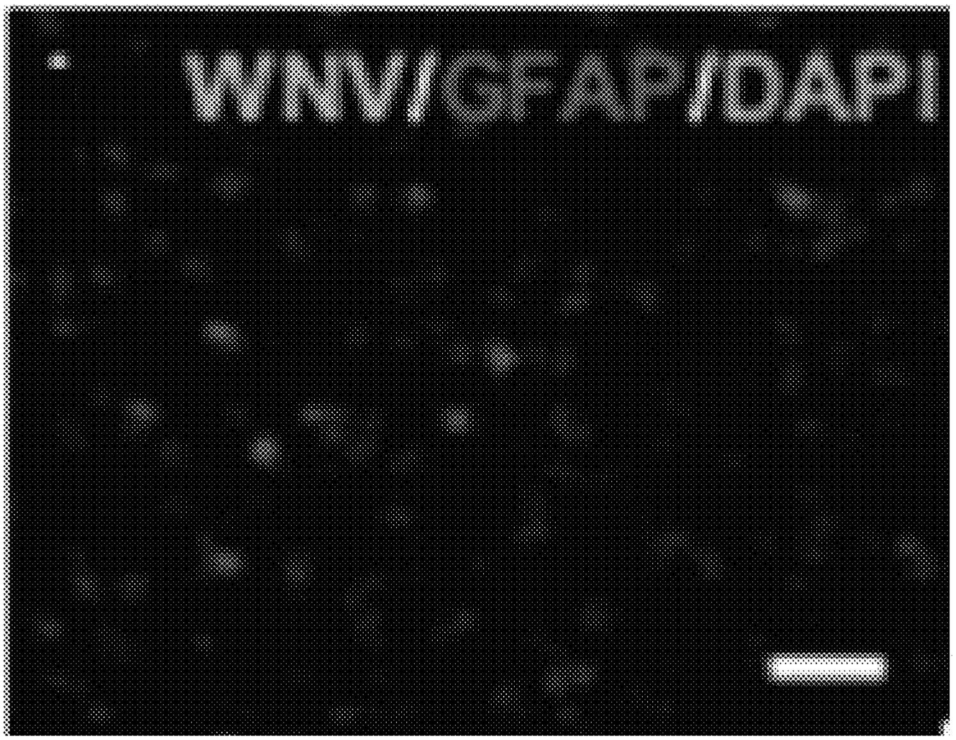
Figure 8K:
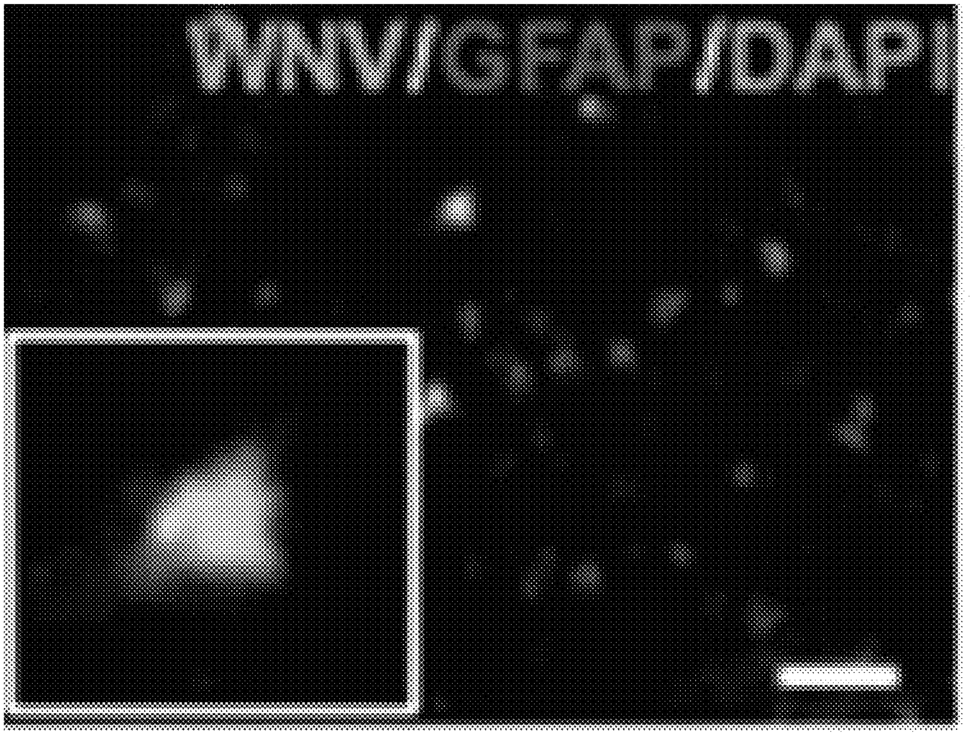
Figure 8L:
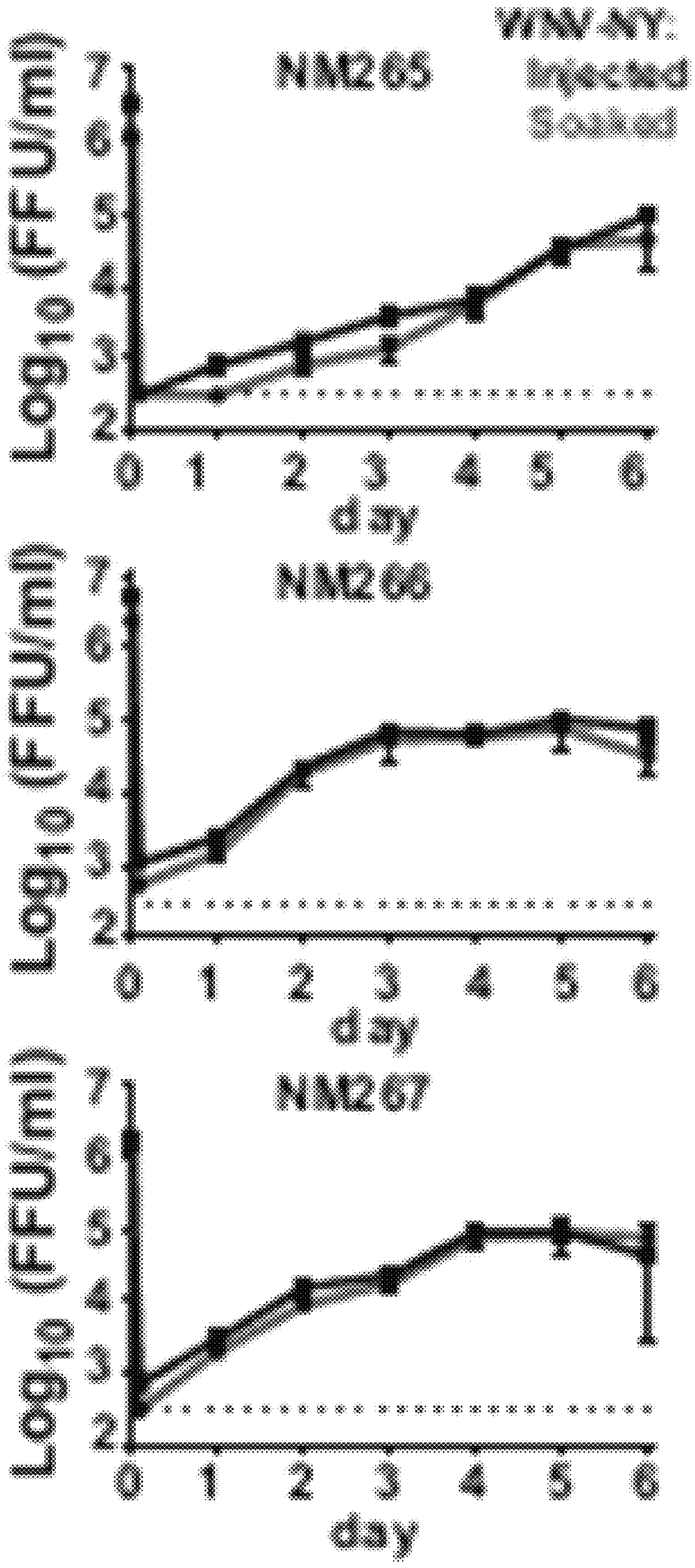
Figure 8M:
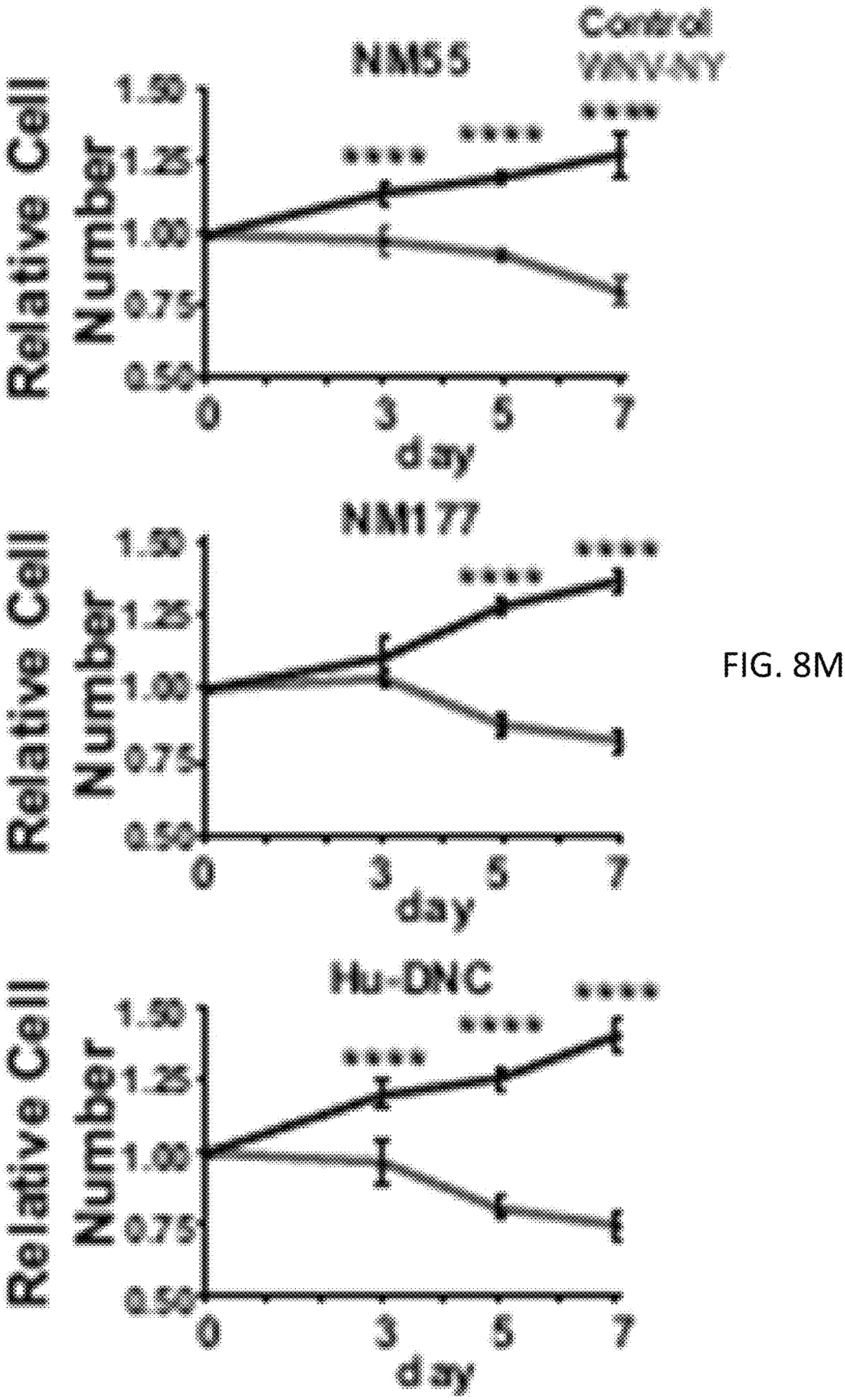

More than 60 years ago, WNV was tested for its oncolytic efficacy, but instead had substantial toxicity[23, 24]. The effects of WNV (New York, 1999) to ZIKV were compared in the models[25]. WNV infected both GSCs and DGCs to high levels (FIG. 8A-FIG. 8G), inducing cell death indiscriminately (FIG. 8A, FIG. 8B). WNV also infected normal human neural cells in culture and brain slices from freshly resected epilepsy tissues, and targeted both $NeuN^+$ neurons and $GFAP^+$ astrocytes (FIG. 8H-FIG. 8K, Brain slices). WNV infection of normal neural cells induced significant cell death (FIG. 8M). Thus, the GSC specificity of ZIKV is not a general property of related neurotropic flaviviruses[16, 17].

Example 4: Testing ZIKV GSC Specificity Using an In Vitro Organoid Model

Figure 2A:
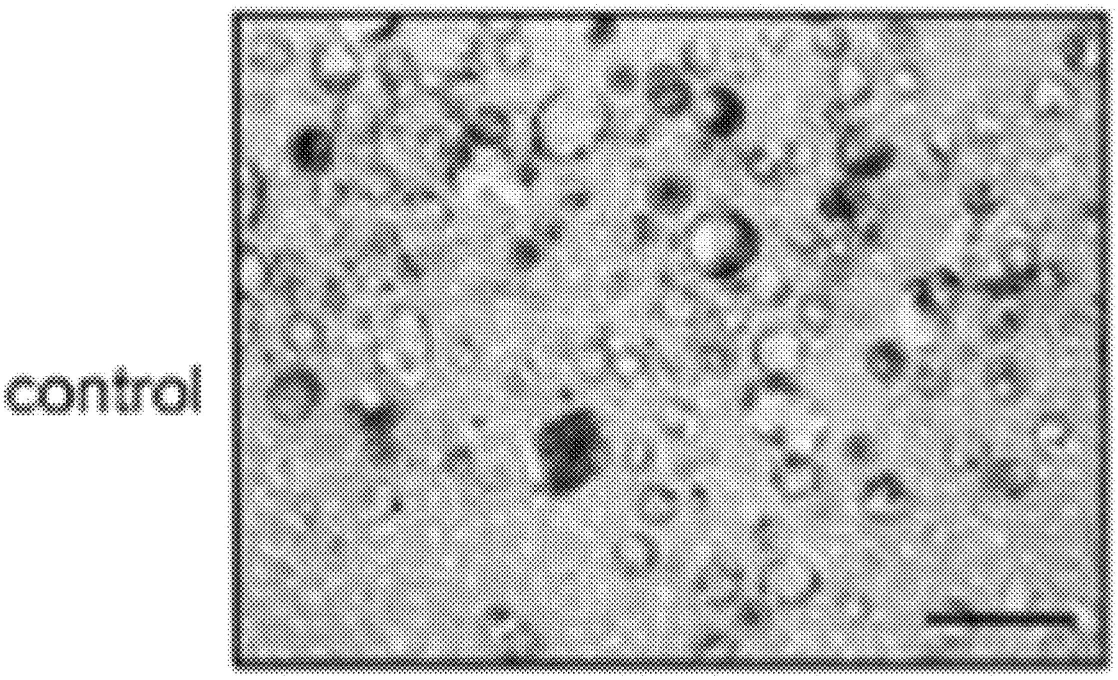
FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, FIG. 2M, FIG. 2N, FIG. 2O and FIG. 2P depict ZIKV infection causes loss of self-renewal and proliferation of human glioblastoma-derived organoids.
Figure 2B:
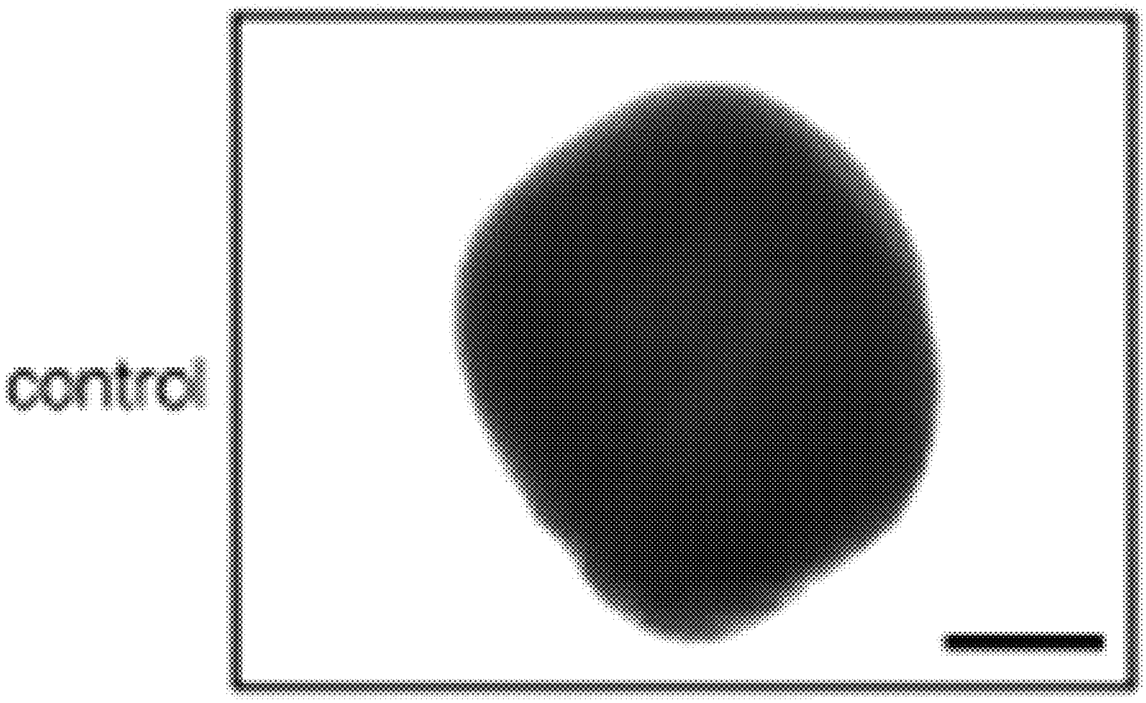
Figure 2C:
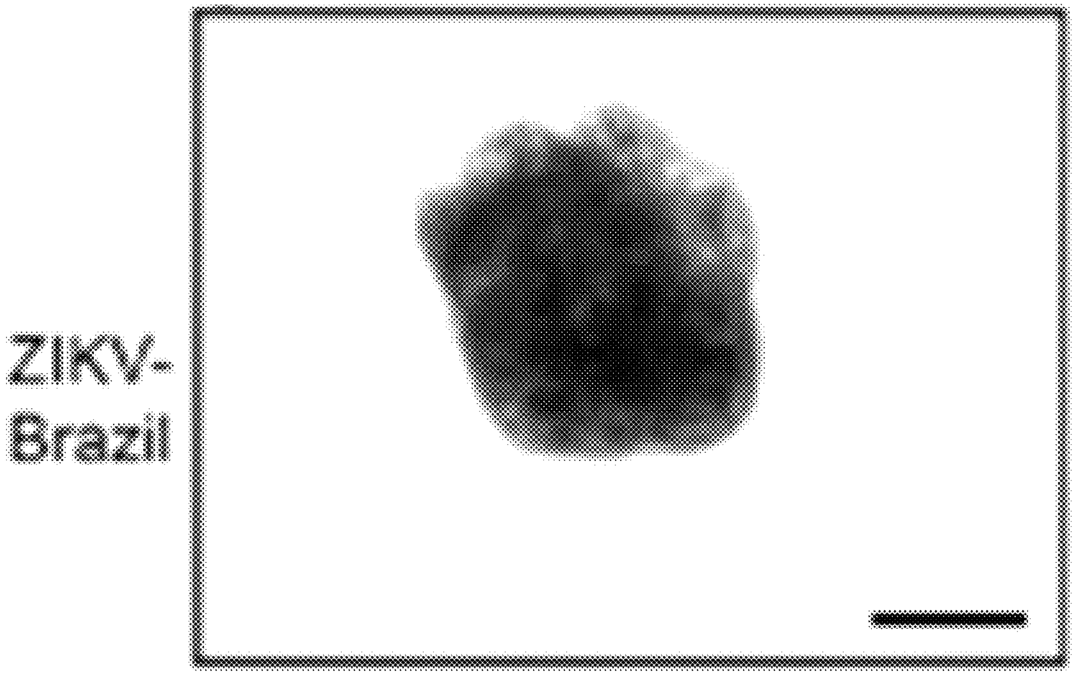
Figure 2D:
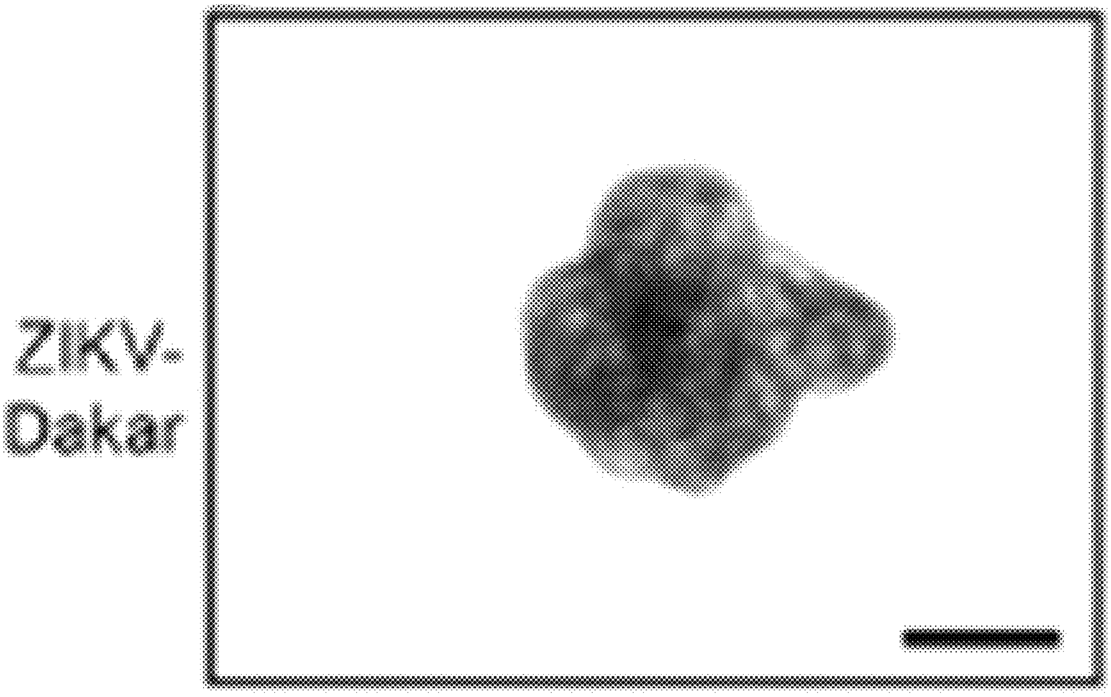
Figure 2E:
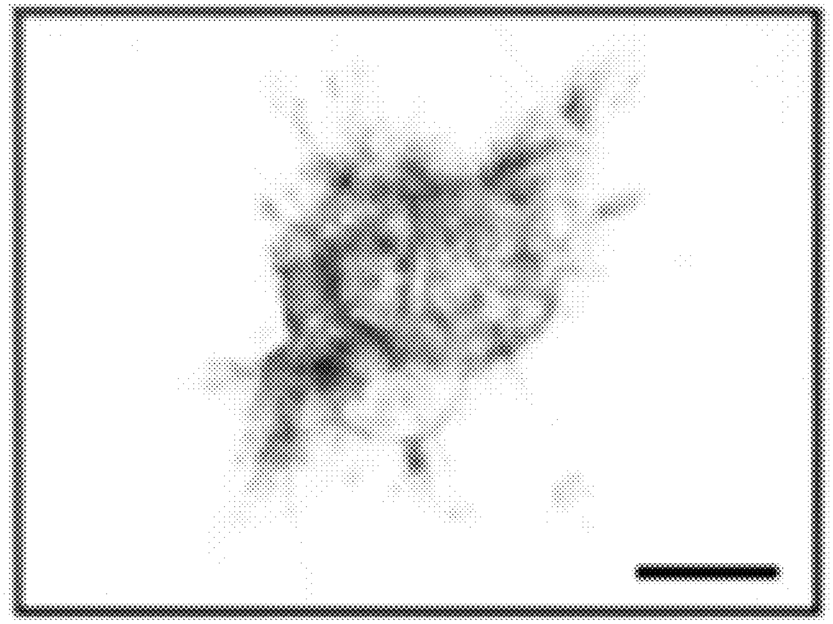
Figure 2F:
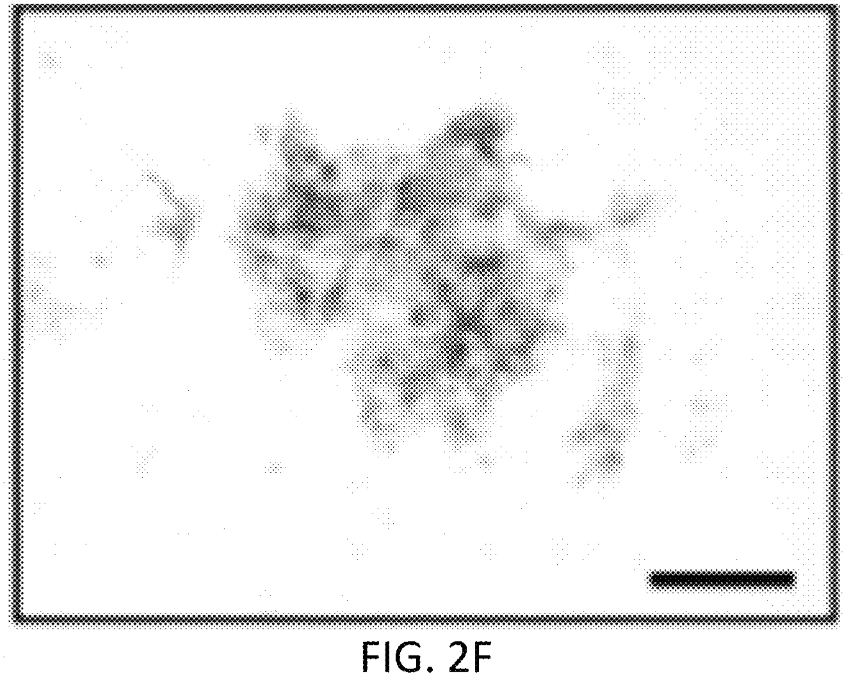
Figure 2G:
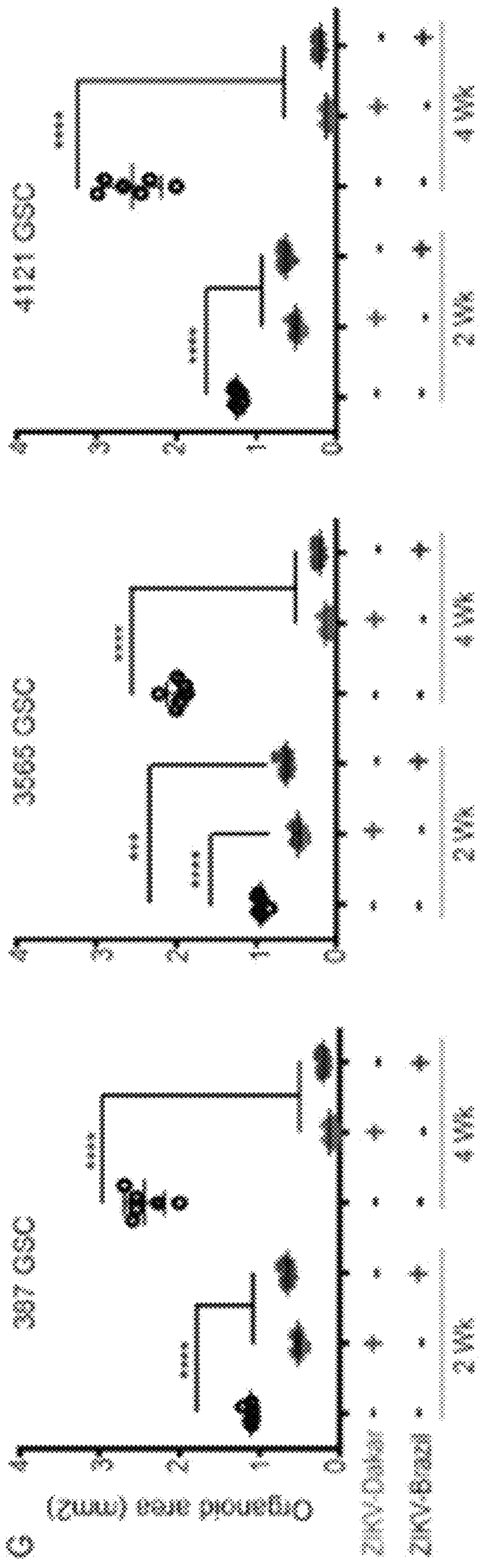
Figure 2H:
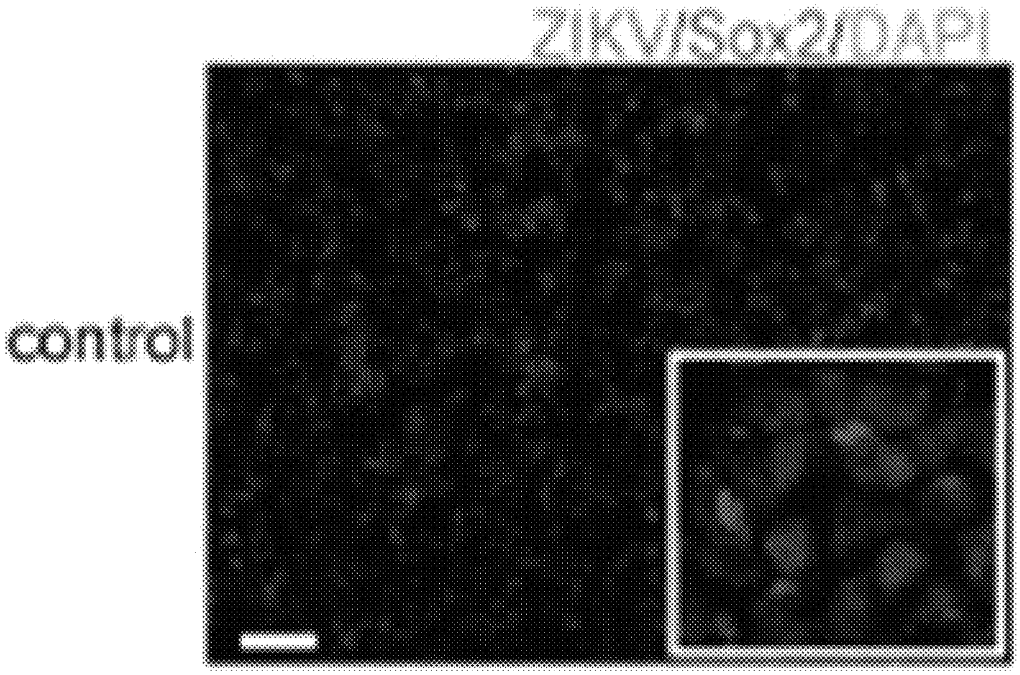
Figure 2I:
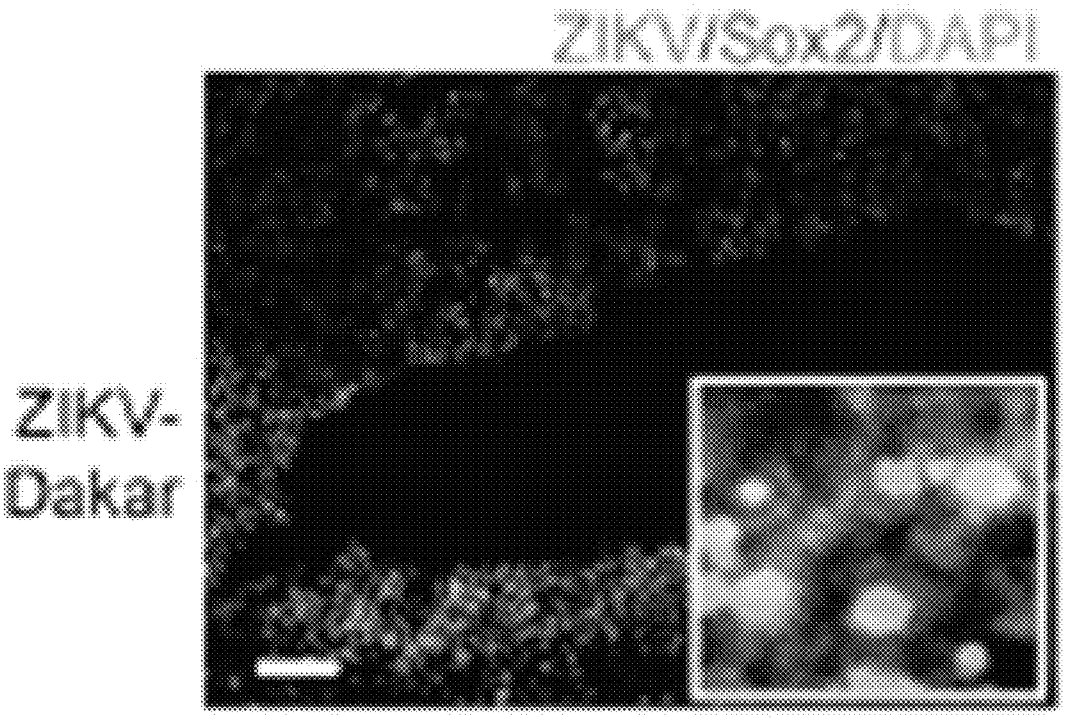
Figure 2J:
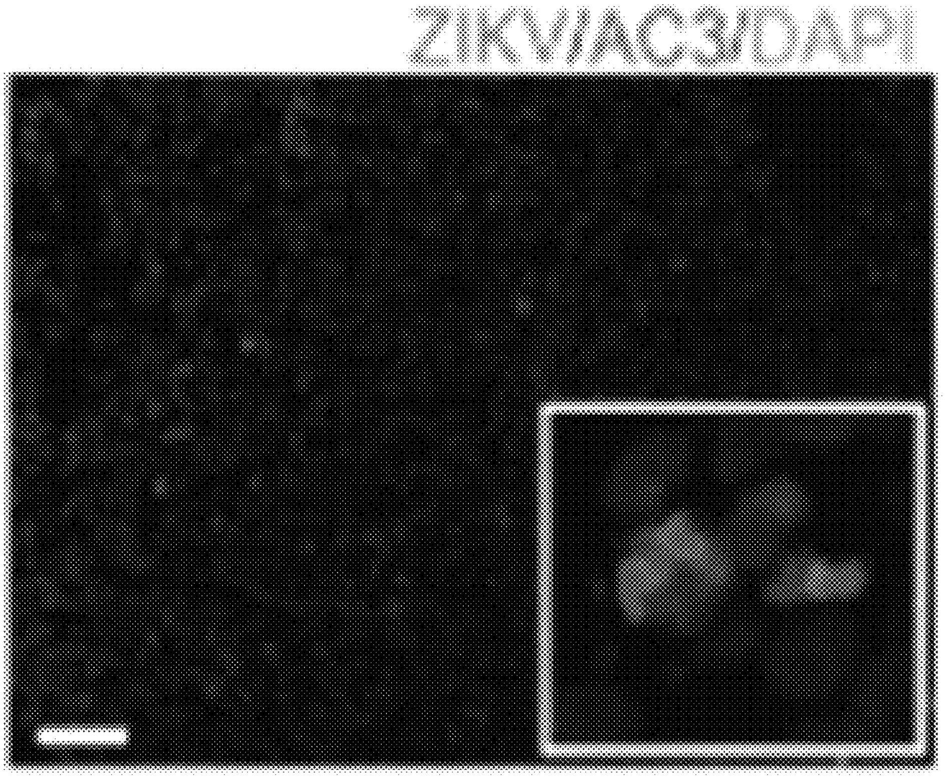
Figure 2K:
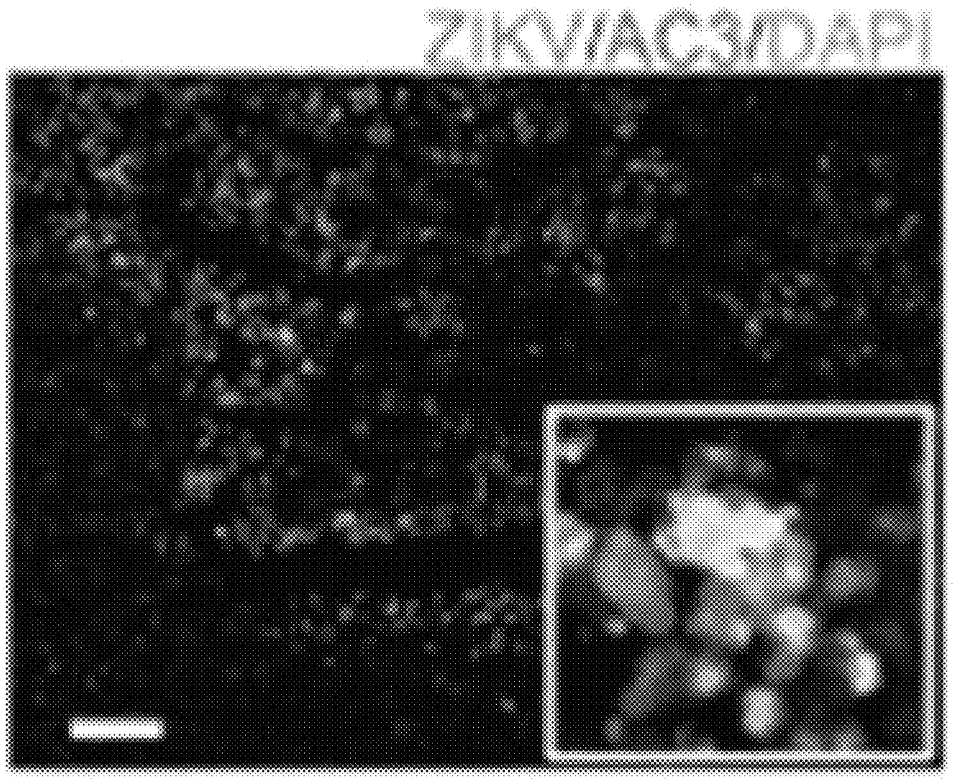
Figure 2L:
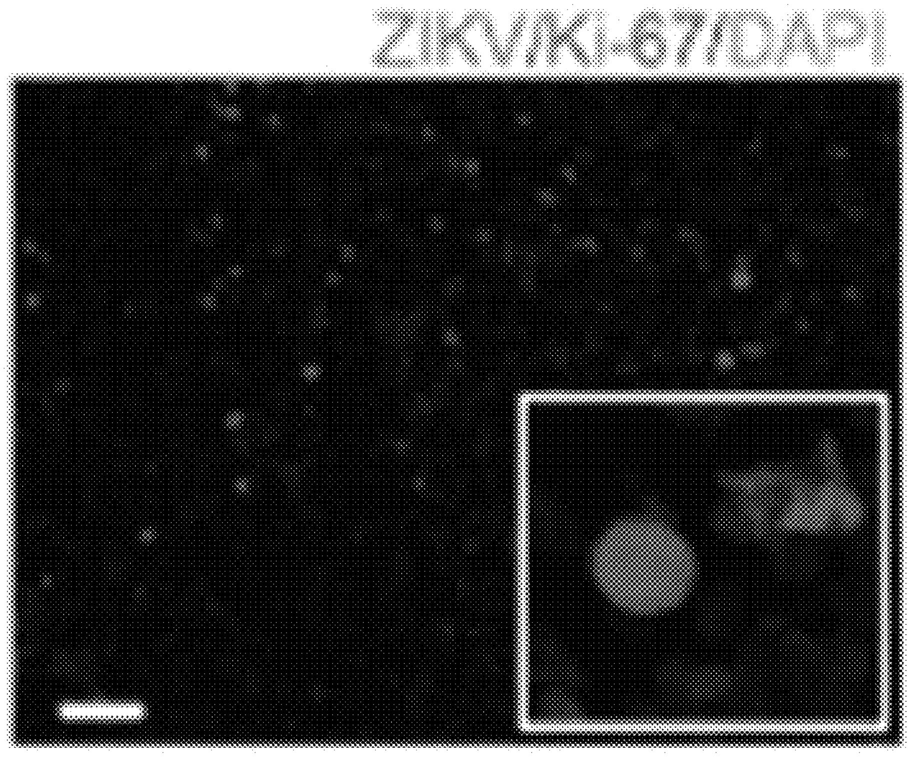
Figure 2M:
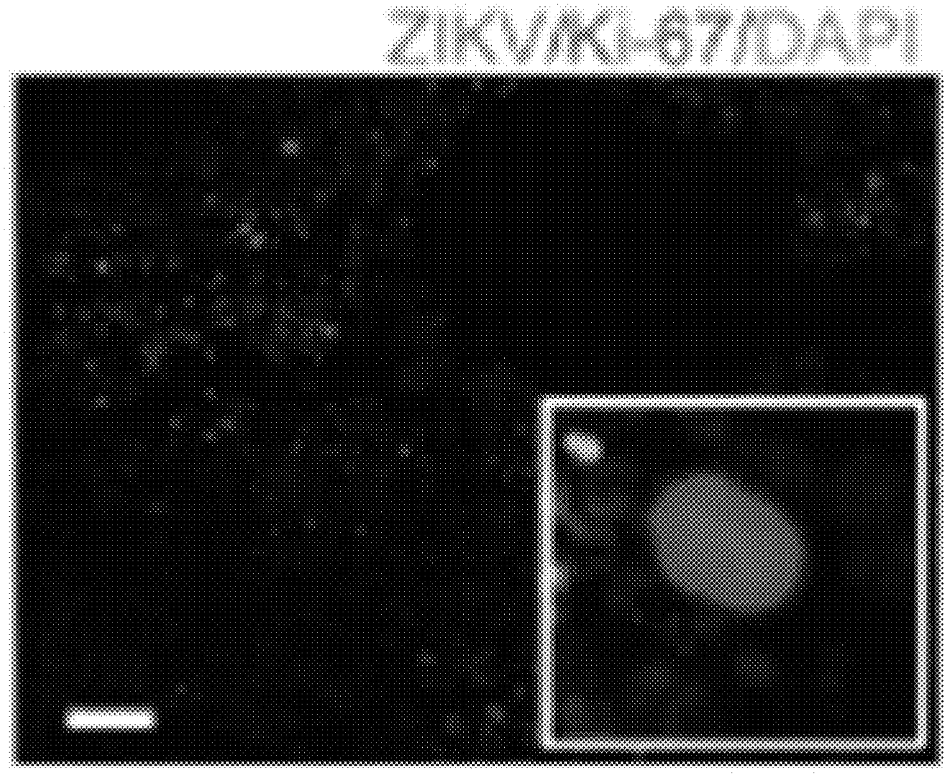
Figure 2N:
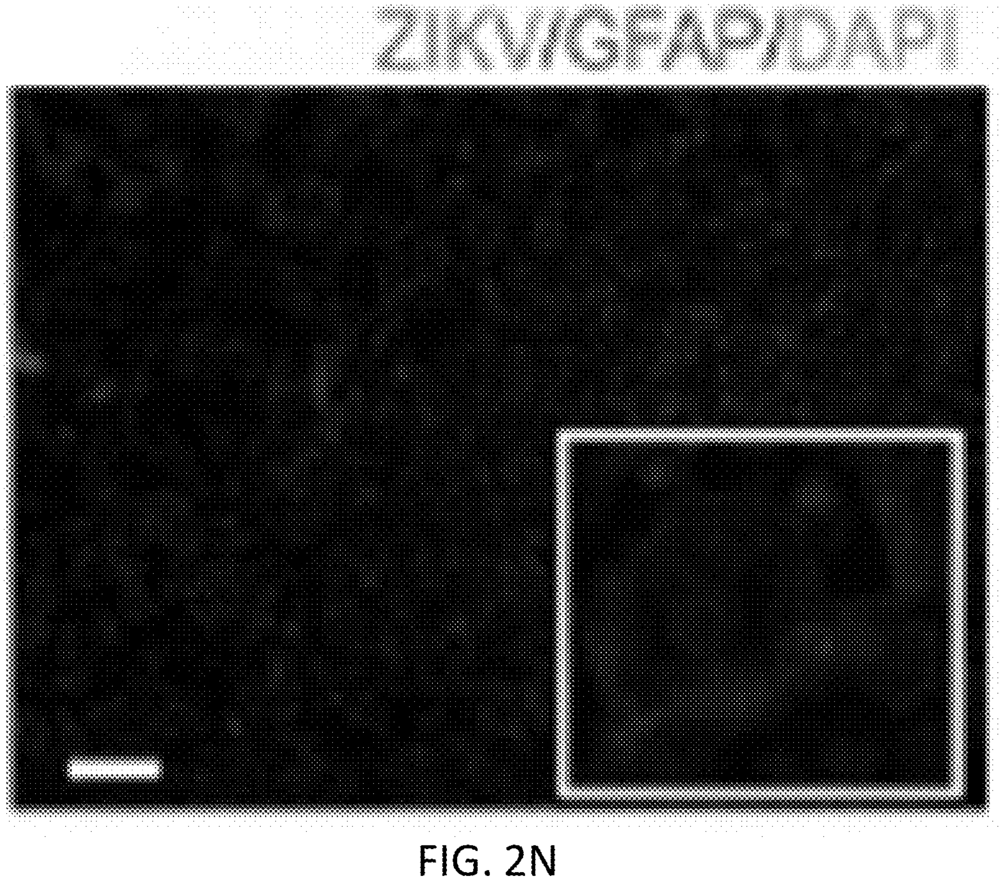
Figure 2O:
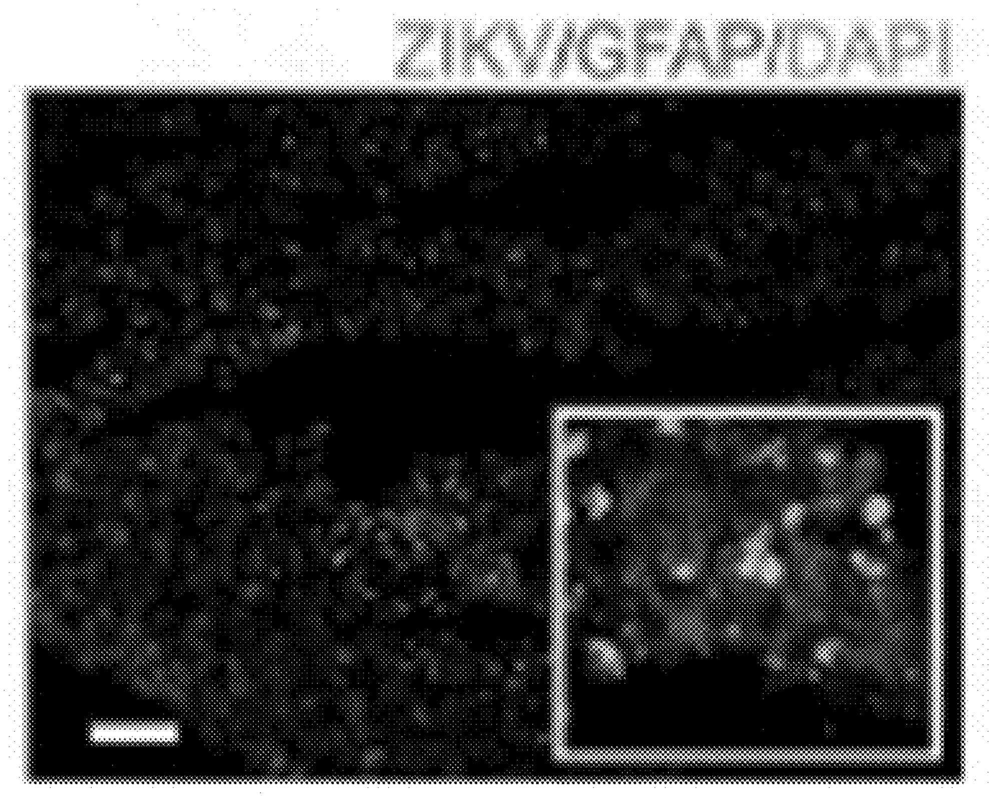
Figure 2P:
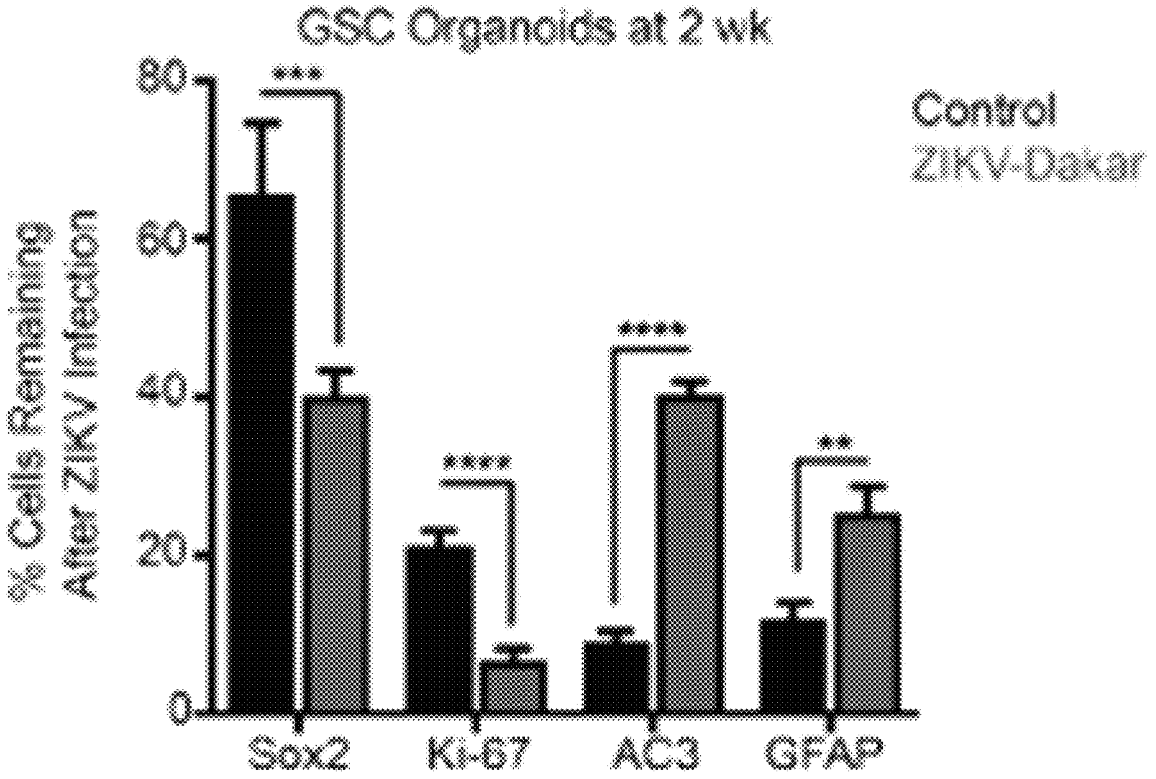

To test ZIKV GSC specificity in the context of the cellular heterogeneity that exists in patients, an in vitro organoid model was used. Cerebral organoids recapitulate normal brain structures, permitting interrogation of human brain responses to perturbation[13]. The creation of brain GBM organoids was recently reported[26]. To determine the potential utility of ZIKV in human GBM organoids, three GSC models (T387, T3565, and T4121) were coated in Matrigel, forming small organoids by 3 days (FIG. 2A), which grew into mature organoids within 3 weeks (FIG. 26)[13, 26]. The three GSCs were infected at the mature organoid stage with ZIKV-Brazil or ZIKV-Dakar. Infection with ZIKV slowed organoid growth at 2 (FIG. 2C, FIG. 2D) and 4 weeks (FIG. 2E, FIG. 2F) as assessed by measuring organoid area (FIG. 2G). The tumour cell populations infected by ZIKV in the GBM organoids were examined next. ZIKV infected tumour cells in organoids with high efficiency within 2 weeks (FIG. 2I, FIG. 2K, FIG. 2M, and FIG. 2O), with preference for cells expressing the GSC marker, SOX2 (FIG. 2I). Co-localization of ZIKV-infected cells and the apoptotic marker, AC3, confirmed that ZIKV induced tumour cell death (FIG. 2M and FIG. 2P). In GBM organoids, ZIKV did not infect proliferating tumour cells, as marked by Ki67, efficiently (FIG. 2K), or differentiated tumour cells (FIG. 2O). ZIKV infection significantly reduced undifferentiated GSCs in GBM organoids, as shown by changes in SOX2 (FIG. 2H, FIG. 2I, and FIG. 2P) and Ki67 (FIG. 2J, FIG. 2K and FIG. 2P) staining, and increased apoptosis (marked by AC3, FIG. 2L, FIG. 2M, and FIG. 2P) staining, which resulted in a relative increase in DGCs (marked by GFAP, FIG. 2N-FIG. 2P) compared to the uninfected control. Collectively, these results demonstrate that ZIKV targets undifferentiated, quiescent GBM GSCs, which represent the most malignant tumour cells, for infection, differentiation, and apoptosis[27].

Example 5: Testing ZIKV GSC Specificity in Patient-Derived GBM Tumors

Figure 3A:
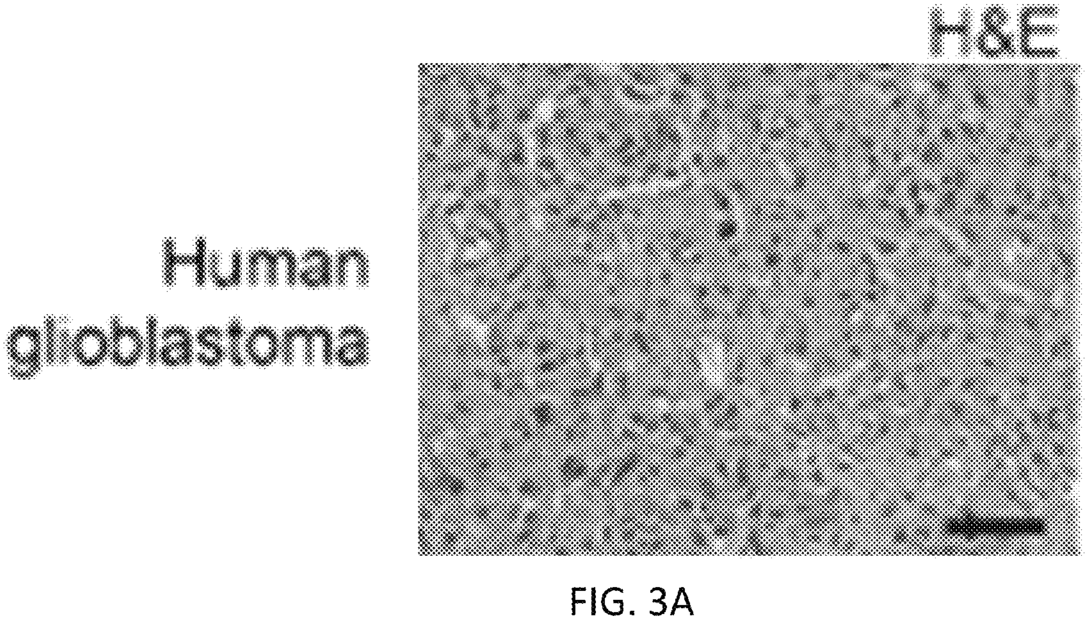
Figure 3B:
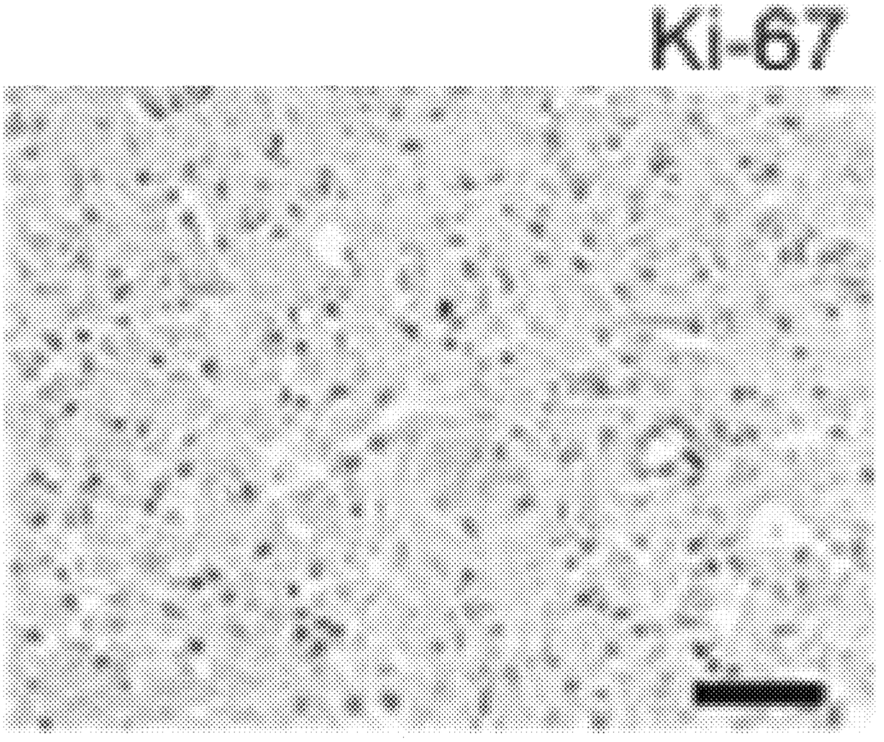
Figure 3C:
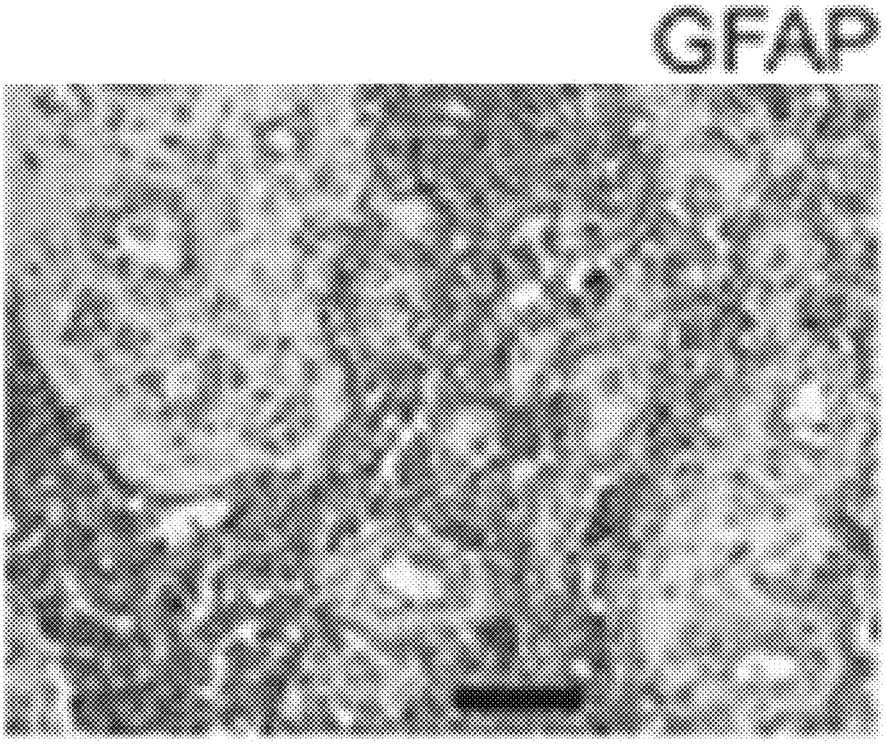
Figure 3D:
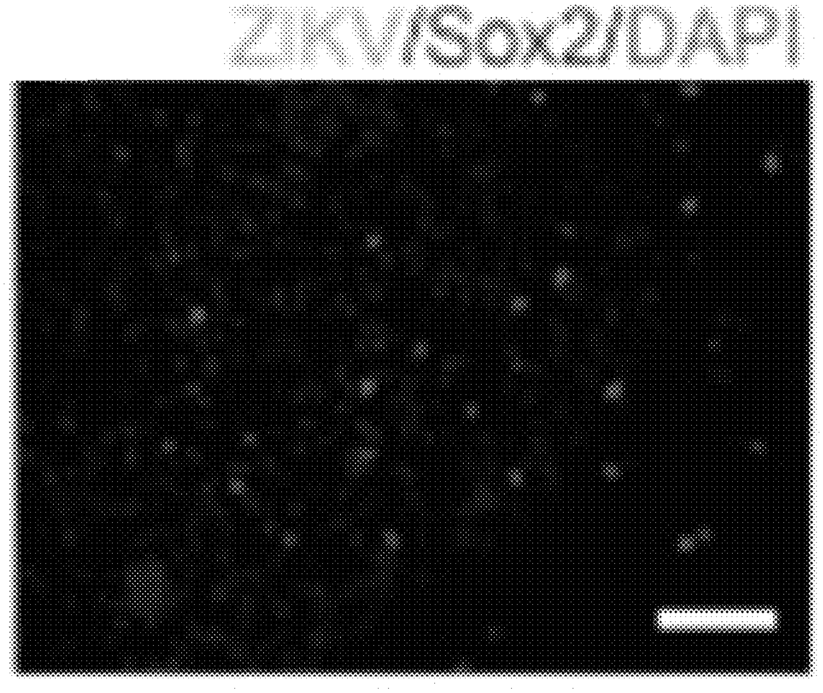
Figure 3E:
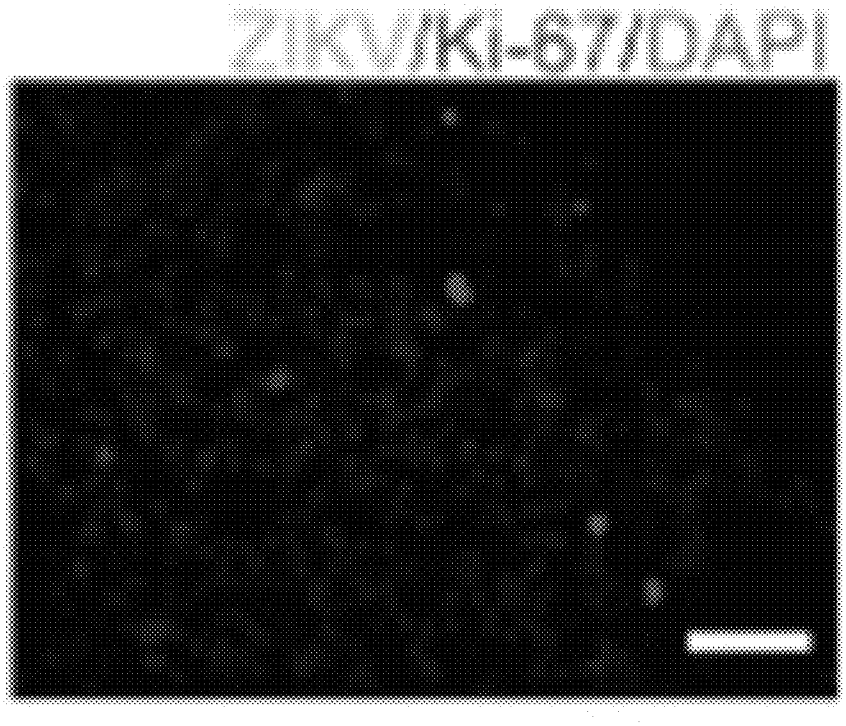
Figure 3F:
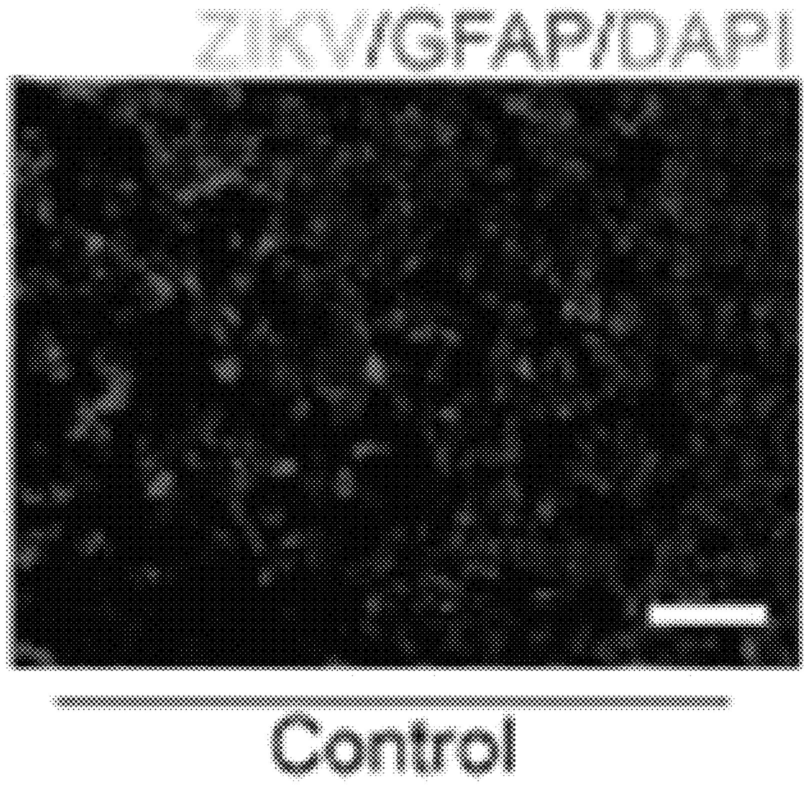
Figure 3G:
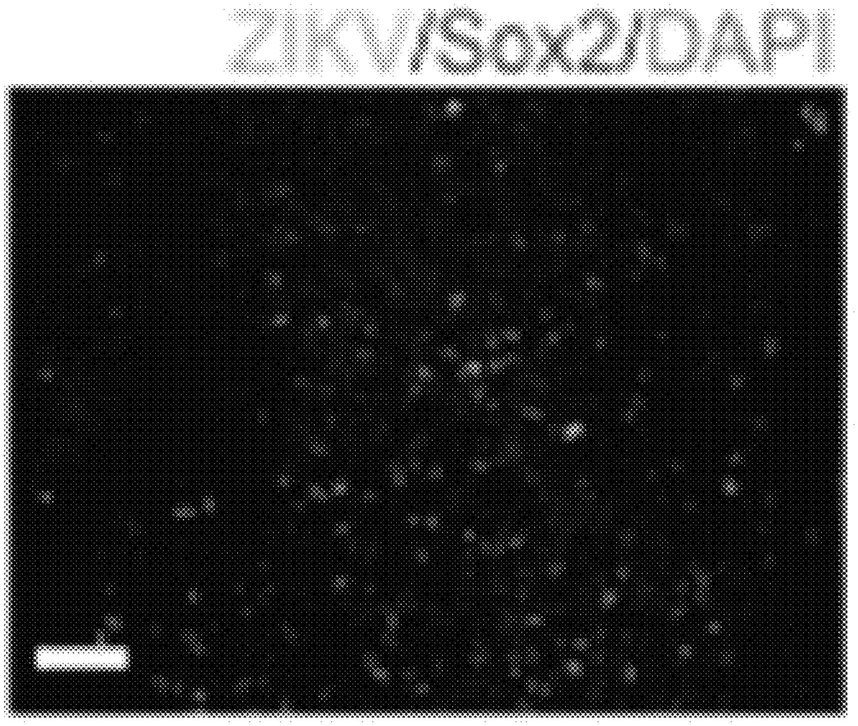
Figure 3H:
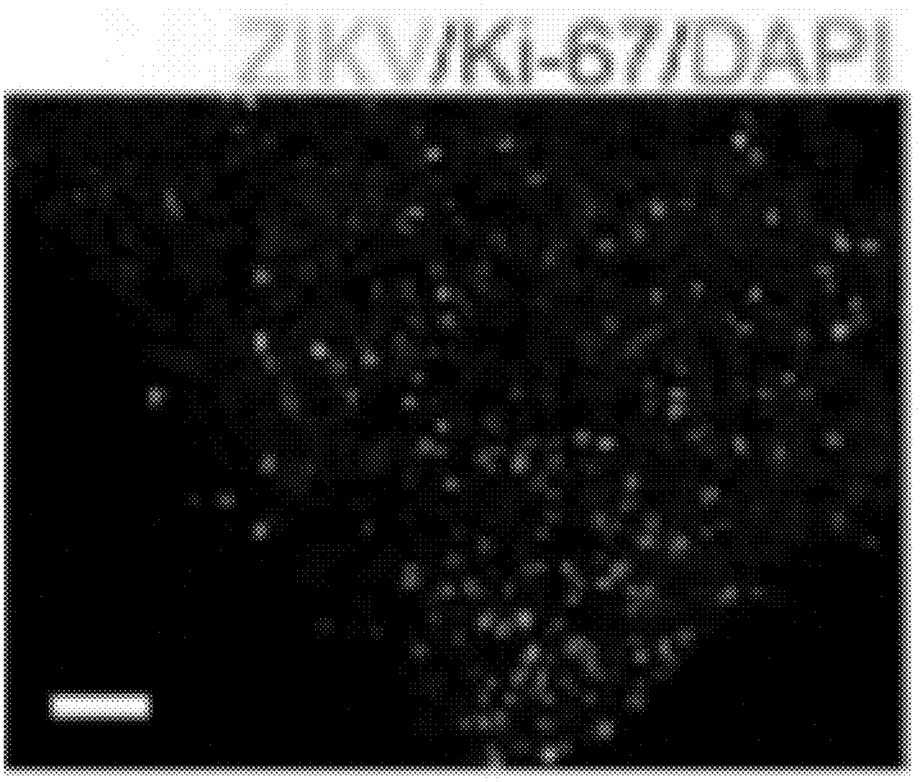
Figure 3I:
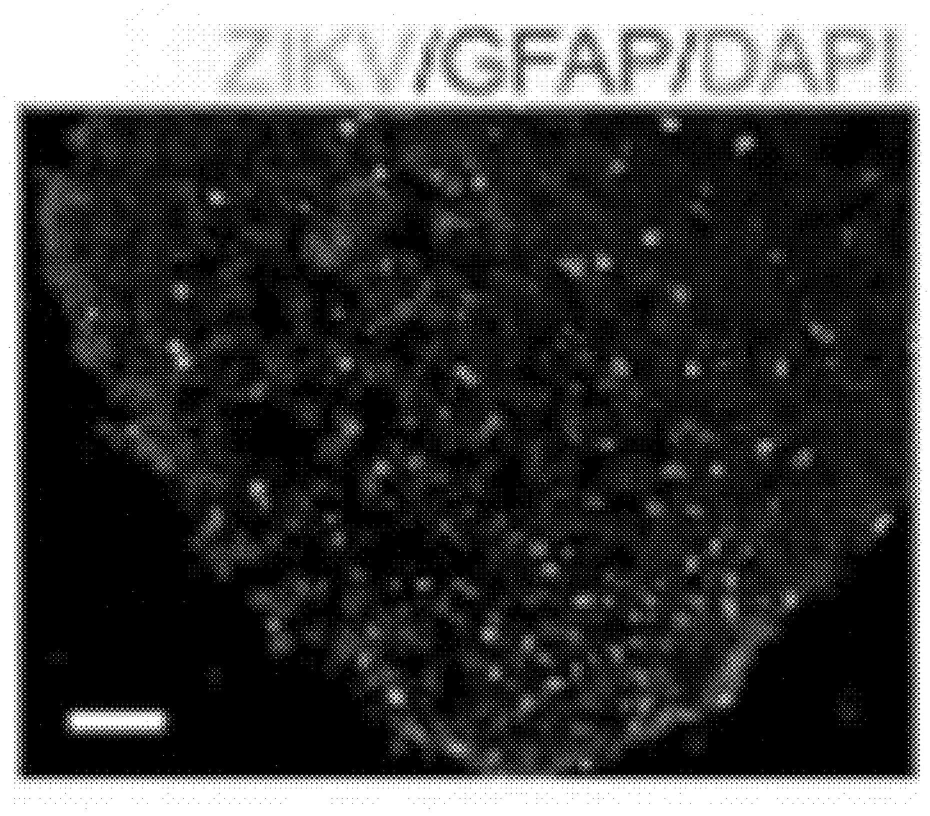
Figure 3J:
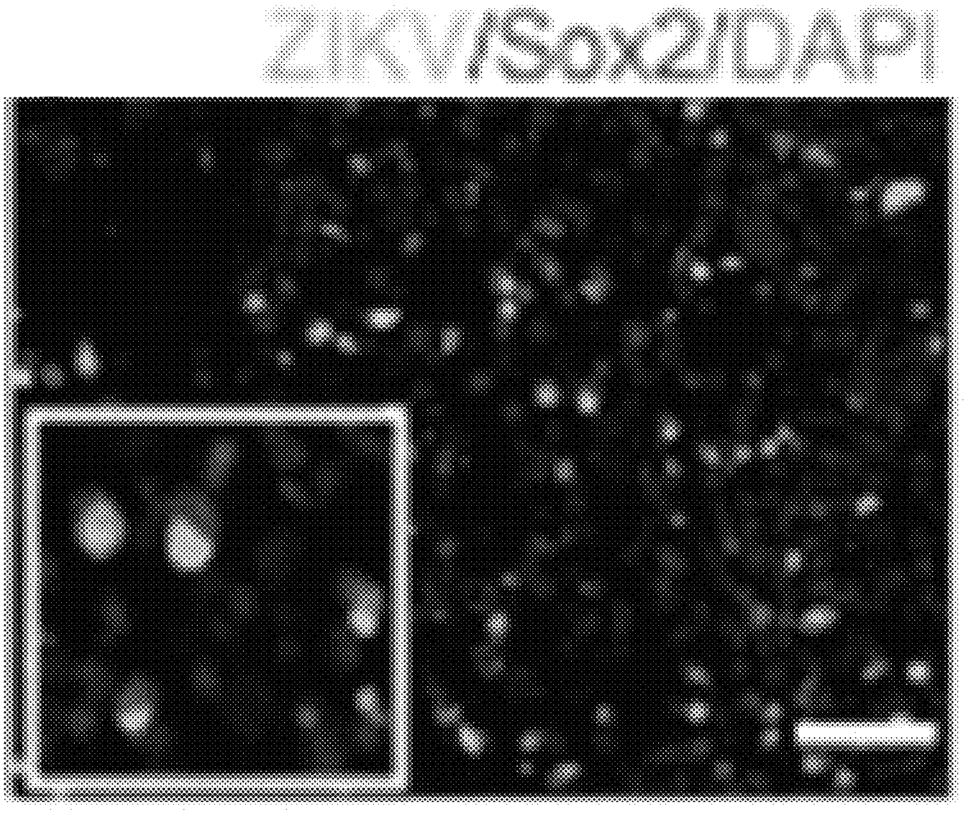
Figure 3K:
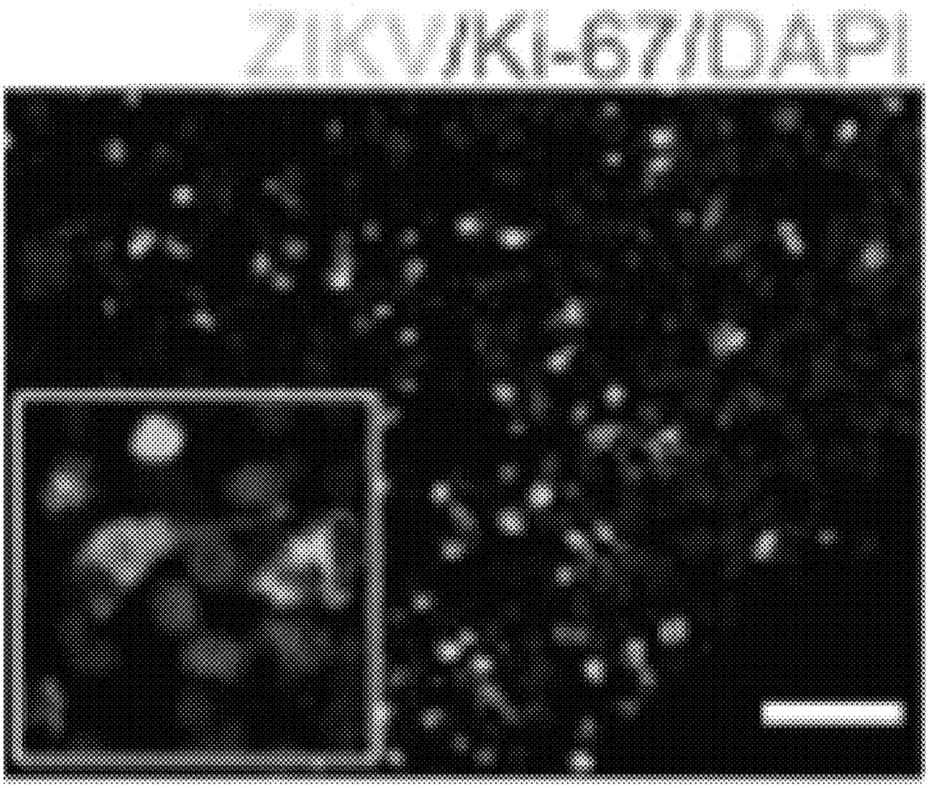
Figure 3L:
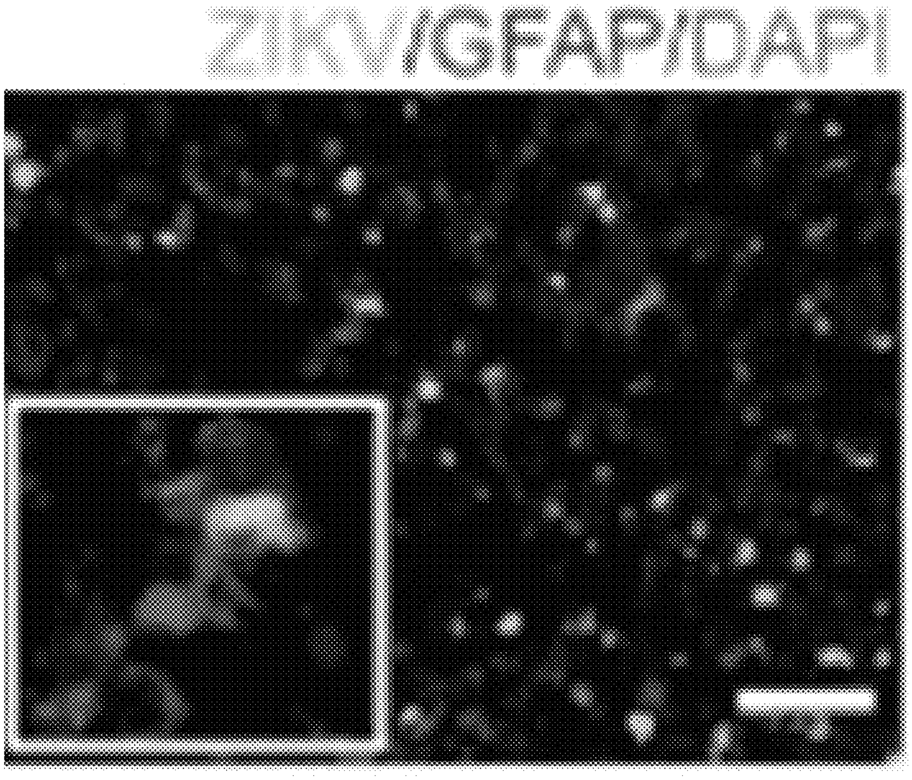
Figure 3M:
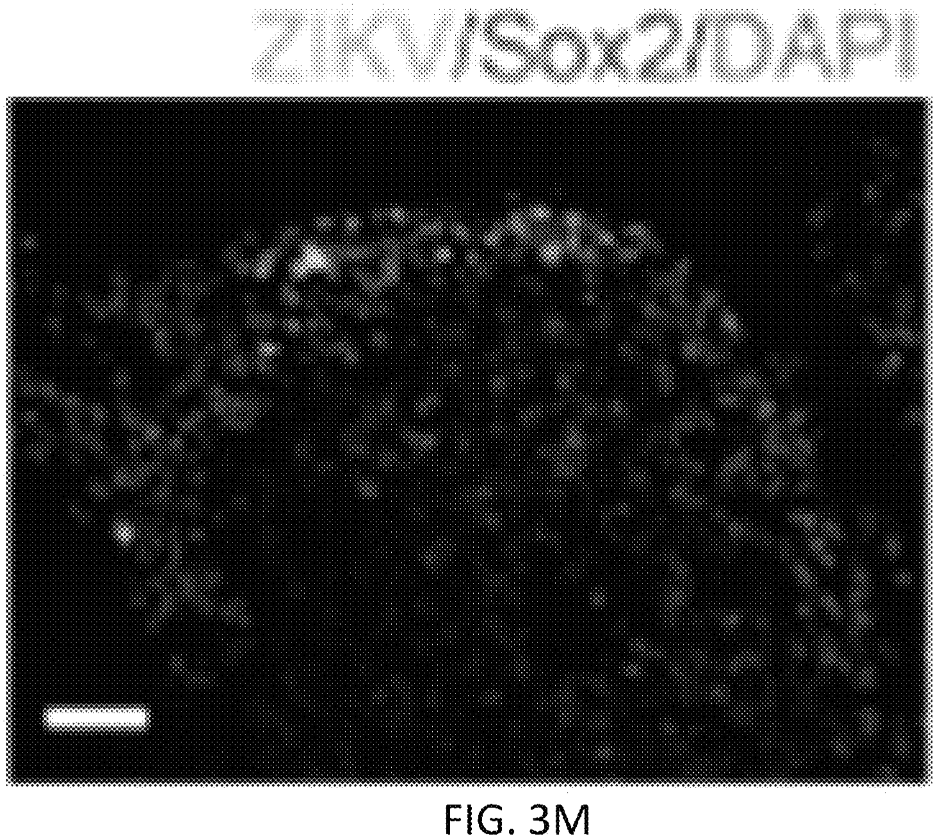
Figure 3N:
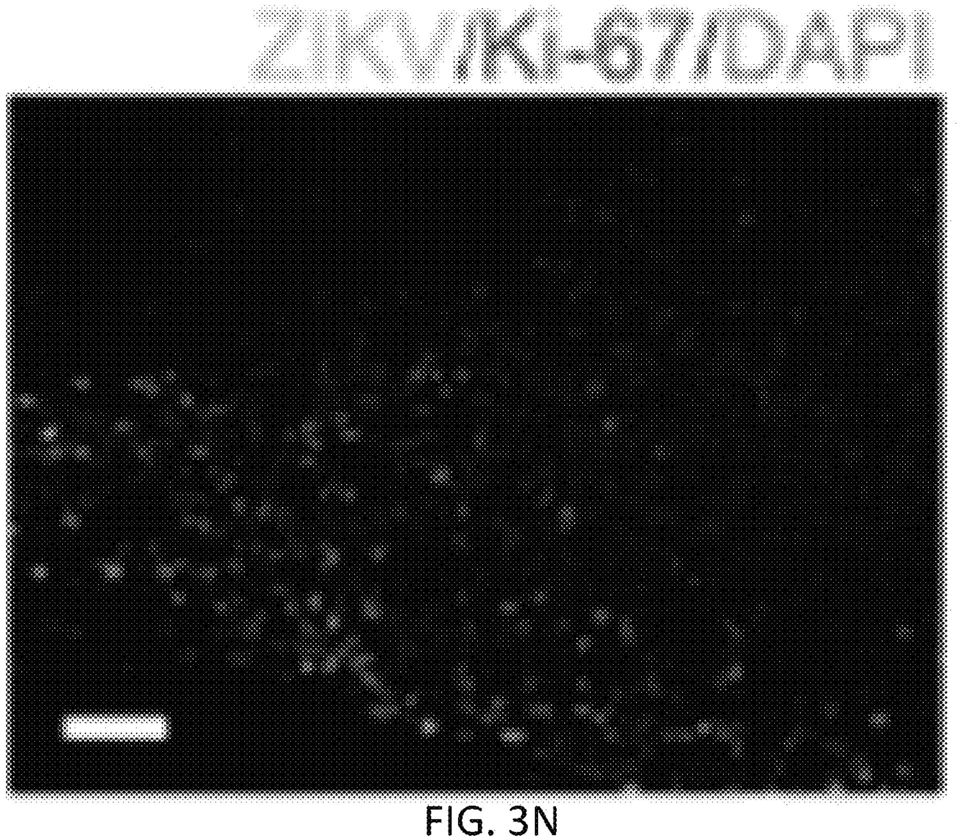
Figure 3O:
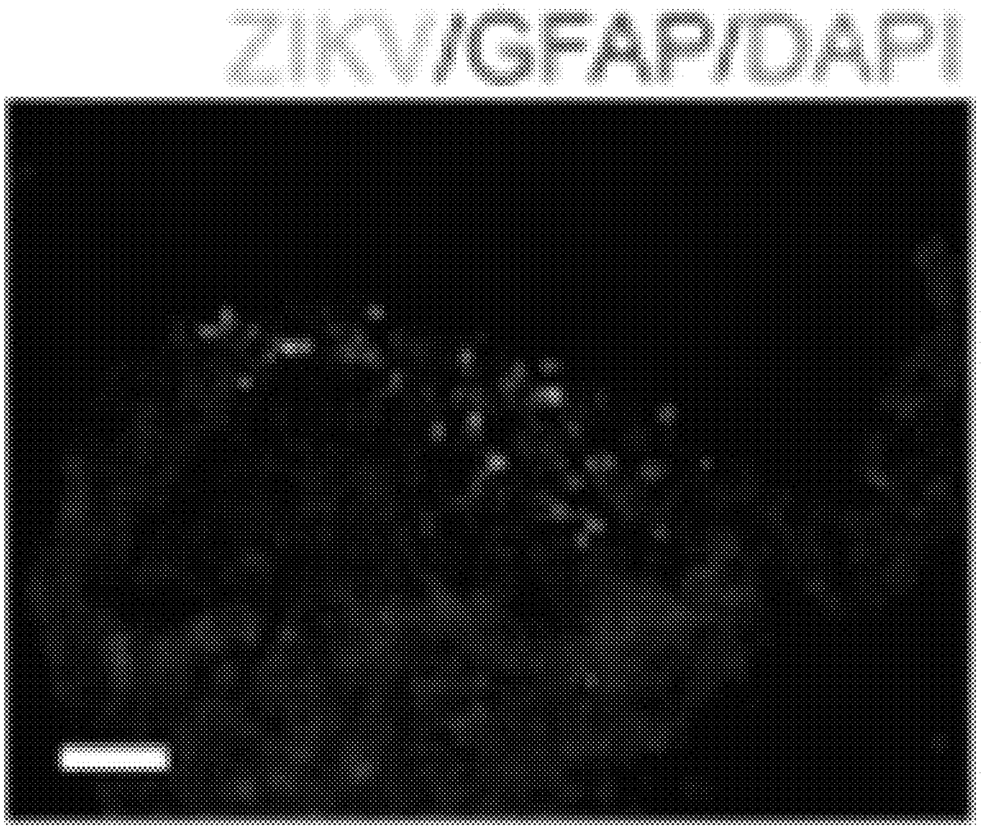
Figure 3P:
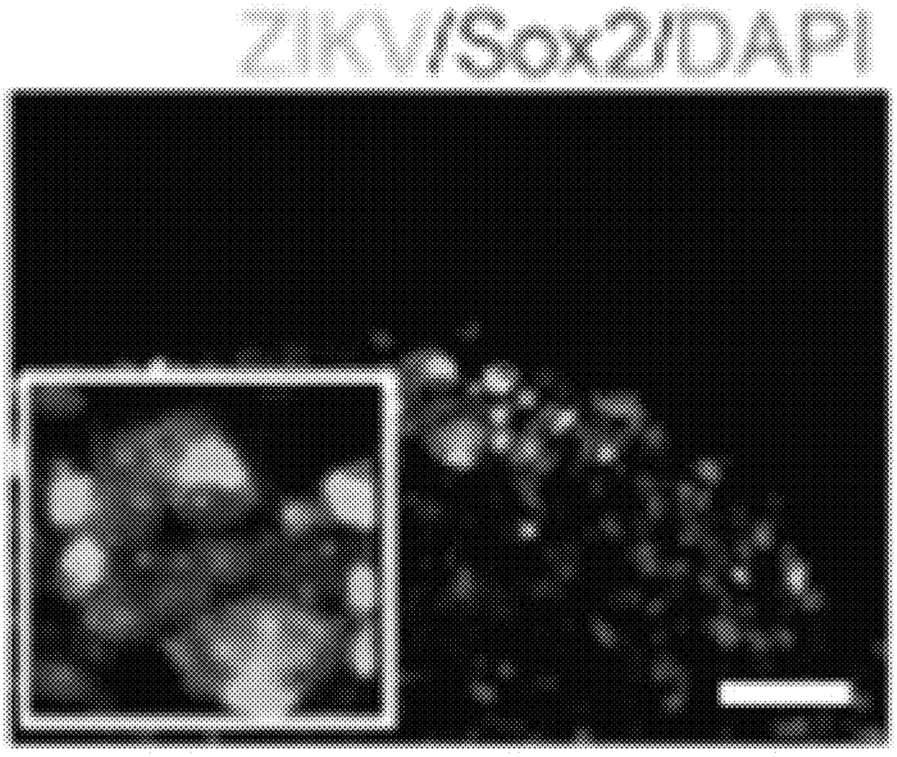
Figure 3Q:
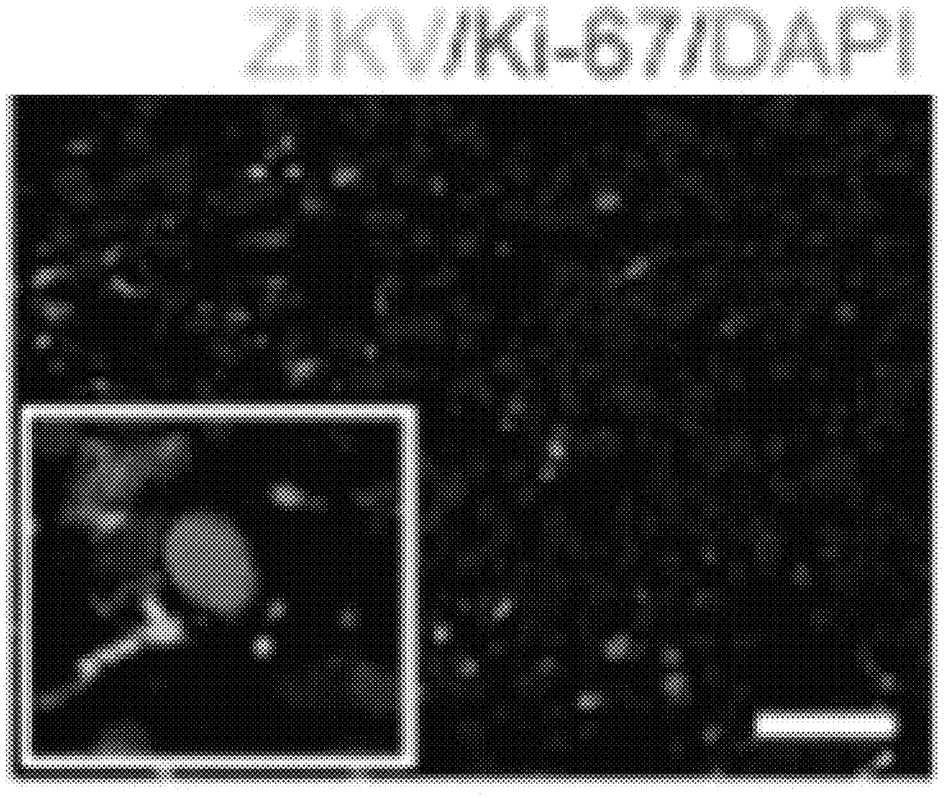
Figure 3R:
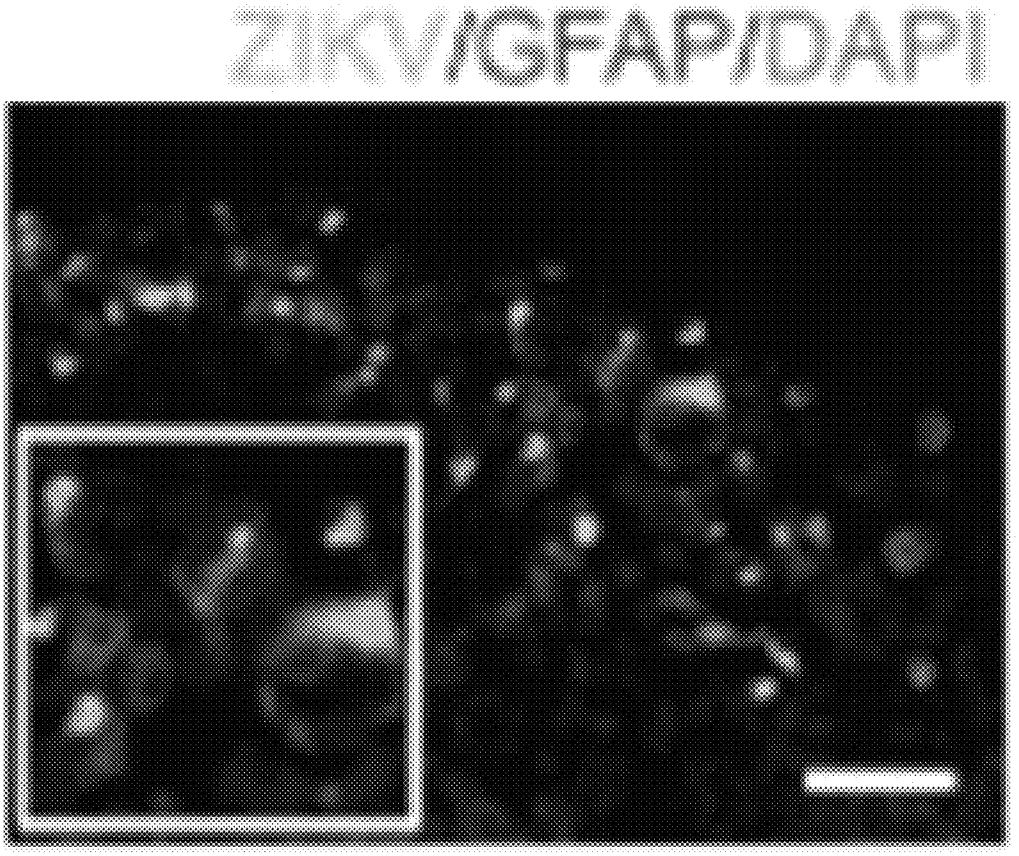
Figure 3T:
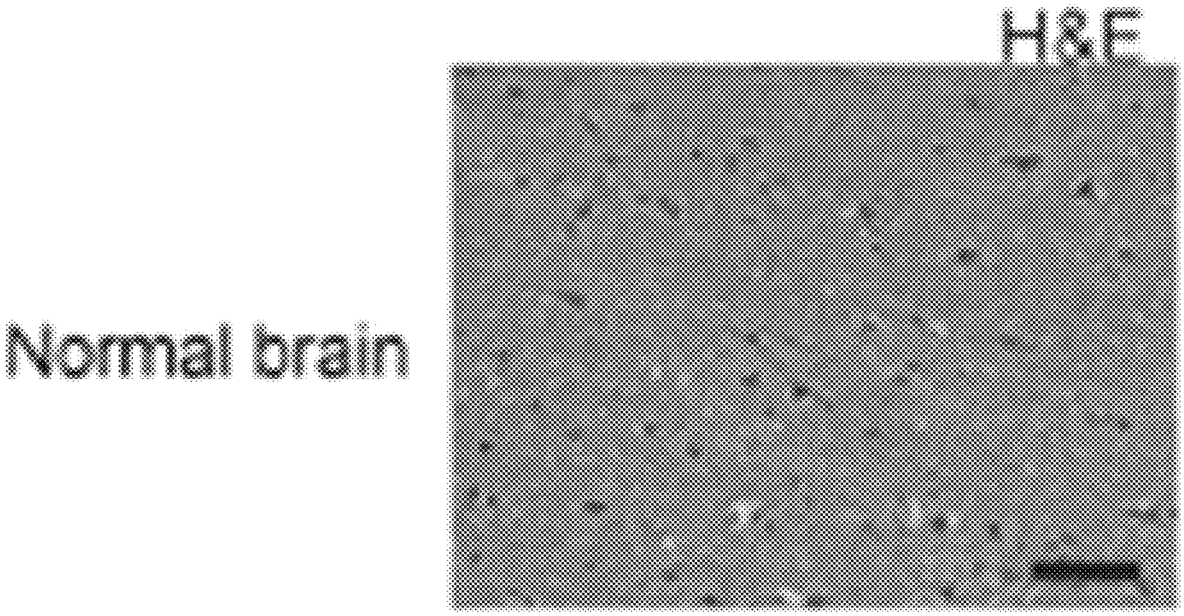
Figure 3U:
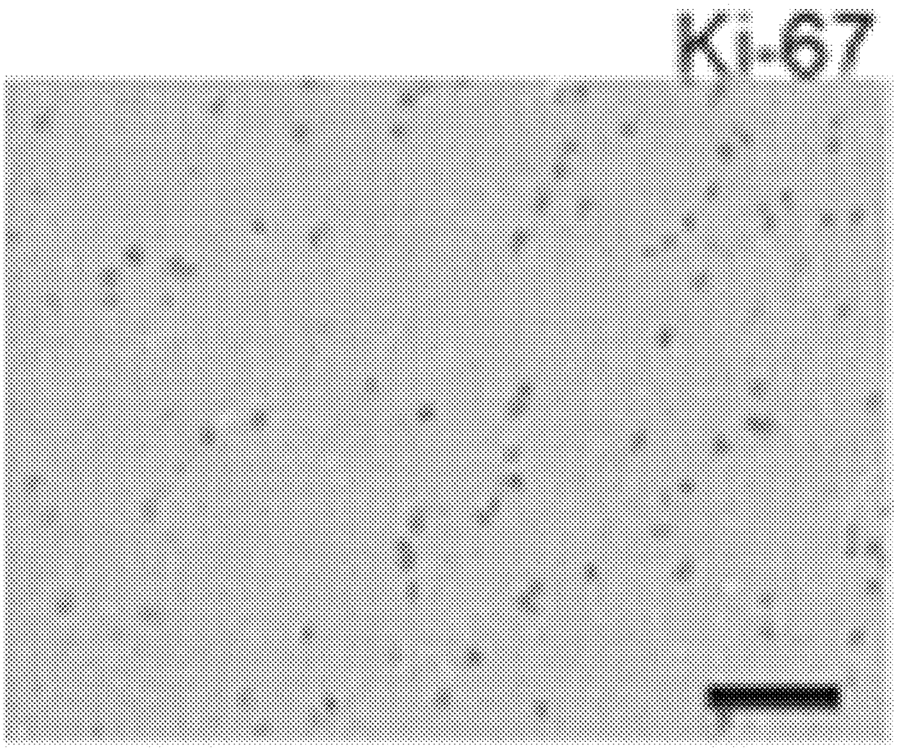
Figure 3V:
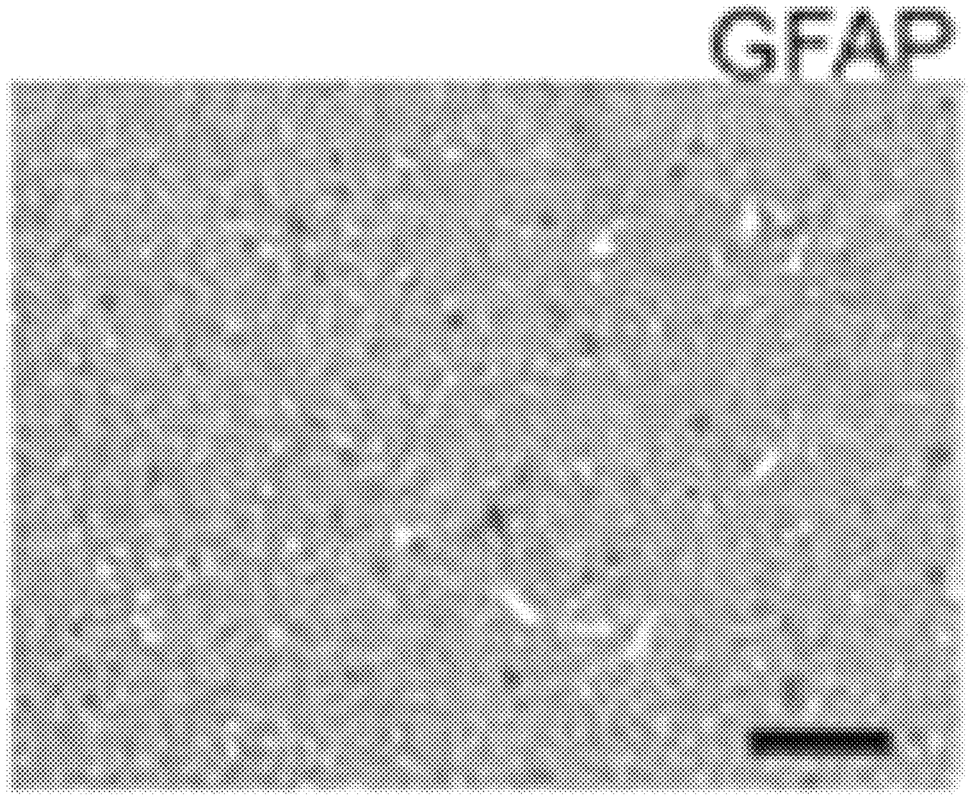
Figure 3W:
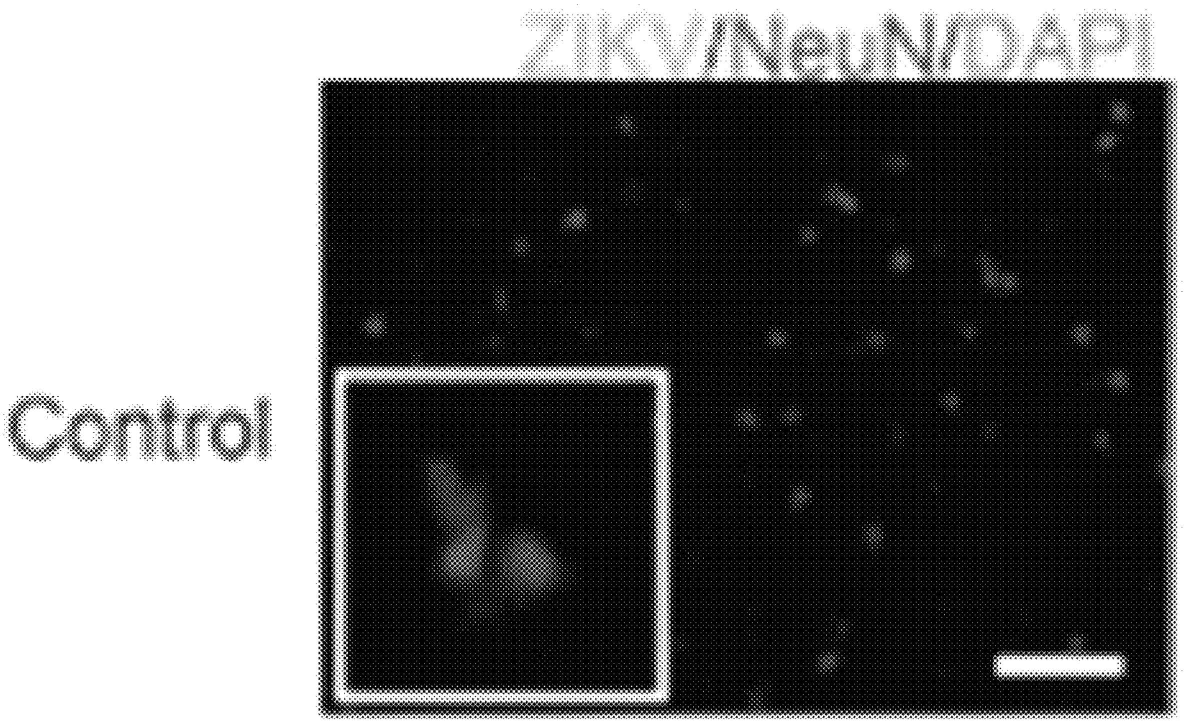
Figure 3X:
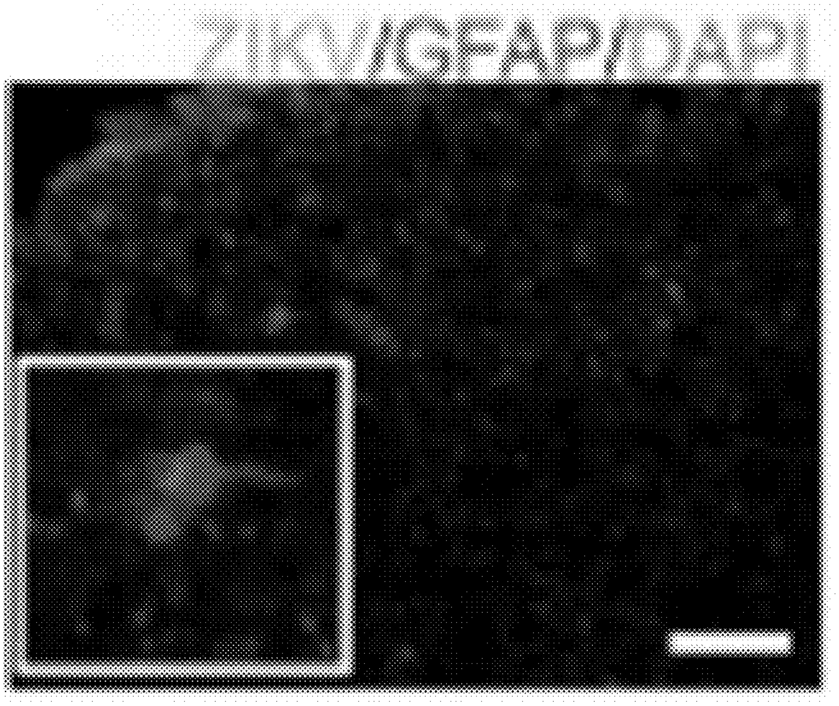
Figure 3Y:
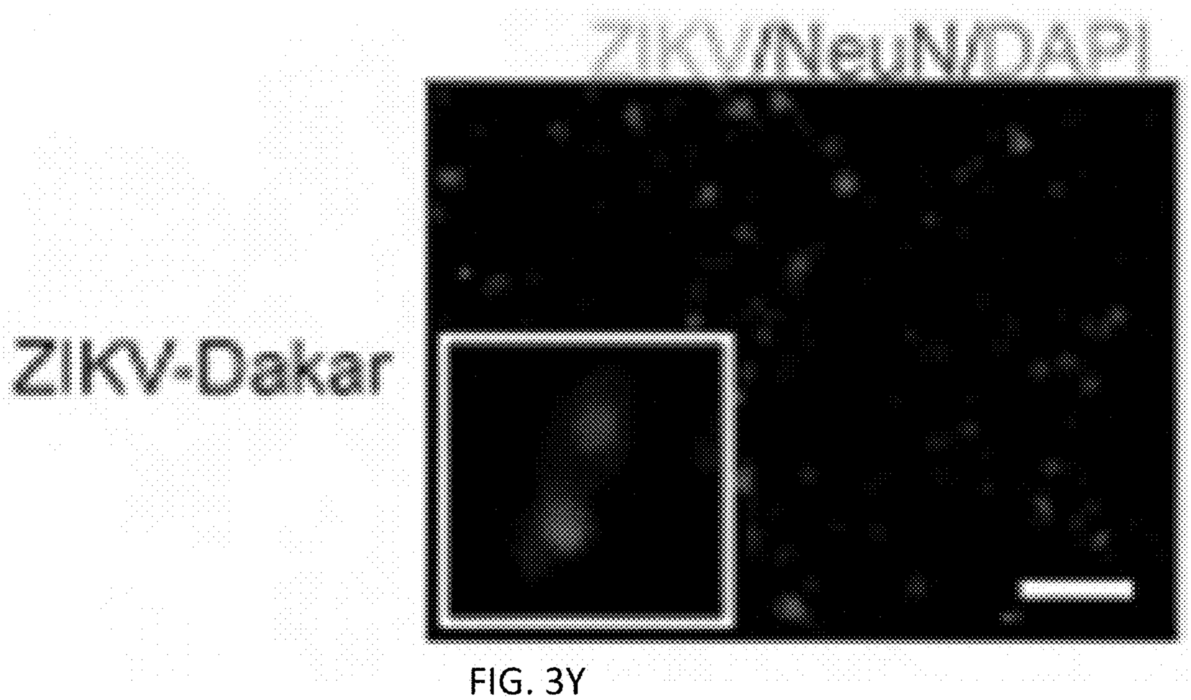
Figure 3Z:
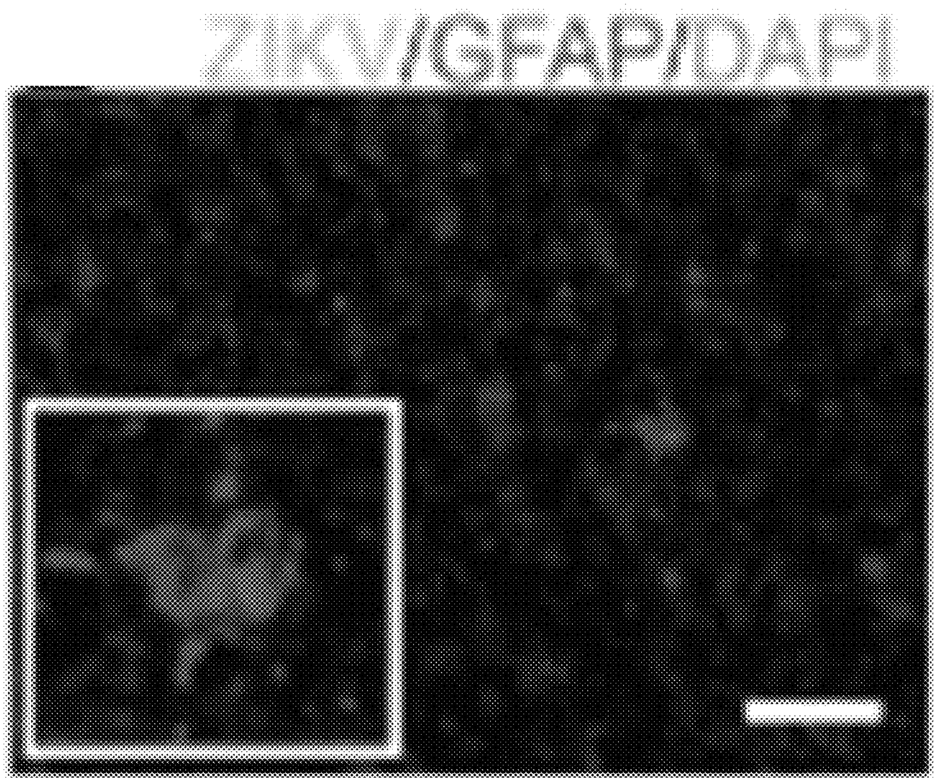
Figure 6F:
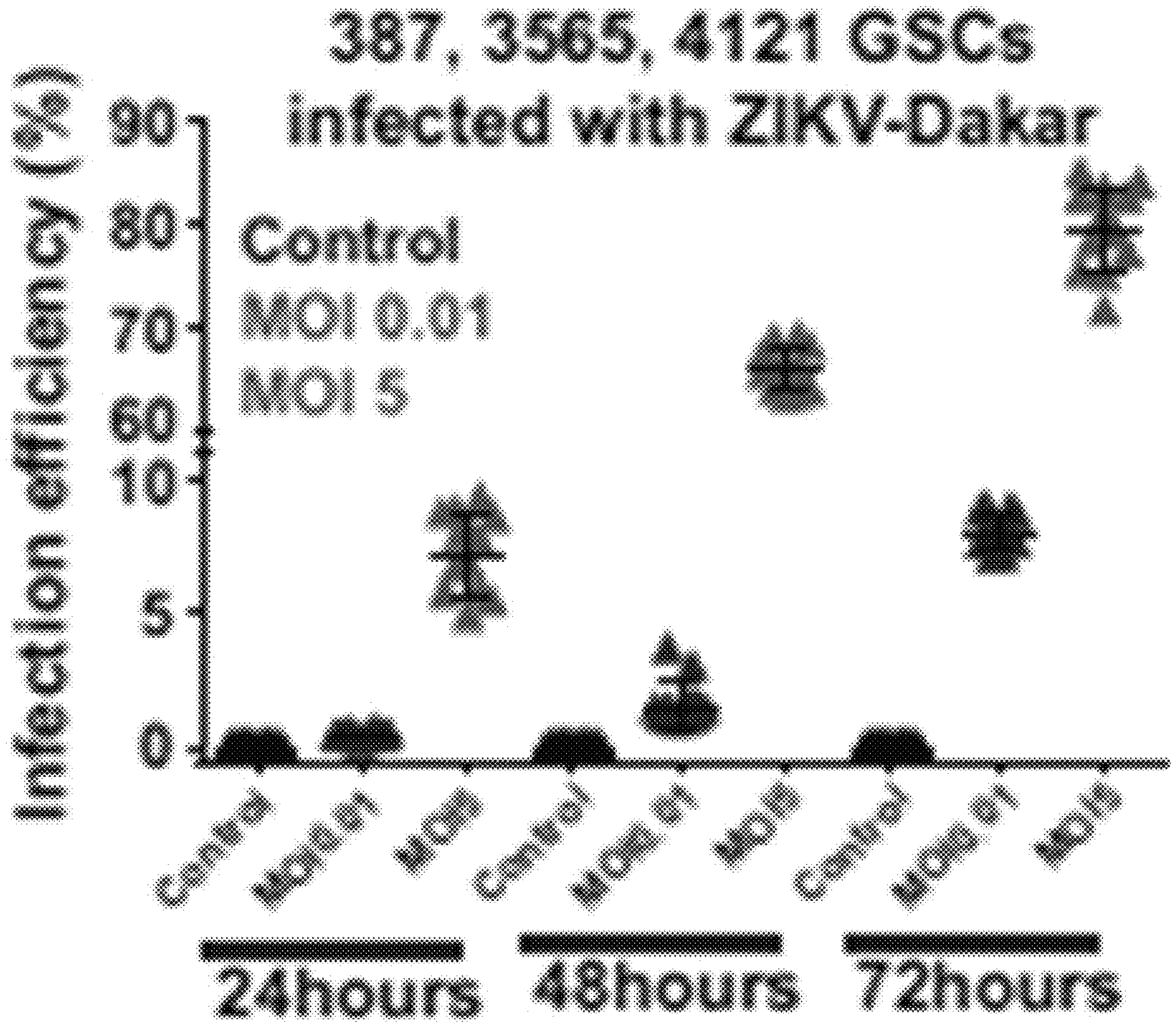
Figures 6G, 6H, 6I:
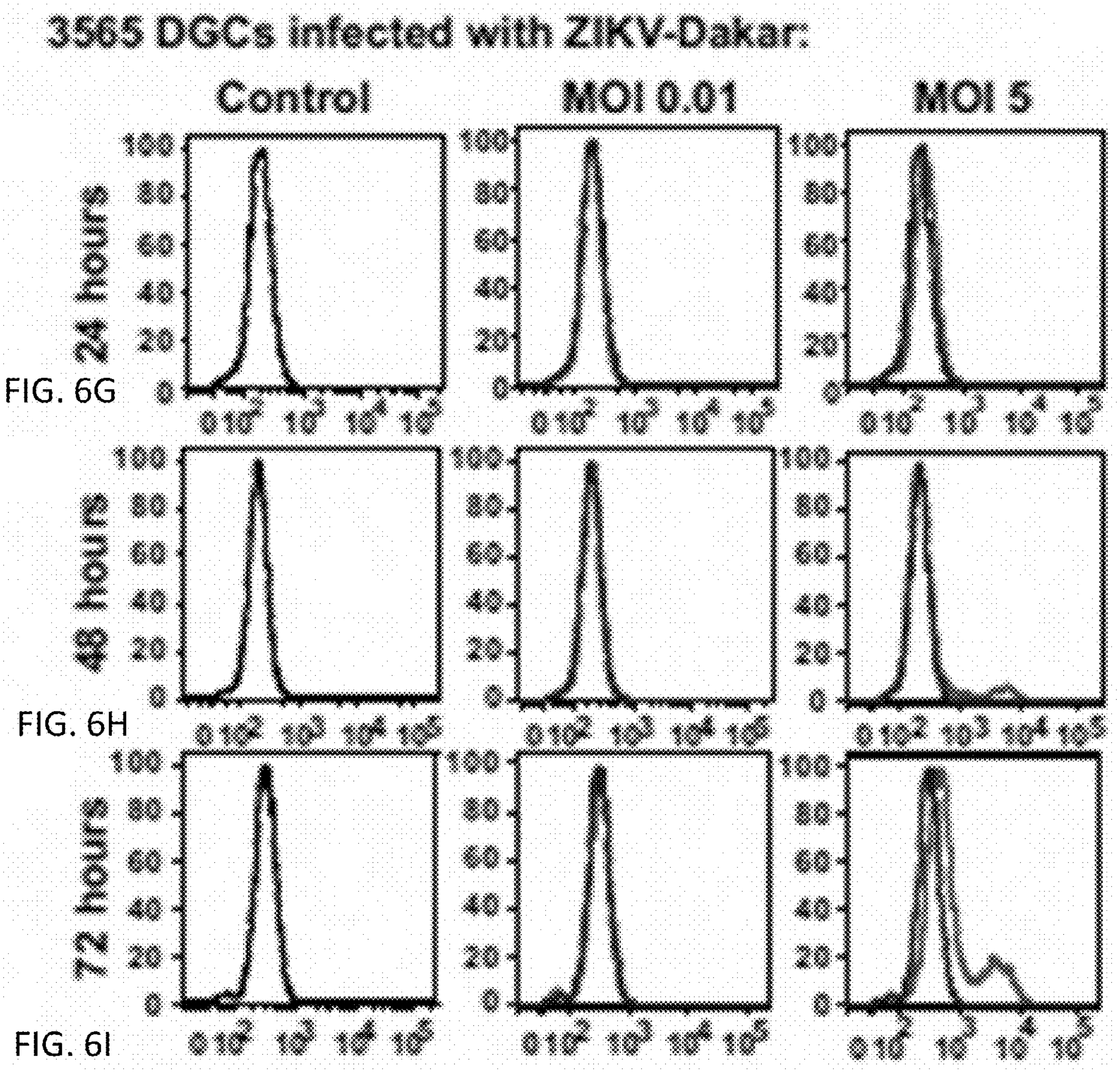
Figure 6J:
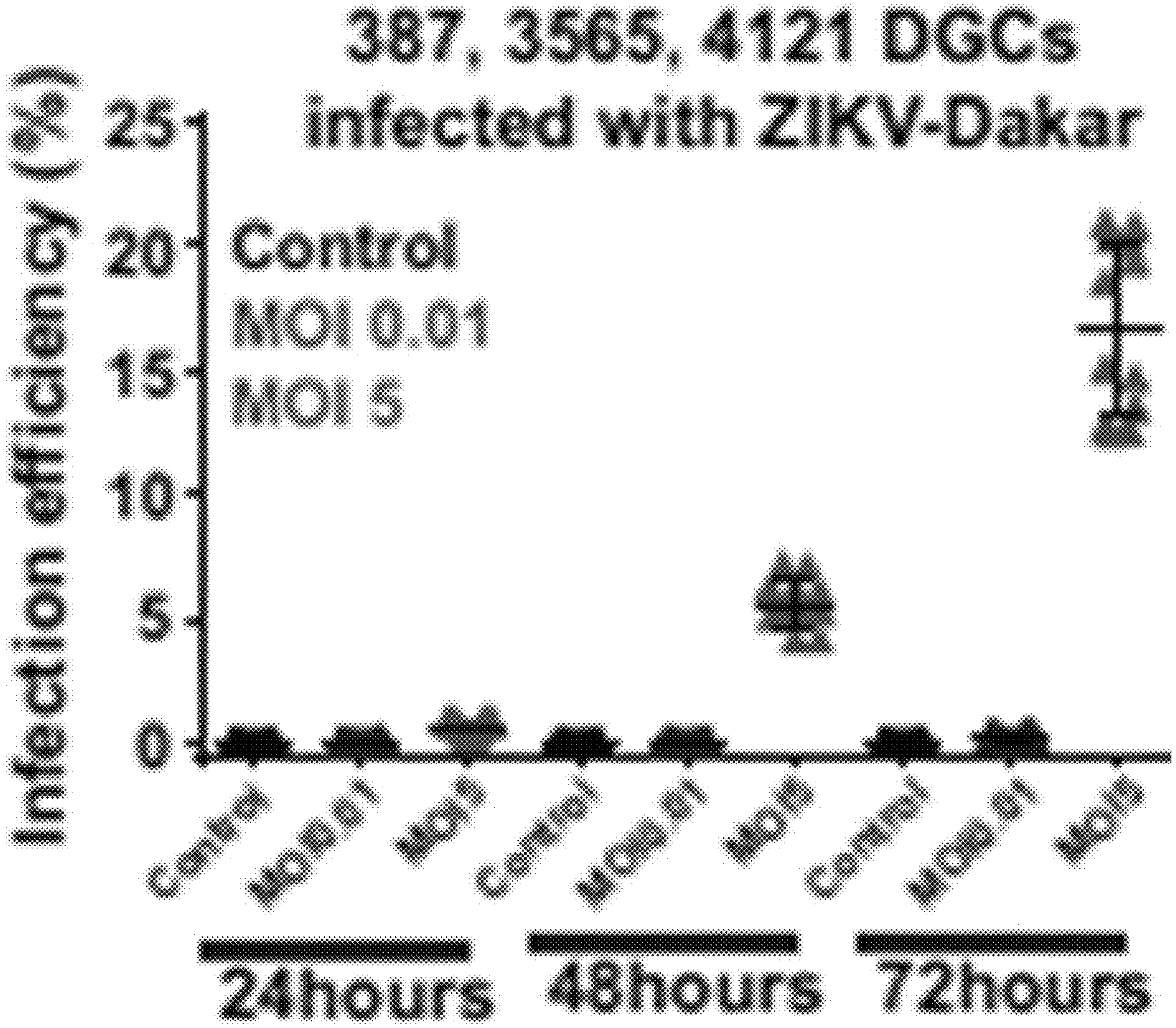
Figure 7A:
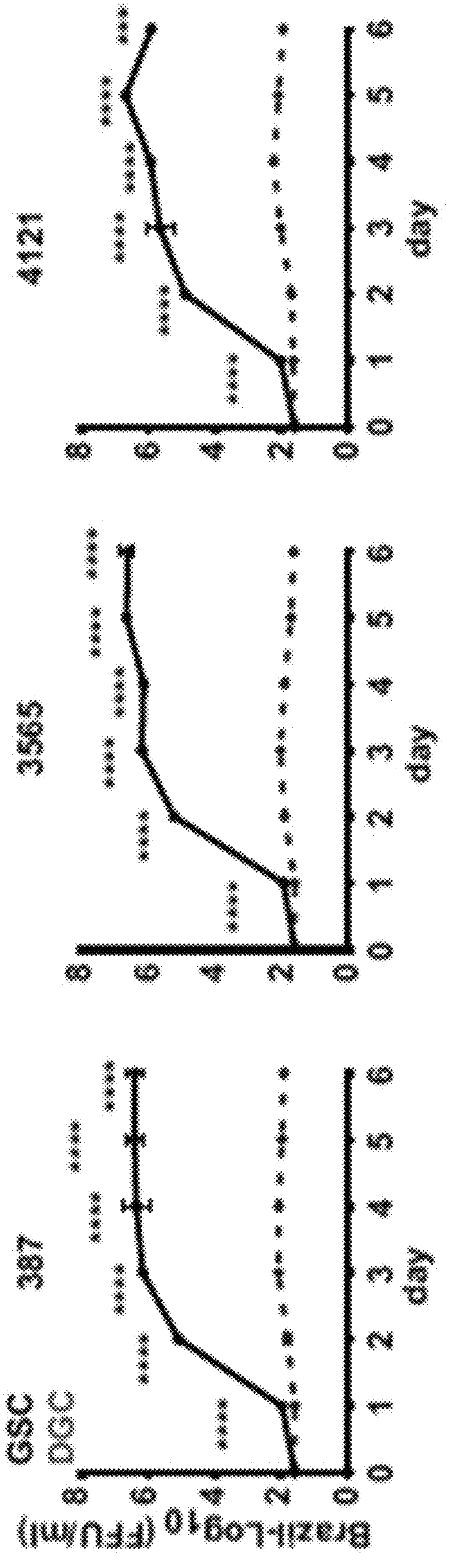
FIG. 7A and FIG. 7B show ZIKV production is better in GSCs than DGCs. Viral titres in supernatants were determined by FFA one week after infection of GSCs 387, 3565, and 4121 with ZIKV-Brazil (FIG. 7A) or ZIKV-Dakar (FIG. 7B). For each experiment, data was pooled from four independent experiments. Values represent mean±SD (Two-tailed unpaired t-test for FIG. 7A and FIG. 7B: ****, P<0.0001).
Figure 7B:
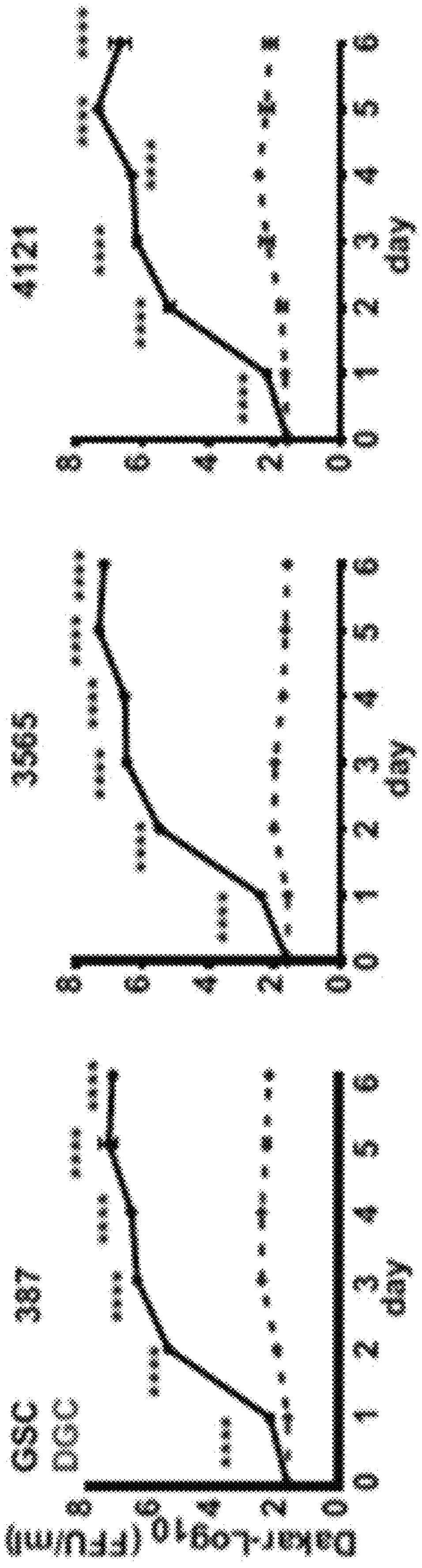

To confirm these results in the absence of culture, patient-derived GBM tumour slices immediately after surgical resection were collected (FIG. 3H-FIG. 3J) and infected with the two ZIKV strains. Over a one-week period, ZIKV progressively infected these tumour cells (FIG. 3K-FIG. 3Z, FIG. 6F). Co-staining sections for ZIKV antigen and the GSC marker, SOX2 (FIG. 3N, FIG. 3O, FIG. 3T, FIG. 3U) revealed that the majority of ZIKV infected cells expressed SOX2, albeit with some variation between two ZIKV strains (FIG. 3Z). ZIKV infected rapidly-dividing tumour cells (FIG. 3P, FIG. 3Q, FIG. 3V, and FIG. 3W) at a lower percentage compared to $SOX2^+$ GBM cells (FIG. 3Z) and rarely infected differentiated GBM cells (FIG. 3R, FIG. 3S, FIG. 3X-FIG. 3Z). These results support the hypothesis that ZIKV specifically targets and kills GSCs.

Example 6: Testing the Effects of ZIKV on Normal Human Neural Cells

Figure 9A:
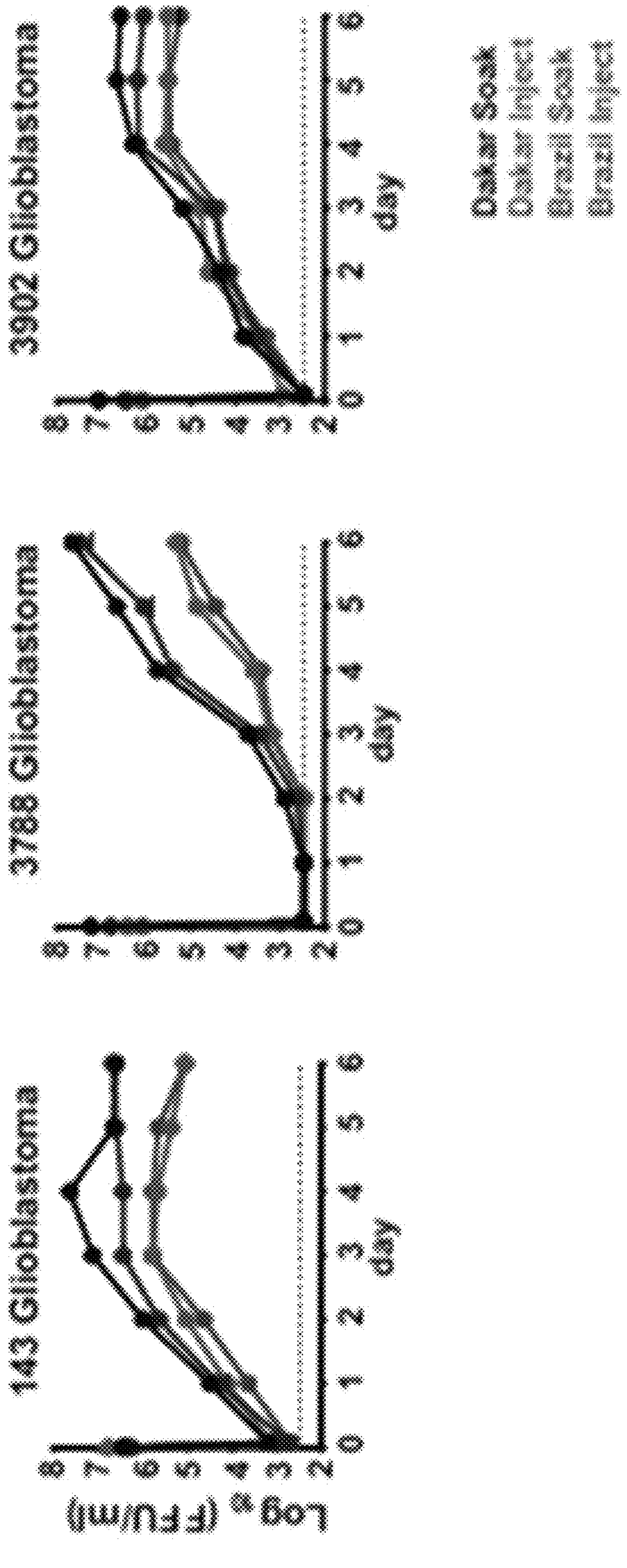
FIG. 9A, FIG. 9B, FIG. 9C, FIG. 9D, FIG. 9E, FIG. 9F, FIG. 9G, FIG. 9H, FIG. 9I, FIG. 9J and FIG. 9K show ZIKV minimally effects normal adult brain compared to GSCs and DGCs.
Figure 9B:
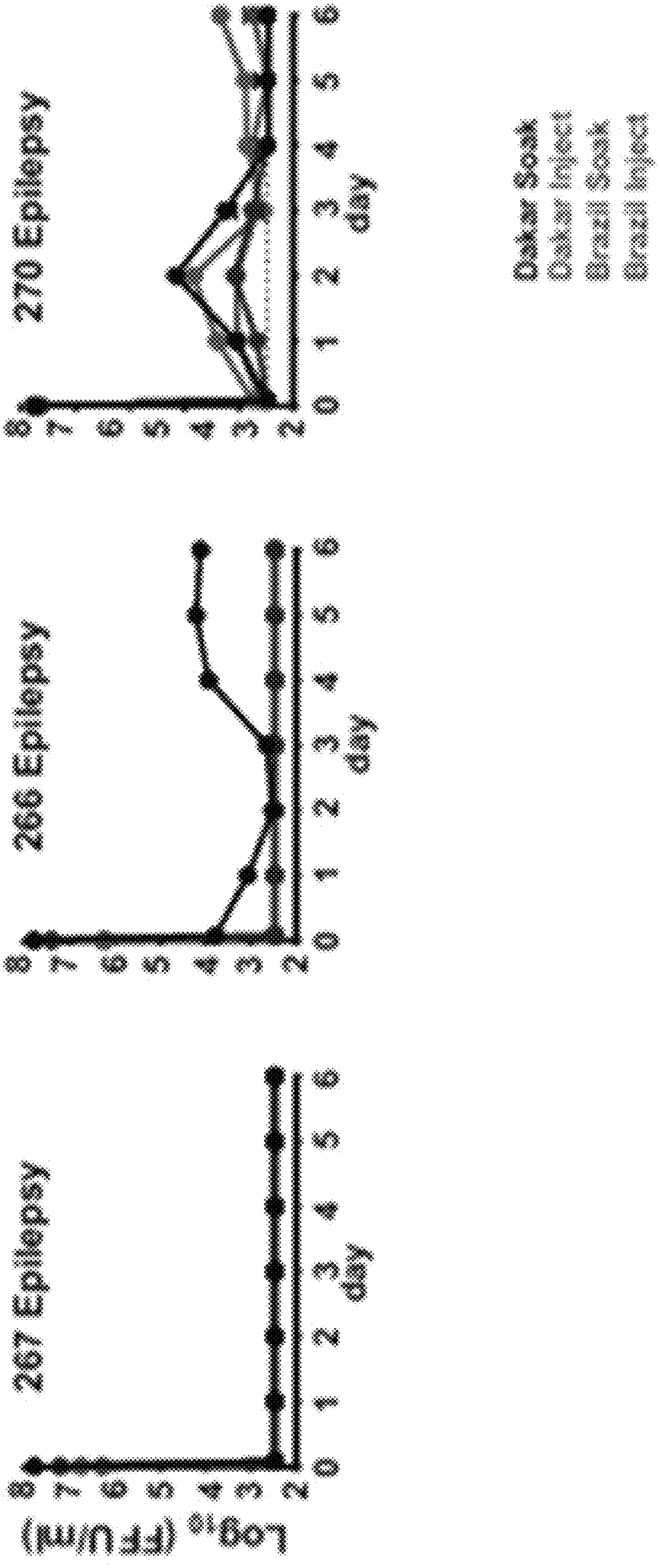
Figure 9C:
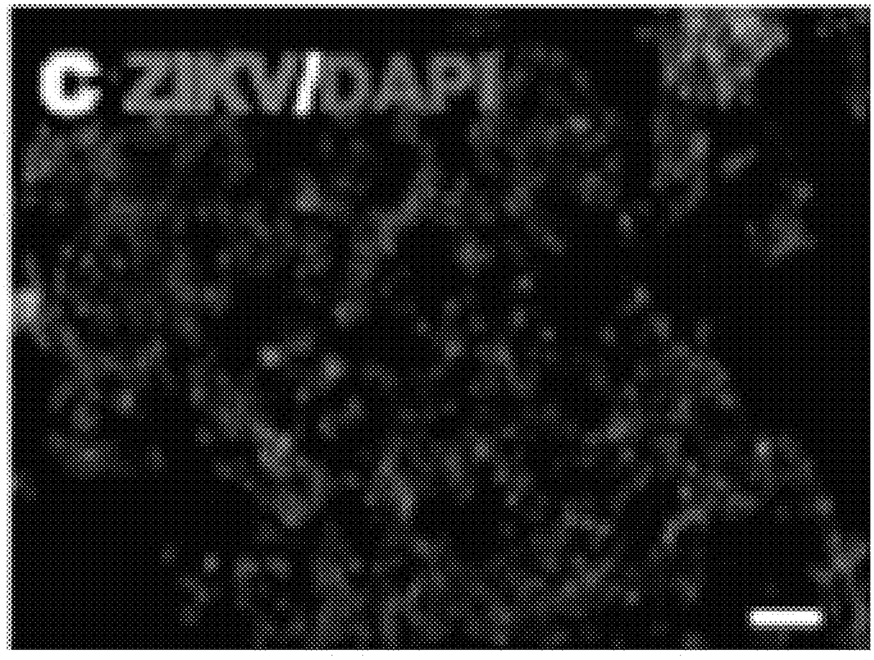
Figure 9D:
Figure 9E:
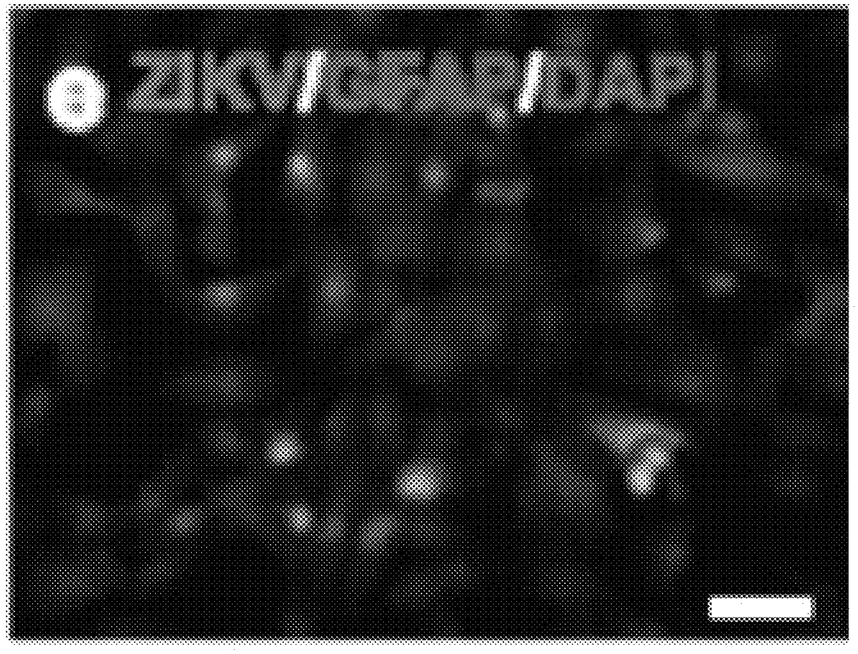
Figure 9F:
Figure 9G:
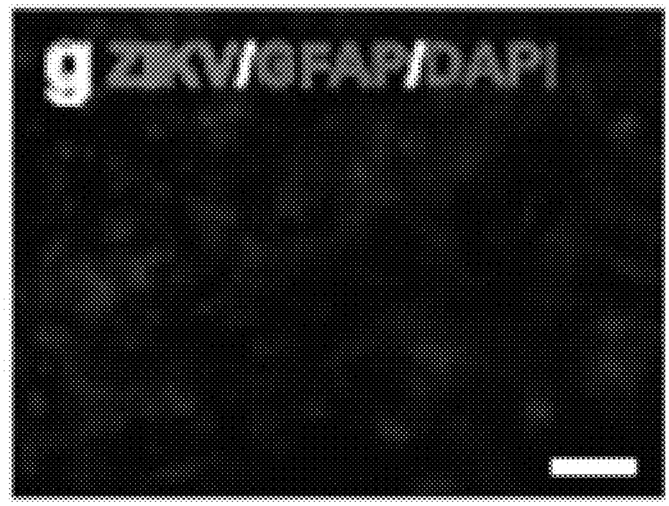
Figure 9H:
Figure 9I:
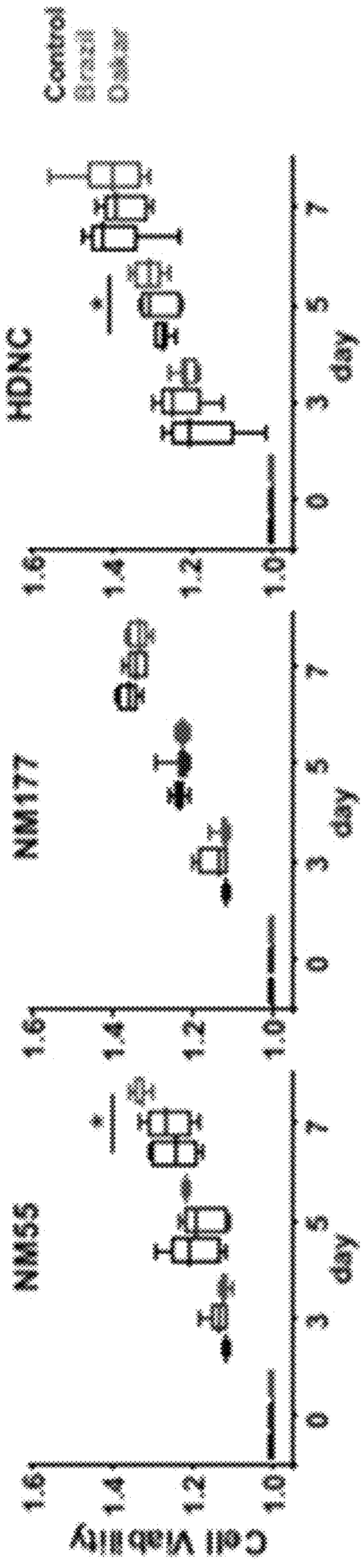
Figure 9J:
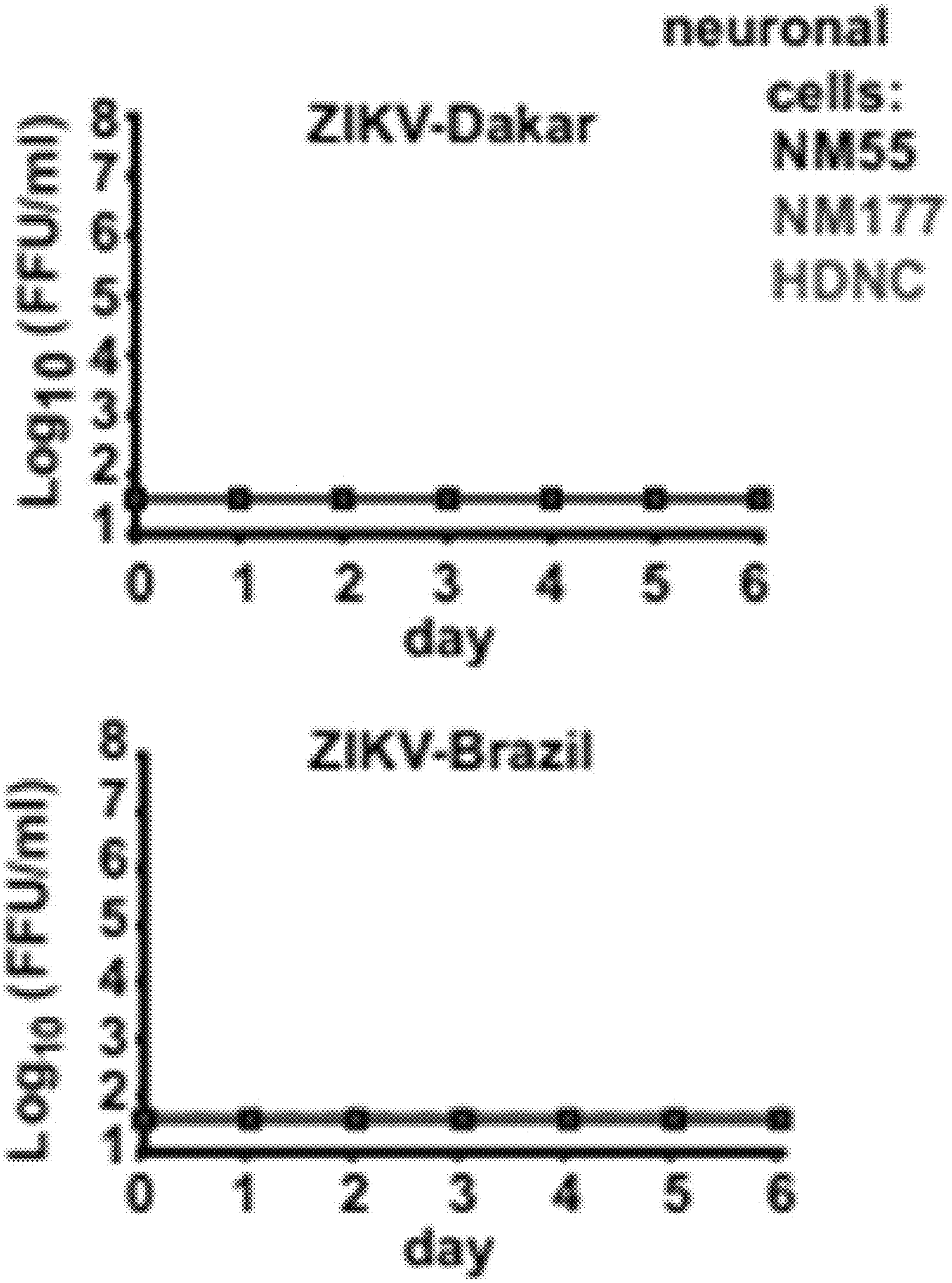
Figure 9K:
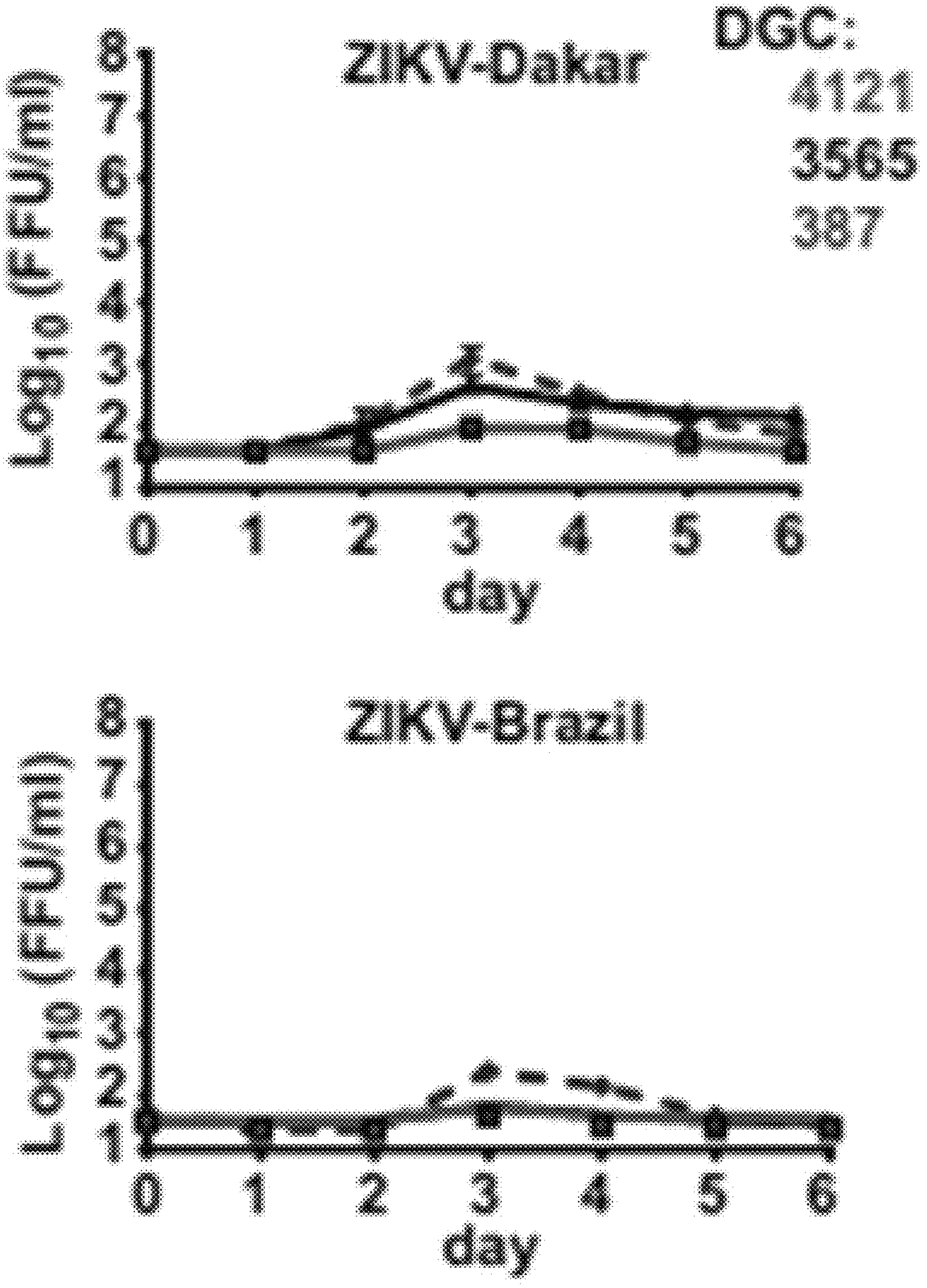

The therapeutic index of an oncolytic virus derives from its ability to infect and kill tumour cells, with limited effects on normal cells[6, 8]. To test the effects of the ZIKV on normal adult human neural cells, non-malignant neural tissues were derived from surgical specimens of adults undergoing epilepsy surgery (brain primary tissue from epilepsy patients 266, 267, and 270; FIG. 3A-FIG. 3C). In contrast to effects on GBM tissues, ZIKV did not infect normal human brain tissues, including $NeuN^+$ neurons (FIG. 3D and FIG. 3*f*) or $GFAP^+$ glial cells (FIG. 3E and FIG. 3G), as limited viral replication was detected (FIG. 6E) compared to GBM (FIG. 6F). In addition, the human brain neuronal cell lines that were freshly derived from epilepsy patients (NM55 and NM 177) or from differentiated human neural stem cells (Hu-DNC) demonstrated limited ZIKV infection (FIG. 7G-FIG. 7I; FIG. 9E, FIG. 9F). Limited toxicity in these neuronal cell models was confirmed using a cell viability assay over a week time course with two ZIKV strains (FIG. 9G), and ZIKV replicated poorly in normal neuronal cell lines in contrast to DGCs (FIG. 9*h*, FIG. 9I).

Figure 4A:
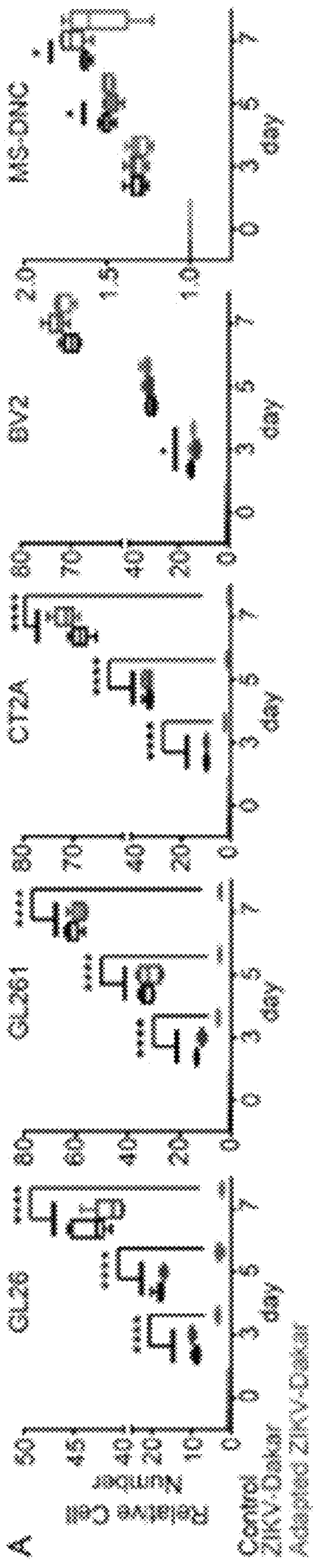

Example 7: Testing Effects of ZIKV in Mice Using a Mouse-Adapted Version of ZIKV-Dakar Oncolytic viruses elicit anti-tumour effects from a combination of direct tumour cell killing and activation of anti-tumour immune response[28]. Relevant conditions for human brain tumour therapy were recapitulated by using mice. As mice are not natural hosts for ZIKV, pathogenesis studies have used animals with acquired or genetic deficiencies of type I interferon (IFN) signalling[12]. However, such immunodeficiencies may fail to model the efficacy of ZIKV as an oncolytic therapy study, which requires an immunocompetent background. To overcome this limitation, a mouse-adapted version of ZIKV-Dakar that had gained virulence through sequential passage through a $Rag1^{-/-}$ host[29] was used. The efficacy of the parental and mouse-adapted ZIKV-Dakar strains was first compared against three murine glioma models developed in the C57BL/6 background (GL261, GL26, CT-2A)[20] and two normal murine CNS lines (BV2 and MS-DNC) in vitro. The mouse-adapted ZIKV-Dakar strain attenuated the growth of the murine glioma cells, whereas the parental ZIKV strain was less effective over a one-week time course (FIG. 4A). In contrast, neither the parental nor the mouse-adapted Dakar ZIKV inhibited the growth of normal mouse CNS cells (BV2 and MS-DNC) or other murine cell types (M. Gorman and M. Diamond, unpublished data). These results were confirmed by virus titration at one week with murine glioblastoma cells (GL26, GL261, and CT-2A), which demonstrated increased viral titre, but not with normal mouse neuronal cells (BV2 and MS-DNC) or other wild type mouse cells (FIG. 4B and data not shown). Thus, mouse-adapted ZIKV retains specificity against mouse GSCs with limited toxicity for normal neuronal cells.

Example 8: Assessing Oncolytic Effects of ZIKV In Vivo

Figure 4F:
Figure 4G:
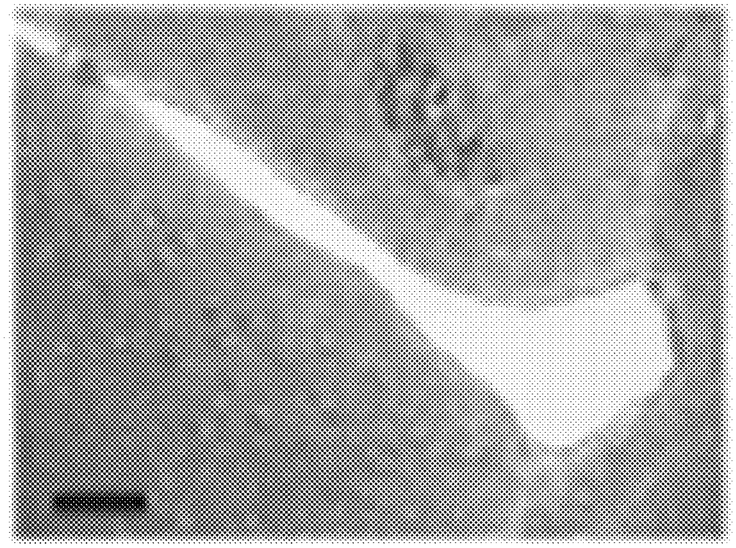
Figure 4H:
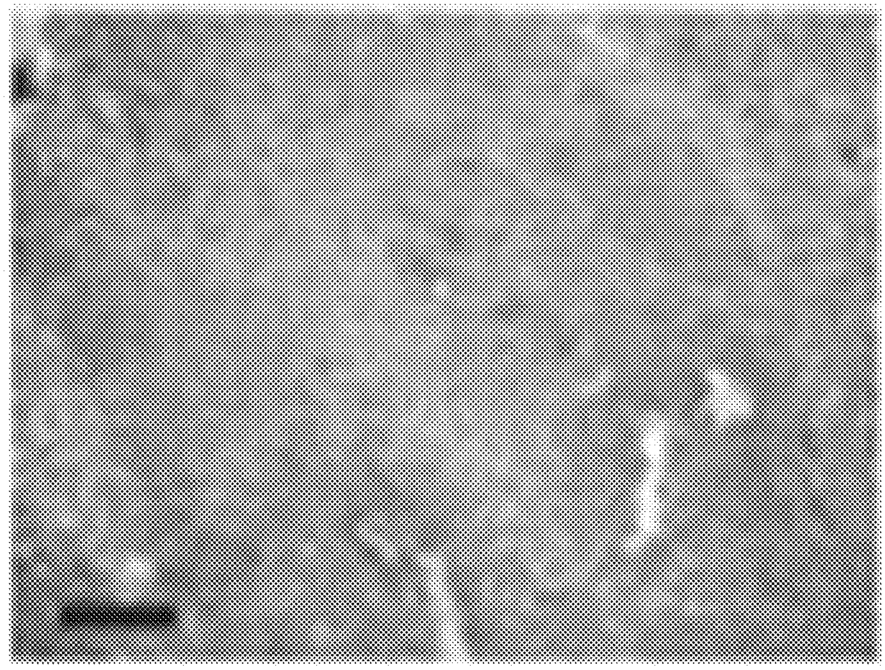
Figure 4I:
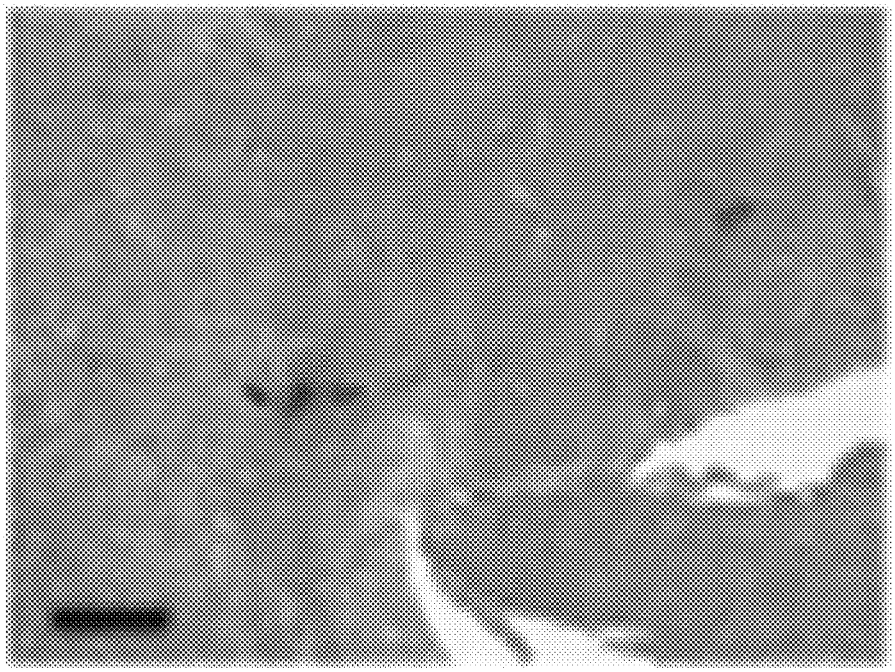
Figure 4J:
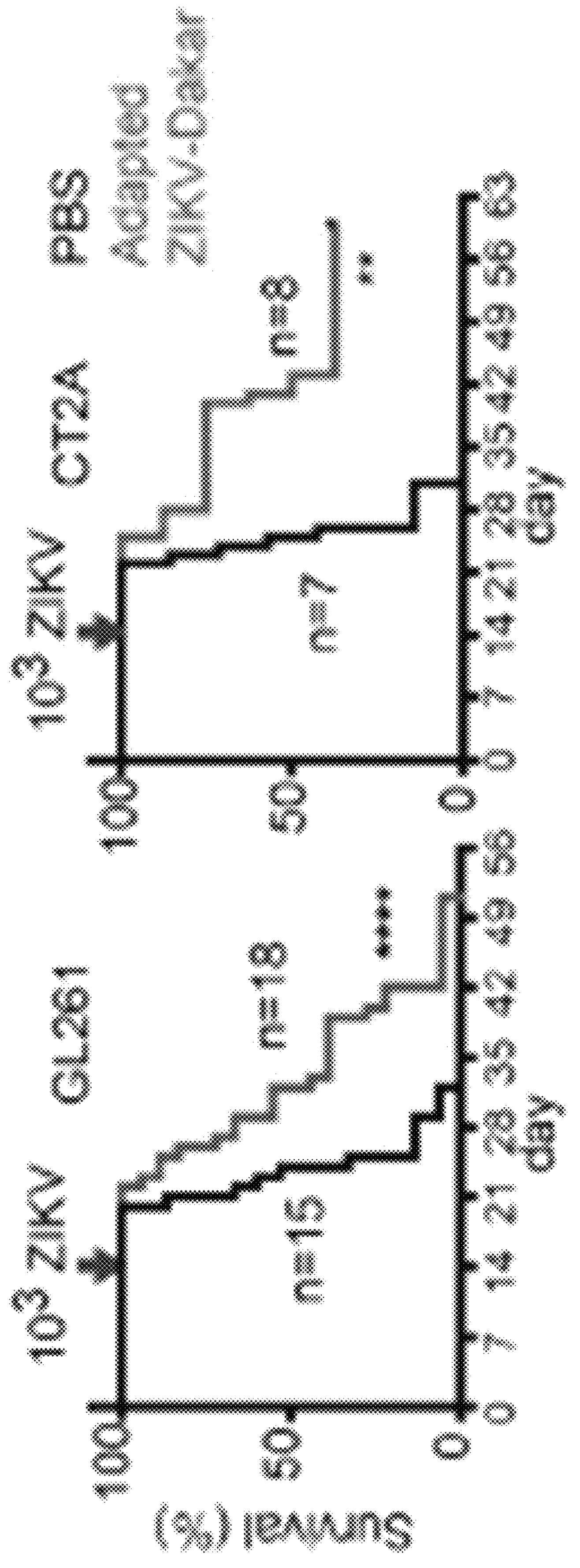
Figure 4K:
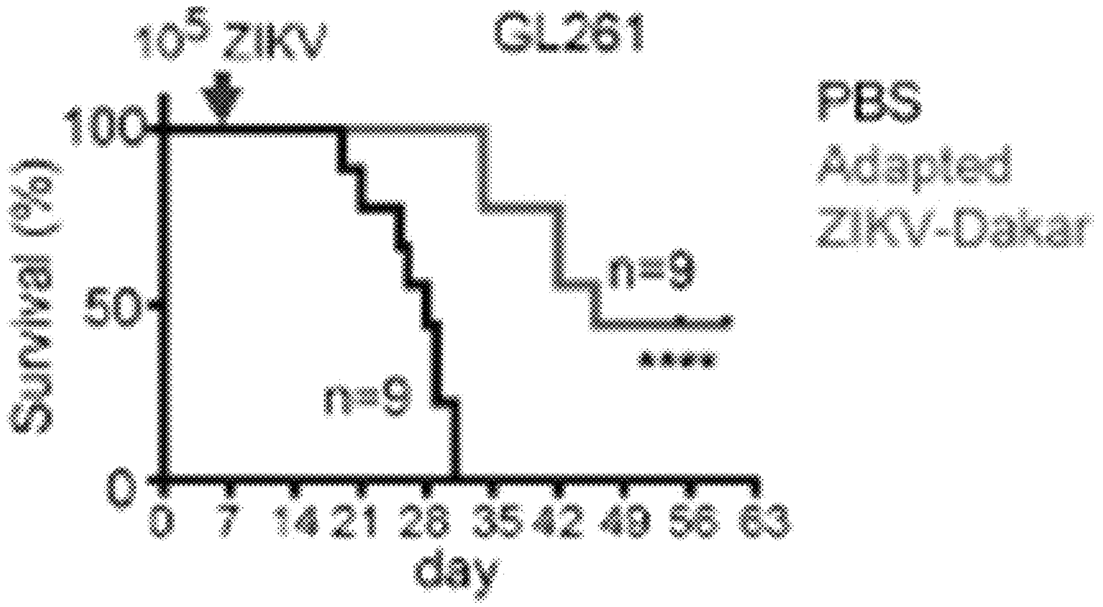
Figure 4L:
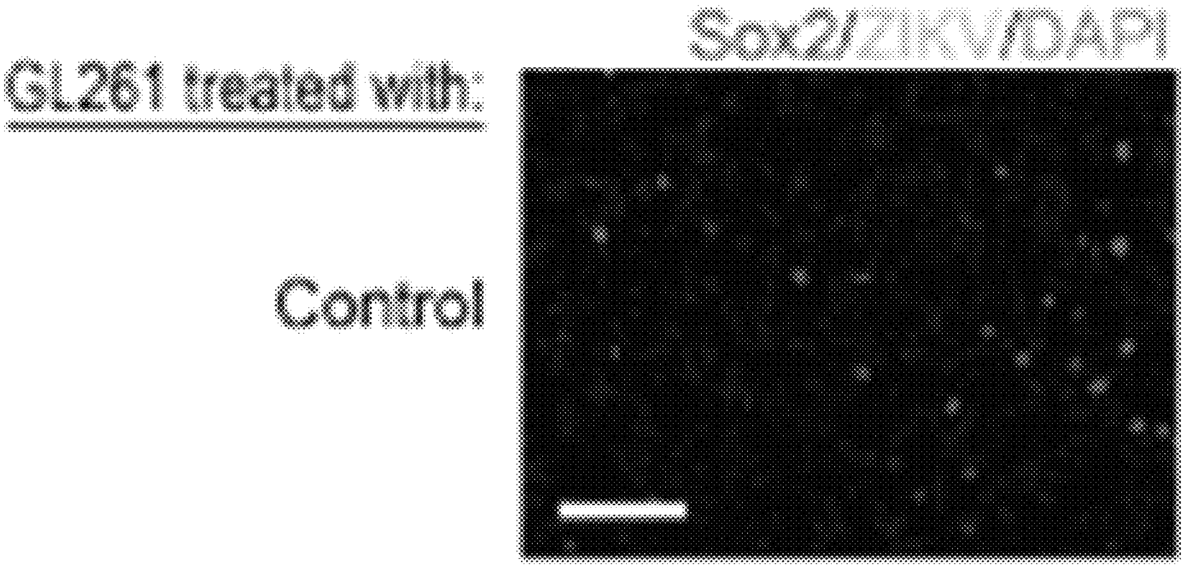
Figure 4M:
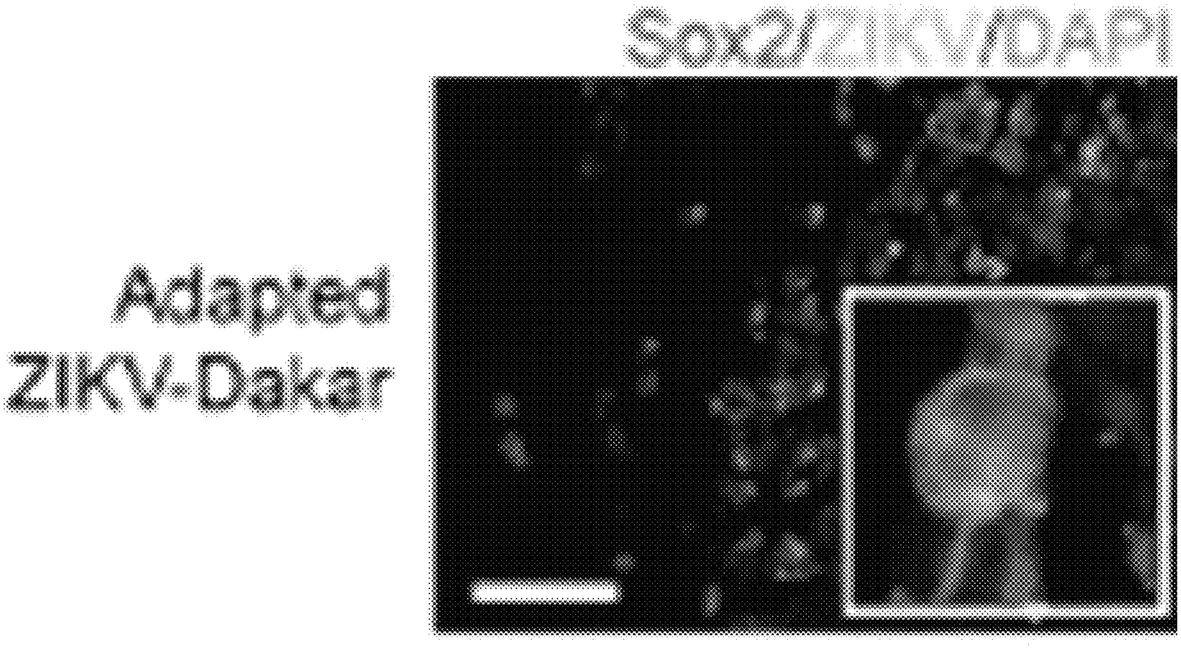
Figure 4N:
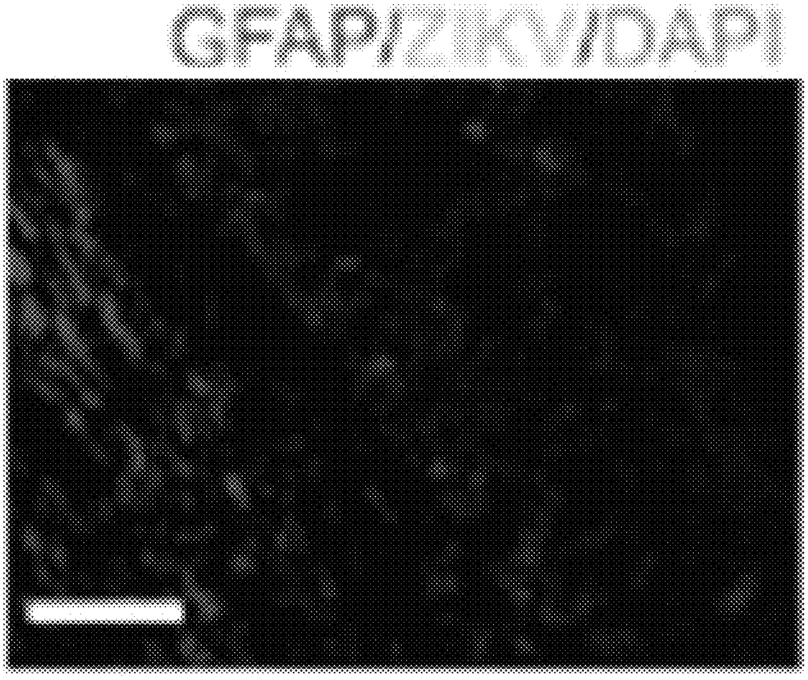
Figure 4O:
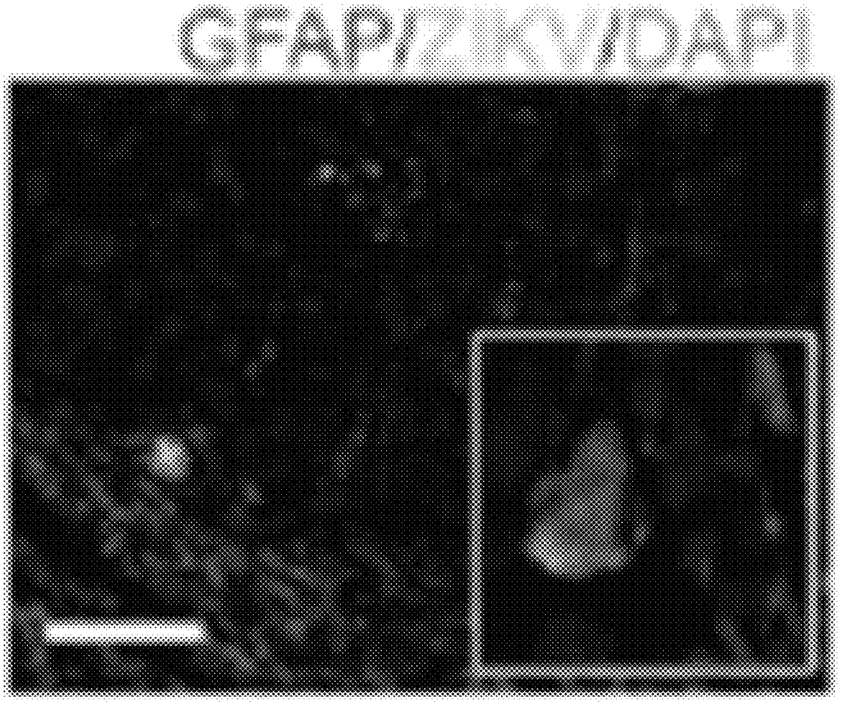
Figure 4P:
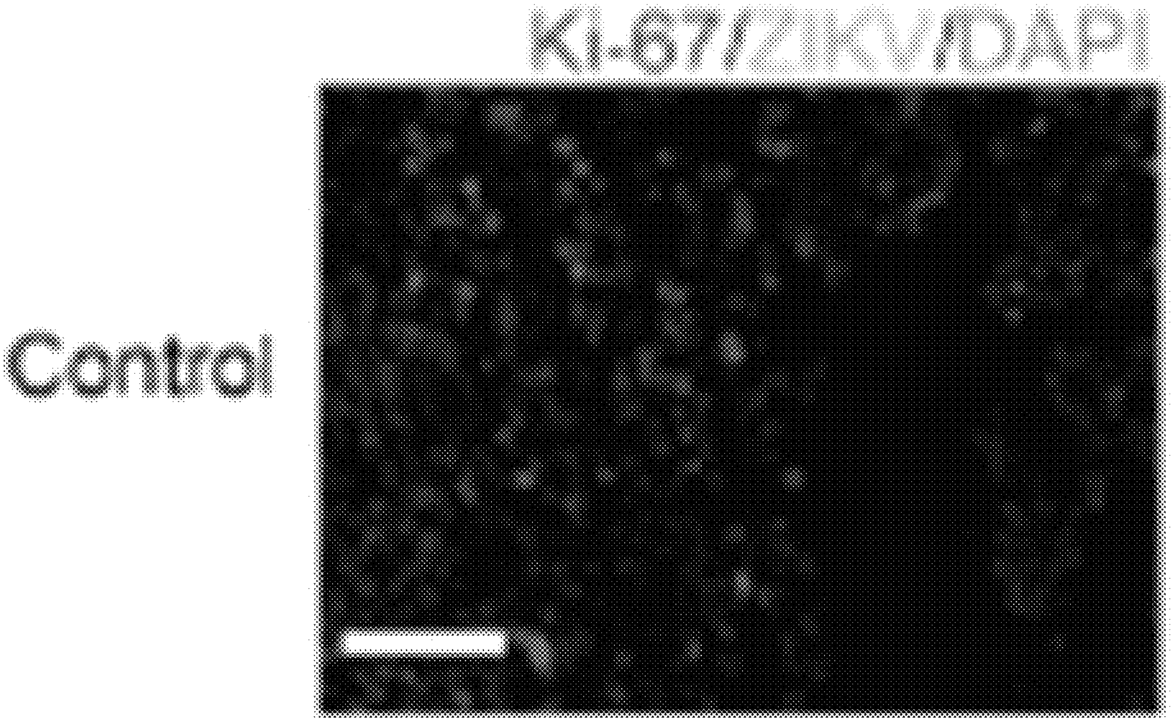
Figure 4Q:
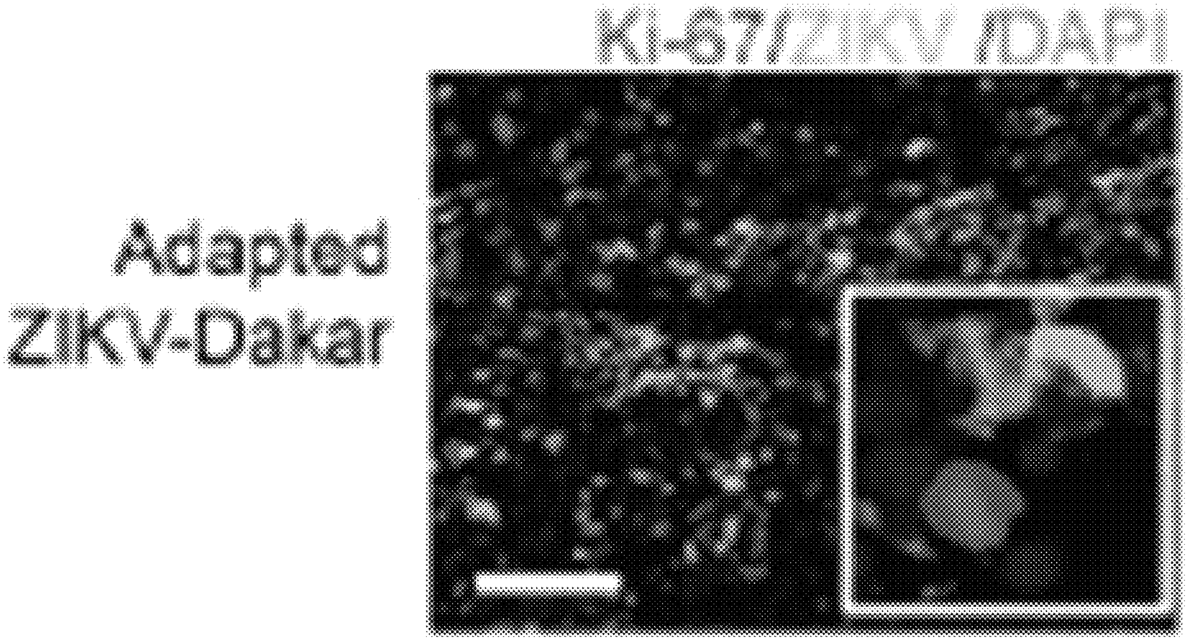
Figure 4R:
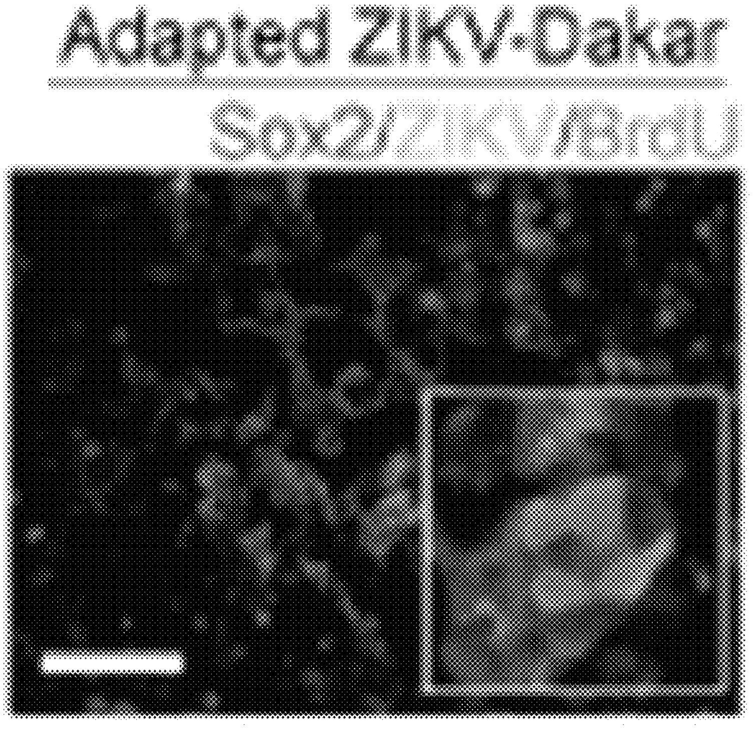
Figure 4S:
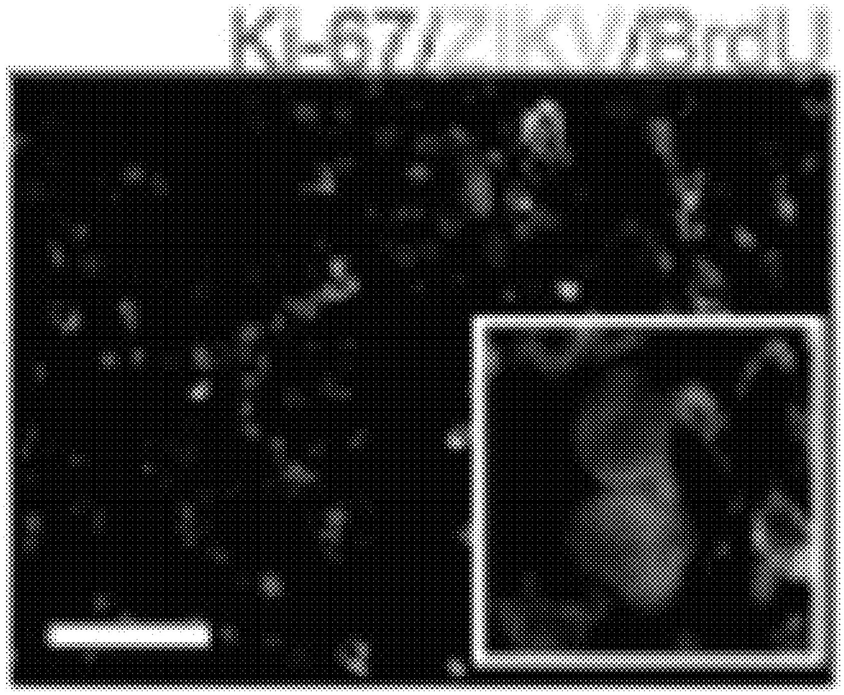
Figure 4T:
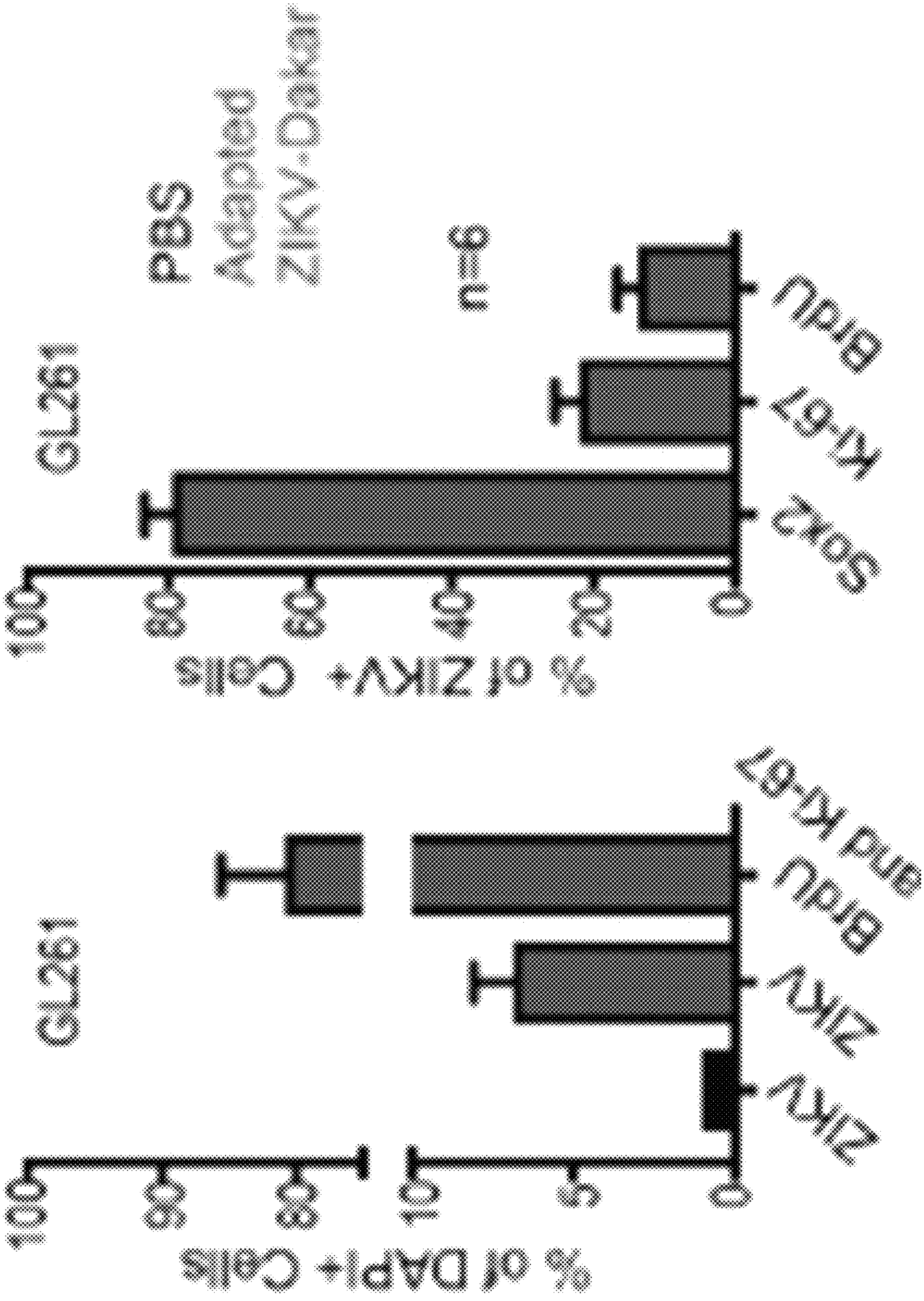
Figure 4U:
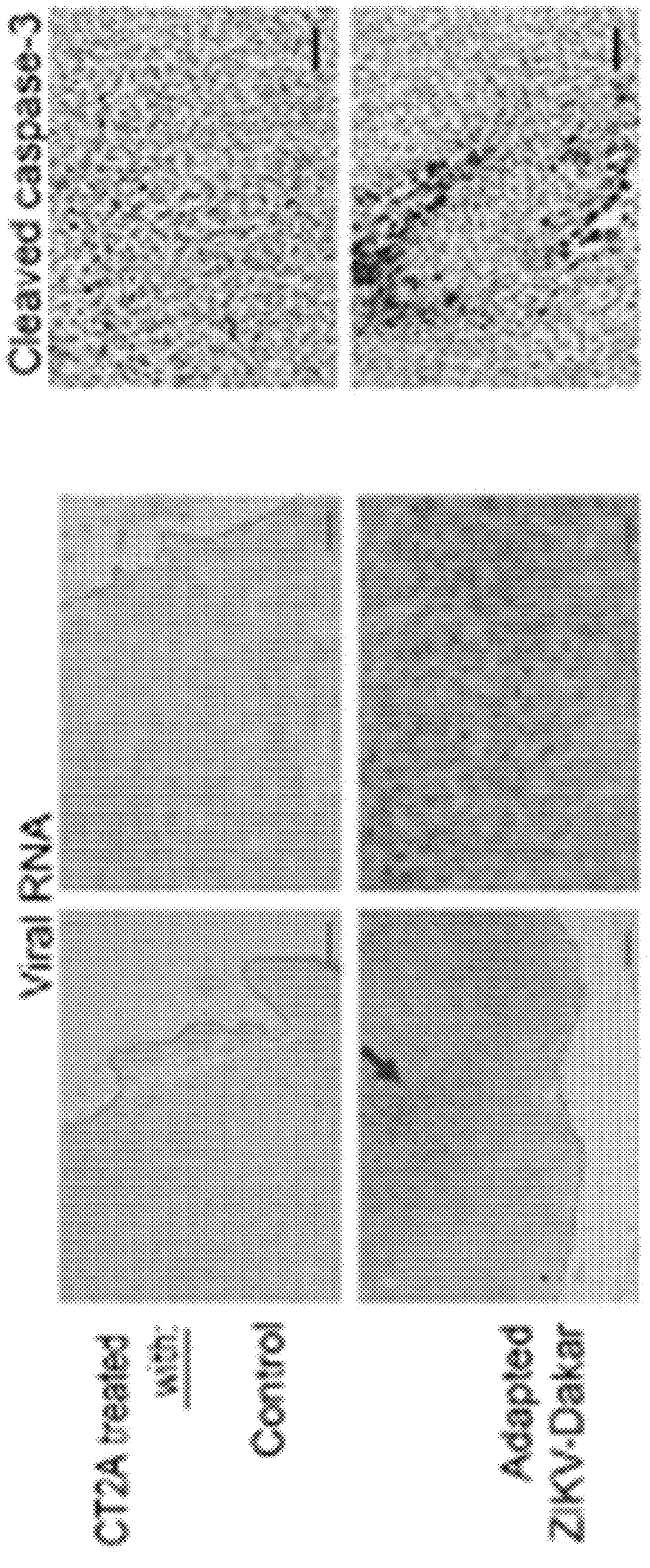

To assess the oncolytic effects of ZIKV in vivo, two murine GBMs (GL261 and CT-2A) grown in syngeneic hosts were generated. GBM cells were transduced with a luciferase reporter and permitted to form tumours, which was validated by bioluminescence imaging (FIG. 4C). Mice with evidence of tumour (one-week post implantation, FIG. 4D, FIG. 4E) were randomized into two groups and treated two weeks after implantation with either PBS control or mouse-adapted ZIKV-Dakar ($10^3$ FFU in 10 μl). Notably, ZIKV infection extended the lifespan of tumour-bearing mice significantly (FIG. 4J). Histological examination at one week after implantation of GBM showed that the virus-treated GBM (FIG. 4G and FIG. 4I) were smaller in volume, compared to PBS treated mice GBM (FIG. 4F and FIG. 4H). To see if the tumour bearing mice could benefit from higher dose of virus $10^5$ FFU of mouse-adapted ZIKV-Dakar were inoculated at one week post implantation. Intriguingly, the survival time of tumour bearing mice was prolonged compared to the control or the $10^3$ FFU dose (FIG. 4K). To determine the specificity of cell targeting, ZIKV antigen and markers of stem cells, proliferation and differentiation were stained (FIG. 4L-FIG. 4T). ZIKV infected approximately 6% of glioma cells at the endpoint (FIG. 4T), with the majority of these cells expressing the precursor markers, Sox2 (FIG. 4M, FIG. 4T). In contrast, $GFAP^+$ differentiated tumour cells were less infected (FIG. 4Q). Effects on proliferating cell populations were measured by Ki67 staining and BrdU treatment and staining. The majority of ZIKV-positive cells were negative for (>70%) Ki67 (FIG. 4O, FIG. 4T) or (>80%) BrdU (FIG. 4R-FIG. 4T). These results support the efficacy of ZIKV in vivo against quiescent, stem-like cells[13, 15].

Example 9: Whole Genome Sequencing of GSC and DGC

Figure 10A:
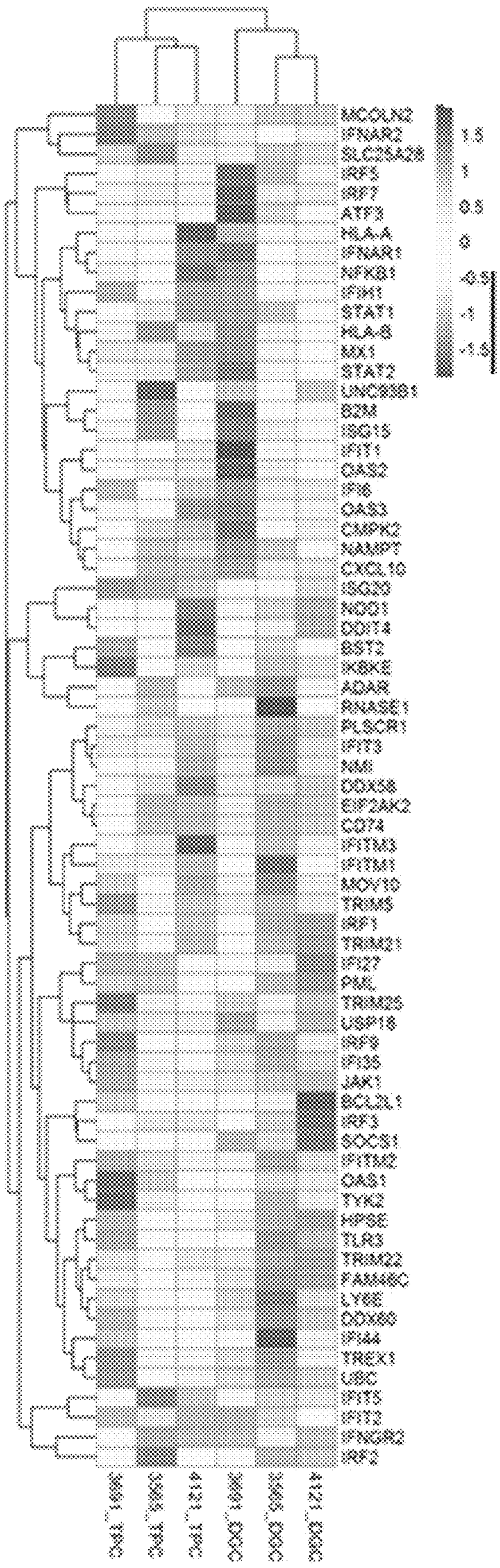
FIG. 10A, FIG. 10B, FIG. 10C, FIG. 10D, FIG. 10E, FIG. 10F and FIG. 10G show RNA-Sequencing of GSCs and DCCs reveals differences in IFN signalling.
Figure 10B:
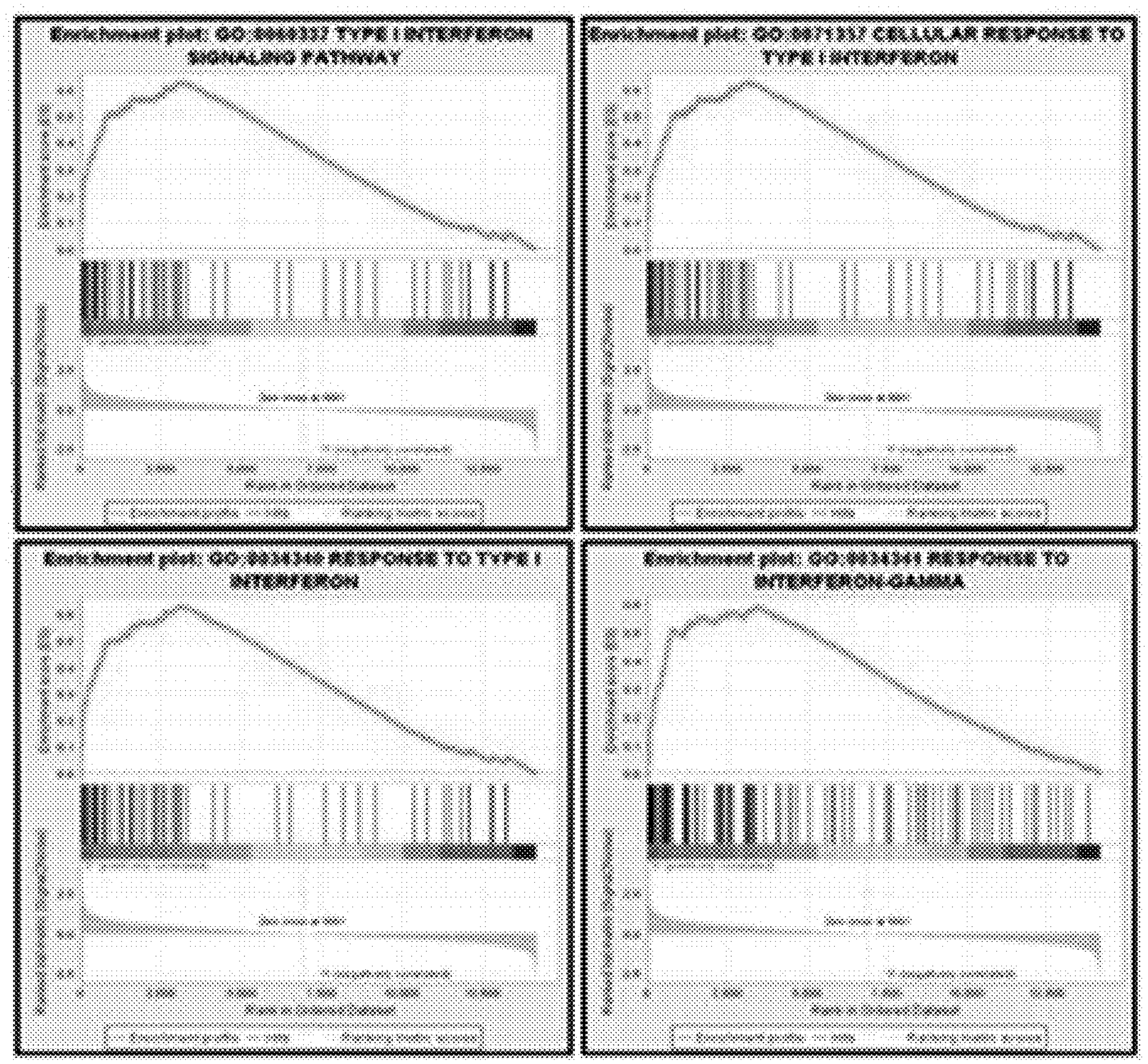
Figures 10C, 10D:
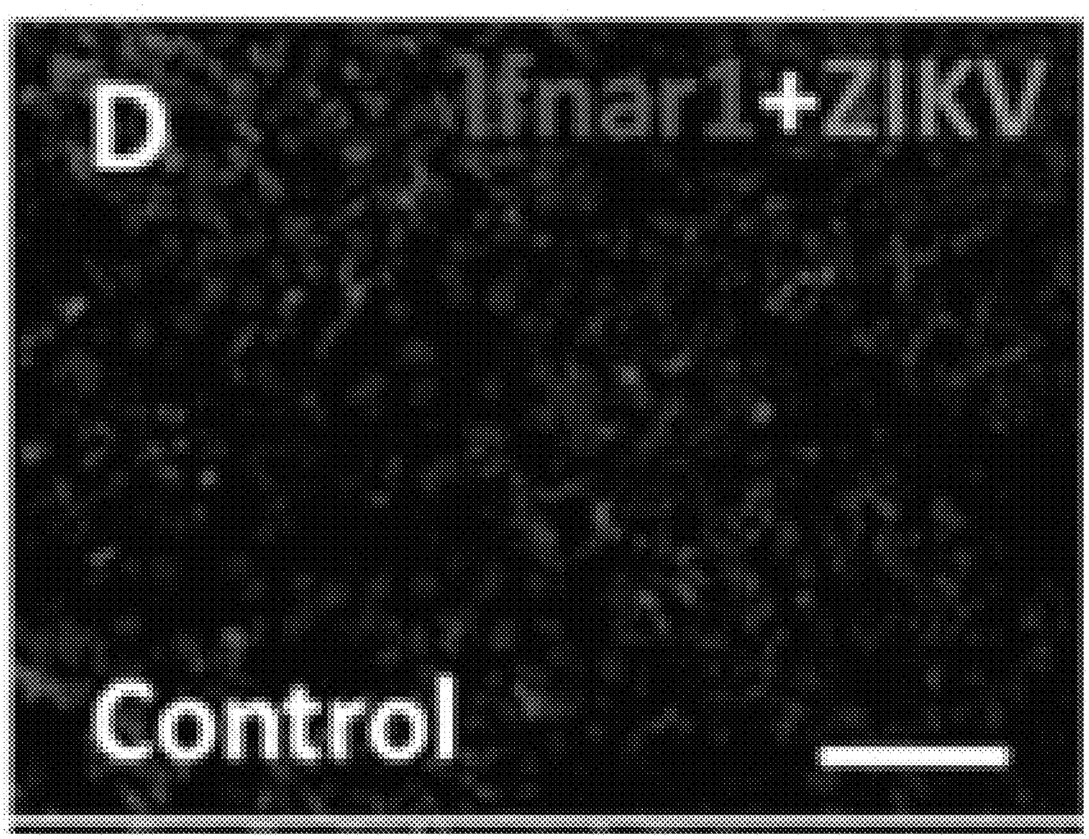
Figure 10E:
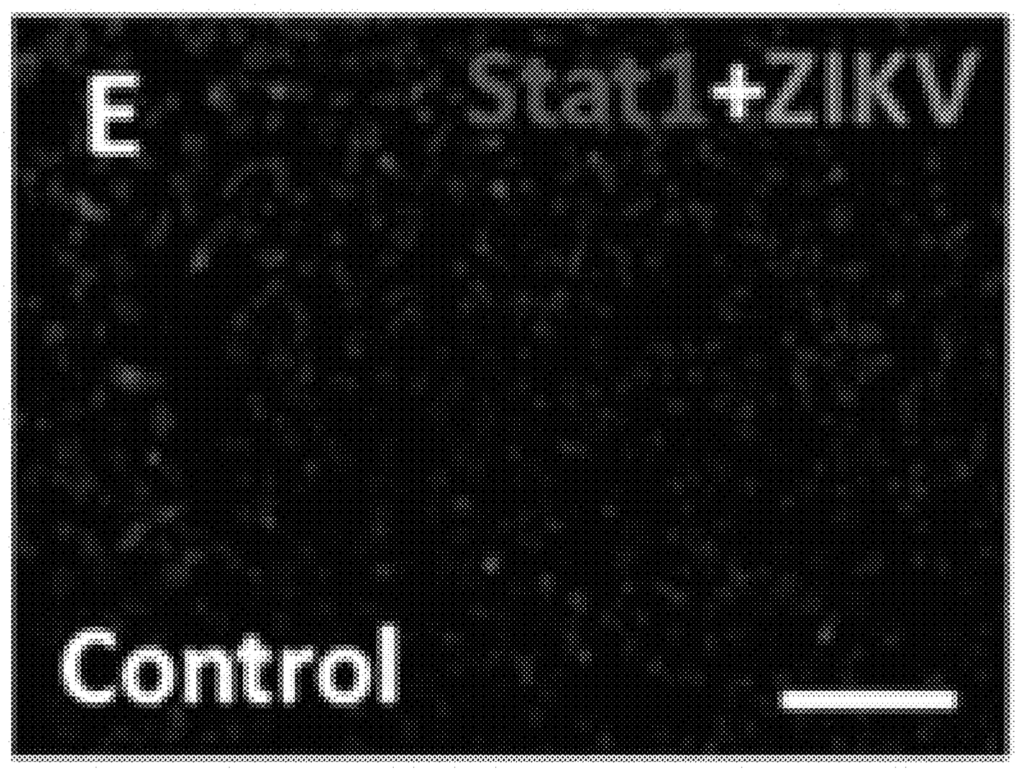
Figure 10F:
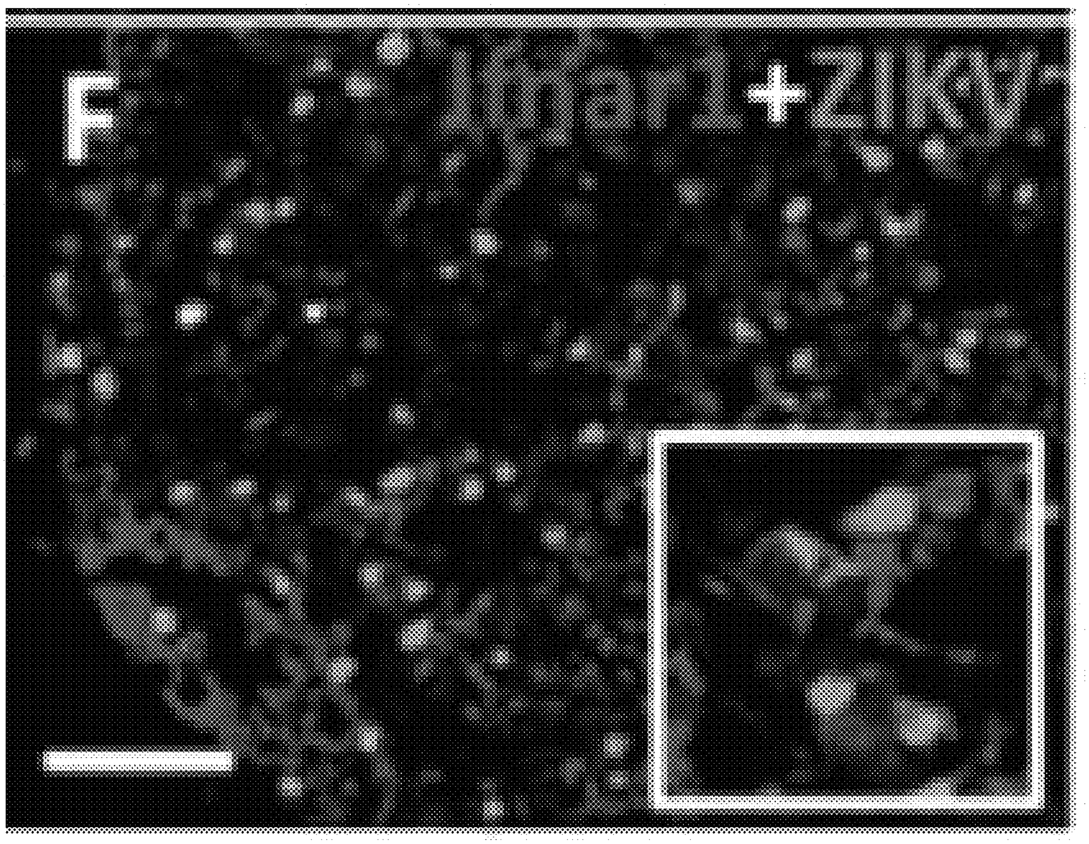
Figure 10G:
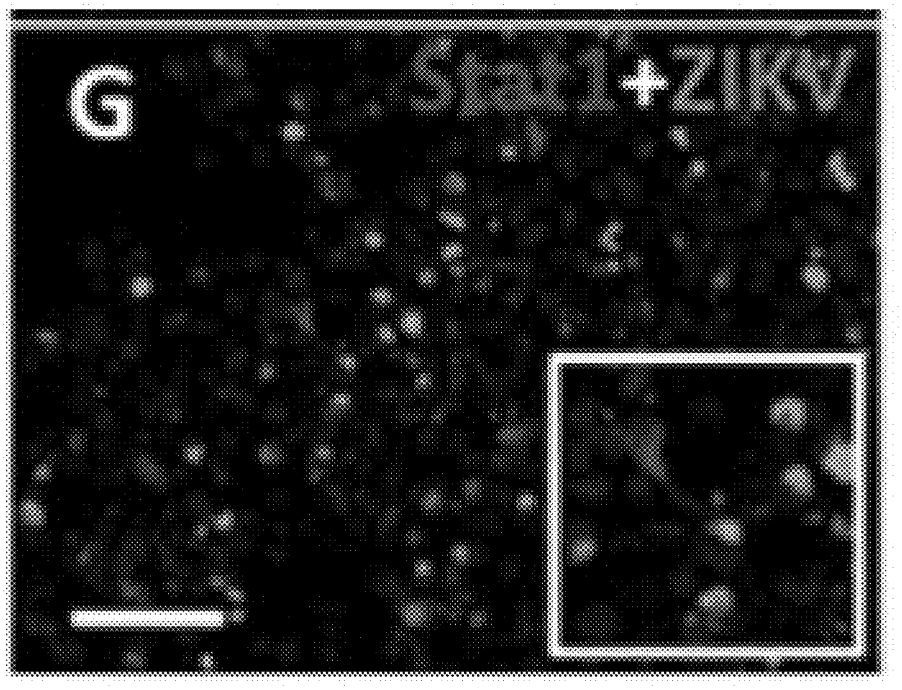
Figure 11A:
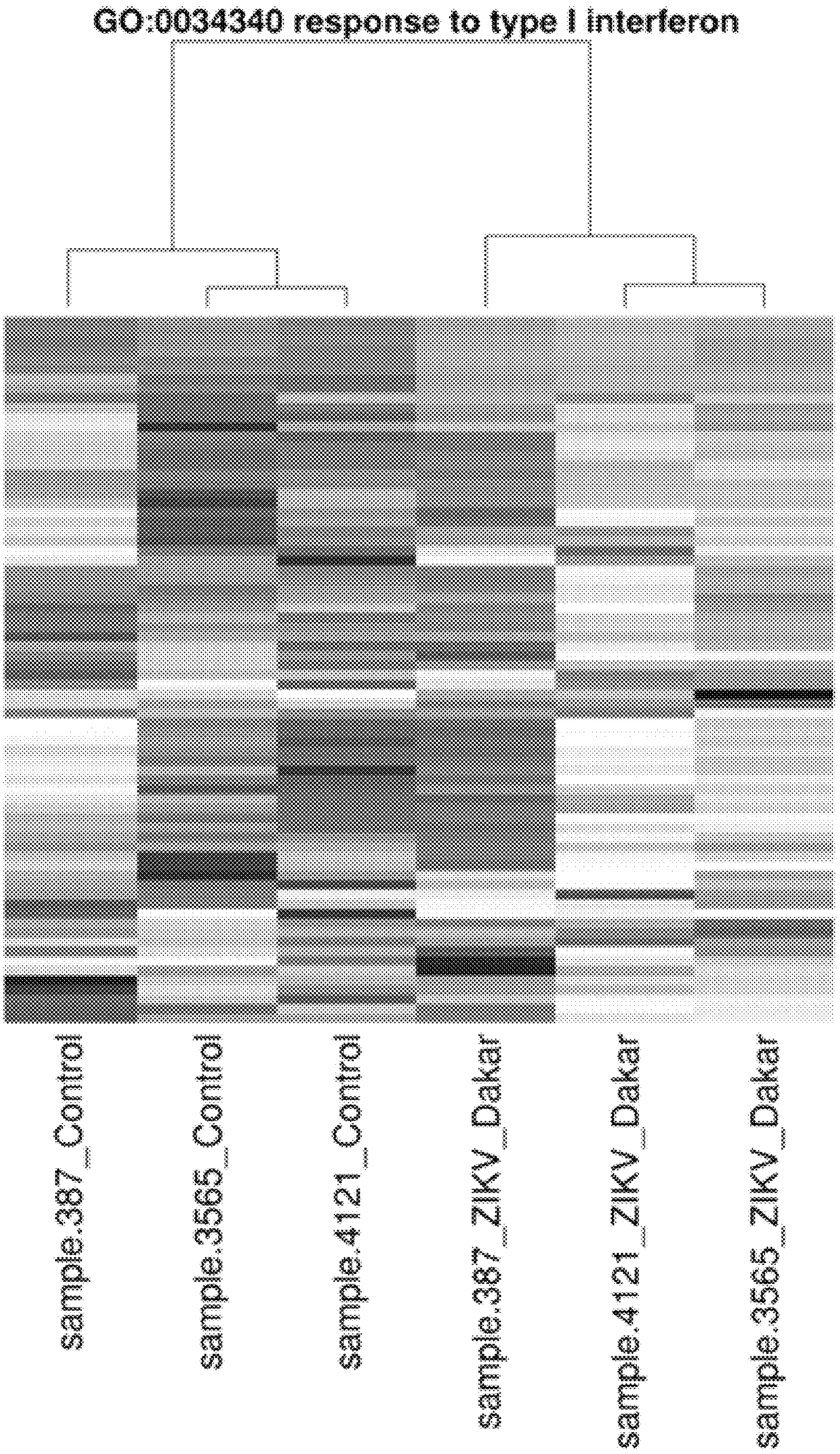
FIG. 11A, FIG. 11B, FIG. 11C and FIG. 11D shows RNA-Sequencing of GSCs infected with ZIKV-Dakar reveals transcriptional activation of ISGs.
Figure 11B:
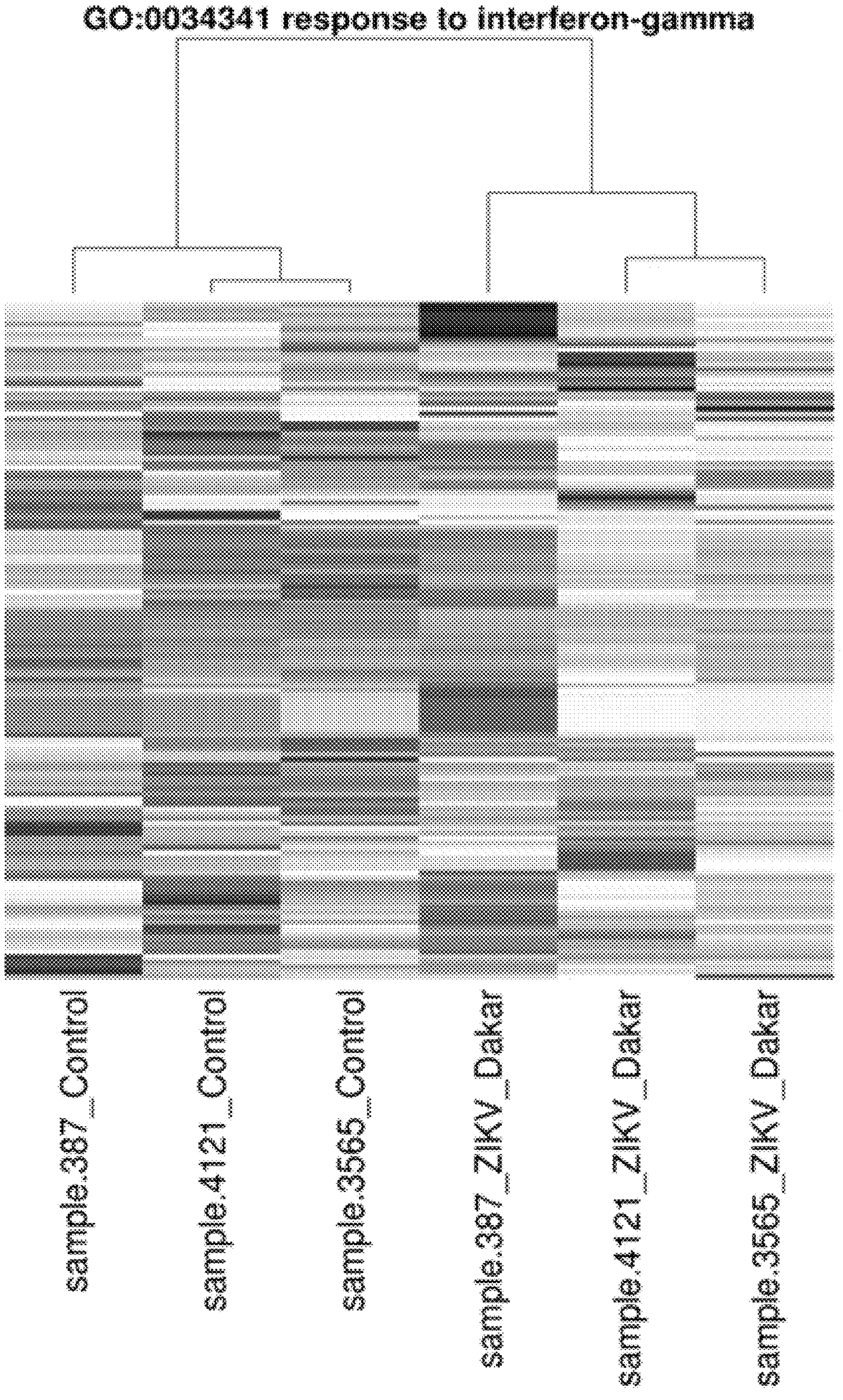
Figure 11C:
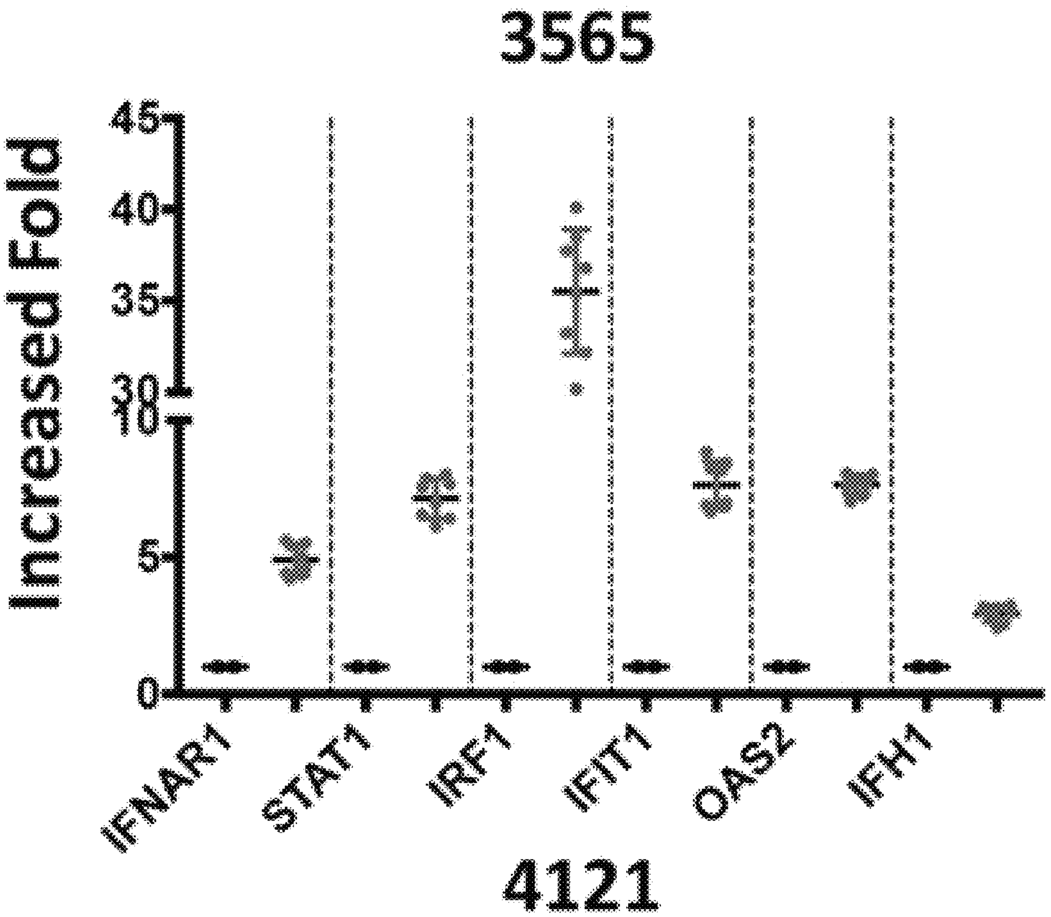
Figure 11C:
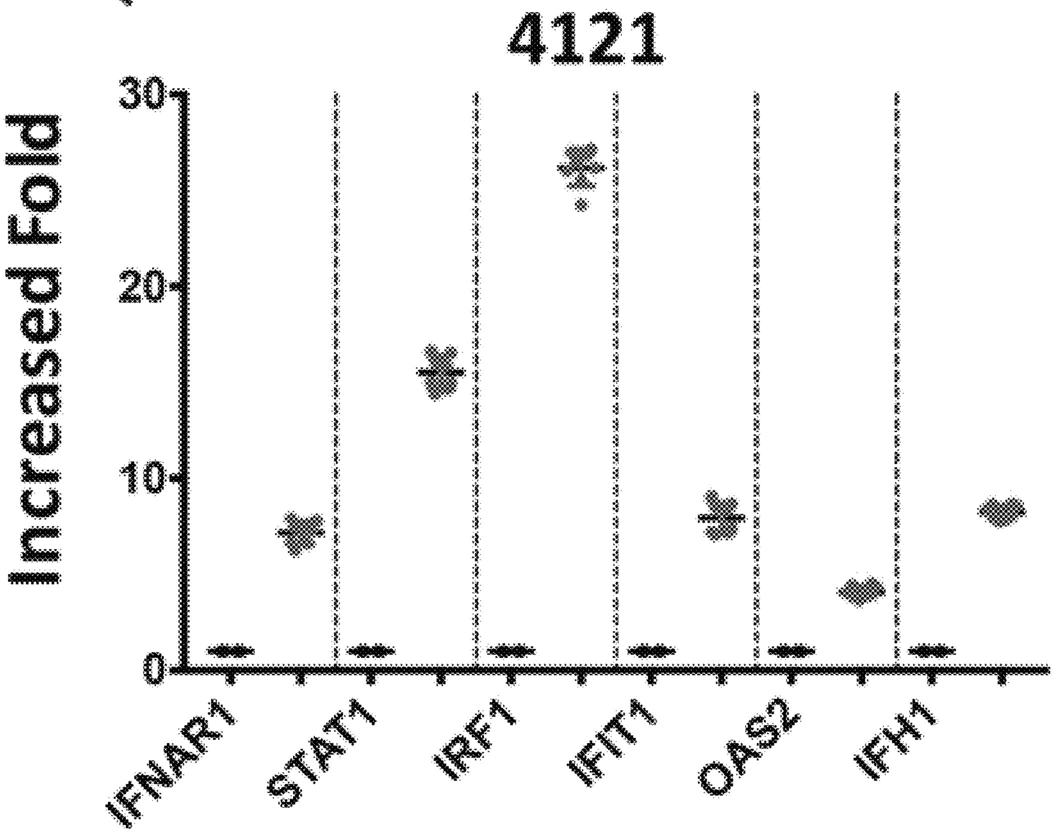
Figure 11D:
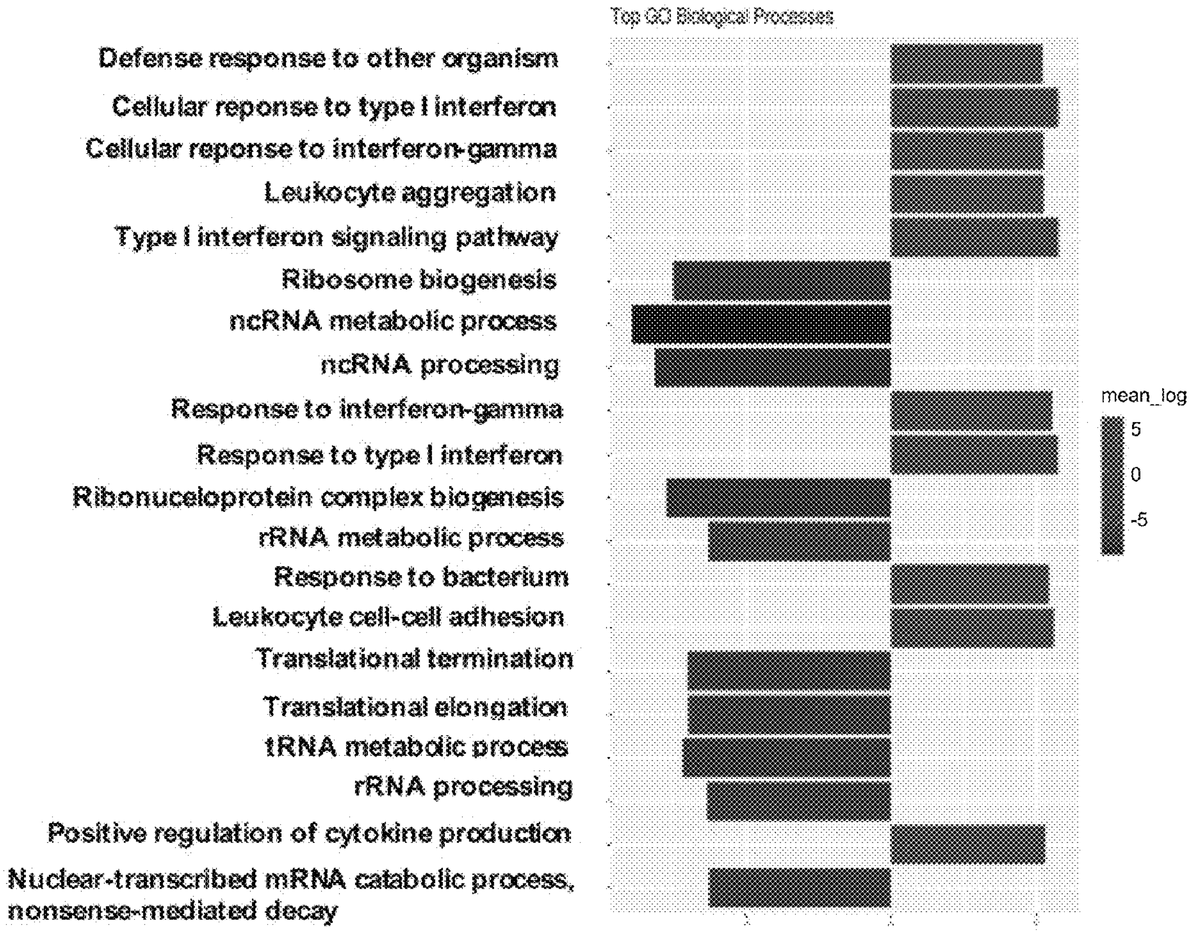

Although the mechanism by which ZIKV preferentially targets GSCs for infection and killing occur remains unknown, GSCs can strongly suppress anti-tumour immune responses[3]. To address the possible target specificity of ZIKV, whole transcriptome RNA sequencing (RNA-seq) was performed, comparing GSCs and DGC and defined a group of differentially expressed immune genes including type I IFN-stimulated genes (ISGs) (FIG. 10). Type I IFN responses are critical for controlling viral infection in regions of the brain[25]. GESA enrichment maps of type I and II IFN signalling pathway genes revealed that many ISGs were upregulated in DGCs (FIG. 10*a*-FIG. 10C). Staining for Ifnar1 or Stat1 with ZIKV E showed that an absence of colocalization in human GBM cells (FIG. 10D-FIG. 10G). To further elucidate the signalling pathways that regulated ZIKV targeting of GSCs, we infected three GSC models (T387, T3565, T4121) with the ZIKV-Dakar strain for 48-56 hours, and then performed RNA-seq. IFN signalling was the top Gene Ontology pathway activated by ZIKV infection (FIG. 11). The RNA-seq data were validated by qPCR (FIG. 11C). As ZIKV cannot fully antagonize ISGs, IFN responses may contribute to the specificity of ZIKV inhibiting GSC growth, but more limited killing of DGCs or normal brain neurons and glial cells.

Figure 5A:
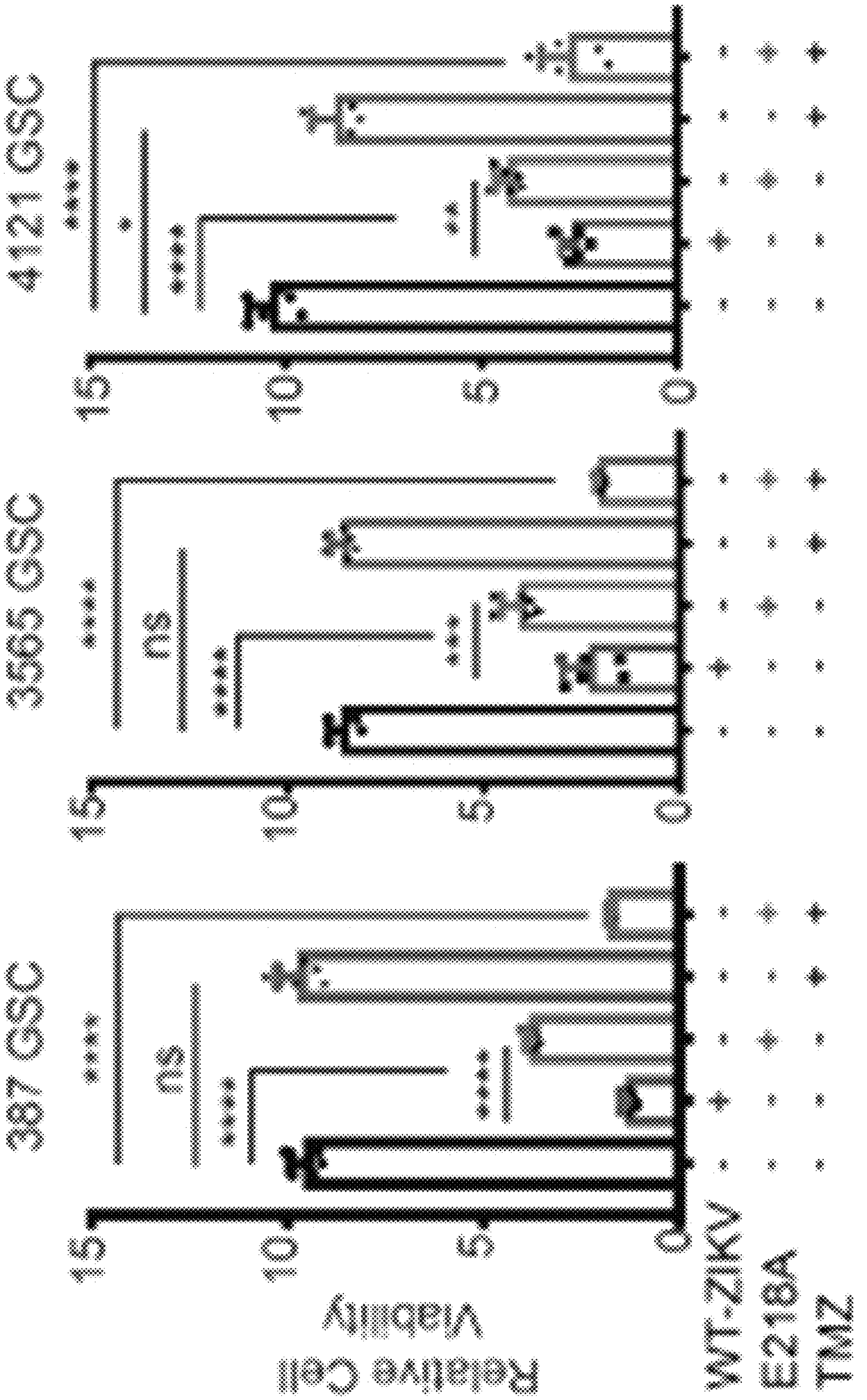
FIG. 5A, FIG. 5B, FIG. 5C, FIG. 5D, FIG. 5E, FIG. 5F, FIG. 5G, FIG. 5H, FIG. 5I and FIG. 5J show ZIKV-E218A inhibits the growth of GSCs and has additive effects with temozolomide.
Figure 5B:
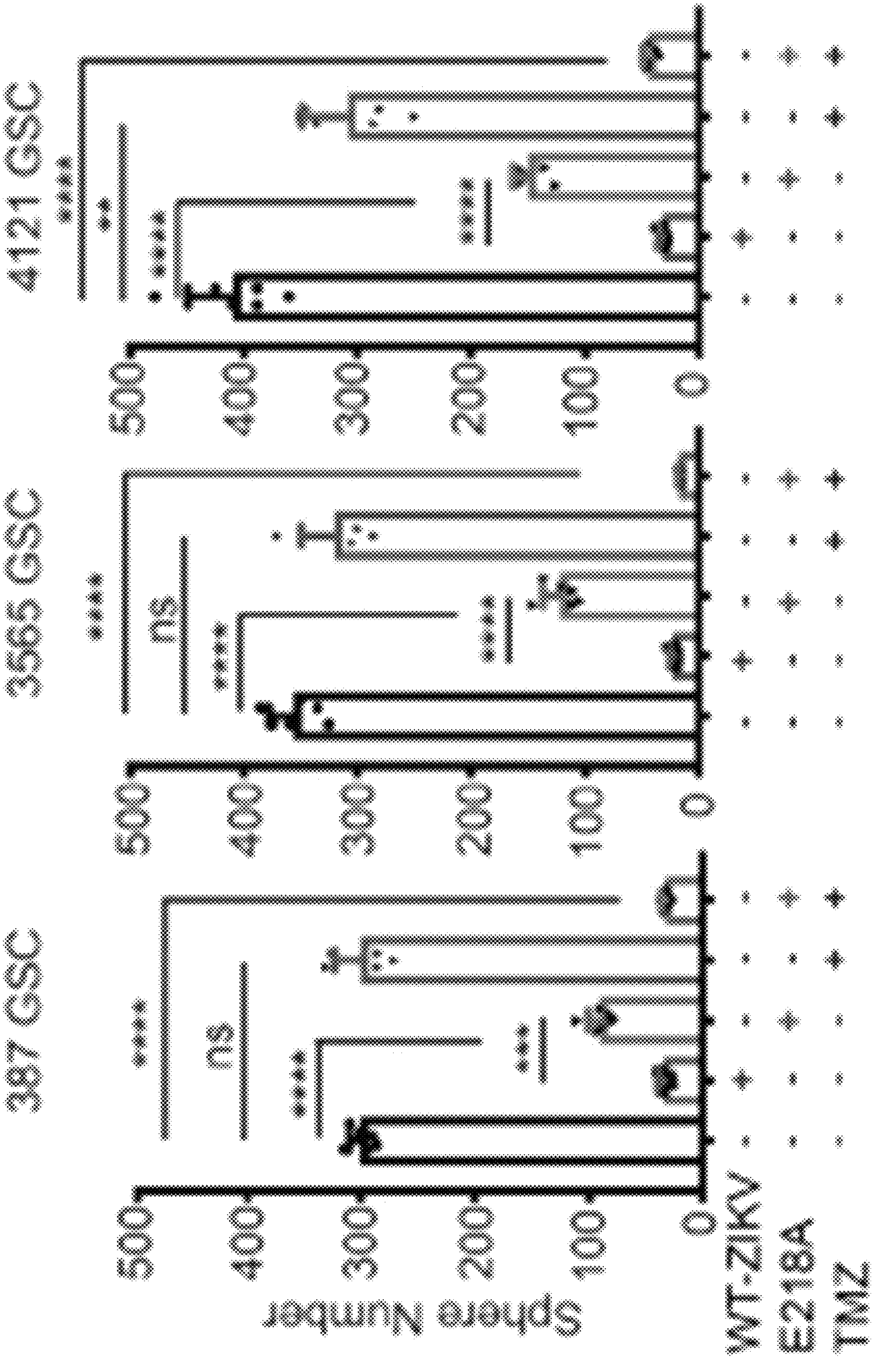
Figure 5C:
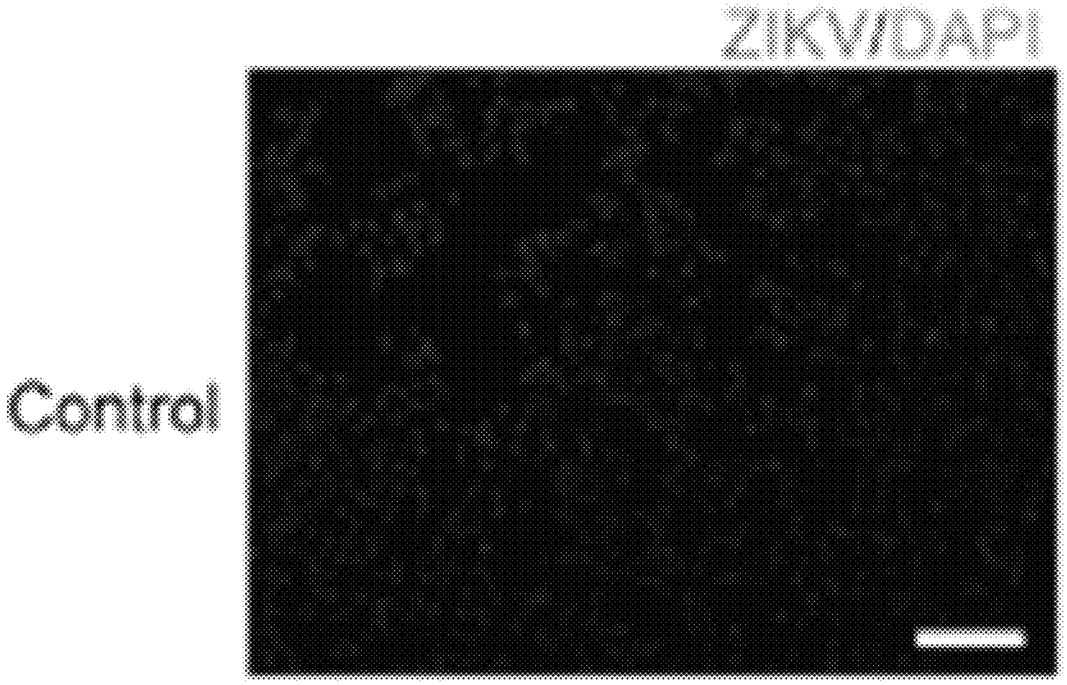
Figure 5D:
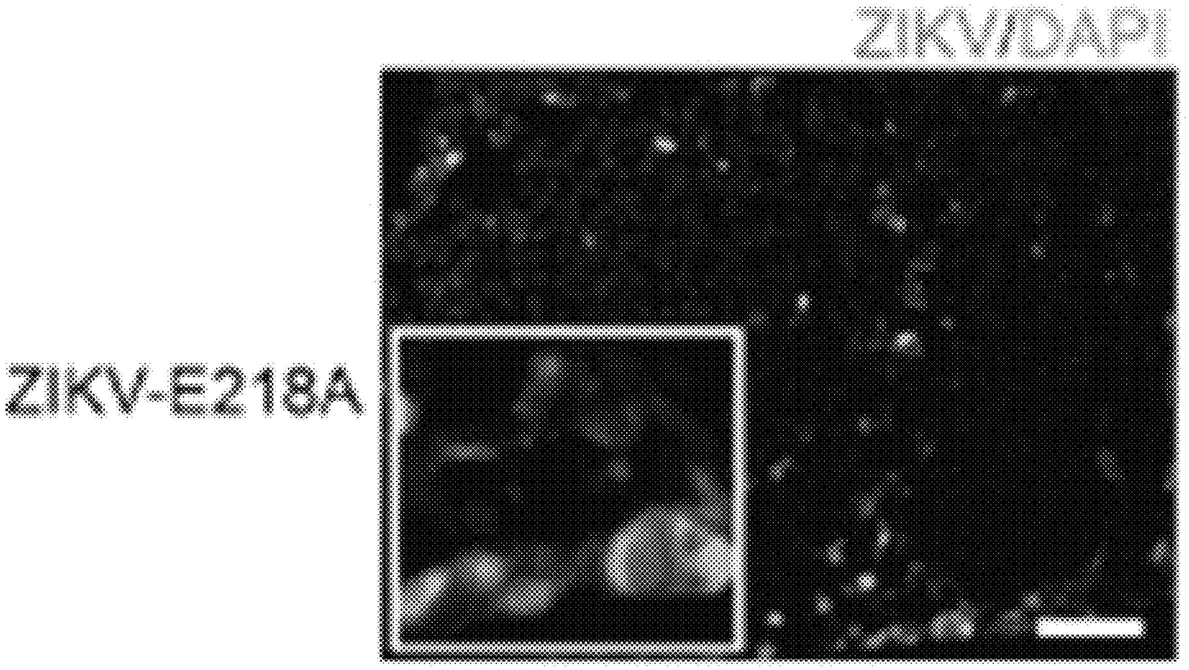
Figure 5E:
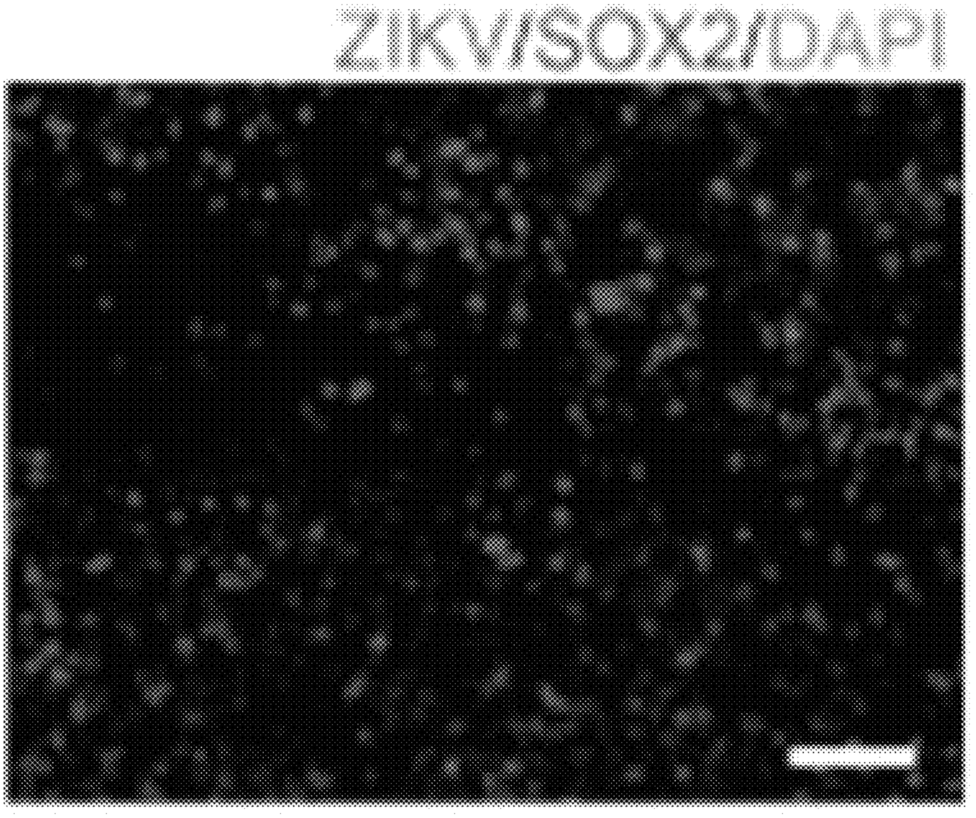
Figure 5F:
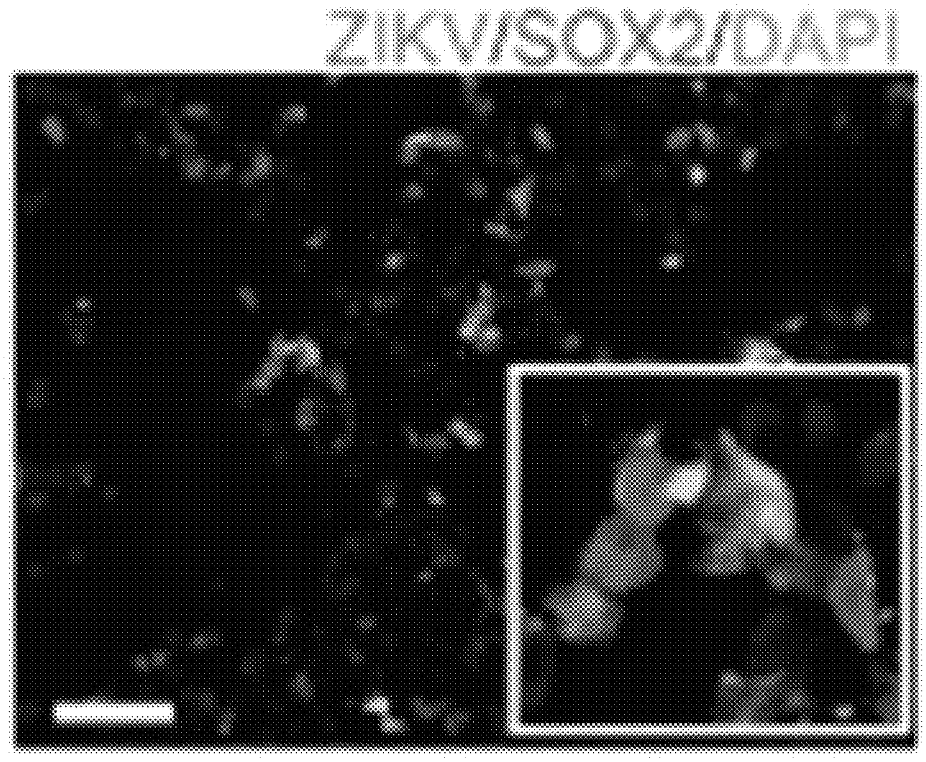
Figure 5G:
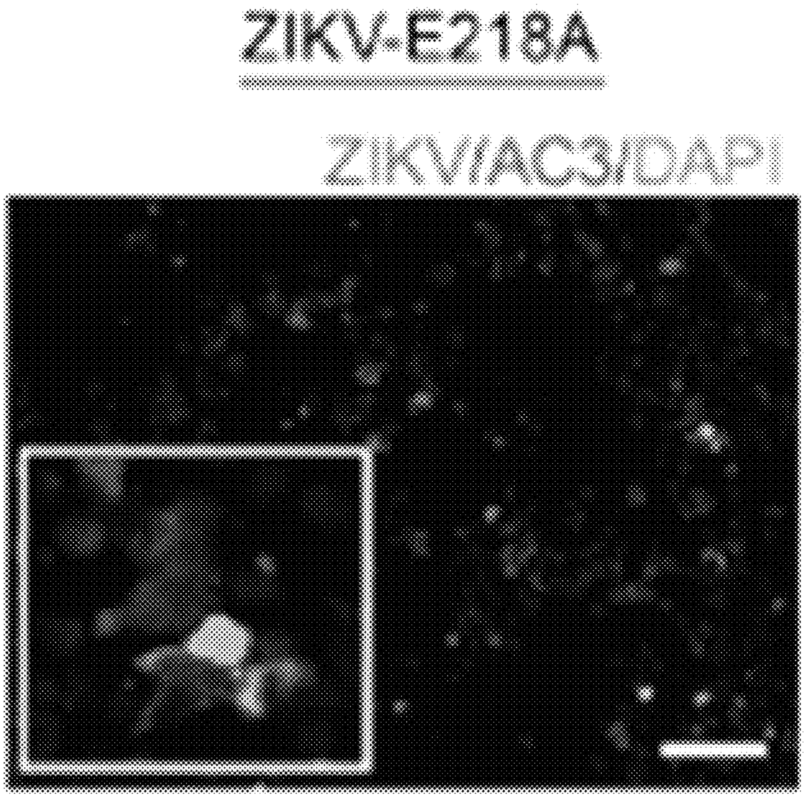
Figure 5H:
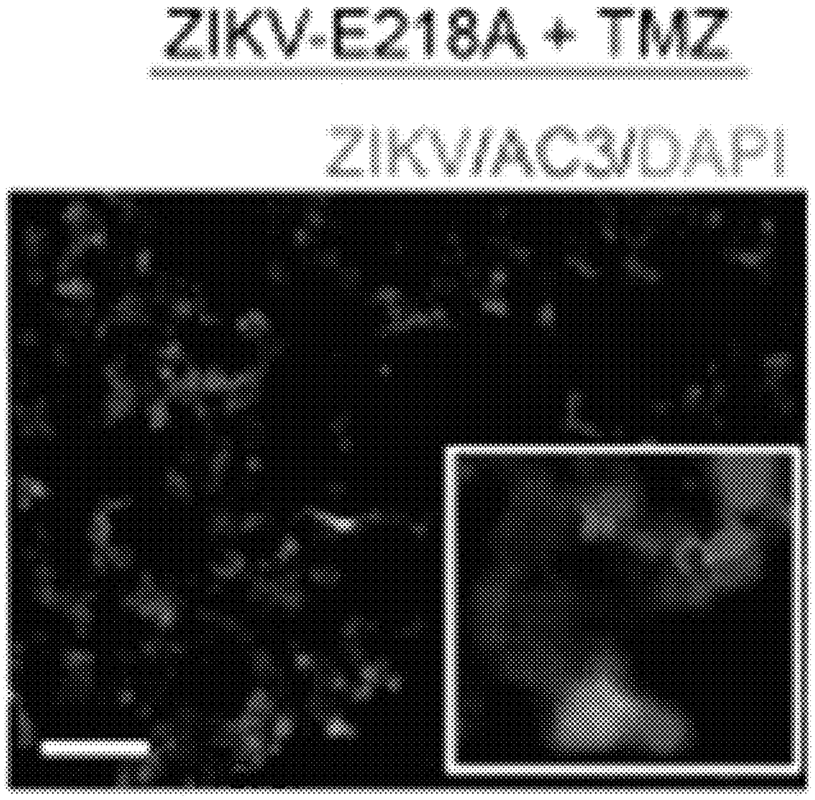
Figure 5I:
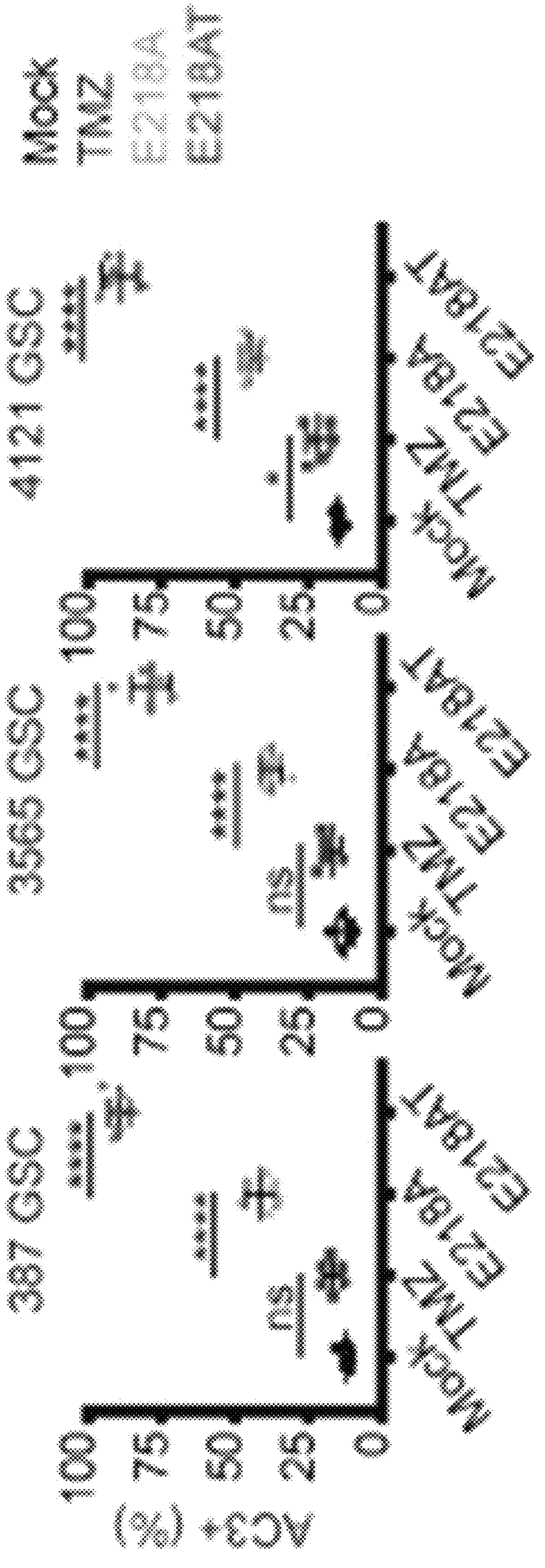
Figure 5J:
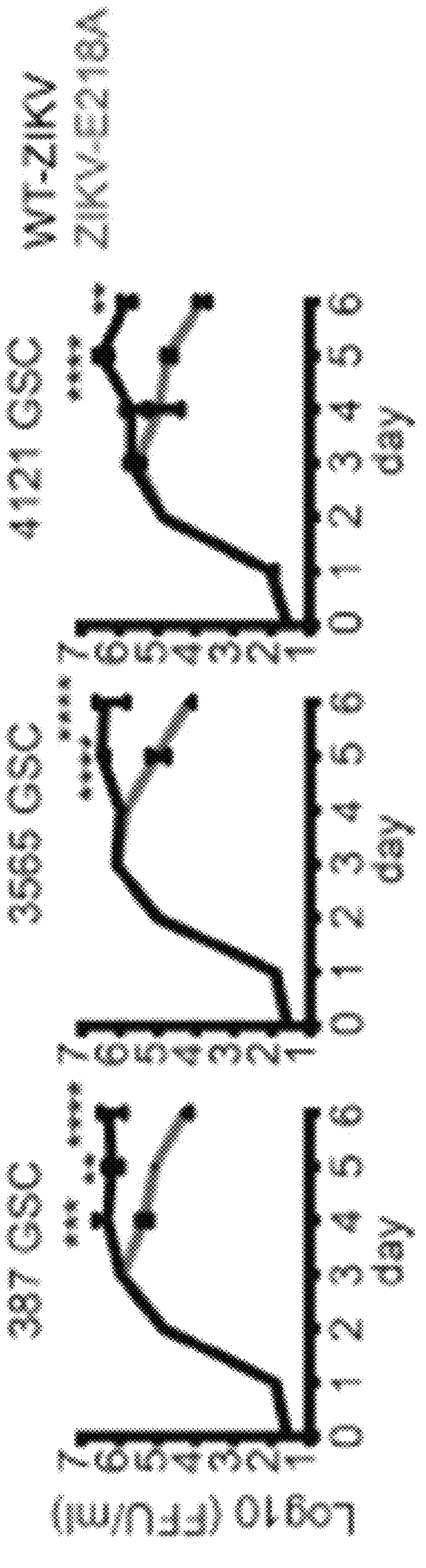
Figure 12A:
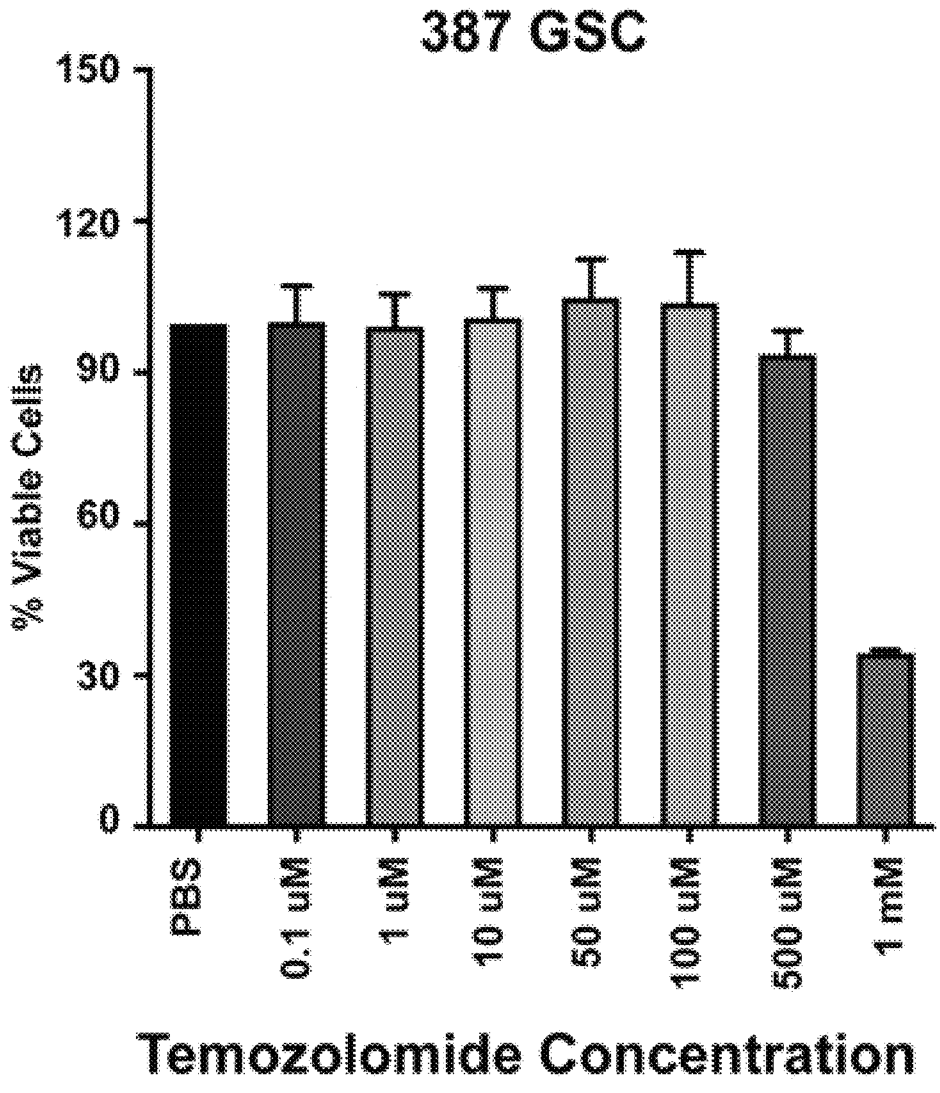
FIG. 12 shows a Temozolomide cytotoxicity assay. Two GSC lines (387 and 3565) were treated with indicated concentrations of temozolomide for 7 days. Relative cell number was assayed by CellTiter-Glo on day 7 and normalized to PBS control.
Figure 12B:
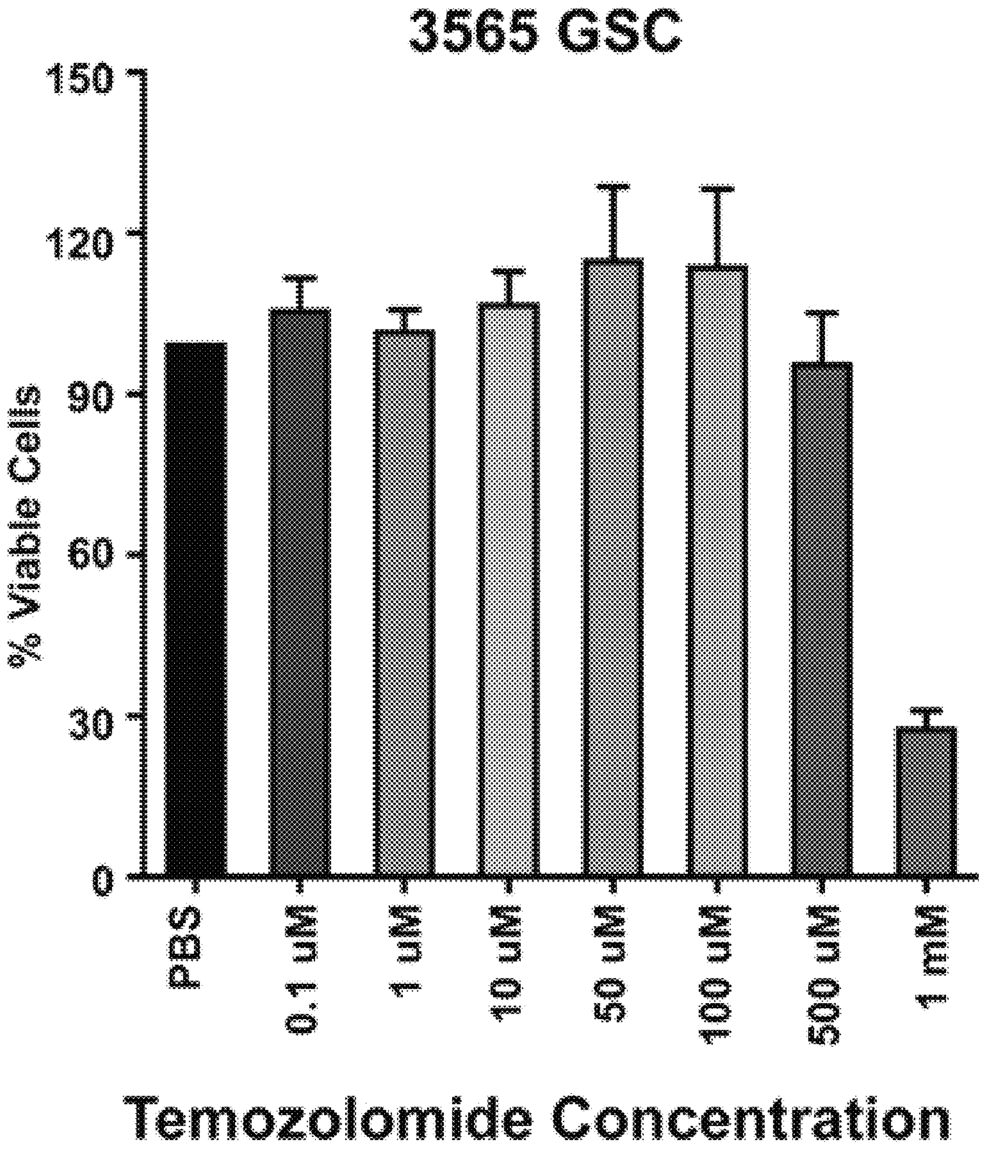
Figure 13:
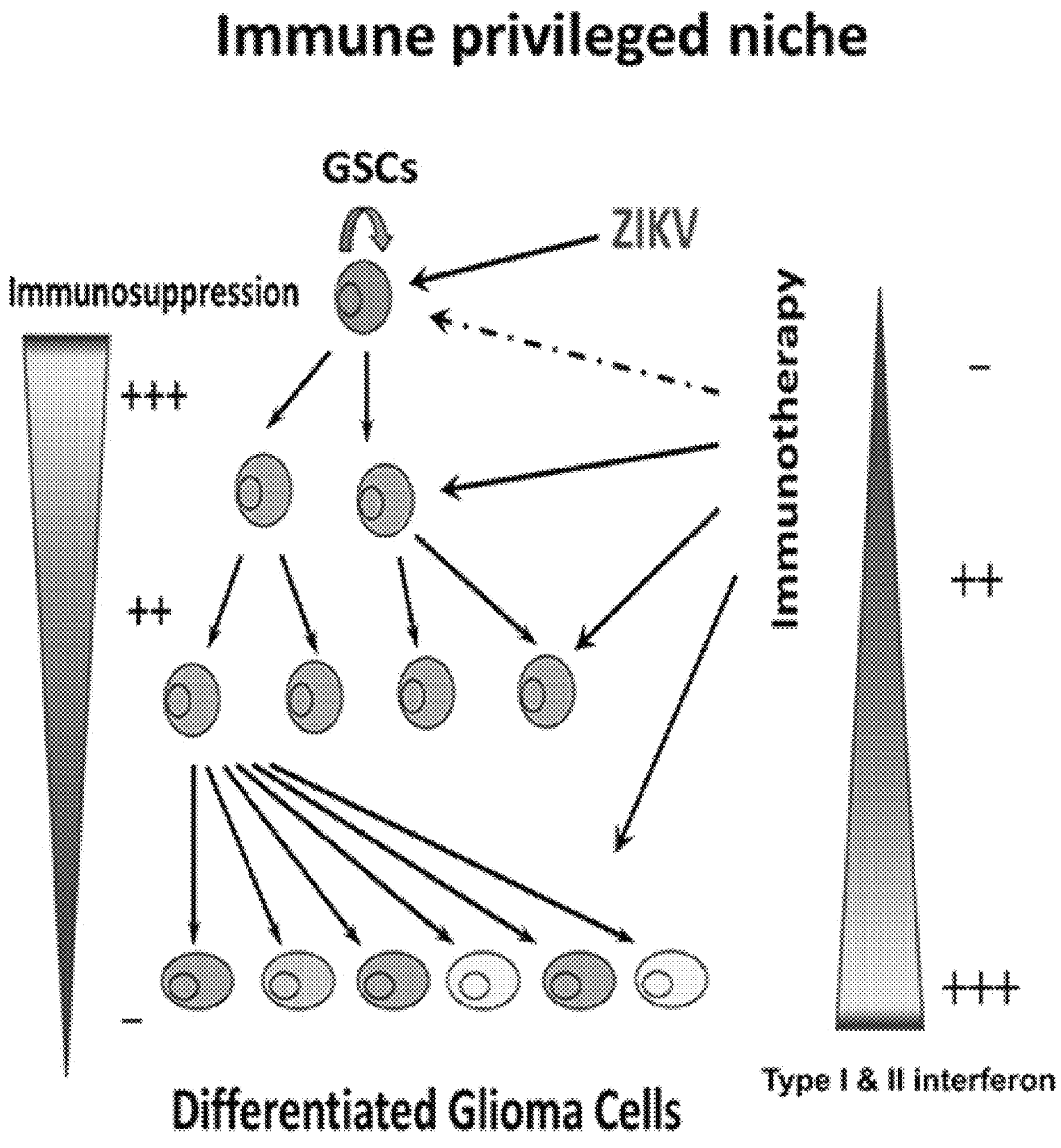
FIG. 13 shows a model of GSCs as an immune privileged niche. Therapeutic refractoriness of GSCs residing in glioblastoma is attributed to the immunosuppressive microenvironment that protects malignant GSCs from cytotoxic effects of the immune response. We found that the downregulation of type I and II IFN signalling in human GSCs, which plays a key role in formation of the immune-privileged niche. This provides a rationale for infection with oncolytic ZIKV to attenuate GSC viability and thus suggests an alternative approach to treat human glioblastomas.

Example 10: Comparing Tumoricidal Effects of Wild-Type ZIKV and its Recombinant Derivative ZIKV-E218A Most oncolytic viruses require genetic engineering to maximize efficacy against tumour cells and minimize toxicity to normal cells[8-10]. It was previously reported that a mutation of the flavivirus NS5 gene (E218A) sensitizes the virus to translational inhibition by type I IFN and IFIT1[30], resulting in attenuated replication in cells responsive to type I IFNs. As such, and to potentially enhance safety of an oncolytic ZIKV, the tumoricidal effects of a wild-type ZIKV (FSS13025, Cambodian 2010) and its recombinant derivative ZIKV-E218A was compared against three GSC models[14] (FIG. 5). Both the parental and E218A mutant ZIKV strains displayed anti-GSC activity, as measured by cell viability and sphere formation (FIG. 5A, FIG. 5B). Although the parental ZIKV strain was more potent in reducing GSCs growth, both strains were effective. Both the parental strain and E218A attenuated strain preferentially infected SOX2-positive tumour cells and induced apoptosis (FIG. 5C-FIG. 5H). As GSCs often display resistance to chemotherapy, including the standard-of-care temozolomide (TMZ)[1, 2] the combinatorial efficacy of TMZ and ZIKV E218A was evaluated. An effective TMZ concentration (250 μM) was determined by cytotoxicity assay (FIG. 12). Whereas TMZ alone had limited effect against GSCs, ZIKV-E218A combined with TMZ for one week showed greater anti-tumour efficacy (FIG. 5A, FIG. 5B) and induction of apoptosis (FIG. 5G-FIG. 5I). In consideration of safety of ZIKV-E218A for GBM patients, its replication capacity over a one-week time course was tested. ZIKV-E218A had self-limited replication capacity in three GSC models (T387, T3565, T4121) relative to the parental ZIKV strain (FIG. 5J). These data suggest that engineered mutant ZIKV strains may promote infection and lysis of GSCs with less toxicity to surrounding differentiated neuronal cells.

Materials and Methods for Examples 1-10

Ethics Statement

This study was carried out in accordance with the recommendations in the Guide for the Care and Use of Laboratory Animals of the National Institutes of Health. The protocols were approved by the Institutional Animal Care and Use Committee at the Washington University School of Medicine (Assurance number A338101). Inoculations were performed under anaesthesia induced and maintained with ketamine hydrochloride and xylazine, and all efforts were made to minimize animal suffering.

Isolation and Culture of Glioblastoma Stem Cells and Differentiated Cells.

Glioblastoma tissues were obtained from excess surgical materials from patients at the Cleveland Clinic after neuropathology review with appropriate informed consent, in accordance with an IRB-approved protocol (2559). To prevent culture-induced drift, patient-derived subcutaneous xenografts were generated in NOD-scid $IL2Rg^{null}$ mice (Jackson Laboratory) and maintained as a recurrent source of tumour cells for study. Upon xenograft removal, a papain dissociation system (Worthington Biochemical) was used to dissociate tumours according to the manufacturer's instructions. Cells were then cultured in Neurobasal complete media (Neurobasal medium (Life Technologies) supplemented with 1×B27 without vitamin A (ThermoFisher), 2 mM L-glutamine (ThermoFisher), 1 mM sodium pyruvate (ThermoFisher), 10 ng/ml basic fibroblast growth factor (bFGF), and 10 ng/ml epidermal growth factor (EGF) (R&D Systems). Since no marker uniformly defines glioblastoma stem cells (GSCs), we used several criteria to validate GSCs. Both GSCs and differentiated glioblastoma cells (DGCs) were derived immediately after dissociation or after transient xenograft passage in immunocompromised mice using prospective sorting followed by assays to confirm stem cell marker expression, sphere formation, and secondary tumour initiation[20]. For experiments using matched GSCs and DGCs cultures, we segregated AC133 marker-positive and marker-negative populations using CD133/1 antibody conjugated magnetic beads (Miltenyi Biotech), as previously described[20]. The GSCs phenotype was validated by stem cell marker expression OLIG2 (R&D, AF2418, stock: 0.2 mg/ml, working dilution 1/1000) and SOX2 (R&D, AF2018, stock: 0.2 mg/ml, working dilution 1/1000), functional assays of self-renewal (serial neurosphere passage), and tumour propagation using in vivo limiting dilution.

Proliferation and Sphere Formation Assay

Cell viability was measured using Cell-Titer Glo (Promega). After addition of ZIKV, all data were normalized to day 0, and expressed as relative cell number. Neurosphere formation was measured as previously described[20]. Briefly, GSCs (1,000 cells) were plated into 96-well plates. The presence and number of neurospheres in each well were recorded on days 0, 3, 5, 7.

ZIKV Strains

ZIKV Dakar 41519 strain (Senegal, 1984) and Brazil (Paraiba 2015) were provided by the World Reference Center for Emerging Viruses and Arboviruses (University of Texas Medical Branch) and S. Whitehead (National Institutes of Health, Bethesda, Md.). Parental and ZIKV-E218A (mutation in NS5 gene) were generated from an infectious cDNA clone of the Cambodian strain FSS13025 (2010) (Accession No. KU955593.1) using site-directed mutagenesis, as described previously[14]. ZIKV stocks were propagated in Vero cells after inoculating at an MOI of 0.01 and incubating for 72 h. Viral titres were quantified by plaque assay as previously described[31] and stocks were stored at −80° C. in single-use aliquots. ZIKV strain Dakar 41519 was passaged three times in $Rag1^{-/-}$ mice to create a mouse-adapted, more pathogenic variant of ZIKV-Dakar[31].

Cells

Vero (African Green Monkey kidney epithelial, ATCC CCL-81) cells, BV2 cells (microglia), GL261 (mouse glioma), GL26 (mouse glioma, a gift from Maria Castro, University of Michigan), CT2A[32] (mouse glioma, Thomas Seyfried, Boston College), NM55, NM177, or DGCs were maintained in Dulbecco's Modified Eagle Medium supplemented with 10% foetal bovine serum (Atlas). For animal studies, GL261 and CT2A cells were virally transduced with a luciferase construct, and selected with puromycin (1 μg/mL). GSCs, epilepsy tissues and glioblastoma tissues were maintained in Neurobasal complete media. All cells were incubated at 37° C. in humidified incubators supplemented with 5% CO2. All cell lines were negative for *mycoplasma*. Human brain specimens were not tested for *mycoplasma*.

In Vitro Viral Infection and Drug Treatment Experiments

GSCs were plated at 1,000 cells/well in 96-well tissue culture treated plates (TPP) and allowed to attach overnight. For viral infection and growth inhibition assays, wild-type ZIKV-Dakar, ZIKV-Brazil, or mouse adapted ZIKV-Dakar were used at an MOI of 5. For combined drug+virus therapy experiments, wild-type parental ZIKV-Cambodia and its derivative ZIKV-E218A were used for infection. Temozolomide (TMZ, Sigma) was dissolved in PBS and diluted in Neurobasal complete media. ZIKV was added at an MOI of 5 by itself or 4 h before TMZ (250 μM) addition. Cell supernatants were stored at −80° C. for subsequent analysis.

Infectious Virus Titration

Focus formation assays (FFA) were performed with Vero cells as described previously[31]. Supernatant samples containing ZIKV were serially diluted and added to Vero cell monolayers in 96-well plates. Virus was allowed to infect for 2-4 h and then 100 μl of a 1:1 solution of 2×DMEM with 8% FBS and 2% methylcellulose was added to cells. Plates were incubated for 48 h, then fixed by the addition of 2% paraformaldehyde (PFA). Cells then were incubated with 500 ng/mL of the flavivirus cross-reactive mouse monoclonal antibody E60[31] for 2 h at room temperature. After incubation for 1 h with a 1:5,000 dilution of horseradish peroxidase (HRP)-conjugated goat anti-mouse IgG (Sigma), foci were detected by addition of TrueBlue substrate (KPL). Foci were analysed with a CTL Immunospot instrument.

Histology

Sections (5 μm) of paraffin-embedded tissues were analysed for haematoxylin and eosin (H & E, Thermo Fisher Scientific), Picro-Sirius Red (Sigma-Aldrich) and Masson's Trichrome (Diagnostic Biosystems) according to the manufacturer's instructions. 4×, 10× and 20× images were captured on a Nikon Eclipse 80i bright field microscope (Nikon). Image analysis was performed by thresholding for positive staining and normalizing to total tissue area, using ImageJ (NIH) and Metamorph v7.7.0.0 (Molecular Devices) software[33].

Immunofluorescence Staining and Microscopy

Cryosections (8 μm-thick) were air-dried and fixed in 4% PFA for 15 min before being washed twice with PBS. Tissues were permeabilized by incubating the slides with 1% Triton X-100 in PBS for 15 min at RT, and peroxidase-quenched by incubating in 1% hydrogen peroxide (Invitrogen) for 10 min at RT. After blocking for 1 h at RT in blocking buffer (5% goat serum, 2.5% BSA in 1×PBS), slides were incubated overnight in a humidified chamber at 4° C. with primary antibodies, ZIKV (Millipore, AB10216, working dilution 1/1000), Sox2 (Millipore, AB5603, stock: 1 mg/ml, working dilution 1/400), Ki-67 (Millipore, AB9620, working dilution 1/400), GFAP (Sigma, G9269, working dilution 1/1000), PAX6 (Abcam, #AB5790, stock: 1 mg/ml, working dilution 1/200), NeuN (Abcam, AB177487, working dilution 1/500), Stat1 (Abcam, AB31369, stock: 1 mg/ml, working dilution 1/1000), BrdU (Abcam, AB6326, stock: 1 mg/ml, working dilution 1/1000), Ifnar1 (Sino Biological, 50469, stock: 1 mg/ml, working dilution 1/1000), following PBST (1×PBS with 0.05% Tween-20) washes, slides were incubated with Alexa Fluor 488, 594- or 647-conjugated anti-mouse, rat or rabbit secondary antibodies (Thermo Fisher Scientific). Slides subsequently were washed and mounted using Vectashield w/DAPI (Vector Labs). For cell immunofluorescence staining, $10^5$ cells were seeded into a 12-well chamber slide (Thermo Fisher Scientific) and cultured overnight. Slides were then processed as described above for tissue staining. 10×, 20× and 40× Images were collected on a Nikon Eclipse 80i Epifluorescence microscope (Nikon)[33]. The cells were identified based on DAPI. Image analysis was performed by thresholding for positive staining and normalizing to total tissue area, using ImageJ (NIH) and Metamorph v7.7.0.0 (Molecular Devices) software. Quantitation initially was performed in an unblinded manner. However, many of the key results were re-quantitated by a second individual in blinded manner to eliminate bias.

Immunohistochemistry

Tissues were fixed in 10% formalin, embedded in paraffin, and incubated with antibodies as previously described[33]. Briefly, 6 μm-thick sections were deparaffinized in xylene, rehydrated in graded ethanol, and subjected to antigen retrieval by steam heating in Citra antigen retrieval solution (BioGenex). After blocking for 1 h at RT in blocking buffer (5% goat serum, 2.5% BSA in 1×PBS), slides were incubated overnight in a humidified chamber at 4° C. with primary antibodies Ki-67 (Millipore, AB9620, working dilution 1/400) or GFAP (Sigma, G9269, working dilution 1/1000). Slides were then incubated at RT for 30 minutes with anti-rabbit or anti-mouse secondary antibodies (EnVision+System-HRP Labelled Polymer, Dako). Staining was detected using 3,3'-diaminobenzidine (DAB). Image acquisition and analysis was similar to that of immunofluorescence imaging.

Organoids

Organoids were formed by suspending tumour cells in Matrigel and forming 20 ml pearls on Parafilm molds prior to culture. Organoids were cultured in 6-well or 10-cm plates, shaking in Neurobasal complete media. Images of growing organoids were acquired using an EVOS FL Cell Imaging System (Invitrogen) for microscopic imaging. Organoids were grown until 35 days under these conditions. Organoids were infected with ZIKV-Dakar or ZIKV-Brazil at $10^6$ FFU for 2 h and then the media was removed. Organoids subsequently were washed three times with PBS, and fresh Neurobasal complete media was added[20]. Images were acquired using an EVOS Cell Imaging System 3 (Thermo Fisher Scientific). Areas of individual organoids were measured with ImageJ.

Immunoblotting

Cells were collected and lysed in RIPA buffer (50 mM Tris-HCl, pH 7.5; 150 mM NaCl; 0.5% NP-40; 50 mM NaF with protease inhibitors (Thermofisher, EDTA-free), and incubated on ice for 30 min. Lysates were centrifuged at 14,000×rpm at 4° C. for 10 min, and supernatants were collected. Protein concentration was determined using a Bradford assay (Bio-Rad Laboratories). Equal amounts of protein samples were mixed with SDS Laemmli loading buffer, boiled and electrophoresed using NuPAGE Bis-Tris Gels (Life Technologies), then transferred onto PVDF membranes (Millipore). Blocking was performed for 45 min using TBST supplemented with 5% non-fat dry milk and blotting performed with primary antibodies at 4° C. for 16 h. The following antibodies were used: Sox2 (R&D, AF2018, stock: 0.2 mg/ml, working dilution 1/1000), Olig2 (R&D, AF2418, stock: 0.2 mg/ml, working dilution 1/1000), GFAP (Biolegend, PRB-571C, working dilution 1/1000), and α-tubulin (Sigma, T6074, stock: 2 mg/ml, working dilution 1/1000).

Animal Experiments (a) Mice and tumour implantation. Mouse glioblastoma cells (GL261 and CT2A) transduced with luciferase were grown in DMEM supplemented with 10% serum. Cells were harvested by trypsinization, and then washed and resuspended in PBS. A total of $2\times10^4$ cells were implanted into six week-old C57BL/6 female mice (Jackson Laboratory). Briefly, animals were anesthetized by intraperitoneal injection of ketamine (10 mg/kg) and xylazine (100 mg/kg), placed in a stereotactic apparatus (Stoelting) and an incision was made over the cranial midline. A burrhole was made 1.5 mm anterior to lambda and 2.5 mm right of midline. A 29.5 gauge Hamilton syringe was inserted to a depth of 3 mm and withdrawn 0.5 mm to a depth of 2.5 mm. 3 μl of GL261 or CT-2A-luc2 cells were injected over the course of 5 min. The incision site was closed by Vetbond (3M).

(b) Treatment and animal monitoring. One (GL261) or two weeks (GL261 or CT2A) following tumour implantation, animals were placed into two groups, for mouse-adapted ZIKV-Dakar inoculation or saline injection. There was no formal animal randomization process; animals were taken from serial cages and treated with control or virus. $10^3$ or $10^5$ FFU of mouse-adapted ZIKV-Dakar was diluted in 10 μl volume. The same coordinates from surgery were used for this treatment. Animals were monitored daily for signs of neurological impairment. The monitor was not blinded to the treatment received.

Flow Cytometry

At different time points after ZIKV infection, cells were fixed with 2% PFA diluted in PBS for 10 min at room temperature and permeabilized with HBSS buffer (10 mM HEPES, 0.1% (w/v) saponin (Sigma), and 0.025% $NaN_3$ for 10 min at room temperature). GSCs were transferred to a V-bottom plate (Costar) and incubated for 1 h at 4° C. with 2 μg/mL of ZV-64 mAb[34]. After washing, cells were incubated with an Alexa Fluor 647-conjugated goat anti-mouse IgG (Invitrogen) for 30 min at 4° C., washed twice with HBSS buffer, processed on a FACS Array (BD Biosciences), and analysed using FlowJo software (Tree Star).

Bioluminescence Imaging

Beginning one week after tumour cell implantation, brain tumour formation was detected using bioluminescence imaging. Mice, under isoflurane anaesthesia (2% vaporized in $O_2$), were injected intraperitoneally with D-luciferin (150 mg/kg in PBS; Gold Biotechnology) and imaged using an IVIS50 (PerkinElmer). Exposure times were 10 sec or 60 sec, and software-defined contour regions of interest were used to measure total photon flux (photons/sec) using Living Image 2.6.

Quantitative RT-PCR for ZIKV RNA

ZIKV RNA levels were determined by one-step quantitative reverse transcriptase PCR (qRT-PCR) (ThermoFisher) on an ABI 7500 Fast instrument using standard cycling conditions. Viral burden was expressed on a $\log_{10}$ scale as viral RNA equivalents per g after comparison with a standard curve produced using serial tenfold dilutions of ZIKV RNA. For ZIKV, the following primer sets were used:

```
For:
                                    (SEQ ID NO: 1)
5'-CCACCAATGTTCTCTTGCAGACATATTG-3';

Rev:
                                    (SEQ ID NO: 2)
5'-TTCGGACAGCCGTTGTCCAACACAAG-3';
and

Probe:
                                    (SEQ ID NO: 3)
5'-56-FAM/AGCCTACCT TGACAAGCAGTC/3IABkFQ-3'.
```

Quantitative RT-PCR for GSCs and DGCs

Total cellular RNA was isolated using Trizol reagent (Sigma-Aldrich), followed by reverse transcription into cDNA using the qScript cDNA Synthesis Kit (Quanta BioSciences). Real-time PCR was performed using an Applied Biosystems 7900HT cycler using SYBR-Green PCR Master Mix (Thermo Fisher Scientific), Sequences for gene-specific primer sets were as follows:

```
human IFNAR1
forward
                                    (SEQ ID NO: 4)
5'-AAC AGG AGC GAT GAG TCI GTC-3'
and

reverse
                                    (SEQ ID NO: 5)
5'-TGC GAA ATG GTG TAA ATG AGT CA-3';

human STAT1
forward
                                    (SEQ ID NO: 6)
5'-CAG CTT GAC TCA AAA TTC CTG GA-3'
and
```

-continued

```
reverse
                                    (SEQ ID NO: 7)
5'-TGA AGA TTA CGC TTG CTT TTC CT-3';

human IRF1
forward
                                    (SEQ ID NO: 8)
5'-ATG CCC ATC ACT CGG ATG C-3'
and

reverse
                                    (SEQ ID NO: 9)
5'-CCC TGC TTT GTAICG GCC TG-3';

human IFIT1
forward
                                   (SEQ ID NO: 10)
5'-ATG ACG ATG AAA TGC CTG A'
and

reverse
                                   (SEQ ID NO: 11)
5'-CAG GTC ACC AGA CTC CTC AC-3';

human OAS2-1
forward
                                   (SEQ ID NO: 12)
5'-CTCAGAAGCTGGGTTGGTTTAT-3'
and

reverse
                                   (SEQ ID NO: 13)
5'-ACCATCTCGTCGATCAGTGTC-3';

human IFIH1
forward
                                   (SEQ ID NO: 14)
5'- TCG AAT GGG TAT TCC ACA GAC G-3'
and

reverse
                                   (SEQ ID NO: 15)
5'- GTG GCG ACT GTCCTC TGA A-3';

18S RNA
                                   (SEQ ID NO: 16)
forward 5'-AACCCGTTGAACCCCATT-5'
and

reverse
                                   (SEQ ID NO: 17)
5'-CCATCCAATCGGTAGTAGCG-3';

GAPDH
forward
                                   (SEQ ID NO: 18)
5'-CCTGTTCGACAGTCAGCCG-3'
and

reverse
                                   (SEQ ID NO: 19)
5'-CGACCAAATCCGTTGACTCC-3';
```

RNA-Sequencing Data Acquisition, Quality Control, and Processing

RNA was obtained from GSCs infected with ZIKV-Dakar for 48-56 h. Total cellular RNA was isolated using the RNeasy kit (Qiagen). RNA-seq reads were aligned to the Ensembl release 76 assembly with STAR version 2.5.1a. Gene counts were derived from the number of uniquely aligned unambiguous reads by Subread:feature Count version 1.4.6p5. Transcript counts were produced by Sailfish version 0.6.3. Sequencing performance was assessed for total number of aligned reads, total number of uniquely aligned reads, genes and transcripts detected, ribosomal fraction, known junction saturation, and read distribution over known gene models with RSeQC version 2.6.2.

All gene-level and transcript counts were imported into the R/Bioconductor package EdgeR and TMM normalization size factors were calculated to adjust for samples for differences in library size. Genes or transcripts not expressed in any sample were excluded from further analysis. The TMM size factors and the matrix of counts were imported into R/Bioconductor package Limma and weighted likelihoods based on the observed mean-variance relationship of every gene/transcript were calculated for all samples with the Voom function. Performance of the samples was assessed with a Spearman correlation matrix and multi-dimensional scaling plots. Gene/transcript performance was assessed with plots of residual standard deviation of every gene to their average log-count with a robustly fitted trend line of the residuals. Generalized linear models were created to test for gene/transcript level differential expression. Differentially expressed genes and transcripts were then filtered for FDR adjusted P values less than or equal to 0.05.

To enhance the biological interpretation of the large set of transcripts, grouping of genes/transcripts based on functional similarity was achieved using the R/Bioconductor packages GAGE and Pathview. GAGE and Pathview also were used to generate pathway maps on known signalling and metabolism pathways curated by KEGG.

For the matched GSC and DGC lines, RNA-sequencing data was evaluated for type I and II IFN signatures between GSCs and DGCs using gene set enrichment analysis and was validated using RNA-sequencing data on additional matched cell lines derived from Suva et al[36]. IFN signatures were derived from the Molecular Signature Database curated by the Broad Institute[36] (http://www.broad.mit.edu/gsea/). Unsupervised hierarchical clustering was performed using FPKM values from matched TPC and DGC lines.

Statistical Analysis

All statistical analysis was performed using Prism 7.0 software (Graphpad). The number of animals and replicate in vitro experiments is specified in each figure legend. No statistical methods were used to predetermine sample sizes, but our choice of sample sizes is similar to those reported in previous publications[20, 33]. All animals that survived tumour implantation and virus injection surgeries were included in the analyses. All grouped data were presented as mean±SD or SEM as indicated in figure legends. Student's t-tests, one-way ANOVA with multiple comparison correction, and two-way ANOVA with multiple comparison correction were used to assess significance of differences between groups. These tests were performed when the sample size was large enough to assume that the means were normally distributed or that the distribution of residuals was normal, respectively. For groups being statistically compared, variance in data was similar. For animal survival analysis, Kaplan-Meier curves were generated and the log-rank test was performed to assess statistical significance between groups.

Data Availability

Upon acceptance, all RNA sequencing data will be deposited in the Gene Expression Omnibus (GEO) data repository.

Discussion for Examples 1-10

In GBM and other cancer types, cancer stem cells contribute tumour malignancy due to resistance to radiotherapy, chemotherapy, molecularly targeted therapies, and immunotherapies, supporting the urgent need for effective anti-CSC therapies[3]. The findings suggest that ZIKV, because of its unique tropism for neuroprogenitor cells, may offer a tailored therapy that could be used in combination with more conventional therapies (e.g. cytotoxic chemotherapy) that target bulk tumour cell populations. Future engineering could render ZIKV an important tool in neuro-oncology.

Example 11: Immune Checkpoint Blockade to Enhance Zika Virus Treatment of Glioblastoma As described above, we recently showed the first use of ZIKV to kill GSCs. We showed that the virus kills patient-derived GSCs and minimally affects differentiated (non-GSC) tumor cells or normal human brain cells. ZIKV treatment prolongs survival of mice bearing syngeneic brain tumors two-to three-fold, and the virus remains within the tumor bed. Our in vitro findings were replicated using patient-derived GBM organoids and brain slices: while ZIKV targeted GSCs within fresh brain slices, there was no effect on normal brain slices taken from epilepsy surgeries. Importantly, the survival results and shrinkage of tumors we observed in mice suggest that there were indirect effects of ZIKV treatment, beyond death of GSCs. We propose that ZIKV initiates a tumor-directed immune response.

Immune checkpoint inhibitors have significant effects on brain metastases, suggesting that they have activity in the brain or activity on immune cells that get into the brain. However, checkpoint inhibitor trials in GBM have been so far unsuccessful. For example, preliminary results of a randomized phase III study testing the efficacy and safety of nivolumab (the CheckMate 143 study) were presented at the annual meeting of the American Society of Clinical Oncology in June 2017. Reardon, et al. demonstrated that nivolumab was safe, but the overall response rate in recurrent GBM was lower than the current standard, bevacizumab, a monoclonal antibody that blocks angiogenesis. Interestingly, in patients that did respond, their responses were significantly more durable in the nivolumab group. This suggests that checkpoint blockade can be safe and possibly effective, but we hypothesize that efficacy requires a stronger immune stimulus.

Here, we propose using attenuated Zika virus followed by immune checkpoint blockade to treat GBM. This research is significant because we are developing a new treatment paradigm for the most aggressive brain tumor. This work is innovative because it uses the honing capacity of ZIKV to target and kill GSCs and a unique, attenuated ZIKV that we have genetically engineered to be safer while still effective. Additionally, no other oncolytic virus has ever been combined with checkpoint blockade to treat brain tumors.

Our therapeutic regimen would be beneficial to all patients with recurrent glioblastoma, and if we find benefit, we would move the regimen in the upfront setting at diagnosis, in combination with standard temozolomide and radiation. In a phase I trial, the primary endpoint will be the maximal safe Zika virus concentration (up to $10^8$ FFU) delivered intracranially, combined with the known maximal checkpoint blockade dose, delivered intravenously beginning two weeks later. Secondary endpoints will be determination of the immune infiltration in treated tumors and correlation with activated T cell populations in blood. In situ hybridization will detect Zika virus distribution within the tumor, and in relationship to injection sites. For a phase II trial, the primary endpoint will be time to GBM recurrence. For this trial, we will compare ZIKV plus checkpoint blockade to bevacizumab, the current standard treatment at recurrence. No other study has tested the combination of oncolytic virus with immune checkpoint blockade in GBM.

Example 12: Generation of Attenuated Zika Virus Strains

Figure 14:
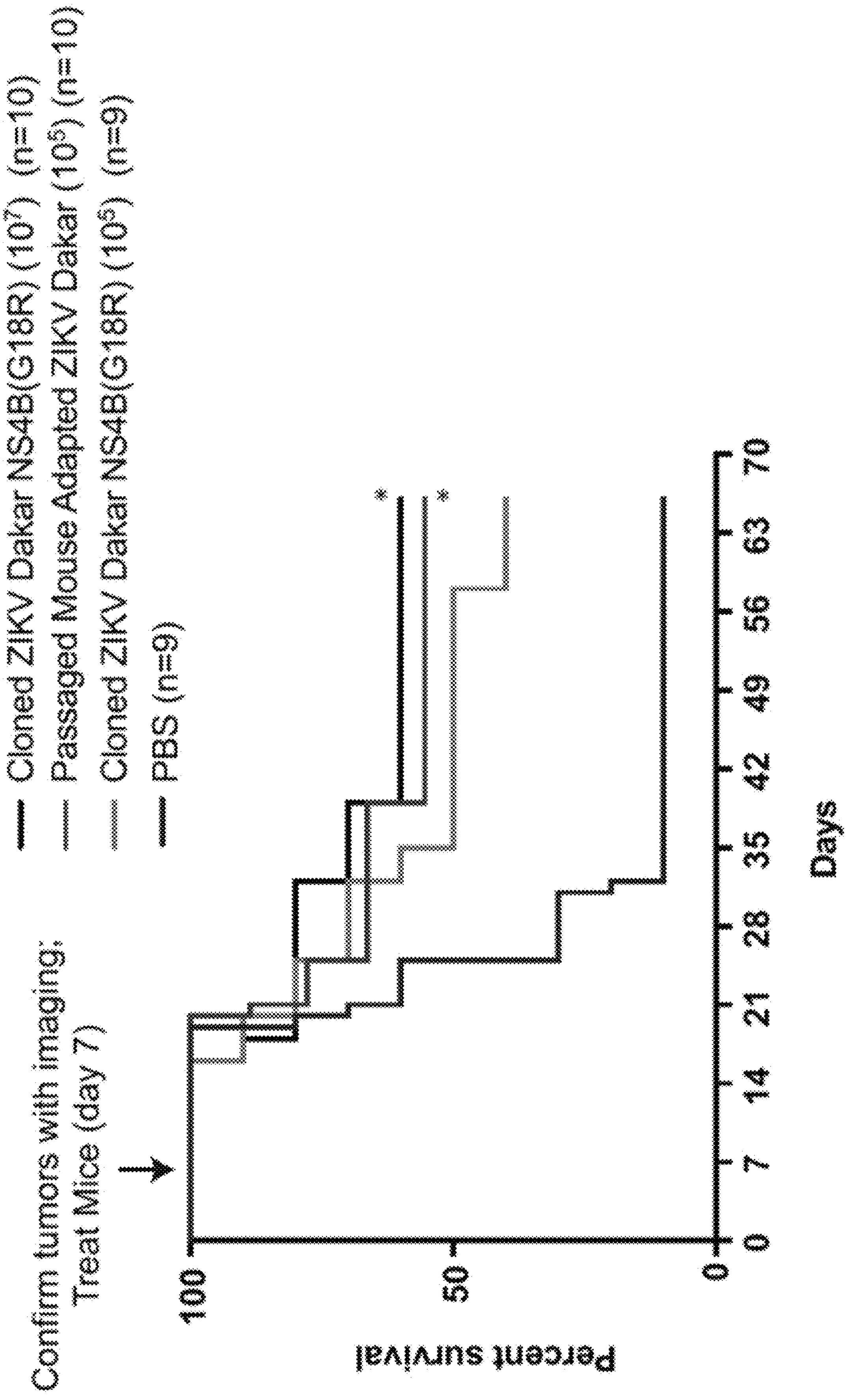
FIG. 14 shows ZIKV generated from a cDNA clone prolongs survival of mice with glioma. Mice bearing GL261 glioma were treated with PBS (n=9) or 105 FFU of mouse-adapted ZIKV Dakar (n=10)(Zhu et al., 2017), or 105 FFU or 107 FFU of ZIKV Dakar NS4B(G18R) produced from cDNA (n=10 each). Significance was analyzed by log-rank test, (*, P<0.05).

We've generated a Zika virus strains from a cloned cDNA backbone (ZIKV Dakar 41525 strain, Accession No. KU955591). Into this clone, we made an NS4B (G18R) mutation, which confers mouse adaptation while maintaining virulence in human cells (Gorman et al., 2018). Such generation from a cDNA clone makes our product consistent and safer. We confirmed this Zika virus strain performed as well as the passaged strain (FIG. 14). We've successfully generated attenuated strains from the cloned cDNA backbone and have produced the following:

a) ZIKV Dakar NS4B(G18R)-NS3 (K399R)
b) ZIKV Dakar NS3 (K399R)
c) ZIKV Dakar NS4B(G18R)-NS5 (E218A)
d) ZIKV Dakar NS4B(G18R)-E(N154Q T156V)
e) ZIKV Dakar NS4B(G18R)-Δ3'UTR The NS3 (K399R) mutation is found in the passaged mouse adapted strain but not likely required for adaptation (Gorman et al., 2018). The NS5 (E218A) mutation sensitizes the virus to translational inhibition by type I interferon and IFIT1 and results in attenuation in cells responsive to type I interferons (Daffis et al., 2010). The envelope protein E (N154Q T156V) mutations limit viral dissemination across endothelial barriers. The deletion of 10 nucleotides in the 3' untranslated regions (Δ3'UTR) disrupts short flaviviral RNA productions and as such also results in attenuation in cells responsive to type I interferons.

Figure 15:
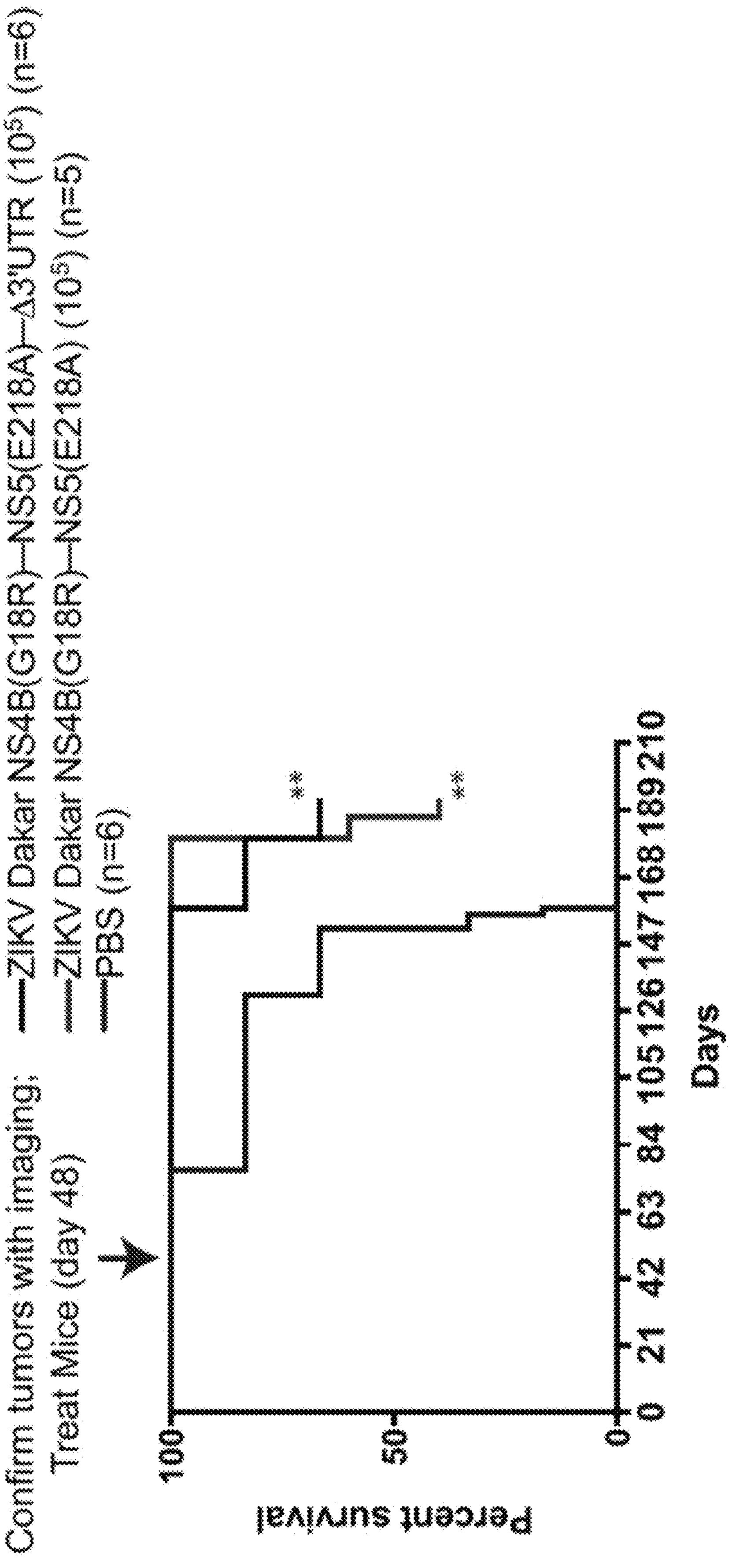
FIG. 15 shows attenuated ZIKV generated from a cDNA clone prolongs survival of mice harboring human glioblastoma. Immunodeficient mice (NOD-scidIL2R$\gamma^{null}$) bearing human 0308 glioblastoma stem cells (Lee et al., 2006) were treated with PBS (n=6), $10^5$ FFU of ZIKV Dakar NS4B (G18R)-NS5(E218A)-Δ3'UTR (n=6), or 105 FFU ZIKV Dakar NS4B(G18R)-NS5(E218A)-Δ3'UTR (n=5).

We have confirmed activity of the NS5 mutant virus in human GBM cells (Zhu et al., 2017). We also tested and confirmed that attenuated ZIKV strains generated from the cloned cDNA have significant efficacy in human glioblastoma stem cells in vivo (FIG. 15).

Figure 16:
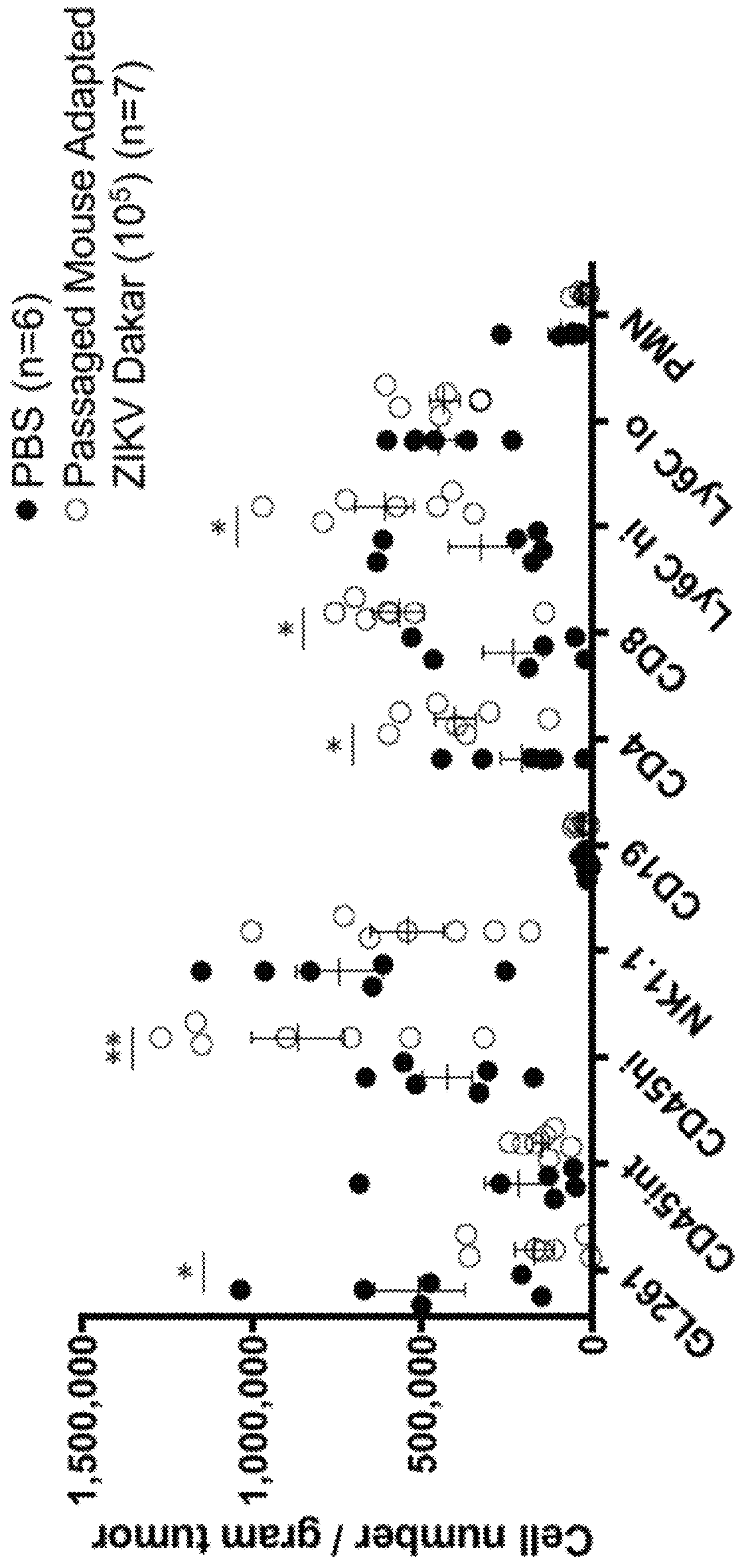
FIG. 16 shows treatment with ZIKV results in immune cell infiltration into tumor. Mice bearing GL261 glioma were treated with PBS (n=6) or 105 FFU of mouse-adapted ZIKV Dakar (n=7). At 14 days after treatment, brains were harvested and subjected to flow cytometry. Significance was analyzed by unpaired student's 2-tailed t-test, (*, P<0.05; **, P<0.01).

We have found that in addition to direct oncolytic effects on tumor cells, ZIKV treatment results in immune cell infiltration (FIG. 16) in the region of the tumor. This suggests use of ZIKV treatment combined with therapies that leverage the immune system may provide a new treatment paradigm for cancer.

Figure 17:
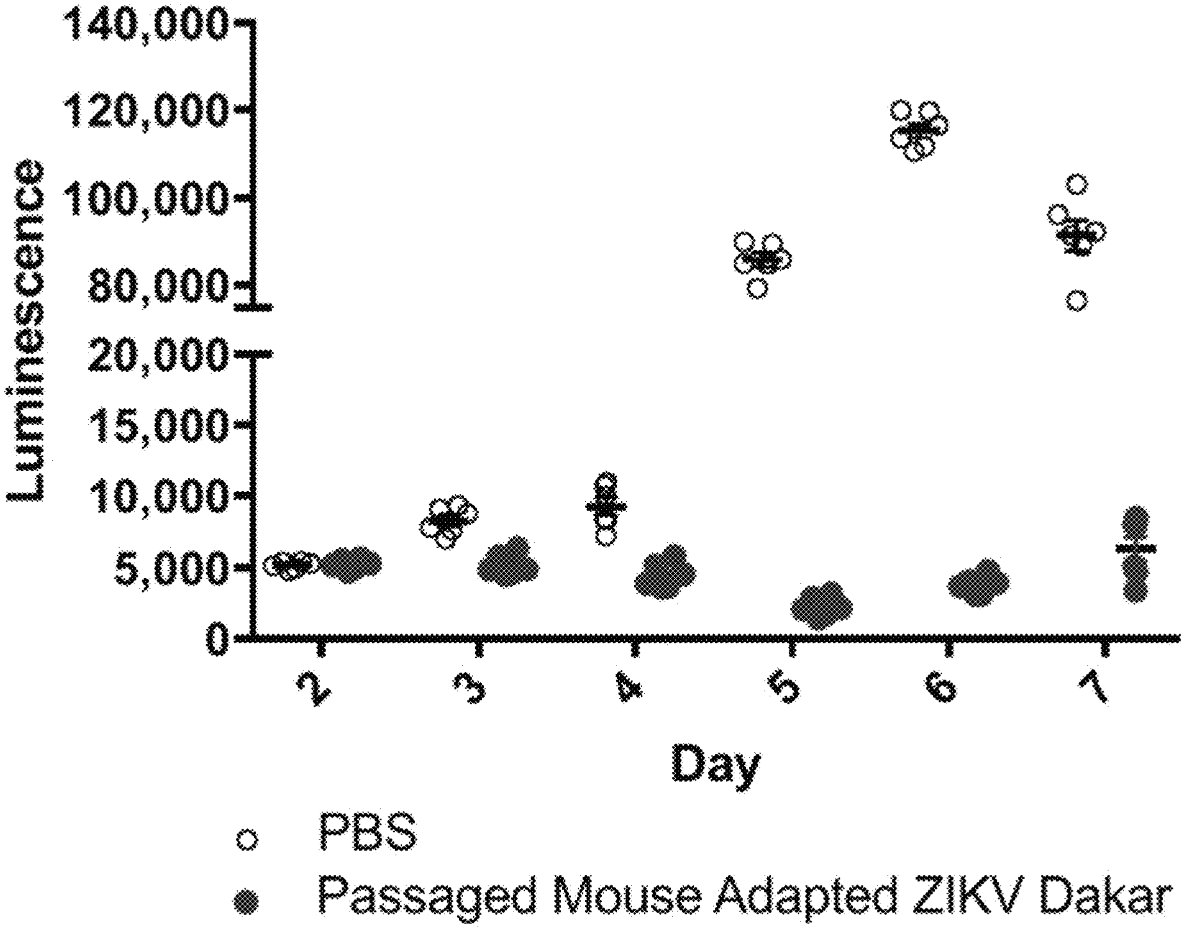
FIG. 17 shows ZIKV has oncolytic activity in multiple myeloma cells. MM1S human multiple myeloma cells were treated with PBS control or treated with ZIKV-Dakar (MOI=5) on day 0. Relative cell number was assessed by luminescence using Celltiter Glo assay (Promega).

Attenuated ZIKV for use in treating cancer include a) All mutations affecting ZIKV 2'-O methyltransferase activity (e.g., NS5 E218A)
b) All mutations affecting ZIKV E and NS1 protein N-linked glycosylations
c) All mutations for deletions in the 3'-UTR affect sfRNA generation or interferon antagonism
d) All mutations in NS4B that affect interferon antagonism or autophagy pathways Lastly, we have found that ZIKV has activity in multiple myeloma (FIG. 17).

REFERENCES TO EXAMPLES

1. Stupp, R. et al. Effects of radiotherapy with concomitant and adjuvant temozolomide versus radiotherapy alone on survival in glioblastoma in a randomised phase III study: 5-year analysis of the EORTC-NCIC trial. *The Lancet. Oncology* 10, 459-466, doi:10.1016/s1470-2045(09)70025-7 (2009).
2 Chen, J. et al. A restricted cell population propagates glioblastoma growth after chemotherapy. *Nature* 488, 522-526, doi:10.1038/nature11287 (2012).
3 Alvarado, A. G. et al. Glioblastoma Cancer Stem Cells Evade Innate Immune Suppression of Self-Renewal through Reduced TLR4 Expression. *Cell stem cell* 20, 450-461.e454, doi:10.1016/j.stem.2016.12.001 (2017).
4 Bao, S. et al. Glioma stem cells promote radioresistance by preferential activation of the DNA damage response. *Nature* 444, 756-760, doi:10.1038/nature05236 (2006).
5 Wallner, K. E., Galicich, J. H., Krol, G., Arbit, E. & Malkin, M. G. Patterns of failure following treatment for glioblastoma multiforme and anaplastic astrocytoma. *International Journal of Radiation Oncology*Biology*Physics* 16, 1405-1409, doi: 10.1016/0360-3016(89)90941-3 (1989).

6 Kaufmann, J. K. & Chiocca, E. A. Glioma virus therapies between bench and bedside. *Neuro-oncology* 16, 334-351, doi:10.1093/neuonc/not310 (2014).

7 Miska, J. et al. Anti-GITR therapy promotes immunity against malignant glioma in a murine model. *Cancer Immunology, Immunotherapy* 65, 1555-1567, doi: 10.1007/s00262-016-1912-8 (2016).

8 Cattaneo, R. et al. How to develop viruses into anticancer weapons. *PLOS Pathogens* 13, e1006190, doi:10.1371/journal.ppat.1006190 (2017).

9 Martuza, R., Malick, A., Markert, J., Ruffner, K. & Coen, D. Experimental therapy of human glioma by means of a genetically engineered virus mutant. *Science* (New York, N.Y.) 252 (1991).

10 Alonso, M. M., Jiang, H., Gomez-Manzano, C. & Fueyo, J. Targeting brain tumor stem cells with oncolytic adenoviruses. *Methods in molecular biology* (Clifton, N.J.) 797, 111-125, doi:10.1007/978-1-61779-340-0_9 (2012).

11 Cassady, K. A. et al. *Pre-clinical Assessment of* C134, a Chimeric Oncolytic Herpes Simplex Virus, in Mice and Non-human Primates. *Molecular therapy oncolytics* 5, 1-10, doi:10.1016/j.omto.2017.02.001 (2017).

12 Lazear, H. M. et al. A Mouse Model of Zika Virus Pathogenesis. *Cell host & microbe* 19, 720-730, doi: 10.1016/j.chom.2016.03.010 (2016).

13 Qian, X. et al. Brain-Region-Specific Organoids Using Mini-bioreactors for Modeling ZIKV Exposure. *Cell* 165, 1238-1254, doi:10.1016/j.cell.2016.04.032 (2016).

14 Shan, C. et al. An Infectious cDNA Clone of Zika Virus to Study Viral Virulence, Mosquito Transmission, and Antiviral Inhibitors. *Cell Host & Microbe* 19, 891-900, doi:10.1016/j.chom.2016.05.004 (2016).

15 Li, H. et al. in *Cell stem cell* Vol. 19 593-598 (2016).

16 Ming, G.-I., Tang, H. & Song, H. Advances in Zika *Virus Research*: Stem Cell Models, Challenges, and Opportunities. *Cell stem cell* 19, 690-702, doi:10.1016/j.stem.2016.11.014 (2016).

17 Garcez, P. P. et al. Zika virus impairs growth in human neurospheres and brain organoids. *Science* (New York, N.Y.) 352 (2016).

18 Gabriel, E. et al. in *Cell stem cell* Vol. 20 397-406.e395 (2017).

19 Parra, B. et al. Guillainé Barré Syndrome Associated with Zika Virus Infection in Colombia. *New England Journal of Medicine* 375, 1513-1523, doi:10.1056/NEJMoa1605564 (2016).

20 Wang, X. et al. Purine synthesis promotes maintenance of brain tumor initiating cells in glioma. *Nature neuroscience*, doi:10.1038/nn.4537 (2017).

21 Liu, C. et al. Mosaic analysis with double markers reveals tumor cell of origin in glioma. *Cell* 146, 209-221, doi: 10.1016/j.cell.2011.06.014 (2011).

22 Pastrana, E., Silva-Vargas, V. & Doetsch, F. Eyes wide open: a critical review of sphere-formation as an assay for stem cells. *Cell stem cell* 8, 486-498, doi:10.1016/j.stem.2011.04.007 (2011).

23 Southam, C. M. & Moore, A. E. Clinical studies of viruses as antineoplastic agents, with particular reference to egypt 101 virus. *Cancer* 5, 1025-1034, doi:10.1002/1097-0142(195209)5:5<1025::AID-CNCR2820050518>3.0.CO; 2-Q (1952).

24 Moore, A. E. Effects of Viruses on Tumors. *Annual Review of Microbiology* 8, 393-410, doi:10.1146/annurev.mi.08.100154.002141 (1954).

25 Cho, H. et al. Differential innate immune response programs in neuronal subtypes determine susceptibility to infection in the brain by positive-stranded RNA viruses. *Nature medicine* 19, 458-464, doi: 10.1038/nm.3108 (2013).

26 Hubert, C. G. et al. A Three-Dimensional Organoid Culture System Derived from Human Glioblastomas Recapitulates the Hypoxic Gradients and Cancer Stem Cell Heterogeneity of Tumors Found In Vivo. *Cancer research* 76, 2465-2477, doi:10.1158/0008-5472.can-15-2402 (2016).

27 Singh, S. K. et al. Identification of human brain tumour initiating cells. *Nature* 432, 396-401, doi:10.1038/nature03128 (2004).

28 Brown, M. C. & Gromeier, M. Cytotoxic and immunogenic mechanisms of recombinant oncolytic poliovirus. *Current opinion in virology* 13, 81-85, doi:10.1016/j.coviro.2015.05.007 (2015).

29 Sapparapu, G. et al. Neutralizing human antibodies prevent Zika virus replication and fetal disease in mice. *Nature* 540, 443-447, doi:10.1038/nature20564 (2016).

30 Daffis, S. et al. 2'-O methylation of the viral mRNA cap evades host restriction by IFIT family members. doi: 10.1038/nature09489.

31 Govero, J. et al. Zika virus infection damages the testes in mice. *Nature* 540, 438-442, doi:10.1038/nature20556 (2016).

32 Oh, T. et al. Immunocompetent murine models for the study of glioblastoma immunotherapy. *Journal of Translational Medicine* 12, 107, doi:10.1186/1479-5876-12-107 (2014).

33 Jiang, H. et al. Targeting focal adhesion kinase renders pancreatic cancers responsive to checkpoint immunotherapy. *Nature medicine* 22, 851-860, doi:10.1038/nm.4123 (2016).

34 Zhao, H. et al. Structural Basis of Zika Virus-Specific Antibody Protection. *Cell* 166, 1016-1027, doi:10.1016/j.cell.2016.07.020 (2016).

35 Suvà, M. L. et al. Reconstructing and reprogramming the tumor-propagating potential of glioblastoma stem-like cells. *Cell* 157, 580-594, doi:10.1016/j.cell.2014.02.030 (2014).

36 Subramanian, A. et al. Gene set enrichment analysis: a knowledge-based approach for interpreting genome-wide expression profiles. *Proceedings of the National Academy of Sciences of the United States of America* 102, 15545-15550, doi:10.1073/pnas.0506580102 (2005).

What is claimed is:

1. A method of treating a glioma in a subject in need thereof, the method comprising: intratumorally administering a composition comprising an engineered ZIKV to the subject, wherein the engineered ZIKV comprises a 10 nucleotide deletion in the 3' UTR of the ZIKV genome, wherein the 10 nucleotide deletion disrupts short flaviviral RNA production by the engineered ZIKV as compared to a ZIKV without the 10 nucleotide deletion, wherein (a) the ZIKV is strain FSS13025 comprising the sequence of SEQ ID NO: 21 and the deletion comprises nucleotides 10650 to 10659 of SEQ ID NO: 21; or (b) the ZIKV is strain Dakar 41525 comprising the sequence of SEQ ID NO: 22 and the deletion comprises nucleotides 10649 to 10658 of SEQ ID NO: 22.

2. The method of claim 1, wherein the engineered ZIKV selectively kills glioma stem cells or renders the glioma stem cells more susceptible to chemotherapy or radiation therapy.

3. The method of claim 1, further comprising the step of administrating a chemotherapeutic agent, an immune checkpoint blockade, radiation, a CAR T-cell therapy, an interferon-based therapy or an interleukin-based therapy to the subject.

4. The method of claim 1, wherein the glioma is selected from the group consisting of astrocytoma, oligodendroglioma, and glioblastoma.

* * * * *